(12) United States Patent
Marineau et al.

(10) Patent No.: US 9,975,896 B2
(45) Date of Patent: May 22, 2018

(54) INHIBITORS OF TRANSCRIPTION FACTORS AND USES THEREOF

(71) Applicants: Dana-Farber Cancer Institute, Inc., Boston, MA (US); University of Massachusetts, Boston, MA (US)

(72) Inventors: Jason J. Marineau, Franklin, MA (US); James E. Bradner, Weston, MA (US); Wei Zhang, Sharon, MA (US); Jun Qi, Sharon, MA (US); Michael R. McKeown, Brookline, MA (US); Harry Hongning Fu, Newton, MA (US); Shuai Liu, Dorchester, MA (US)

(73) Assignees: Dana-Farber Cancer Institute, Inc., Boston, MA (US); University of Massachusetts, Boston, MA (US)

( * ) Notice: Subject to any disclaimer, the term of this patent is extended or adjusted under 35 U.S.C. 154(b) by 0 days. days.

(21) Appl. No.: 14/907,339

(22) PCT Filed: Jul. 25, 2014

(86) PCT No.: PCT/US2014/048230
§ 371 (c)(1),
(2) Date: Jan. 25, 2016

(87) PCT Pub. No.: WO2015/013635
PCT Pub. Date: Jan. 29, 2015

(65) Prior Publication Data
US 2016/0168154 A1 Jun. 16, 2016

Related U.S. Application Data

(60) Provisional application No. 61/858,521, filed on Jul. 25, 2013.

(51) Int. Cl.
*A61K 31/519* (2006.01)
*C07D 487/04* (2006.01)
(Continued)

(52) U.S. Cl.
CPC .......... *C07D 487/04* (2013.01); *A61K 31/519* (2013.01); *C07D 413/10* (2013.01); *C07D 471/04* (2013.01); *C07D 491/048* (2013.01)

(58) Field of Classification Search
CPC ............................ A61K 31/519; C07D 487/04
See application file for complete search history.

(56) References Cited

U.S. PATENT DOCUMENTS 3,681,343 A  8/1972 Hester, Jr.
3,709,898 A  1/1973 Hester, Jr.
(Continued)

FOREIGN PATENT DOCUMENTS

CA  2020806 A1  1/1991
CA  2710740 A1  7/2009
(Continued)

OTHER PUBLICATIONS

International Search Report and Written Opinion for PCT/US2014/023386, dated Jul. 9, 2014.
(Continued)

*Primary Examiner* — Craig D Ricci
*Assistant Examiner* — Christopher R Stone
(74) *Attorney, Agent, or Firm* — Wolf, Greenfield & Sacks, P.C.

(57) ABSTRACT

The present invention provides novel compounds of any one of Formulae (I) to (IV), and pharmaceutically compositions thereof. Compounds of any one of Formulae (I) to (IV) are believed to be inhibitors of bromodomain-containing proteins (e.g., bromo and extra terminal proteins (BETs)). Also provided are methods, uses, and kits using the inventive compounds and pharmaceutical compositions for inhibiting the activity of the bromodomain-containing proteins and for treating and/or preventing in a subject in need thereof diseases associated with bromodomain-containing proteins, such as proliferative diseases.

(Continued)

-continued

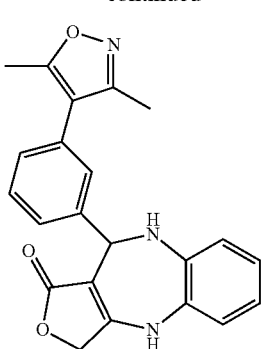

(IV)

33 Claims, 15 Drawing Sheets

(51) Int. Cl.
  *C07D 413/10* (2006.01)
  *C07D 471/04* (2006.01)
  *C07D 491/048* (2006.01)

(56) References Cited

U.S. PATENT DOCUMENTS

| | | |
|---|---|---|
| 3,812,259 A | 5/1974 | Collins |
| 4,621,083 A | 11/1986 | Casals-Stenzel et al. |
| 5,104,543 A | 4/1992 | Brandt et al. |
| 5,593,988 A | 1/1997 | Tahara et al. |
| 5,712,274 A | 1/1998 | Sueoka et al. |
| 5,721,231 A | 2/1998 | Moriwaki et al. |
| 5,753,649 A | 5/1998 | Taha, III et al. |
| 5,760,032 A | 6/1998 | Kitajima et al. |
| 5,846,972 A | 12/1998 | Buckman et al. |
| 5,854,238 A | 12/1998 | Kempen |
| 6,444,664 B1 | 9/2002 | Princen et al. |
| 6,806,272 B2 | 10/2004 | Bauer et al. |
| 6,861,422 B2 | 3/2005 | Hoffmann et al. |
| 7,015,213 B1 | 3/2006 | Bigg et al. |
| 7,371,753 B2 | 5/2008 | Stadtmueller et al. |
| 7,528,143 B2 | 5/2009 | Noronha et al. |
| 7,528,153 B2 | 5/2009 | Noronha et al. |
| 7,589,167 B2 | 9/2009 | Zhou et al. |
| 7,750,152 B2 | 7/2010 | Hoffman et al. |
| 7,786,299 B2 | 8/2010 | Hoffman et al. |
| 7,816,530 B2 | 10/2010 | Grauert |
| 7,825,246 B2 | 11/2010 | Noronha et al. |
| 8,003,786 B2 | 8/2011 | Hoffman et al. |
| 8,044,042 B2 | 10/2011 | Adachi et al. |
| 8,133,900 B2 | 3/2012 | Hood et al. |
| 8,138,199 B2 | 3/2012 | Noronha et al. |
| 8,338,464 B2 | 12/2012 | Melnick et al. |
| 8,476,260 B2 | 7/2013 | Miyoshi et al. |
| 8,604,042 B2 | 12/2013 | Noronha et al. |
| 8,981,083 B2 | 3/2015 | Bradner et al. |
| 9,301,962 B2 | 4/2016 | Bradner et al. |
| 9,320,741 B2 | 4/2016 | Bradner et al. |
| 9,695,172 B2 | 7/2017 | Bradner et al. |
| 9,714,946 B2 | 7/2017 | Bradner et al. |
| 9,789,120 B2 | 10/2017 | Bradner et al. |
| 2002/0032200 A1 | 3/2002 | Cai et al. |
| 2002/0169158 A1 | 11/2002 | Hunt, III et al. |
| 2003/0130268 A1 | 7/2003 | Saga, III et al. |
| 2003/0216758 A1 | 11/2003 | Signore |
| 2004/0176380 A1 | 9/2004 | Hoffmann et al. |
| 2006/0035902 A1 | 2/2006 | Linz et al. |
| 2006/0074088 A1 | 4/2006 | Munzert et al. |
| 2006/0142257 A1 | 6/2006 | Nieschlag et al. |
| 2006/0223055 A1 | 10/2006 | Howley et al. |
| 2007/0105839 A1 | 5/2007 | Imbach et al. |
| 2007/0179178 A1 | 8/2007 | Buettelmann et al. |
| 2007/0218135 A1 | 9/2007 | Mukharya et al. |
| 2008/0004308 A1 | 1/2008 | Dhanak et al. |
| 2008/0081781 A1 | 4/2008 | Lippa et al. |
| 2008/0305113 A1 | 12/2008 | Kwon et al. |
| 2009/0012064 A1 | 1/2009 | Sagara et al. |
| 2009/0238828 A1 | 9/2009 | Munzert et al. |
| 2009/0280115 A1 | 11/2009 | Maier et al. |
| 2009/0281191 A1 | 11/2009 | Rangwala et al. |
| 2009/0318408 A1 | 12/2009 | Cai et al. |
| 2010/0041643 A1 | 2/2010 | Adachi et al. |
| 2010/0249412 A1 | 9/2010 | Linz et al. |
| 2010/0286127 A1 | 11/2010 | Miyoshi et al. |
| 2011/0028405 A1 | 2/2011 | Harrison et al. |
| 2011/0098288 A1 | 4/2011 | Major et al. |
| 2011/0172231 A1 | 7/2011 | Baenteli et al. |
| 2011/0201606 A1 | 8/2011 | Garcia-Cheverria et al. |
| 2011/0212077 A1 | 9/2011 | Noronha et al. |
| 2011/0230460 A1 | 9/2011 | Kempen et al. |
| 2011/0245245 A1 | 10/2011 | Mortensen et al. |
| 2012/0014979 A1 | 1/2012 | Dent |
| 2012/0040961 A1 | 2/2012 | Gray et al. |
| 2012/0202798 A1 | 8/2012 | Sagara |
| 2012/0329803 A1 | 12/2012 | Linz et al. |
| 2013/0184264 A1 | 7/2013 | Bradner et al. |
| 2013/0210813 A1 | 8/2013 | Bradner et al. |
| 2013/0245013 A1 | 9/2013 | Mohr et al. |
| 2013/0252331 A1 | 9/2013 | Bradner et al. |
| 2013/0274239 A1 | 10/2013 | Gangloff et al. |
| 2013/0280332 A1 | 10/2013 | Moss et al. |
| 2014/0011862 A1 | 1/2014 | Bradner et al. |
| 2014/0243322 A1 | 8/2014 | Arnold et al. |
| 2016/0033519 A1 | 2/2016 | Bradner et al. |
| 2016/0231314 A1 | 8/2016 | Bradner et al. |
| 2016/0317547 A1 | 11/2016 | Bradner et al. |
| 2016/0332993 A1 | 11/2016 | Bradner et al. |
| 2016/0347749 A1 | 12/2016 | Bradner et al. |
| 2017/0008895 A1 | 1/2017 | Bradner et al. |
| 2017/0145013 A1 | 5/2017 | Bradner et al. |
| 2017/0145023 A1 | 5/2017 | Bradner et al. |

FOREIGN PATENT DOCUMENTS

| | | |
|---|---|---|
| CH | 622019 A5 | 3/1981 |
| CN | 1227555 A | 9/1999 |
| CN | 101022809 A | 8/2007 |
| CN | 101420955 A | 4/2009 |
| CN | 102341394 A | 2/2012 |
| CN | 103037865 A | 4/2013 |
| DE | 3724164 A1 | 2/1988 |
| EP | 0 087 850 A1 | 9/1983 |
| EP | 0 368 175 A1 | 5/1990 |
| EP | 0 387 613 A1 | 9/1990 |
| EP | 0 934 940 A1 | 8/1999 |
| EP | 0 989 131 B1 | 11/2002 |
| EP | 1 297 836 A1 | 4/2003 |
| EP | 2 112 152 A1 | 10/2009 |
| EP | 2 239 264 A1 | 10/2010 |
| EP | 2 481 739 A1 | 8/2012 |
| ES | 2 351 367 T3 | 2/2011 |
| FR | 2329668 A1 | 5/1977 |
| JP | 61-87684 A | 5/1986 |
| JP | 1-299231 | 12/1989 |
| JP | 6-157316 | 6/1994 |
| JP | H10500998 A | 1/1998 |
| JP | 11-228576 | 8/1999 |
| JP | 11-512107 A | 10/1999 |
| JP | 3001979 | 11/1999 |
| JP | 3096299 | 8/2000 |
| JP | 2008-156311 | 7/2008 |
| JP | 5913292 B2 | 4/2016 |
| PT | 2 139 892 E | 11/2011 |
| WO | WO 97/47622 A1 | 12/1997 |
| WO | WO 98/11111 A1 | 3/1998 |
| WO | WO 01/95912 A1 | 12/2001 |
| WO | WO 2003/020722 A1 | 3/2003 |
| WO | WO 2006/018185 A2 | 2/2006 |
| WO | WO 2007/095188 A2 | 8/2007 |

(56) References Cited

FOREIGN PATENT DOCUMENTS

| | | |
|---|---|---|
| WO | WO 2008/009909 A1 | 1/2008 |
| WO | WO 2008/083056 A2 | 7/2008 |
| WO | WO 2008/113711 A1 | 9/2008 |
| WO | WO 2008/137081 A1 | 11/2008 |
| WO | WO 2009/023269 A2 | 2/2009 |
| WO | WO 2009/040556 A1 | 4/2009 |
| WO | WO 2009/067547 A1 | 5/2009 |
| WO | WO 2009/084693 A1 | 7/2009 |
| WO | WO 2010/015387 A1 | 2/2010 |
| WO | WO 2010/049466 A1 | 5/2010 |
| WO | WO 2010/080712 A1 | 7/2010 |
| WO | WO 2011/036566 A1 | 3/2011 |
| WO | WO 2011/054553 A1 | 5/2011 |
| WO | WO 2011/054841 A1 | 5/2011 |
| WO | WO 2011/054843 A1 | 5/2011 |
| WO | WO 2011/054844 A1 | 5/2011 |
| WO | WO 2011/054845 A1 | 5/2011 |
| WO | WO 2011/054846 A1 | 5/2011 |
| WO | WO 2011/054848 A1 | 5/2011 |
| WO | WO 2011/101369 A1 | 8/2011 |
| WO | WO 2011/143651 A1 | 11/2011 |
| WO | WO 2011/143657 A1 | 11/2011 |
| WO | WO 2011/143660 A2 | 11/2011 |
| WO | WO 2011/143669 A2 | 11/2011 |
| WO | WO 2011/161031 A1 | 12/2011 |
| WO | WO 2012/072505 A1 | 6/2012 |
| WO | WO 2012/075383 A2 | 6/2012 |
| WO | WO 2012/075456 A1 | 6/2012 |
| WO | WO 2012/116170 A1 | 8/2012 |
| WO | WO 2012/118812 A2 | 9/2012 |
| WO | WO 2012/120048 A1 | 9/2012 |
| WO | WO 2013/033268 A2 | 3/2013 |
| WO | WO 2013/033269 A1 | 3/2013 |
| WO | WO 2013/033270 A2 | 3/2013 |
| WO | WO 2013/097601 A1 | 7/2013 |
| WO | WO 2013/148197 A1 | 10/2013 |
| WO | WO 2014/071247 A1 | 5/2014 |
| WO | WO 2014/095774 A1 | 6/2014 |
| WO | WO 2014/139324 A1 | 9/2014 |
| WO | WO 2015/081284 A1 | 6/2015 |
| WO | WO 2015/117083 A1 | 8/2015 |
| WO | WO 2016/022902 A1 | 2/2016 |

OTHER PUBLICATIONS

International Preliminary Report on Patentability for PCT/US2014/023386, dated Sep. 24, 2015.
Invitation to Pay Additional Fees for PCT/US2014/48230, dated Nov. 17, 2014.
International Search Report and Written Opinion for PCT/US2014/48230, dated Jan. 30, 2015.
International Preliminary Report on Patentability for PCT/US2014/48230, dated Feb. 4, 2016.
Invitation to Pay Additional Fees for PCT/US2015/14109, dated Apr. 20, 2015.
International Search Report and Written Opinion for PCT/US2015/14109, dated Jul. 6, 2015.
International Preliminary Report on Patentability for PCT/US2015/14109, dated Aug. 11, 2016.
International Search Report and Written Opinion for PCT/US2015/14044, dated Apr. 23, 2015.
International Preliminary Report on Patentability for PCT/US2015/14044, dated Aug. 11, 2016.
International Search Report and Written Opinion for PCT/US2015/14039, dated Apr. 23, 2015.
International Preliminary Report on Patentability for PCT/US2015/14039, dated Aug. 11, 2016.
International Search Report and Written Opinion for PCT/US2015/14120, dated Apr. 23, 2015.
International Preliminary Report on Patentability for PCT/US2015/14120, dated Aug. 11, 2016.
International Search Report and Written Opinion for PCT/US2015/044180, dated Nov. 5, 2015.
Invitation to Pay Additional Fees for PCT/US2015/44303, dated Oct. 21, 2015.
International Search Report and Written Opinion for PCT/US2015/44303, dated Dec. 31, 2015.
Invitation to Pay Additional Fees for PCT/US2015/051017, dated Oct. 31, 2016.
[No Author Listed], PubChem SID 225027960. Available date/deposit date: Feb. 2, 2015. pubchem.ncbi.nlm.nih.gov/substance/225027960. Last accessed Nov. 28, 2016.
[No Author Listed], PubChem CID 5325760. Published Jan. 25, 2006. pubchem.ncbi.nlm.nih.gov//compound/5325760?from=summary#section=Top. Last accessed Oct. 20, 2014.
CAPLUS Database Result for Deng et al., Structural determinants for ERK5 (MAPK7) and leucine rich repeat kinase 2 activities of benzo[e]pyrimido-[5,4-b]diazepine-6(11H)-ones. Eur J Med Chem. 2013;70:758-67. doi: 10.1016/j.ejmech.2013.10.052. Epub Oct. 29, 2013. Accession No. 2013:1979798. Abstract Only.
Deng et al., Structural determinants for ERK5 (MAPK7) and leucine rich repeat kinase 2 activities of benzo[e]pyrimido-[5,4-b]diazepine-6(11H)-ones. Eur J Med Chem. 2013;70:758-67. doi: 10.1016/j.ejmech.2013.10.052. Epub Oct. 29, 2013.
Zuercher et al., Identification and structure-activity relationship of phenolic acyl hydrazones as selective agonists for the estrogen-related orphan nuclear receptors ERRbeta and ERRgamma.. J Med Chem. May 5, 2005;48(9):3107-9.
Extended European Search Report for PCT/US2014/048230, dated Jan. 31, 2017.
International Preliminary Report on Patentability for PCT/US2015/044180, dated Feb. 23, 2017.
International Preliminary Report on Patentability for PCT/US2015/044303, dated Feb. 23, 2017.
International Search Report and Written Opinion for PCT/US2016/051017, dated Jan. 10, 2017.
International Search Report and Written Opinion for PCT/US2016051107, dated Nov. 22, 2016.
Invitation to Pay Additional Fees for PCT/US2016/63502, dated Feb. 9, 2017.
International Search Report and Written Opinion for PCT/US2016/63502, dated May 10, 2017.
International Search Report and Written Opinion for PCT/US2011/036667, dated Aug. 15, 2011.
International Preliminary Report on Patentability for PCT/US2011/036667, dated Nov. 29, 2012.
International Search Report and Written Opinion for PCT/US2011/036647, dated Aug. 17, 2011.
International Preliminary Report on Patentability for PCT/US2011/036647, dated Nov. 29, 2012.
International Search Report and Written Opinion for PCT/US2011/036672, dated Jan. 27, 2012.
International Preliminary Report on Patentability for PCT/US2011/036672, dated Nov. 29, 2012.
International Search Report and Written Opinion for PCT/US2011/036701, dated Feb. 1, 2012.
International Preliminary Report on Patentability for PCT/US2011/036701, dated Nov. 29, 2012.
GENBANK Submission; NH/NCBI, Accession No. H86170. Hillier et al., Nov. 21, 1995. 2 pages.
GENBANK Submission; NH/NCBI, Accession No. NP_001003694. Lubula et al., Oct. 6, 2016. 4 pages.
GENBANK Submission; NH/NCBI, Accession No. NP_001420. Ledsaak et al., Sep. 15, 2016. 8 pages.
GENBANK Submission; NH/NCBI, Accession No. NP_001717. Barda et al., Feb. 2, 2014. 2 pages.
GENBANK Submission; NH/NCBI, Accession No. NP_003061. Agaimy et al., Dec. 10, 2016. 5 pages.
GENBANK Submission; NH/NCBI, Accession No. NP_003063. Liao et al., May 2, 2016. 5 pages.
GENBANK Submission; NH/NCBI, Accession No. NP_003843. Yuan et al., Dec. 20, 2003. 3 pages.

(56) References Cited

OTHER PUBLICATIONS

GENBANK Submission; NH/NCBI, Accession No. NP_003875. Li et al., Oct. 7, 2016. 3 pages.
GENBANK Submission; NH/NCBI, Accession No. NP_004371. Liu et al., Dec. 10, 2006. 3 pages.
GENBANK Submission; NH/NCBI, Accession No. NP_004597. Herzfeld et al., Aug. 26, 2016. 5 pages.
GENBANK Submission; NH/NCBI, Accession No. NP_005095. Xiao et al., Oct. 6, 2016. 4 pages.
GENBANK Submission; NH/NCBI, Accession No. NP_005753. Dalgaard et al., Oct. 6, 2016. 6 pages.
GENBANK Submission; NH/NCBI, Accession No. NP_009168. DiBernardo et al., Sep. 28, 2008. 2 pages.
GENBANK Submission; NH/NCBI, Accession No. NP_031397. Shao et al., Jan. 4, 2017. 4 pages.
GENBANK Submission; NH/NCBI, Accession No. NP_038478. Jones et al., Sep. 23, 2005. 2 pages.
GENBANK Submission; NH/NCBI, Accession No. NP_054828. Hou et al., Sep. 15, 2016. 5 pages.
GENBANK Submission; NH/NCBI, Accession No. NP_055392. Aberg et al., Mar. 22, 2014. 3 pages.
GENBANK Submission; NH/NCBI, Accession No. NP_060404. Bezrookove et al., Oct. 7, 2016. 5 pages.
GENBANK Submission; NH/NCBI, Accession No. NP_060635. Varela et al., Dec. 18, 2011. 3 pages.
GENBANK Submission; NH/NCBI, Accession No. NP_060959. Kuryshev et al., Mar. 26, 2006. 2 pages.
GENBANK Submission; NH/NCBI, Accession No. NP_061836. Perry et al., Feb. 21, 2016. 7 pages.
GENBANK Submission; NH/NCBI, Accession No. NP_066564. Wiper-Bergeron et al., Jun 3, 2007. 3 pages.
GENBANK Submission; NH/NCBI, Accession No. NP_076413. Clark et al., Jun. 27, 2007. 2 pages.
GENBANK Submission; NH/NCBI, Accession No. NP_113601. Knijnenburg et al., Jan. 17, 2014. 3 pages.
GENBANK Submission; NH/NCBI, Accession No. NP_490597. Duan et al., Oct. 6, 2016. 5 pages.
GENBANK Submission; NH/NCBI, Accession No. NP_612411. Saare et al., Aug. 25, 2016. 2 pages.
GENBANK Submission; NH/NCBI, Accession No. NP_722516. Xia et al., Nov. 22, 2015. 3 pages.
GENBANK Submission; NH/NCBI, Accession No. NP_872579. Lee et al., Oct. 6, 2016. 4 pages.
GENBANK Submission; NH/NCBI, Accession No. XP_039676. [No Author Listed], Aug. 19, 2004. 3 pages.
[No Author Listed], Methanesulfonyl chloride: Difference between revisions. Wikipedia entry. http://en.wikipedia.org/w/index.phptitle=Methanesulfonyl_chloride&diff=602110747 &oldid=601684911. Last accessed Feb. 23, 2016. 2 pages.
[No Author Listed], PubChem CID-55504609. Create date Jan. 25, 2012. https://pubchem.ncbi.nlm.nih.gov/compound/55504609. Last accessed Feb. 23, 2016.
[No Author Listed], PubChem CID-56267130. Create date Jan. 25, 2012. https://pubchem.ncbi.nlm.nih.gov/compound/56267130. Last accessed Feb. 23, 2016.
[No Author Listed], PubChem SID 235048169. Feb. 13, 2015. Retrieved on Oct. 24, 2016. Available at https://pubchem.ncbi.nlm.nih.gov/substance/235048169.
[No Author Listed], PubChem SID 235671906. Feb. 13, 2015. Retrieved on Oct. 24, 2016. Available at https://pubchem.ncbi.nlm.nih.gov/substance/235671906#section=Top>.
Abbate et al., "Structure of the papillomavirus DNA-tethering complex E2:Brd4 and a peptide that ablates HPV chromosomal association," Mol Cell 24, 877-889, (2006).
Anders et al., Genome-wide localization of small molecules. Nat Biotechnol. Jan. 2014;32(1):92-6. doi: 10.1038/nbt.2776. Epub Dec. 15, 2013.
Arango et al., "Reversible Azoospermia in a Patient Treated with Triazolam," Eur J Contracept Reprod Health Care, 1(3):293-294 (1996).

Bartholomeeusen et al., Bromodomain and extra-terminal (BET) bromodomain inhibition activate transcription via transient release of positive transcription elongation factor b (P-TEFb) from 7SK small nuclear ribonucleoprotein. J Biol Chem. Oct. 19, 2012;287(43):36609-16. doi: 10.1074/jbc.M112.410746. Epub Sep. 5, 2012.
Baud et al., Chemical biology. A bump-and-hole approach to engineer controlled selectivity of BET bromodomain chemical probes. Science. Oct. 31, 2014;346(6209):638-41. doi: 10.1126/science.1249830. Epub Oct. 16, 2014.
Berge et al., Pharmaceutical salts. J Pharm Sci. Jan. 1977;66(1):1-19.
Berkovits et al., "The First Bromodomain of the Testis-Specific Double Bromodomain Protein Brdt is Required for Chromocenter Organization That is Modulated by Genetic Background," Dev Biol., 360(2):358-368 (2011).
Berkovits et al., "The Role of the Double Bromodomain-Containing BET Genes During Mammalian Spermatogenesis," Current Topics in Developmental Biology, 102: 293-326 (2013).
Buchdinger et al., "Selective inhibition of the platelet-derived growth factor signal transduction pathway by a protein-tyrosine kinase inhibitor of the 2-phenylaminopyrimidine class," Proc Natl Acad Sci, 92:2558-2562 (1995).
Buchdinger et al.,"Inhibition of the Abl Protein-Tyrosine Kinase in Vitro and in Vivo by a 2-Phenylaminopyrimidine Derivative," Cancer Res, 56:100-104 (1996).
Bullock et al., "Structural basis of Inhibitor Specificity of the Human Protooncogene Proviral Insertion site in Moloney Murine lLeukemia virus (PIM-1) kinase," J Med Chem, 48:7604-7614 (2005).
Cellai et al., Mechanistic Insight Into WEB-2170-induced Apoptosis in Human Acute Myelogenous Leukemia Cells: the Crucial Role of PTEN, Exp Hematol, 37(10):1176-1185 (2009).
Cellai et al., Specific PAF Antagonist WEB-2086 Induces Terminal Differentiation of Murine and Human Leukemia Cells. FASEB, 16:733-735 (2002).
Chaidos et al., Potent antimyeloma activity of the novel bromodomain inhibitors I-BET151 and I-BET762. Blood. Jan. 30, 2014;123(5):697-705. doi: 10.1182/blood-2013-01-478420. Epub Dec. 13, 2013.
Cheng et al., Adjudin disrupts spermatogenesis via the action of some unlikely partners: Eps8, Arp2/3 complex, drebrin E, PAR6 and 14-3-3. Spermatogenesis. Oct. 2011;1(4):291-297. Epub Oct. 1, 2011.
Choi et al., Brain Penetrant LRRK2 Inhibitor. ACS Med Chem Lett. Aug. 9, 2012;3(8):658-662.
Cole, "Chemical probes for histone-modifying enzymes," Nat Chem Biol 4, 590-597 (2008).
Crawford et al., "Bromodomain 4 activation predicts breast cancer survival," Proc Natl Acad Sci, 105, 6380-6385, (2008).
Dawson et al., Inhibition of BET recruitment to chromatin as an effective treatment for MLL-fusion leukaemia. Nature. Oct. 2, 2011;478(7370):529-33. doi: 10.1038/nature10509.
Delbroek et al., Development of an enzyme-linked immunosorbent assay for detection of cellular and in vivo LRRK2 S935 phosphorylation. J Pharm Biomed Anal. Mar. 25, 2013;76:49-58.
Delmore et al., BET bromodomain inhibition as a therapeutic strategy to target c-Myc. Cell. Sep. 16, 2011;146(6):904-17. doi: 10.1016/j.cell.2011.08.017. Epub Sep. 1, 2011.
Deng et al., Characterization of a selective inhibitor of the Parkinson's disease kinase LRRK2. Nat Chem Biol. Apr. 2011;7(4):203-5.
Deng et al., Discovery of a benzotetyrimido-[5,4-b][1,4]diazepin-6(11H)-one as a Potent and Selective Inhibitor of Big MAP Kinase 1. ACS Med Chem Lett. Mar. 10, 2011;2(3):195-200.
Denis et al., "An Emerging Role for Bromodomain-Containing Proteins in Chromatin Regulation and Transcriptional Control of Adipogenesis," FEBS Lett., 584(15):3260-3268 (2010).
Dey et al., "Brd4 Marks Select Genes of Mitotic Chromatin and Directs Postmitotic Transcription," Molecular Biology of the Cell, 20:4899-4909 (2009).
Druker et al, "Effects of a selective inhibitor of the Abl Tyrosine kinase on the Growth of Bcr-Abl positive cells," Nat Med, 2:561-566 (1996).

(56) References Cited

OTHER PUBLICATIONS

Druker et al., "Efficacy and safety of a specific inhibitor of the BCR-ABL tyrosine kinase in chronic myeloid leukemia," N Engl J Med 344, 1031-1037 (2001).
Elkins et al., X-ray crystal structure of ERK5 (MAPK7) in complex with a specific inhibitor. J Med Chem. Jun. 13, 2013;56(11):4413-21.
Fedorov et al., "A Systematic Interaction Map of Validated Kinase Inhibitors with Ser/Thr kinases," Proc Natl Acad Sci., 104(51):20523-20528 (2007).
Filippakopoulos et al., Targeting bromodomains: epigenetic readers of lysine acetylation. Nat Rev Drug Discov. May 2014;13(5):337-56. doi: 10.1038/nrd4286. Epub Apr. 22, 2014.
French et al., "BRD4 Bromodomain Gene Reanangement in Aggressive Carcinoma with Translocation t(15;19)," $A_T$ J Pathol, 159(6):1987-1992 (2001).
French et al., BRD4-NUT fusion oncogene: a novel mechanism in aggressive carcinoma. Cancer Res. Jan. 15, 2003;63(2):304-7.
French et al., BRD-NUT oncoproteins: a family of closely related nuclear proteins that block epithelial differentiation and maintain the growth of carcinoma cells. Oncogene. Apr. 3, 2008;27(15):2237-42. Epub Oct. 15, 2007.
French, "Demystified Molecular pathology of NUT Midline Carcinomas," J Clin Pathol, 63:492-496 (2010).
Greenwald et al., "E.u-BRD2 Transgenic Mice Develop B-Cell Lymphoma and Leukemia," Blood, 103(4):1475-1484 (2004).
Haack et al., "Diagnosis of NUT Midline Carcinoma Using a NUT-specific Monoclonal Antibody," $A_T$ J Surg Pathol, 33:984-991 (2009).
He et al., The histone methyltransferase Ezh2 is a crucial epigenetic regulator of allogeneic T-cell responses mediating graft-versus-host disease. Blood. Dec. 12, 2013;122(25):4119-28. Doi: 10.1182/blood-2013-05-505180. Epub Oct. 18, 2013.
Houzelstein et al., Growth and early postimplantation defects in mice deficient for the bromodomain-containing protein Brd4. Mol Cell Biol. Jun. 2002;22(11):3794-802.
Hu et al., Adjudin targeting rabbit germ cell adhesion as a male contraceptive: a pharmacokinetics study. J Androl. Jan.-Feb. 2009;30(1):87-93. doi: 10.2164/jandrol.108.004994. Epub Sep. 18, 2008.
Huang et al., "Brd4 Coactivates Transcriptional Activation of $NF-_KB$ via Specific Binding to Acetylated RelA," Mol Cell Biol, 29(5):1375-1387 (2009).
Kadota et al., "Identification of Novel Gene Amplifications in Breast Cancer and Coexistence of Gene Amplification With an Activating Mutation of PIK3CA," Cancer Res, 69: 7357-7365 (2009).
Kavanagh et al., The development of CNS-active LRRK2 inhibitors using property-directed optimisation.Bioorg Med Chem Lett. Jul. 1, 2013;23(13):3690-6.
Kim et al., "Berberine Improves Lipid Dysregulation in Obesity by Controlling Central and Peripheral AMPK Activity," $A_T$. J. Physiol. Endocrinol. Metab., 296: E812-E819 (2009).
Konze et al., An orally bioavailable chemical probe of the Lysine Methyltransferases EZH2 and EZH1. ACS Chem Biol. 2013;8(6):1324-34. Doi: 10.1021/cb400133j. Epub Apr. 24, 2013.
Krueger et al., The mechanism of release of P-TEFb and HEXIM1 from the 7SK snRNP by viral and cellular activators includes a conformational change in 7SK. PLoS One. Aug. 23, 2010;5(8):e12335. doi: 10.1371/journal.pone.0012335.
Lawless et al., Histone Deacetylase Inhibitors Target Diabetes Via Chromatin Remodeling or as Chemical Chaperones? Curr Diabetes Rev, 5(3):201-209 (2009).
Le Coutre et al., In vivo eradication of human BCR/ABL-positive leukemia cells with an ABL kinase inhibitor. J Natl Cancer Inst, 91:163-168 (1999).
Lee et al., "Berberine, a Natural Plant Product, Activates AMP-Activated Protein Kinase with Beneficial Metabolic Effects in Diabetic and Insulin-Resistant States," Diabetes, 55: 2256-2264 (2006).
Lotti et al., Ultrasound of the male genital tract in relation to male reproductive health. Hum Reprod Update. Jan.-Feb. 2015;21(1):56-83. doi: 10.1093/humupd/dmu042. Epub Jul. 19, 2014.
Marushige, Activation of Chromatin by Acetylation of Histone Side Chains, Proc. Nat'l. Acad. Sci., 73(11): 3937-3941 (1976).
Matzuk, "Small-Molecule Inhibition of BRDT for Male Contraception," Cell: 150:673-684 (2012).
McKeown et al., Biased multicomponent reactions to develop novel bromodomain inhibitors. J Med Chem. Nov. 13, 2014;57(21):9019-27. doi: 10.1021/jm501120z. Epub Oct. 31, 2014.
Meguro et al., "Heterocycles. VI. Synthesis of 4H-s-Triazolo[4,3-a][1,4]benzodiazepines, Novel Tricyclic Psychosedatives," Chem. Pharm. Bull.,21(11):2382-2390 (1973).
Men-Ger et al., "Use of All-Trans Retinoic Acid in the Treatment of Acute Promyelocytic Leukemia," Blood, 72(2): 567-572 (1988).
Mochizuki et al., "The Bromodomain Protein Brd4 Stimulates G1 Gene Transcription and Promotes Progression to S Phase," J Biol Chem, 283(14):9040-9048 (2008).
Niesen et al., "The use of Differential Scanning Fluorimetry to Detect Ligand Interactions that Promote Protein Stability," Nat Protoc, 2(9):2212-2221 (2007).
Nishimura et al., Fertility and Reproduction Studies of Apafant (WEB 2086 BS) in Rats Dosed Orally. Oyo Yakuri/Pharmacometrics. Oct. 1, 1996. 52(3/4):185-200.
Owen et al., "The Structural Basis for the Recognition of Acetylated Histone R4 by the Bromodomain of Histone Acetyltransferase Gcn5p," The EMBO Journal, 19(22):6141-6149 (2000).
Patani et al., "Bioisosterism: A Rational Approach in Drug Design," Chem. Rev., 96:3147-3176 (1996).
Phelps et al., "Clinical Response and Pharmacokinetics :from a Phase 1 Study of an Active Dosing Schedule of Flavopiridol in Relapsed Chronic Lymphocytic Leukemia," Blood, 113(12):2637-2645 (2009).
Presiler et al., "Assessment of c-myc Expression in Individual Leukemic Cells," Leuk Res, 12(6): 507-516 (1988).
Ptashne, "Binding Reactions: Epigenetic Switches, Signal Transduction and Cancer," Current Biology, 19(6):R234-R241 (2009).
Quinn et al., "A homogeneous method for investigation of methylation-dependent protein-protein interactions in epigenetics," Nucleic Acids Res, 38(2):el 1(1-10) (2010).
Rahl et al., "c-Myc Regulates Transcriptional Pause Release," Cell, 141 :432-445 (2010).
Roberts et al., A Bead-Based Proximity Assay for BRD4 Ligand Discovery. Curr Protoc Chem Biol. Dec. 2, 2015;7(4):263-78. doi: 10.1002/9780470559277.ch150024.
Santillan et al., "Bromodomain and Histone Acetyltransferase Domain Specificities Control Mixed Lineage Leukemia Phenotype," Cancer Res, 66(20):10032-10039 (2006).
Schindler et al., "Structural mechanism for STI-571 Inhibition of Abelson Tyrosine kinase. Science," 289:1938-1942 (2000).
Schreiber et al., "Signaling Network Model of Chromatin," Cell, 111:771-778 (2002).
Schroder et al., Two-pronged binding with bromodomain-containing protein 4 liberates positive transcription elongation factor b from inactive ribonucleoprotein complexes. J Biol Chem. Jan. 6, 2012;287(2):1090-9. doi: 10.1074/jbc.M111.282855. Epub Nov. 14, 2011.
Seyrig et al., "Effects of a Chronic Administration of Two Benzodiazepines on Food Intake in Rats Given a Highly Palatable Diet," Pharmacology Biochemistly & Behavior, 25:913-918 (1986).
Shang et al., "The First Bromodomain of Brdt, a Testis-Specific Member of the BET Sub-Family of Double-Bromodomain-Containing Proteins, is Essential for Male Germ Cell Differentiation," Development, 134: 3507-3515 (2007).
Smith et al., The Bromodomain: A New Target in Emerging Epigenetic Medicine. ACS Chem Biol. Mar. 18, 2016;11(3):598-608. doi: 10.1021/acschembio.5b00831. Epub Dec. 3, 2015.
Tanaka et al., Inhibitors of emerging epigenetic targets for cancer therapy: a patent review (2010-2014). Pharm Pat Anal. 2015;4(4):261-84. doi: 10.4155/ppa.15.16.
Taskinen et al., "A High Tumor-Associated Macrophage Content Predicts Favorable Outcome in Follicular Lymphoma Patients

(56) References Cited

OTHER PUBLICATIONS

Treated with Rituximab and Cyclophosphamide-Doxorubicin-Vincristine-Prednisone," Clin Cancer Res, 13(19): 5784-5785 (2007).
Verma et al., Identification of Potent, Selective, Cell-Active Inhibitors of the Histone Lysine Methyltransferase EZH2. ACS Med Chem Lett. Oct. 19, 2012;3(12):1091-6. Doi: 10.1021/ml3003346. eCollection 2012.
Vollmuth et al., "Structures of the dual bromodomains of the P-TEFb-activating protein Brd4 at atomic resolution," J Biol Chem, 284:36547-36556 (2009).
Von Voigtlander et al., "Alprazolam: Review of Pharmacological, Pharmacokinetic and Clinical Data," Drug Development Research, 6:1-12 (1985).
Wang et al., "Brd2 Disruption in Mice Causes Severe Obesity Without Type 2 Diabetes," Biochem. J., 425:71-83 (2010).
Wang et al., A seamless trespass: germ cell migration across the seminiferous epithelium during spermatogenesis. J Cell Biol. Aug. 13, 2007;178(4):549-56.
Wehner et al., Effects of natalizumab, an alpha4 integrin inhibitor, on fertility in male and female guinea pigs. Birth Defects Res B Dev Reprod Toxicol. Apr. 2009;86(2):108-16. doi: 10.1002/bdrb.20191.
Yang et al., "Brd4 recruits P-TEFb to chromosomes at late mitosis to promote G1 gene expression and cell cycle progression," Mol Cell Biol, 28(3):967-976 (2008).
Yang et al., "Multisite Protein Modification and Intramolecular Signaling," Oncogene, 24:1653-1662 (2005).
Yang et al., Recruitment of P-TEFb for stimulation of transcriptional elongation by the bromodomain protein Brd4. Mol Cell. Aug. 19, 2005;19(4):535-45.
You et al., "Kaposi's sarcoma-associated herpesvirus latency-associated nuclear antigen interacts with bromodomain protein Brd4 on host mitotic chromosomes," J Virol 80, 8909-8919, (2006).
You et al., "Regulation of Aurora B Expression by the Bromodomain Protein Brd4," Mol Cell Biol. 29:5094-5103 (2009).
Zeng et al., Bromodomain: an acetyl-lysine binding domain. FEBS Lett. Feb. 20, 2002;513(1):124-8.
Zhang et al., "Down-Regulation of NF-$_\kappa$B Transcriptional Activity in HIV-Associated Kidney Disease by BRD4 Inhibition," J. Biol Chem, 287(34):28840-28851 (2012).
Zhang et al., "Down-Regulation of NF-$_\kappa$B Transcriptional Activity in HIV-Associated Kidney Disease by BRD4 Inhibition," J. Biol Chem, 287(46):38956 (2012).
Zhao et al., "Research Development on Fusion Protein Transcription Factor siRNA Specifically Targeting Leukemia," Sciencepaper• Online: 1-6 and J. J Med Res., 39(2):6-9 (Feb. 2010) (English-language translation entitled "Progiess ofResearch on siRNA that Targets Leukemia Specific Transcription Regulation Factor Fusion Proteins," pp. 1-10).
Zuber et al., "RNAi Screen Identifies Brd4 as a Therapeutic Target in Acute Myeloid Leukaemia," Nature: 478: 524-528 (2011), with "Supplementary Information" from www.nature.com/nature, pp. 1-33.
U.S. Appl. No. 15/426,708, filed Feb. 7, 2017, Bradner et al.
U.S. Appl. No. 15/426,660, filed Feb. 7, 2017, Bradner et al.
U.S. Appl. No. 13/698,006, filed Apr. 26, 2013, Bradner et al.
U.S. Appl. No. 14/977,343, filed Dec. 21, 2015, Bradner et al.
U.S. Appl. No. 13/697,963, filed Jun. 3, 2013, Bradner et al.
PCT/US2014/048230, Jan. 31, 2017, Extended European Search Report.
PCT/US2015/044180, Feb. 23, 2017, International Preliminary Report on Patentability.
PCT/US2015/044303, Feb. 23, 2017, International Preliminary Report on Patentability.
PCT/US2016/051017, Jan. 10, 2017, International Search Report and Written Opinion.
PCT/US2016/051107, Nov. 22, 2016, International Search Report and Written Opinion.
PCT/US2016/63502, Feb. 9, 2017, Invitation to Pay Additional Fees.
PCT/US2016/63502, May 10, 2017, International Search Report and Written Opinion.
PCT/US2011/036667, Aug. 15, 2011, International Search Report and Written Opinion.
PCT/US2011/036667, Nov. 29, 2012, International Preliminary Report on Patentability.
PCT/US2011/036647, Aug. 17, 2011, International Search Report and Written Opinion.
PCT/US2011/036647, Nov. 29, 2012, International Preliminary Report on Patentability.
PCT/US2011/036672, Jan. 27, 2012, International Search Report and Written Opinion.
PCT/US2011/036672, Nov. 29, 2012, International Preliminary Report on Patentability.
PCT/US2011/036701, Feb. 1, 2012, International Search Report and Written Opinion.
PCT/US2011/036701, Nov. 29, 2012, International Preliminary Report on Patentability.
Extended European Search Report for EP 15744026.4, dated Jun. 7, 2017.
Extended European Search Report for EP 15743171.9, dated Jul. 10, 2017.
Extended European Search Report for EP 15742537, dated Jun. 22, 2017.
Extended European Search Report for EP 15743564.5, dated Jul. 13, 2017.
CAPLUS Database Result for Hoffman et al., WO 2003/020722 A1 (Mar. 13, 2003). Caplus Accession No. 2003:202640.
Ember et al., Acetyl-lysine binding site of bromodomain-containing protein 4 (BRD4) interacts with diverse kinase inhibitors. ACS Chem Biol. May 16, 2014;9(5):1160-71. doi: 10.1021/cb500072z. Epub Mar. 13, 2014.
Knapp et al., Selective Targeting of Protein Interactions. Mediated by Epigenetic Effector Domains. SGC Sep. 5, 2013;1-35.

| Compound | R | BRD4--IC$_{50}$ (μM) |
|---|---|---|
| 1a | H | >100 |
| 2a | 2-CHO | >100 |
| 3a | 3-CHO | 79.4 |
| 4a | 4-CHO | 1.89 |
| 5a | 4-Ac | 16.1 |

INHIBITORS OF TRANSCRIPTION FACTORS AND USES THEREOF

RELATED APPLICATIONS

The present application is a national stage filing under 35 U.S.C. § 371 of international PCT application, PCT/US2014/048230, filed Jul. 25, 2014, which claims priority under 35 U.S.C. § 119(e) to U.S. provisional patent application, U.S. Ser. No. 61/858,521, filed Jul. 25, 2013, each of which is incorporated herein by reference.

GOVERNMENT SUPPORT

This invention was made with U.S. Government support under grants CA156732 and HD076508 awarded by the National Institutes of Health. The U.S. Government has certain rights in the invention.

BACKGROUND OF THE INVENTION

Bromodomain-containing proteins are of substantial biological interest, as components of transcription factor complexes and determinants of epigenetic memory. For example, the bromo and extra terminal protein (BET) family (e.g., bromodomain-containing protein 2 (BRD2), bromodomain-containing protein 3 (BRD3), bromodomain-containing protein 4 (BRD4), and bromodomain testis-specific protein (BRDT)) shares a common domain architecture featuring two amino-terminal bromodomains that exhibit high levels of sequence conservation, and a more divergent carboxy-terminal recruitment domain (Filippakopoulos et al., Nature 2010, 468, 1067-1073). BRD2 and BRD3 are reported to associate with histones along actively transcribed genes and may be involved in facilitating transcriptional elongation (Leroy et al., Mol. Cell. 2008, 30, 51-60). It has also been reported that BRD4 or BRD3 may fuse with nuclear protein in testis (NUT), forming novel fusion oncogenes BRD4-NUT or BRD3-NUT, in a highly malignant form of epithelial neoplasia (French et al., Cancer Res., 2003, 63, 304-307; French et al., J. Clin. Oncol. 2004, 22, 4135-4139). Data suggests that BRD-NUT fusion proteins contribute to carcinogenesis (French et al., Oncogene 2008, 27, 2237-2242). BRDT is uniquely expressed in the testes and ovary. All family members of BET have been reported to have some function in controlling or executing aspects of the cell cycle and have been shown to remain in complex with chromosomes during cell division, suggesting a role in the maintenance of epigenetic memory. In addition, some viruses make use of BET proteins to tether their genomes to the host cell chromatin, as part of the process of viral replication (You et al., Cell 2004, 117, 349-360). BRD4 appears to be involved in the recruitment of the pTEF-b complex to inducible genes, resulting in phosphorylation of RNA polymerase and increased transcriptional output (Hargreaves et al., Cell 2009, 138, 129-145). In humans, BRD2, BRD3, BRD4, and BRDT exhibit similar gene arrangements, domain organizations, and some functional properties (Wu et al., J. Biol. Chem. 2007, 282, 13141-13145).

Recently, some compounds have been reported to be bromodomain binding agents, e.g., WO 2012/075383, WO 2011/054553, WO 2011/054841, WO 2011/054844, WO 2011/054845, WO 2011/054846, WO 2011/054848, WO 2011/143669, and WO 2011/161031. Moreover, Japanese patent application publication JP 2008/156311 discloses a benzimidazole derivative which is said to be a BRD2 bromodomain binding agent which has utility with respect to virus infection and/or proliferation. International PCT publication WO 2009/084693 discloses a series of thienotriazolodiazepine derivatives that are said to inhibit the binding between an acetylated histone and a bromodomain-containing protein which are said to be useful as anti-cancer agents. International PCT publication WO 2011/054843 suggests compounds which inhibit the binding of a bromodomain with its cognate acetylated proteins may have utility in the treatment of a range of autoimmune and inflammatory diseases or conditions.

BET proteins, however, are just one branch of the bromodomain containing protein family. There are dozens of undrugged bromodomains, and novel probe molecules against these targets would be invaluable tools both for improved biological studies and potential leads for drug development. Transcription initiation factor TFIID subunit 1 (TAF1) and TAF1L are two such proteins. As a part of the STAGA complex containing TRRAP, GCN5, TFIID, CBP/P300, mediator (Liu et al., Molecular Cell Biology 2008, 28, 108), and Sp1 (Schroder et al., J. Biol. Chem. 2012, 287, 1090), TAF1 is susceptible to oncogenic activation by MYC. Moreover, TAF1 has been shown to block p53 activity (Li et al., Molecular Cell. 2004, 13, 867), and inactivation of TAF1 triggers a DNA damage response (Buchmann et al., Molecular Cell Biology 2004, 24, 5332). In addition, the TFIID complex, of which TAF1 is a significant member, is vital to stem cell reprogramming (Pijnappel et al., Nature 2013, 495, 516). Inhibitors of TAF1 may help further elucidate its biological role and potentially be an inhibitor of cancer cell growth. With such promising studies related to drugging the epigenome, it is of the utmost importance to develop new chemistry capable of reaching these targets.

SUMMARY OF THE INVENTION

Compound JQ1 (e.g., (+)-JQ1, (−)-JQ1, or a mixture thereof; below) and certain compounds related to JQ1 have been reported as inhibitors of bromodomain-containing proteins (e.g., BET proteins). See, e.g., international PCT patent application publication, WO 2011/143669. It has been demonstrated that JQ1 may bind to the acetyl-lysine binding cavity of a bromodomain-containing protein (e.g., BRD4). Binding of JQ1 to the tandem bromodomains of BRD4 has been shown to be acetyl-lysine competitive and able to displace BRD4 from chromatin in human cells. It is expected that JQ1 may be useful in treating a disease associated with bromodomain-containing proteins, such as cancer (e.g., human squamous cell carcinoma). Similar properties of compound I-BET (below), another bromodomain inhibitor, have also been reported (Nicodeme et al., Nature 2010, 468, 1119-1123).

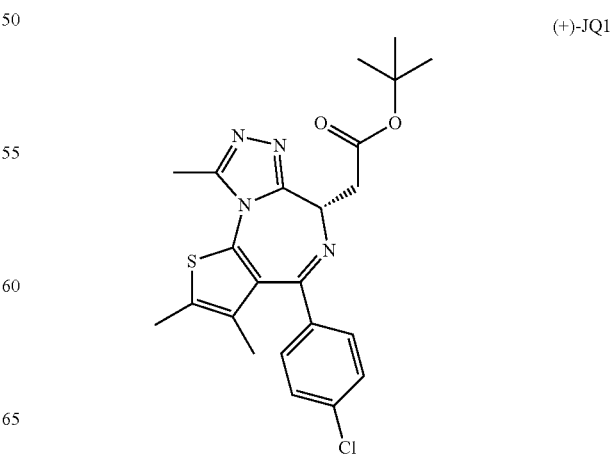

-continued (-)-JQ1

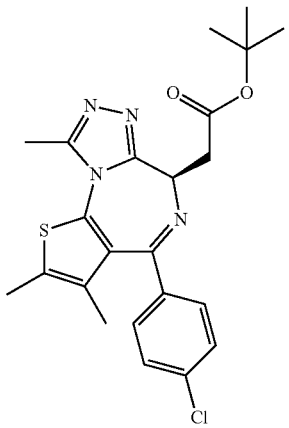

I-BET

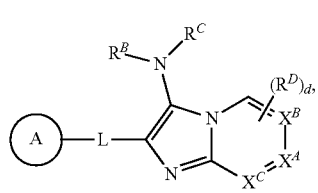

Exemplary compounds of Formula (I) include, but are not limited to:

(UMB11)

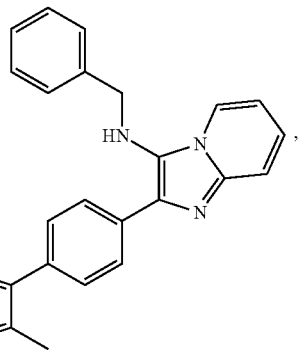

(UMB20)

(UMB21)

(UMB22)

The present invention provides novel compounds of Formulae (I)-(IV). The inventive compounds are thought to be inhibitors of transcription factors, such as bromodomain-containing proteins (e.g., BET proteins) and may be useful in treating diseases associated with bromodomain-containing proteins, such as proliferative diseases (e.g., cancers, benign neoplasms, angiogenesis, inflammatory diseases, and autoimmune diseases). Also provided in the present invention are pharmaceutical compositions, kits, methods, and uses involving a compound of the invention.

In one aspect, the present invention provides compounds of Formula (I):

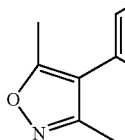

(I)

and pharmaceutically acceptable salts, solvates, hydrates, polymorphs, co-crystals, tautomers, stereoisomers, isotopically labeled derivatives, and prodrugs thereof, wherein $X^A$, $X^B$, $X^C$, Ring A, L, $R^B$, $R^C$, $R^D$, and d are as described herein.

(UMB23)
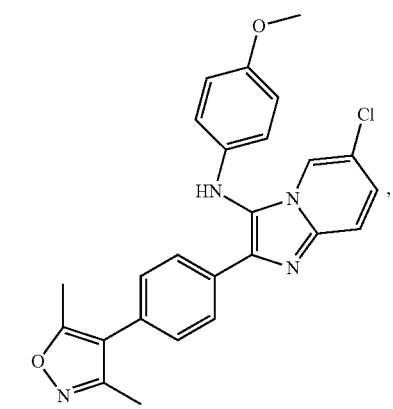
(UMB24)
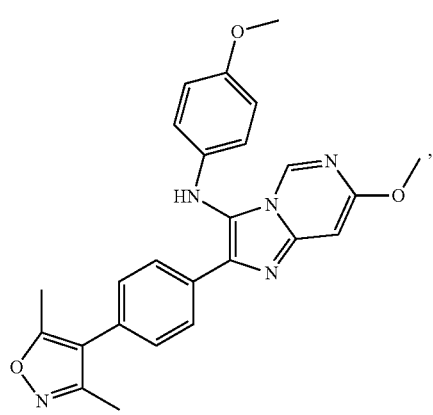
(UMB25)
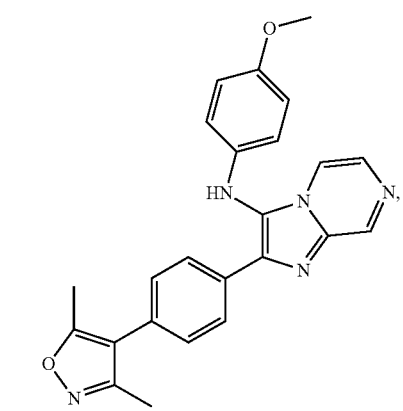
(UMB26)
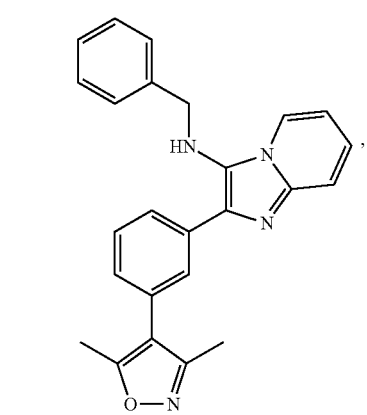
(UMB28)
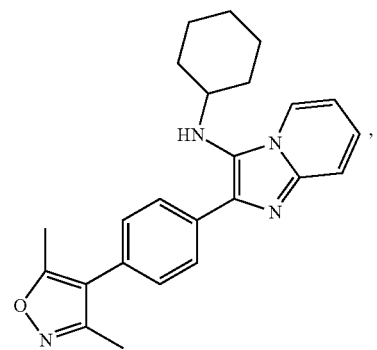
(UMB29)
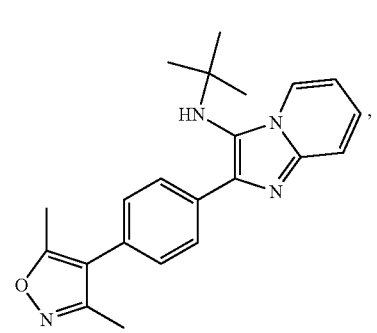
(UMB30)
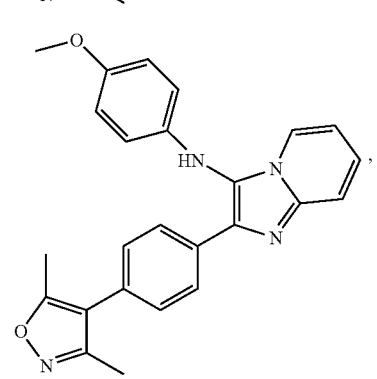
(UMB31)
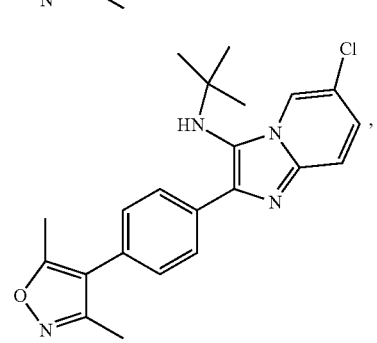
(UMB32)
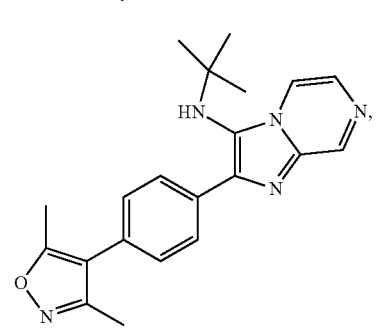

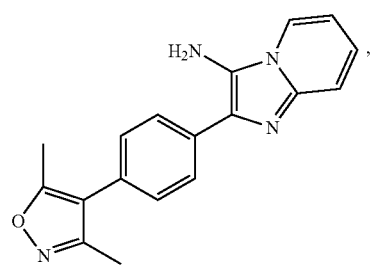
(12a)
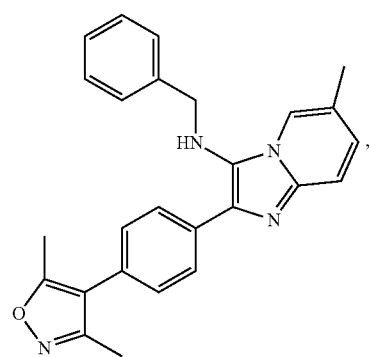
(13a)
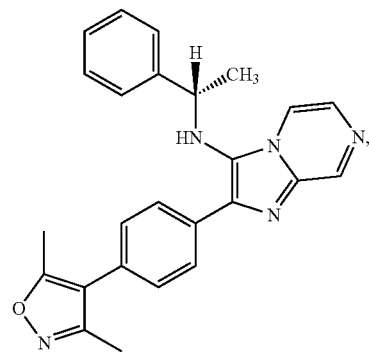
(21a)
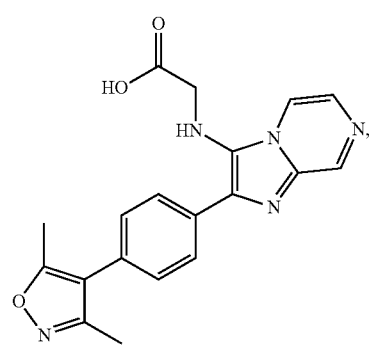
(22a)
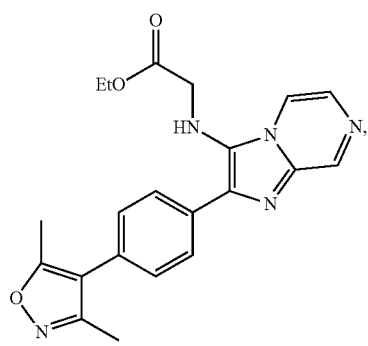
(23a)
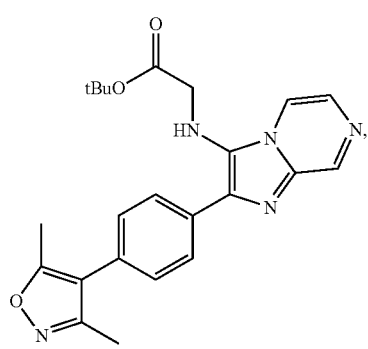
(24a)
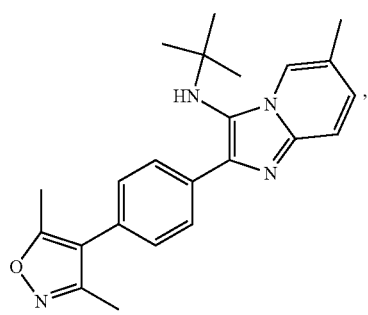
(27a)
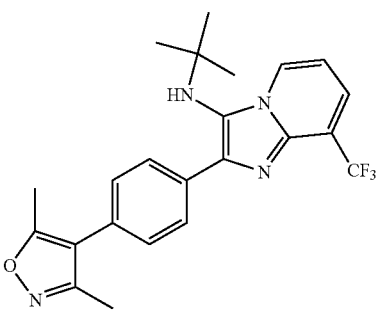
(28a)
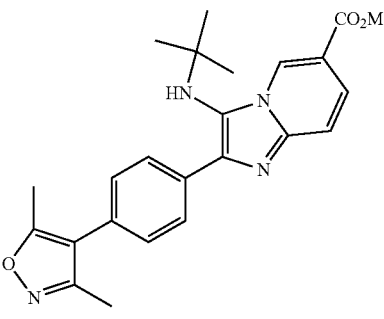
(29a)

-continued
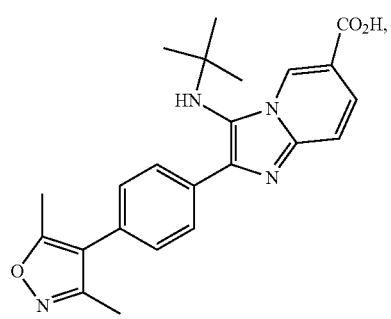
(30a)
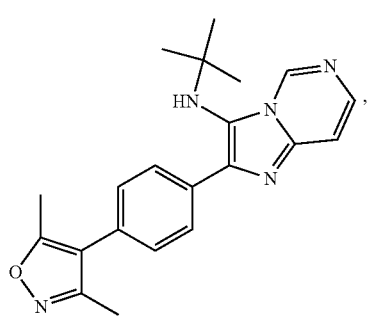
(UMB56)
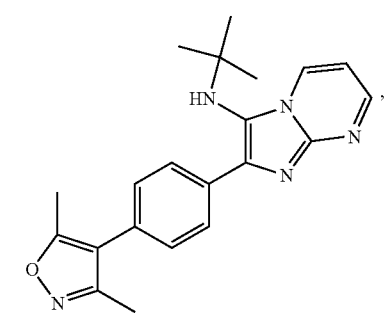
(33a)
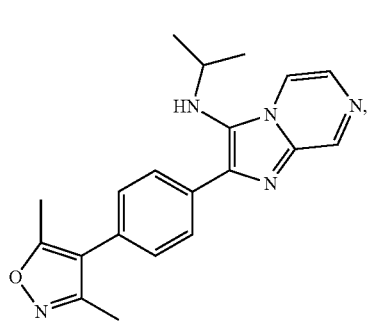
(UMB57)
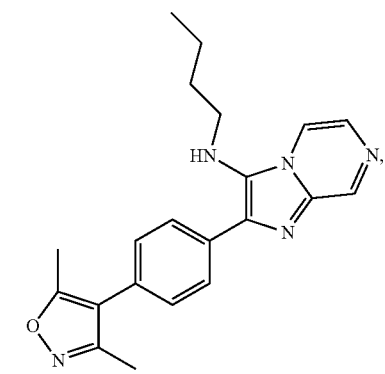
(35a)
-continued
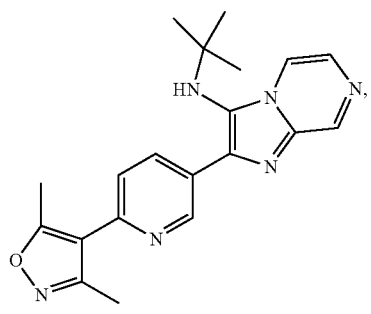
(UMB53)
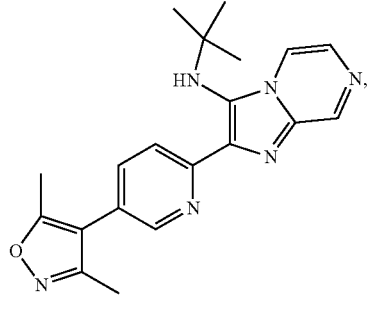
(UMB54)
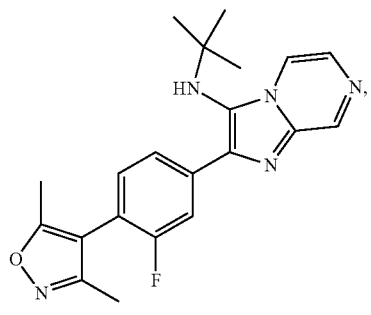
(UMB55)
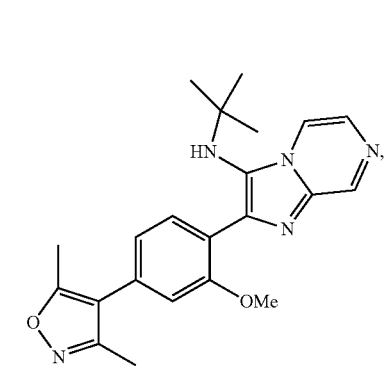
(39a)
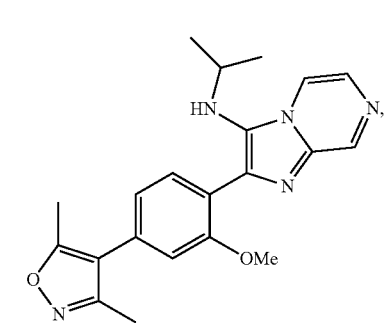
(40a)

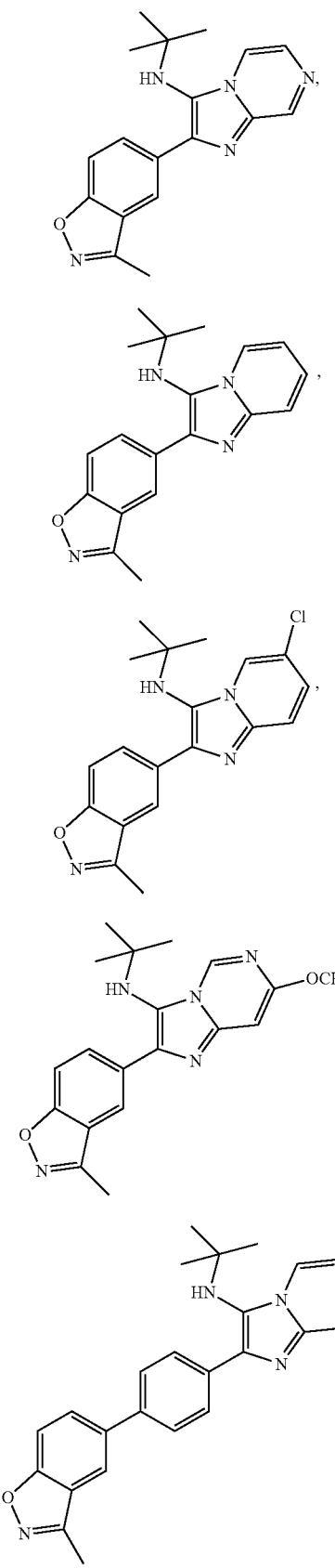

(UMB-33)

(UMB-34)

(UMB-35)

(UMB-36)

(UMB-42)

and pharmaceutically acceptable salts, solvates, hydrates, polymorphs, co-crystals, tautomers, stereoisomers, isotopically labeled derivatives, and prodrugs thereof.

The compounds of the invention are thought to be able to bind bromodomain-containing proteins. In certain embodiments, the compounds of the invention bind to a bromodomain of the bromodomain-containing proteins. The compounds of the invention may inhibit the activity of the bromodomain-containing proteins. The compounds of the invention may also inhibit the function of a bromodomain of the bromodomain-containing proteins.

In another aspect, the present invention provides the compound of Formula (II):

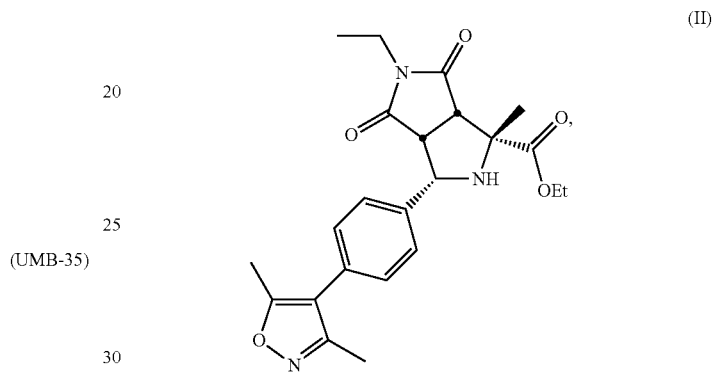

(II)

and pharmaceutically acceptable salts, solvates, hydrates, polymorphs, co-crystals, tautomers, stereoisomers, isotopically labeled derivatives, and prodrugs thereof. The compound of Formula (II) is also referred to as compound UMB17.

In yet another aspect, the present invention provides the compound of Formula (III):

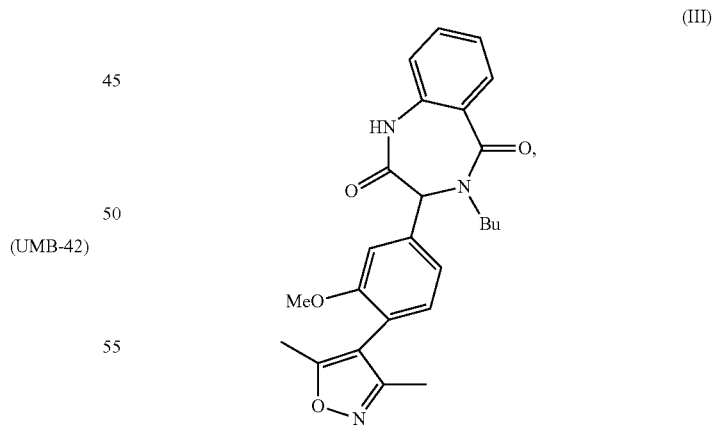

(III)

and pharmaceutically acceptable salts, solvates, hydrates, polymorphs, co-crystals, tautomers, stereoisomers, isotopically labeled derivatives, and prodrugs thereof. The compound of Formula (III) is also referred to as compound UMB18.

In still another aspect, the present invention provides the compound of Formula (IV):

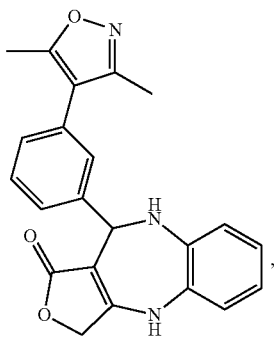

(IV)

and pharmaceutically acceptable salts, solvates, hydrates, polymorphs, co-crystals, tautomers, stereoisomers, isotopically labeled derivatives, and prodrugs thereof. The compound of Formula (IV) is also referred to as compound UMB27.

In still another aspect, the present invention provides pharmaceutical compositions including a compound of the invention, and optionally a pharmaceutically acceptable excipient. In certain embodiments, the pharmaceutical compositions described herein include a therapeutically or prophylactically effective amount of a compound of the invention. The pharmaceutical composition may be useful for treating and/or preventing a disease associated with a bromodomain-containing protein in a subject in need thereof. The pharmaceutical composition may also be useful in inhibiting the activity of a bromodomain-containing protein, in inhibiting the binding of a bromodomain of a bromodomain-containing protein to an acetyl-lysine residue of a histone, and/or in modulating (e.g., down-regulating) the transcription of a gene that is regulated by a bromodomain-containing protein in a subject or cell.

In certain embodiments, the disease associated with a bromodomain-containing protein is a disease associated with the activity of the bromodomain-containing protein. In certain embodiments, the disease associated with a bromodomain-containing protein is a disease associated with the function of a bromodomain of the bromodomain-containing protein. In certain embodiments, the disease associated with a bromodomain-containing protein is a proliferative disease (e.g., cancer, benign neoplasm, angiogenesis, an inflammatory disease, or an autoimmune disease).

In certain embodiments, the subject is a human. In certain embodiments, the subject is a non-human mammal. In certain embodiments, the cell is an in vitro cell.

Another aspect of the present invention relates to methods of treating a disease associated with a bromodomain-containing protein in a subject in need thereof. In another aspect, the present invention provides methods of preventing a disease associated with a bromodomain-containing protein in a subject in need thereof.

Another aspect of the present invention relates to methods of reducing the risk of having a disease associated with a bromodomain-containing protein in a subject in need thereof.

In another aspect, the present invention provides methods of inhibiting the activity of a bromodomain-containing protein in a subject or cell.

In yet another aspect, the present invention provides methods of inhibiting the binding of a bromodomain of a bromodomain-containing protein to an acetyl-lysine residue of a histone in a subject or cell.

In still another aspect, the present invention provides methods of modulating the transcription of a gene that is regulated by a bromodomain-containing protein in a subject or cell. In certain embodiments, the methods of modulating the transcription of a gene are methods of down-regulating the transcription of the gene.

The methods of the present invention include administering to the subject an effective amount of a compound or pharmaceutical composition of the invention. In certain embodiments, the effective amount is a therapeutically effective amount. In certain embodiments, the effective amount is a prophylactically effective amount.

Another aspect of the invention relates to methods of screening a library of compounds to identify a compound that is useful in the methods of the invention (e.g., useful for inhibiting the activity of a bromodomain-containing protein).

Another aspect of the present invention relates to kits comprising a container with a compound or pharmaceutical composition of the invention. The kits of the invention may include a single dose or multiple doses of the inventive compound, or pharmaceutical compositions thereof. The provided kits may be useful in treating and/or preventing a disease associated with a bromodomain-containing protein in a subject in need thereof. The kits may also be useful in inhibiting the activity of a bromodomain-containing protein, in inhibiting the binding of a bromodomain of a bromodomain-containing protein to an acetyl-lysine residue of a histone, and/or in modulating (e.g., down-regulating) the transcription of a gene that is regulated by a bromodomain-containing protein in a subject or cell. In certain embodiments, the kit further includes instructions for administering the compound, or pharmaceutical composition, to the subject.

In yet another aspect, the present invention provides compounds and pharmaceutical compositions of the invention for use in the treatment of a disease associated with a bromodomain-containing protein in a subject in need thereof.

In still another aspect, the present invention provides compounds and pharmaceutical compositions of the invention for use in the prevention of a disease associated with a bromodomain-containing protein in a subject in need thereof.

In still another aspect, the present invention provides compounds and pharmaceutical compositions of the invention for use in reducing the risk of having a disease associated with a bromodomain-containing protein in a subject in need thereof.

The present application refers to various issued patent, published patent applications, journal articles, and other publications, all of which are incorporated herein by reference. The details of one or more embodiments of the invention are set forth herein. Other features, objects, and advantages of the invention will be apparent from the Detailed Description, the Figures, the Examples, and the Claims.

DEFINITIONS

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E.L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1 ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or Spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-romatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5dione. Exemplary 5 -heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6 -heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5 -indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O) (R$^{aa}$)$_2$, —OP(=O)(R$^{aa}$)$_2$, —OP(=O)(OR$^{cc}$)$_2$, —P(=O)$_2$N (R$^{bb}$)$_2$, —OP(=O)$_2$N(R$^{bb}$)$_2$, —P(=O)(NR$^{bb}$)$_2$, —OP(=O) (NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C (=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$) OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O) SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$) R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$) R$^{ee}$, —OC(=NR$^{ff}$)OR$^{ee}$, —C(=NR$^{ff}$)N(R$^{ff}$)$_2$, —OC (=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O) R$^{ee}$, —P(=O)(R$^{ee}$)$_2$, —OP(=O)(R$^{ee}$)$_2$, —OP(=O) (OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-4}$ perhaloalkyl, C$_{2-6}$ alkenyl, C$_{2-6}$ alkynyl, C$_{3-10}$ carbocyclyl, C$_{1-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-4}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$alkyl)$_2$, —OC(=O)NH(C$_{1-6}$alkyl), —NHC(=O)(C$_{1-4}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$alkyl), —NHC(=O)NH$_2$, —C(=NH)O(C$_{1-6}$ alkyl), —OC(=NH)(C$_{1-6}$alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-4}$ alkyl), —SO$_2$NH$_2$, —SO$_2$C$_{1-6}$ alkyl, —SO$_2$OC$_{1-6}$alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —CO$_2R^{aa}$, —C(=O)N($R^{bb}$)$_2$, —C(=NR$^{bb}$)$R^{aa}$, —C(=NR$^{bb}$)OR$^{aa}$, —C(=NR$^{bb}$)N($R^{bb}$)$_2$, —C(=O)NR$^{bb}$SO$_2R^{aa}$, —C(=S)N($R^{bb}$)$_2$, —C(=O)SR$^{aa}$, or —C(=S)SR$^{aa}$, wherein $R^{aa}$ and $R^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2R^{aa}$, —SO$_2R^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2R^{cc}$, —SO$_2$OR$^{aa}$, —SOR$^{aa}$, —C(=S)N(R$^{cc}$)$_2$, —C(=O)SR$^{cc}$, —C(=S)SR$^{cc}$, —P(=O)$_2R^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$alkynyl, C$_{3-10}$ carbocyclyl, 3-14 membered heterocyclyl, C$_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2R^{aa}$, —SO$_2R^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2R^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N diphenylmethyleneamine, N-[(2-pyridyl)mesityl]methyleneamine, N-(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, —R$^{aa}$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxymethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''- dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Exemplary sulfur atom substituents include, but are not limited to, —$R^{aa}$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. In certain embodiments, the sulfur atom substituent present on a sulfur atom is a sulfur protecting group (also referred to as a thiol protecting group). Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

The invention is not intended to be limited in any manner by the above exemplary listing of substituents.

Other Definitions

The following definitions are more general terms used throughout the present application.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\,alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula $R.xH_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R.0.5H_2O$)), and polyhydrates (x is a number greater than 1, e.g., dihydrates ($R.2H_2O$) and hexahydrates ($R.6H_2O$)).

The term "tautomers" or "tautomeric" refers to two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds described herein, which have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "lipophilic" or "hydrophobic" refers to the ability of a compound to dissolve, or the ability of a moiety of a compound to assist the compound in dissolving in fats, oils, lipids, and/or non-polar solvents (e.g., hexane or toluene). Lipophilic moieties include, but are not limited to, substituted or unsubstituted, branched or unbranched alkyl groups having 1 to 50 carbon atoms. In certain embodiments, the lipophilic moiety is an alkyl group including at least 1, at least 6, at least 12, at least 18, at least 24, at least 36, or at least 50 carbon atoms. In certain embodiments, the lipophilic moiety is an alkyl group including at most 50, at most 36, at most 24, at most 18, at most 12, or at most 6 carbon atoms. Combinations of the above-referenced ranges (e.g., at least about 1 and at most about 24 carbon atoms) are also within the scope of the invention. In certain embodiments, the lipophilic moiety is unsubstituted alkyl. In certain embodiments, the lipophilic moiety is unsubstituted and unbranched alkyl. In certain embodiments, the lipophilic moiety is unsubstituted and unbranched $C_{1-24}$ alkyl. In certain embodiments, the lipophilic moiety is unsubstituted and unbranched $C_{6-24}$ alkyl. In certain embodiments, the lipophilic moiety is unsubstituted and unbranched $C_{12-24}$ alkyl.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is at most about 1,000 g/mol, at most about 900 g/mol, at most about 800 g/mol, at most about 700 g/mol, at most about 600 g/mol, at most about 500 g/mol, at most about 400 g/mol, at most about 300 g/mol, at most about 200 g/mol, or at most about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and at most about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

A "protein," "peptide," or "polypeptide" comprises a polymer of amino acid residues linked together by peptide bonds and refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The term "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "chimeric construct" refers to any gene or a construct, not a native gene, comprising regulatory and coding sequences that are not found together in nature. Accordingly, a chimeric gene or chimeric construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer.

Foreign genes can comprise native genes inserted into a non-native organism, or chimeric genes. A "transgene" is a gene that has been introduced into the genome by a transformation procedure.

The term "histone" refers to highly alkaline proteins found in eukaryotic cell nuclei that package and order the DNA into structural units called nucleosomes. They are the chief protein components of chromatin, acting as spools around which DNA winds, and play a role in gene regulation.

The term "bromodomain" refers to a protein domain that recognizes acetylated lysine residues such as those on the N-terminal tails of histones. In certain embodiments, a bromodomain of a BET protein comprises about 110 amino acids and shares a conserved fold comprising a left-handed bundle of four alpha helices linked by diverse loop regions that interact with chromatin.

The term "bromodomain-containing protein" or "bromodomain protein" refers to a protein, whether wild-type or mutant, natural or synthetic, truncated or complete, or a variant thereof, that possesses the minimum amino acid sequence sufficient for a functional bromodomain capable of mediating molecular recognition of acetyl-lysine of acetylated lysine residues on the tails of histones. Bromodomain-containing proteins include, for example, fusion proteins comprising a bromodomain and an additional portion having desired functionality (e.g., a reporter portion).

The terms "composition" and "formulation" are used interchangeably.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is non-human animal. In certain embodiments, the animal is fish. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The terms "administer," "administering," or "administration" refers to implanting, absorbing, ingesting, injecting, inhaling, or otherwise introducing an inventive compound, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyosifis, pemphigus, pemphigoid, diabetes (e.g., Type I), myasthenia gravis, Hashimoto's thyroditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomylitis, optic neuritis, temporal arteritis, transverse myelitis, necrotizing fascilitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodspature's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, perphigus vulgaris, ANCA-associated vasculitis (e.g., Wegener's granulomatosis, microscopic polyangiitis), urveitis, Sjogren's syndrome, Crohn's disease, Reiter's syndrome, ankylosing spondylitis, Lyme disease, Guillain-Barre syndrome, Hashimoto's thyroiditis, and cardiomyopathy.

BRIEF DESCRIPTION OF THE DRAWINGS

FIG. 5 shows inhibitory curves and potency values for small fragment dimethylisoxazole inhibitors 1a-5a.

DETAILED DESCRIPTION OF CERTAIN EMBODIMENTS OF THE INVENTION

Figure 1:
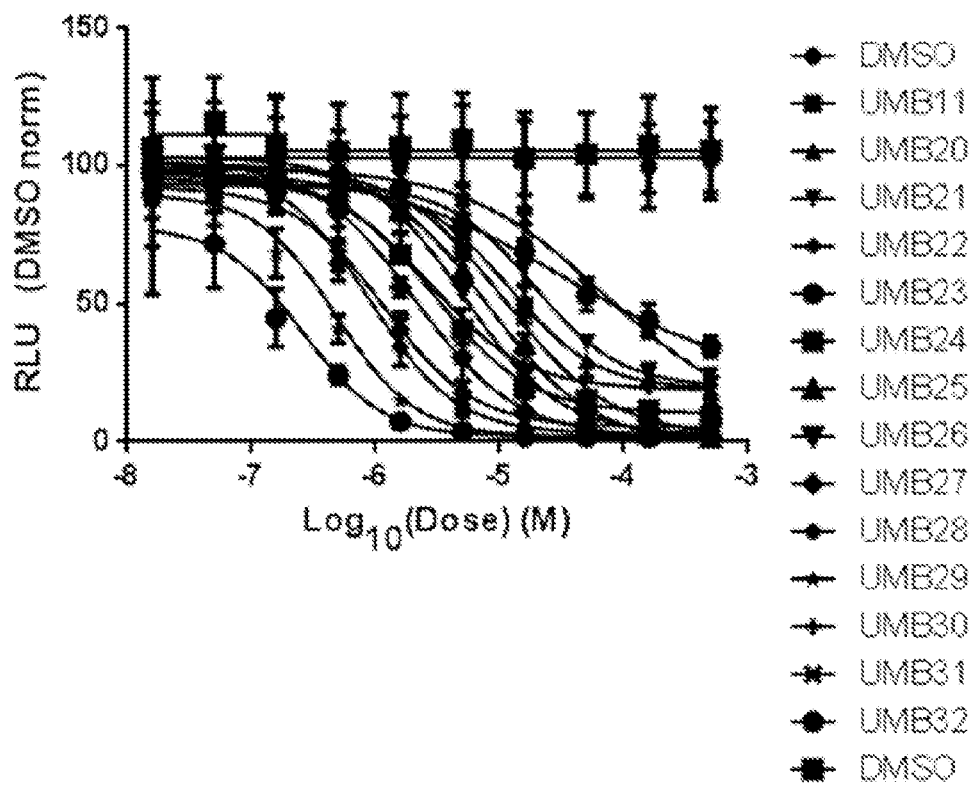
FIG. 1 shows the dose-response curves of exemplary compounds of Formula (I) or (IV) for inhibiting BRD4(1). The response was measured in relative luminescence units (RLUs) and was normalized against DMSO.
Figure 2:
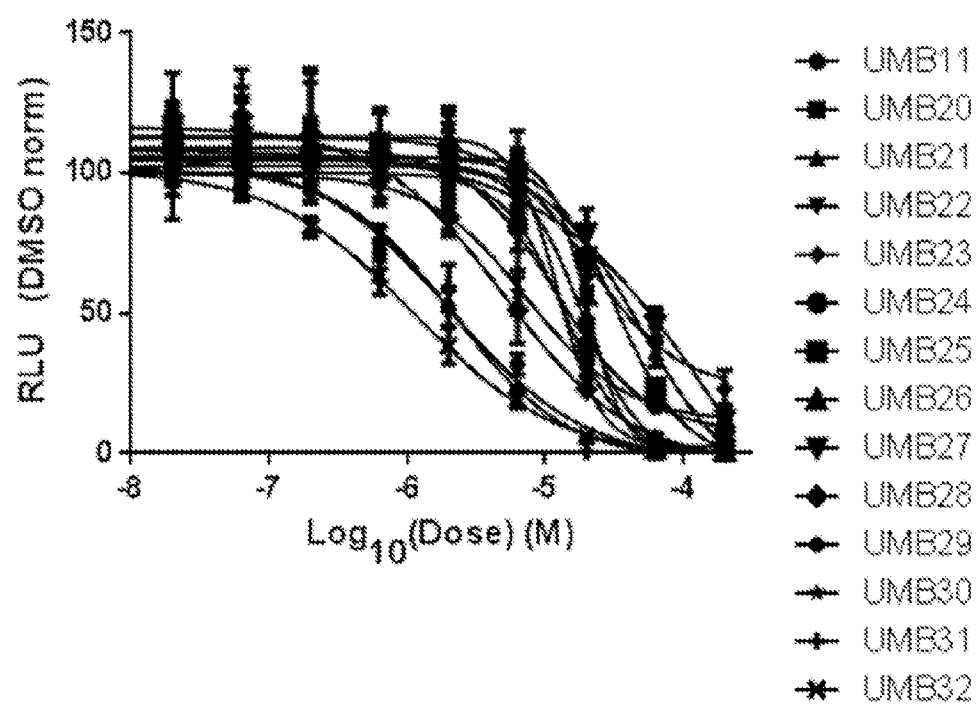
FIG. 2 shows the dose-response curves of exemplary compounds of Formula (I) or (IV) for inhibiting the growth of cancer cell line 797, a nuclear protein in testis (NUT) midline carcinoma. The response was measured in relative luminescence units (RLUs) and was normalized against DMSO.

Inhibitors (e.g., JQ1 and I-BET) of bromodomain-containing proteins (e.g., BET proteins) are useful for treating diseases (such as cancer (e.g., human squamous cell carcinoma)) associated with bromodomain-containing proteins.

The present invention provides compounds of Formulae (I)-(IV), which are novel inhibitors of bromodomain-containing proteins. The compounds of the invention may be able to bind to in a binding pocket of a bromodomain of a bromodomain-containing protein. In certain embodiments, the compounds of the invention bind to the binding pocket of the bromodomain by mimicking the contact between a histone acetyl-lysine residue and the binding pocket. In certain embodiments, the compounds of the invention bind to the apo binding pocket of the bromodomain. Also provided in the present invention are pharmaceutical compositions and kits useful in inhibiting the activity of a transcription factor (e.g., a bromodomain-containing protein). The compounds, pharmaceutical compositions, and kits of the invention may be useful in treating diseases associated with a bromodomain-containing protein, such as proliferative diseases (e.g., cancers, benign neoplasms, angiogenesis, inflammatory diseases, and autoimmune diseases).

Compounds

The present invention provides compounds of Formula (I):

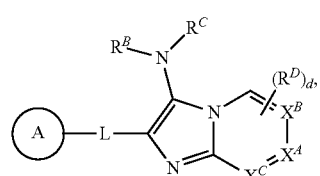

(I)

and pharmaceutically acceptable salts, solvates, hydrates, polymorphs, co-crystals, tautomers, stereoisomers, isotopically labeled derivatives, and prodrugs thereof;

wherein:
$X^A$ is $C(R^D)$ or N;
$X^B$ is $C(R^D)$ or N;
$X^C$ is $C(R^D)$ or N;
wherein no more than two of $X^A$, $X^B$, and $X^C$ can be N;
Ring A is of the formula:

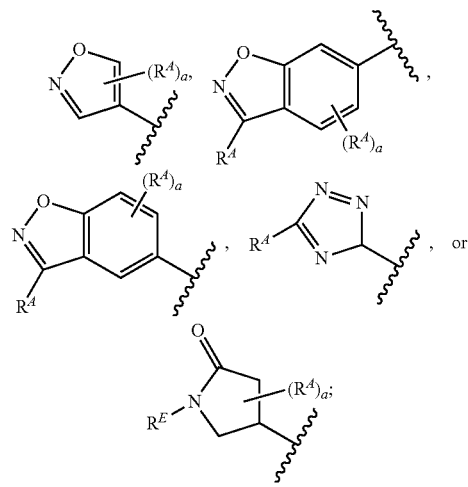

L is a bond or of the formula:

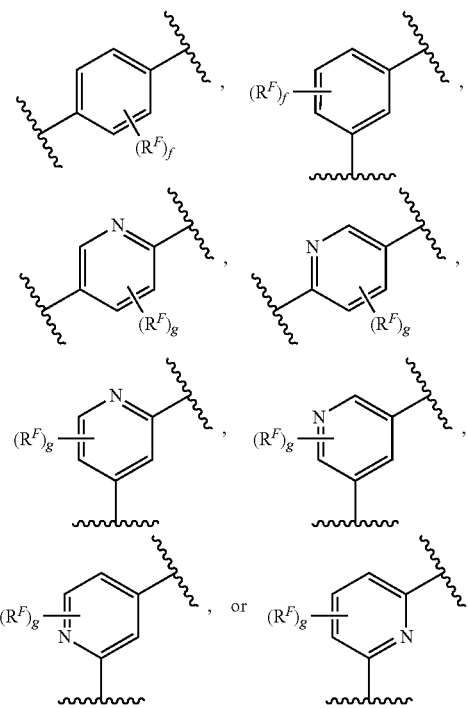

each instance of $R^A$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A1}$, —$N(R^{A1})_2$, —$SR^{A1}$, —CN, —SCN, —$C(=NR^{A1})R^{A1}$, —$C(=NR^{A1})OR^{A1}$, —$C(=NR^{A1})N(R^{A1})_2$, —$C(=O)R^{A1}$, —$C(=O)OR^{A1}$, —$C(=O)N(R^{A1})_2$, —$NO_2$, —$NR^{A1}C(=O)R^{A1}$, —$NR^{A1}C(=O)OR^{A1}$, —$NR^{A1}C(=O)N(R^{A1})_2$, —$OC(=O)R^{A1}$, —$OC(=O)OR^{A1}$, or —$OC(=O)N(R^{A1})_2$, or two instances of $R^A$ are joined to form a substituted or unsubstituted carbocyclic, substituted or unsubstituted heterocyclic, substituted or unsubstituted aryl, or substituted or unsubstituted heteroaryl ring;

each instance of $R^{A1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1}$ are joined to form a substituted or unsubstituted heterocyclic ring;

$R^B$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$C(=O)R^{B1}$, —$C(=O)OR^{B1}$, —$C(=O)N(R^{B1})_2$, or a nitrogen protecting group, or $R^B$ and $R^C$ are joined to form a substituted or unsubstituted heterocyclic ring;

each instance of $R^{B1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or an oxygen protecting group when attached to an oxygen atom, or two instances of $R^{B1}$ are joined to form a substituted or unsubstituted heterocyclic ring;

$R^C$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$C(=O)R^{C1}$, —$C(=O)OR^{C1}$, —$C(=O)N(R^{C1})_2$, or a nitrogen protecting group, or $R^C$ and $R^B$ are joined to form a substituted or unsubstituted heterocyclic ring;

each instance of $R^{C1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or an oxygen protecting group when attached to an oxygen atom, or two instances of $R^{C1}$ are joined to form a substituted or unsubstituted heterocyclic ring;

each instance of $R^D$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{D1}$, —$N(R^{D1})_2$, —$SR^{D1}$, —CN, —SCN, —$C(=NR^{D1})R^{D1}$, —$C(=NR^{D1})OR^{D1}$, —$C(=NR^{D1})N(R^{D1})_2$, —$C(=O)R^{D1}$, —$C(=O)OR^{D1}$, —$C(=O)N(R^{D1})_2$, —$NO_2$, —$NR^{D1}C(=O)R^{D1}$, —$NR^{D1}C(=O)OR^{D1}$, —$NR^{D1}C(=O)N(R^{D1})_2$, —$OC(=O)R^{D1}$, —$OC(=O)OR^{D1}$, or —$OC(=O)N(R^{D1})_2$, or two instances of $R^D$ are joined to form a substituted or unsubstituted carbocyclic, substituted or unsubstituted heterocyclic, substituted or unsubstituted aryl, or substituted or unsubstituted heteroaryl ring;

each instance of $R^{D1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{D1}$ are joined to form a substituted or unsubstituted heterocyclic ring;

$R^E$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$C(=O)R^{E1}$, —$C(=O)OR^{E1}$, —$C(=O)N(R^{E1})_2$, or a nitrogen protecting group;

each instance of $R^{E1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or an oxygen protecting group when attached to an oxygen atom, or two instances of $R^{E1}$ are joined to form a substituted or unsubstituted heterocyclic ring;

each instance of $R^F$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{F1}$, —$N(R^{F1})_2$, —$SR^{F1}$, —CN, —SCN, —$C(=NR^{F1})R^{F1}$, —$C(=NR^{F1})OR^{F1}$, —$C(=NR^{F1})N(R^{F1})_2$, —$C(=O)R^{F1}$, —$C(=O)OR^{F1}$, —$C(=O)N(R^{F1})_2$, —$NO_2$, —$NR^{F1}C(=O)R^{F1}$, —$NR^{F1}C(=O)OR^{F1}$, —$NR^{F1}C(=O)N(R^{F1})_2$, —$OC(=O)R^{F1}$, —$OC(=O)OR^{F1}$, or —$OC(=O)N(R^{F1})_2$, or two instances of $R^F$ are joined to form a substituted or unsubstituted carbocyclic, substituted or unsubstituted heterocyclic, substituted or unsubstituted aryl, or substituted or unsubstituted heteroaryl ring;

each instance of $R^{F1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{F1}$ are joined to form a substituted or unsubstituted heterocyclic ring;

a is 0, 1, 2, 3, 4, or 5;
d is 0, 1, or 2;
f is 0, 1, 2, 3 or 4; and
g is 0, 1, 2, or 3.

In certain embodiments, the present invention provides compounds of Formula (I) and pharmaceutically acceptable salts thereof.

Compounds of Formula (I) include moiety $X^A$. In certain embodiments, $X^A$ is $C(R^D)$. In certain embodiments, $X^A$ is $=C(R^D)-$ or $-C(R^D)=$. In certain embodiments, $X^A$ is CH. In certain embodiments, $X^A$ is $=CH-$ or $-CH=$. In certain embodiments, $X^A$ is N. In certain embodiments, $X^A$ is $=N-$ or $-N=$.

Compounds of Formula (I) include moiety $X^B$. In certain embodiments, $X^B$ is $C(R^D)$. In certain embodiments, $X^B$ is $=C(R^D)-$ or $-C(R^D)=$. In certain embodiments, $X^B$ is CH. In certain embodiments, $X^B$ is $=CH-$ or $-CH=$. In certain embodiments, $X^B$ is N. In certain embodiments, $X^B$ is $=N-$ or $-N=$.

Compounds of Formula (I) include moiety $X^C$. In certain embodiments, $X^C$ is $C(R^D)$. In certain embodiments, $X^C$ is $=C(R^D)-$ or $-C(R^D)=$. In certain embodiments, $X^C$ is CH. In certain embodiments, $X^C$ is $=CH-$ or $-CH=$. In certain embodiments, $X^C$ is N. In certain embodiments, $X^C$ is $=N-$ or $-N=$.

In certain embodiments, each one of $X^A$, $X^B$, and $X^C$ is independently $C(R^D)$. In certain embodiments, each one of $X^A$, $X^B$, and $X^C$ is CH. In certain embodiments, $X^A$ and $X^C$ are $C(R^D)$; and $X^B$ is N. In certain embodiments, $X^A$ and $X^C$ are CH; and $X^B$ is N. In certain embodiments, $X^A$ and $X^B$ are $C(R^D)$; and $X^C$ is N. In certain embodiments, $X^A$ and $X^B$ are CH; and $X^C$ is N. In certain embodiments, $X^B$ and $X^C$ are $C(R^D)$; and $X^A$ is N. In certain embodiments, $X^B$ and $X^C$ are CH; and $X^A$ is N. In certain embodiments, $X^A$ and $X^C$ are N; and $X^B$ is $C(R^D)$. In certain embodiments, $X^A$ and $X^C$ are N; and $X^B$ is CH. In certain embodiments, $X^A$ and $X^B$ are N; and $X^C$ is $C(R^D)$. In certain embodiments, $X^A$ and $X^B$ are N; and $X^C$ is CH. In certain embodiments, $X^B$ and $X^C$ are N; and $X^A$ is $C(R^D)$. In certain embodiments, $X^B$ and $X^C$ are N; and $X^A$ is CH. In certain embodiments, no more than two of $X^A$, $X^B$, and $X^C$ are N. In certain embodiments, no more than one of $X^A$, $X^B$, and $X^C$ are N. In certain embodiments, none of $X^A$, $X^B$, and $X^C$ are N.

Compounds of Formula (I) include Ring A. In certain embodiments, Ring A is of the formula:

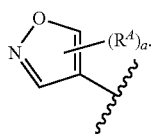

In certain embodiments, Ring A is of the formula:

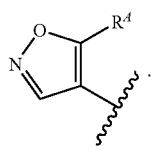

In certain embodiments, Ring A is of the formula:

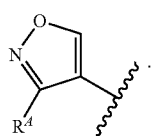

In certain embodiments, Ring A is of the formula:

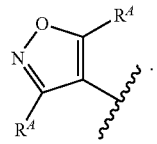

In certain embodiments, Ring A is of the formula:

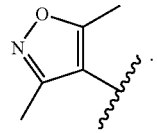 [SMILES: *c1c(C)noc1C]

In certain embodiments, Ring A is of the formula:

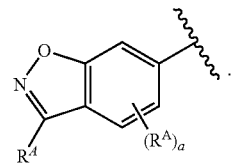

In certain embodiments, Ring A is of the formula:

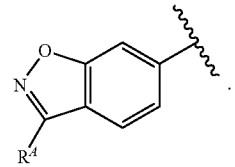

In certain embodiments, Ring A is of the formula:

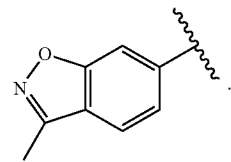

In certain embodiments, Ring A is of the formula:

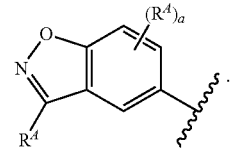

In certain embodiments, Ring A is of the formula:

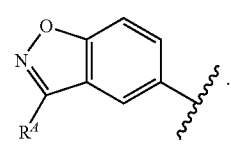

In certain embodiments, Ring A is of the formula:

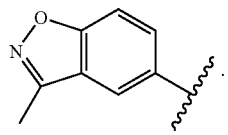 [SMILES: *c1ccc2onc(C)c2c1]

In certain embodiments, Ring A is of the formula:

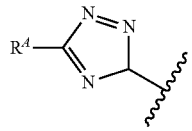

In certain embodiments, Ring A is of the formula:

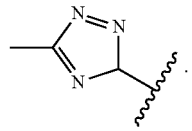

In certain embodiments, Ring A is of the formula:

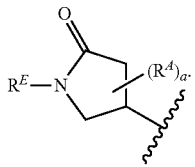

In certain embodiments, Ring A is of the formula:

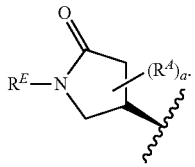

In certain embodiments, Ring A is of the formula:

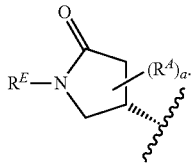

In certain embodiments, Ring A is of the formula:

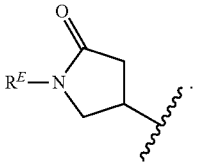

In certain embodiments, Ring A is of the formula:

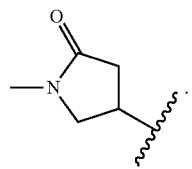

In certain embodiments, Ring A is of the formula:

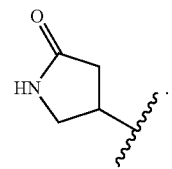

Ring A of Formula (I) may include one or more substituent $R^A$. In certain embodiments, at least one instance of $R^A$ is H. In certain embodiments, at least one instance of $R^A$ is halogen. In certain embodiments, at least one instance of $R^A$ is F. In certain embodiments, at least one instance of $R^A$ is Cl. In certain embodiments, at least one instance of $R^A$ is Br. In certain embodiments, at least one instance of $R^A$ is I (iodine). In certain embodiments, at least one instance of $R^A$ is substituted acyl. In certain embodiments, at least one instance of $R^A$ is unsubstituted acyl. In certain embodiments, at least one instance of $R^A$ is substituted alkyl. In certain embodiments, at least one instance of $R^A$ is unsubstituted alkyl. In certain embodiments, at least one instance of $R^A$ is $C_{1-12}$ alkyl. In certain embodiments, at least one instance of $R^A$ is $C_{1-6}$ alkyl. In certain embodiments, at least one instance of $R^A$ is unsubstituted methyl. In certain embodiments, at least one instance of $R^A$ is substituted methyl. In certain embodiments, at least one instance of $R^A$ is —CH$_2$F. In certain embodiments, at least one instance of $R^A$ is —CHF$_2$. In certain embodiments, at least one instance of $R^A$ is —CF$_3$. In certain embodiments, at least one instance of $R^A$ is Bn. In certain embodiments, at least one instance of $R^A$ is unsubstituted ethyl. In certain embodiments, at least one instance of $R^A$ is substituted ethyl. In certain embodiments, at least one instance of $R^A$ is —(CH$_2$)$_2$Ph. In certain embodiments, at least one instance of $R^A$ is propyl. In certain embodiments, at least one instance of $R^A$ is butyl. In certain embodiments, at least one instance of $R^A$ is pentyl. In certain embodiments, at least one instance of $R^A$ is hexyl. In certain embodiments, at least one instance of $R^A$ is substituted alkenyl. In certain embodiments, at least one instance of $R^A$ is unsubstituted alkenyl. In certain embodiments, at least one instance of $R^A$ is vinyl. In certain embodiments, at least one instance of $R^A$ is substituted alkynyl. In certain embodiments, at least one instance of $R^A$ is unsubstituted alkynyl. In certain embodiments, at least one instance of $R^A$ is ethynyl. In certain embodiments, at least one instance of $R^A$ is substituted carbocyclyl. In certain embodiments, at least one instance of $R^A$ is unsubstituted carbocyclyl. In certain embodiments, at least one instance of $R^A$ is saturated carbocyclyl. In certain embodiments, at least one instance of $R^A$ is unsaturated carbocyclyl. In certain embodiments, at least one instance of $R^A$ is carbocyclyl including one, two, or three double bonds in the carbocyclic ring. In certain embodiments, at least one instance of $R^A$ is monocyclic carbocyclyl. In certain embodiments, at least one instance of $R^A$ is 3- to 7-membered, monocyclic carbocyclyl. In certain embodiments, at least one instance of $R^A$ is cylcopropyl. In certain embodiments, at least one instance of $R^A$ is cyclobutyl. In certain embodiments, at least one instance of $R^A$ is cyclopentyl. In certain embodiments, at least one instance of $R^A$ is cyclohexyl. In certain embodiments, at least one instance of $R^A$ is cycloheptyl. In certain embodiments, at least one instance of $R^A$ is bicyclic carbocyclyl. In certain embodiments, at least one instance of $R^A$ is 5- to 13-membered, bicyclic carbocyclyl. In certain embodiments, at least one instance of $R^A$ is substituted heterocyclyl. In certain embodiments, at least one instance of $R^A$ is unsubstituted heterocyclyl. In certain embodiments, at least one instance of $R^A$ is saturated heterocyclyl. In certain embodiments, at least one instance of $R^A$ is unsaturated heterocyclyl. In certain embodiments, at least one instance of $R^A$ is heterocyclyl including one, two, or three double bonds in the heterocyclic ring. In certain embodiments, at least one instance of $R^A$ is heterocyclyl, wherein one, two, or three atoms in the heterocyclic ring are independently selected from the group consisting of nitrogen, oxygen, and sulfur. In certain embodiments, at least one instance of $R^A$ is monocyclic heterocyclyl. In certain embodiments, at least one instance of $R^A$ is 3- to 7-membered, monocyclic heterocyclyl. In certain embodiments, at least one instance of $R^A$ is bicyclic heterocyclyl. In certain embodiments, at least one instance of $R^A$ is 5- to 13-membered, bicyclic heterocyclyl. In certain embodiments, at least one instance of $R^A$ is substituted aryl. In certain embodiments, at least one instance of $R^A$ is unsubstituted aryl. In certain embodiments, at least one instance of $R^A$ is 6- to 14-membered aryl. In certain embodiments, at least one instance of $R^A$ is 6- to 10-membered aryl. In certain embodiments, at least one instance of $R^A$ is substituted phenyl. In certain embodiments, at least one instance of $R^A$ is unsubstituted phenyl. In certain embodiments, at least one instance of $R^A$ is substituted naphthyl. In certain embodiments, at least one instance of $R^A$ is unsubstituted naphthyl. In certain embodiments, at least one instance of $R^A$ is substituted heteroaryl. In certain embodiments, at least one instance of $R^A$ is unsubstituted heteroaryl. In certain embodiments, at least one instance of $R^A$ is heteroaryl, wherein one, two, three, or four atoms in the heteroaryl ring are independently selected from the group consisting of nitrogen, oxygen, and sulfur. In certain embodiments, at least one instance of $R^A$ is monocyclic heteroaryl. In certain embodiments, at least one instance of $R^A$ is 5-membered, monocyclic heteroaryl. In certain embodiments, at least one instance of $R^A$ is 6-membered, monocyclic heteroaryl. In certain embodiments, at least one instance of $R^A$ is pyridyl. In certain embodiments, at least one instance of $R^A$ is bicyclic heteroaryl, wherein the point of attachment may be on any atom of the bicyclic heteroaryl ring system, as valency permits. In certain embodiments, at least one instance of $R^A$ is 9-membered, bicyclic heteroaryl. In certain embodiments, at least one instance of $R^A$ is 10-membered, bicyclic heteroaryl. In certain embodiments, at least one instance of $R^A$ is $OR^{A1}$. In certain embodiments, at least one instance of $R^A$ is —OMe. In certain embodiments, at least one instance of $R^A$ is —OEt. In certain embodiments, at least one instance of $R^A$ is —OPr. In certain embodiments, at least one instance of $R^A$ is —OBu. In certain embodiments, at least one instance of $R^A$ is —O(pentyl). In certain embodiments, at least one instance of $R^A$ is —O(hexyl). In certain embodiments, at least one instance of $R^A$ is —OPh. In certain embodiments, at least one instance of $R^A$ is —OBn. In certain embodiments, at least one instance of $R^A$ is —O(CH$_2$)$_2$Ph. In certain embodiments, at least one instance of $R^A$ is —OH. In certain embodiments, at least one instance of $R^A$ is —SR$^{A1}$. In certain embodiments, at least one instance of $R^A$ is —SMe. In certain embodiments, at least one instance of $R^A$ is —SH. In certain embodiments, at least one instance of $R^A$ is —N(R$^{A1}$)$_2$. In certain embodiments, at least one instance of $R^A$ is —NMe$_2$. In certain embodiments, at least one instance of $R^A$ is —NH$_2$. In certain embodiments, at least one instance of $R^A$ is —CN. In certain embodiments, at least one instance of $R^A$ is —SCN. In certain embodiments, at least one instance of $R^A$ is —C(=NR$^{A1}$)R$^{A1}$, —C(=NR$^{A1}$)OR$^{A1}$, or —C(=NR$^{A1}$)N(R$^{A1}$)$_2$. In certain embodiments, at least one instance of $R^A$ is —C(=O)R$^{A1}$, —C(=O)OR$^{A1}$, or —C(=O)N(R$^{A1}$)$_2$. In certain embodiments, at least one instance of $R^A$ is —NO$_2$.

In certain embodiments, at least one instance of $R^A$ is —NR$^{A1}$C(=O)R$^{A1}$, —NR$^{A1}$C(=O)OR$^{A1}$ or —NR$^{A1}$C(=O)N(R$^{A1}$)$_2$. In certain embodiments, at least one instance of $R^A$ is —OC(=O)R$^{A1}$, —OC(=O)OR$^{A1}$, or —OC(=O)N(R$^{A1}$)$_2$.

In compounds of Formula (I), two $R^A$ groups may be joined to form a substituted or unsubstituted carbocyclic ring. In certain embodiments, two instances of $R^A$ are joined to form a saturated or unsaturated carbocyclic ring. In certain embodiments, two instances of $R^A$ are joined to form a carbocyclic ring including one, two, or three double bonds in the carbocyclic ring. In certain embodiments, two instances of $R^A$ are joined to form a 3- to 7-membered, monocyclic carbocyclic ring. In certain embodiments, two instances of $R^A$ are joined to form a 3-membered carbocyclic ring. In certain embodiments, two instances of $R^A$ are joined to form a 4-membered carbocyclic ring. In certain embodiments, two instances of $R^A$ are joined to form a 5-membered carbocyclic ring. In certain embodiments, two instances of $R^A$ are joined to form a 6-membered carbocyclic ring. In certain embodiments, two instances of $R^A$ are joined to form a 7-membered carbocyclic ring. In certain embodiments, two instances of $R^A$ are joined to form a 5- to 13-membered, bicyclic carbocyclic ring.

In certain embodiments, two instances of $R^A$ are joined to form a substituted or unsubstituted heterocyclic ring. In certain embodiments, two instances of $R^A$ are joined to form a saturated or unsaturated heterocyclic ring. In certain embodiments, two instances of $R^A$ are joined to form a heterocyclic ring including one, two, or three double bonds in the heterocyclic ring. In certain embodiments, two instances of $R^A$ are joined to form a heterocyclic ring, wherein one, two, or three atoms in the heterocyclic ring are independently selected from the group consisting of nitrogen, oxygen, and sulfur. In certain embodiments, two instances of $R^A$ are joined to form a 3- to 7-membered, monocyclic heterocyclic ring. In certain embodiments, two instances of $R^A$ are joined to form a 5- to 13-membered, bicyclic heterocyclic ring.

In certain embodiments, two instances of $R^A$ are joined to form a substituted or unsubstituted aryl ring. In certain embodiments, two instances of $R^A$ are joined to form a 6- to 14-membered aryl ring. In certain embodiments, two instances of $R^A$ are joined to form a 6-to 10-membered aryl ring. In certain embodiments, two instances of $R^A$ are joined to form a monocyclic aryl ring. In certain embodiments, two instances of $R^A$ are joined to form a phenyl. In certain embodiments, two instances of $R^A$ are joined to form a bicyclic aryl ring. In certain embodiments, two instances of $R^A$ are joined to form a naphthyl.

In certain embodiments, two instances of $R^4$ are joined to form a substituted or unsubstituted heteroaryl ring. In certain embodiments, two instances of $R^4$ are joined to form a monocyclic heteroaryl ring, wherein one, two, or three atoms in the heteroaryl ring are independently selected from the group consisting of nitrogen, oxygen, and sulfur. In certain embodiments, two instances of $R^4$ are joined to form a 5-membered, monocyclic heteroaryl ring. In certain embodiments, two instances of $R^4$ are joined to form a 6-membered, monocyclic heteroaryl ring. In certain embodiments, two instances of $R^4$ are joined to form a pyridyl. In certain embodiments, two instances of $R^4$ are joined to form a bicyclic heteroaryl ring, wherein one, two, three, or four atoms in the heteroaryl ring are independently selected from the group consisting of nitrogen, oxygen, and sulfur. In certain embodiments, two instances of $R^4$ are joined to form a 9-membered, bicyclic heteroaryl ring. In certain embodiments, two instances of $R^4$ are joined to form a 10-membered, bicyclic heteroaryl ring.

In certain embodiments, at least one instance of $R^4$ is halogen or substituted or unsubstituted alkyl. In certain embodiments, at least one instance of $R^4$ is halogen or unsubstituted alkyl. In certain embodiments, at least one instance of $R^4$ is halogen or unsubstituted $C_{1-6}$ alkyl.

In certain embodiments, at least one instance of $R^{41}$ is H. In certain embodiments, at least one instance of $R^{41}$ is substituted acyl. In certain embodiments, at least one instance of $R^{41}$ is unsubstituted acyl. In certain embodiments, at least one instance of $R^{41}$ is acetyl. In certain embodiments, at least one instance of $R^{41}$ is substituted alkyl. In certain embodiments, at least one instance of $R^{41}$ is unsubstituted alkyl. In certain embodiments, at least one instance of $R^{41}$ is $C_{1-12}$ alkyl. In certain embodiments, at least one instance of $R^{41}$ is $C_{1-6}$ alkyl. In certain embodiments, at least one instance of $R^{41}$ is methyl. In certain embodiments, at least one instance of $R^{41}$ is ethyl. In certain embodiments, at least one instance of $R^{41}$ is propyl. In certain embodiments, at least one instance of $R^{41}$ is butyl. In certain embodiments, at least one instance of $R^{41}$ is pentyl. In certain embodiments, at least one instance of $R^{41}$ is hexyl. In certain embodiments, at least one instance of $R^{41}$ is substituted alkenyl. In certain embodiments, at least one instance of $R^{41}$ is unsubstituted alkenyl. In certain embodiments, at least one instance of $R^{41}$ is vinyl. In certain embodiments, at least one instance of $R^{41}$ is substituted alkynyl. In certain embodiments, at least one instance of $R^{41}$ is unsubstituted alkynyl. In certain embodiments, at least one instance of $R^{41}$ is ethynyl. In certain embodiments, at least one instance of $R^{41}$ is substituted carbocyclyl. In certain embodiments, at least one instance of $R^{41}$ is unsubstituted carbocyclyl. In certain embodiments, at least one instance of $R^{41}$ is saturated carbocyclyl. In certain embodiments, at least one instance of $R^{41}$ is unsaturated carbocyclyl. In certain embodiments, at least one instance of $R^{41}$ is carbocyclyl including one, two, or three double bonds in the carbocyclic ring. In certain embodiments, at least one instance of $R^{41}$ is 3- to 7-membered, monocyclic carbocyclyl. In certain embodiments, at least one instance of $R^{41}$ is cylcopropyl. In certain embodiments, at least one instance of $R^{41}$ is cyclobutyl. In certain embodiments, at least one instance of $R^{41}$ is cyclopentyl. In certain embodiments, at least one instance of $R^{41}$ is cyclohexyl. In certain embodiments, at least one instance of $R^{41}$ is cycloheptyl. In certain embodiments, at least one instance of $R^{41}$ is 5- to 13-membered, bicyclic carbocyclyl. In certain embodiments, at least one instance of $R^{41}$ is substituted heterocyclyl. In certain embodiments, at least one instance of $R^{41}$ is unsubstituted heterocyclyl. In certain embodiments, at least one instance of $R^{41}$ is saturated heterocyclyl. In certain embodiments, at least one instance of $R^{41}$ is unsaturated heterocyclyl. In certain embodiments, at least one instance of $R^{41}$ is heterocyclyl including one, two, or three double bonds in the heterocyclic ring. In certain embodiments, at least one instance of $R^{41}$ is heterocyclyl, wherein one, two, or three atoms in the heterocyclic ring are independently selected from the group consisting of nitrogen, oxygen, and sulfur. In certain embodiments, at least one instance of $R^{41}$ is 3- to 7-membered, monocyclic heterocyclyl. In certain embodiments, at least one instance of $R^{41}$ is 5- to 13-membered, bicyclic heterocyclyl. In certain embodiments, at least one instance of $R^{41}$ is substituted or unsubstituted aryl. In certain embodiments, at least one instance of $R^{41}$ is 6- to 14-membered aryl. In certain embodiments, at least one instance of $R^{41}$ is 6- to 10-membered aryl. In certain embodiments, at least one instance of $R^{41}$ is monocyclic aryl. In certain embodiments, at least one instance of $R^{41}$ is phenyl. In certain embodiments, at least one instance of $R^{41}$ is bicyclic aryl. In certain embodiments, at least one instance of $R^{41}$ is naphthyl. In certain embodiments, at least one instance of $R^{41}$ is substituted or unsubstituted heteroaryl. In certain embodiments, at least one instance of $R^{41}$ is heteroaryl, wherein one, two, three, or four atoms in the heteroaryl ring are independently selected from the group consisting of nitrogen, oxygen, and sulfur. In certain embodiments, at least one instance of $R^{41}$ is monocyclic heteroaryl. In certain embodiments, at least one instance of $R^{41}$ is 5-membered, monocyclic heteroaryl. In certain embodiments, at least one instance of $R^{41}$ is 6-membered, monocyclic heteroaryl. In certain embodiments, at least one instance of $R^{41}$ is pyridyl. In certain embodiments, at least one instance of $R^{41}$ is bicyclic heteroaryl, wherein the point of attachment may be on any atom of the bicyclic heteroaryl ring system, as valency permits. In certain embodiments, at least one instance of $R^{41}$ is 9-membered, bicyclic heteroaryl. In certain embodiments, at least one instance of $R^{41}$ is 10-membered, bicyclic heteroaryl. In certain embodiments, at least one instance of $R^{41}$ is a nitrogen protecting group when attached to a nitrogen atom. In certain embodiments, at least one instance of $R^{41}$ is Bn, Boc, Cbz, Fmoc, trifluoroacetyl, triphenylmethyl, acetyl, or Ts when attached to a nitrogen atom. In certain embodiments, $R^{41}$ is an oxygen protecting group when attached to an oxygen atom. In certain embodiments, $R^{41}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{41}$ is a sulfur protecting group when attached to a sulfur atom. In certain embodiments, $R^{41}$ is acetamidomethyl, t-Bu, 3-nitro-2-pyridine sulfenyl, 2-pyridine-sulfenyl, or triphenylmethyl when attached to a sulfur atom.

In certain embodiments, two instances of $R^{41}$ are joined to form a substituted or unsubstituted heterocyclic ring. In certain embodiments, two instances of $R^{41}$ are joined to form a saturated or unsaturated heterocyclic ring. In certain embodiments, two instances of $R^{41}$ are joined to form a heterocyclic ring including one, two, or three double bonds in the heterocyclic ring. In certain embodiments, two instances of $R^{41}$ are joined to form a heterocyclic ring, wherein one, two, or three atoms in the heterocyclic ring are independently selected from the group consisting of nitrogen, oxygen, and sulfur. In certain embodiments, two instances of $R^{41}$ are joined to form a 3- to 7-membered, monocyclic heterocyclic ring. In certain embodiments, two instances of $R^{41}$ are joined to form a 5- to 13-membered, bicyclic heterocyclic ring.

In certain embodiments, a is 0. In certain embodiments, a is 1. In certain embodiments, a is 2. In certain embodiments, a is 3. In certain embodiments, a is 4. In certain embodiments, a is 5.

In certain embodiments, at least one instance of $R^A$ is halogen or substituted or unsubstituted alkyl; and a is 1 or 2. In certain embodiments, at least one instance of $R^A$ is halogen or unsubstituted alkyl; and a is 1 or 2. In certain embodiments, at least one instance of $R^A$ is halogen or unsubstituted $C_{1-6}$ alkyl; and a is 1 or 2. In certain embodiments, at least one instance of $R^A$ is halogen or methyl; and a is 1 or 2. In certain embodiments, at least one instance of $R^A$ is substituted or unsubstituted alkyl; and a is 1 or 2. In certain embodiments, at least one instance of $R^A$ is unsubstituted alkyl; and a is 1 or 2. In certain embodiments, at least one instance of $R^A$ is unsubstituted $C_{1-6}$ alkyl; and a is 1 or 2. In certain embodiments, at least one instance of $R^A$ is methyl; and a is 1 or 2.

When Ring A is of the formula:

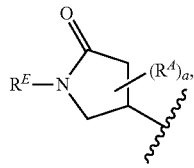

compounds of Formula (I) include substituent $R^E$. In certain embodiments, $R^E$ is H. In certain embodiments, $R^E$ is substituted acyl. In certain embodiments, $R^E$ is unsubstituted acyl. In certain embodiments, $R^E$ is substituted alkyl. In certain embodiments, $R^E$ is unsubstituted alkyl. In certain embodiments, $R^E$ is $C_{1-12}$ alkyl. In certain embodiments, $R^E$ is $C_{1-6}$ alkyl. In certain embodiments, $R^E$ is unsubstituted methyl. In certain embodiments, $R^E$ is substituted methyl. In certain embodiments, $R^E$ is —$CH_2F$. In certain embodiments, $R^E$ is —$CHF_2$. In certain embodiments, $R^E$ is —$CF_3$. In certain embodiments, $R^E$ is Bn. In certain embodiments, $R^E$ is unsubstituted ethyl. In certain embodiments, $R^E$ is substituted ethyl. In certain embodiments, $R^E$ is —$(CH_2)_2Ph$. In certain embodiments, $R^E$ is propyl. In certain embodiments, $R^E$ is butyl. In certain embodiments, $R^E$ is pentyl. In certain embodiments, $R^E$ is hexyl. In certain embodiments, $R^E$ is substituted alkenyl. In certain embodiments, $R^E$ is unsubstituted alkenyl. In certain embodiments, $R^E$ is vinyl. In certain embodiments, $R^E$ is substituted alkynyl. In certain embodiments, $R^E$ is unsubstituted alkynyl. In certain embodiments, $R^E$ is ethynyl. In certain embodiments, $R^E$ is substituted carbocyclyl. In certain embodiments, $R^E$ is unsubstituted carbocyclyl. In certain embodiments, $R^E$ is saturated carbocyclyl. In certain embodiments, $R^E$ is unsaturated carbocyclyl. In certain embodiments, $R^E$ is carbocyclyl including one, two, or three double bonds in the carbocyclic ring. In certain embodiments, $R^E$ is monocyclic carbocyclyl. In certain embodiments, $R^E$ is 3- to 7-membered, monocyclic carbocyclyl. In certain embodiments, $R^E$ is cylcopropyl. In certain embodiments, $R^E$ is cyclobutyl. In certain embodiments, $R^E$ is cyclopentyl. In certain embodiments, $R^E$ is cyclohexyl. In certain embodiments, $R^E$ is cycloheptyl. In certain embodiments, $R^E$ is bicyclic carbocyclyl. In certain embodiments, $R^E$ is 5- to 13-membered, bicyclic carbocyclyl. In certain embodiments, $R^E$ is substituted heterocyclyl. In certain embodiments, $R^E$ is unsubstituted heterocyclyl. In certain embodiments, $R^E$ is saturated heterocyclyl. In certain embodiments, $R^E$ is unsaturated heterocyclyl. In certain embodiments, $R^E$ is heterocyclyl including one, two, or three double bonds in the heterocyclic ring. In certain embodiments, $R^E$ is heterocyclyl, wherein one, two, or three atoms in the heterocyclic ring are independently selected from the group consisting of nitrogen, oxygen, and sulfur. In certain embodiments, $R^E$ is monocyclic heterocyclyl. In certain embodiments, $R^E$ is 3- to 7-membered, monocyclic heterocyclyl. In certain embodiments, $R^E$ is bicyclic heterocyclyl. In certain embodiments, $R^E$ is 5- to 13-membered, bicyclic heterocyclyl. In certain embodiments, $R^E$ is substituted aryl. In certain embodiments, $R^E$ is unsubstituted aryl. In certain embodiments, $R^E$ is 6- to 14-membered aryl. In certain embodiments, $R^E$ is 6- to 10-membered aryl. In certain embodiments, $R^E$ is substituted phenyl. In certain embodiments, $R^E$ is unsubstituted phenyl. In certain embodiments, $R^E$ is substituted naphthyl. In certain embodiments, $R^E$ is unsubstituted naphthyl. In certain embodiments, $R^E$ is substituted heteroaryl. In certain embodiments, $R^E$ is unsubstituted heteroaryl. In certain embodiments, $R^E$ is heteroaryl, wherein one, two, three, or four atoms in the heteroaryl ring are independently selected from the group consisting of nitrogen, oxygen, and sulfur. In certain embodiments, $R^E$ is monocyclic heteroaryl. In certain embodiments, $R^E$ is 5-membered, monocyclic heteroaryl. In certain embodiments, $R^E$ is 6-membered, monocyclic heteroaryl. In certain embodiments, $R^E$ is pyridyl. In certain embodiments, $R^E$ is bicyclic heteroaryl, wherein the point of attachment may be on any atom of the bicyclic heteroaryl ring system, as valency permits. In certain embodiments, $R^E$ is 9-membered, bicyclic heteroaryl. In certain embodiments, $R^E$ is 10-membered, bicyclic heteroaryl. In certain embodiments, $R^E$ is —C(=O)$R^{E1}$. In certain embodiments, $R^E$ is —C(=O)O$R^{E1}$. In certain embodiments, $R^E$ is —C(=O)N($R^{E1}$)$_2$. In certain embodiments, $R^E$ is a nitrogen protecting group. In certain embodiments, $R^E$ is Bn, Boc, Cbz, Fmoc, trifluoroacetyl, triphenylmethyl, acetyl, or Ts.

In certain embodiments, $R^E$ is hydrogen or substituted or unsubstituted alkyl. In certain embodiments, $R^E$ is hydrogen or unsubstituted alkyl. In certain embodiments, $R^E$ is hydrogen or unsubstituted $C_{1-6}$ alkyl.

In certain embodiments, at least one instance of $R^{E1}$ is H. In certain embodiments, at least one instance of $R^{E1}$ is substituted acyl. In certain embodiments, at least one instance of $R^{E1}$ is unsubstituted acyl. In certain embodiments, at least one instance of $R^{E1}$ is acetyl. In certain embodiments, at least one instance of $R^{E1}$ is substituted alkyl. In certain embodiments, at least one instance of $R^{E1}$ is unsubstituted alkyl. In certain embodiments, at least one instance of $R^{E1}$ is $C_{1-12}$ alkyl. In certain embodiments, at least one instance of $R^{E1}$ is $C_{1-6}$ alkyl. In certain embodiments, at least one instance of $R^{E1}$ is methyl. In certain embodiments, at least one instance of $R^{E1}$ is ethyl. In certain embodiments, at least one instance of $R^{E1}$ is propyl. In certain embodiments, at least one instance of $R^{E1}$ is butyl. In certain embodiments, at least one instance of $R^{E1}$ is pentyl. In certain embodiments, at least one instance of $R^{E1}$ is hexyl. In certain embodiments, at least one instance of $R^{E1}$ is substituted alkenyl. In certain embodiments, at least one instance of $R^{E1}$ is unsubstituted alkenyl. In certain embodiments, at least one instance of $R^{E1}$ is vinyl. In certain embodiments, at least one instance of $R^{E1}$ is substituted alkynyl. In certain embodiments, at least one instance of $R^{E1}$ is unsubstituted alkynyl. In certain embodiments, at least one instance of $R^{E1}$ is ethynyl. In certain embodiments, at least one instance of $R^{E1}$ is substituted carbocyclyl. In certain embodiments, at least one instance of $R^{E1}$ is unsubstituted carbocyclyl. In certain embodiments, at least one instance of $R^{E1}$ is saturated carbocyclyl. In certain embodiments, at least one instance of $R^{E1}$ is unsaturated carbocyclyl. In certain embodiments, at least one instance of $R^{E1}$ is carbocyclyl including one, two, or three double bonds in the carbocyclic ring. In certain embodiments, at least one instance of $R^{E1}$ is 3- to 7-membered, monocyclic carbocyclyl. In certain embodiments, at least one instance of $R^{E1}$ is cylcopropyl. In certain embodiments, at least one instance of $R^{E1}$ is cyclobutyl. In certain embodiments, at least one instance of $R^{E1}$ is cyclopentyl. In certain embodiments, at least one instance of $R^{E1}$ is cyclohexyl. In certain embodiments, at least one instance of $R^{E1}$ is cycloheptyl. In certain embodiments, at least one instance of $R^{E1}$ is 5- to 13-membered, bicyclic carbocyclyl. In certain embodiments, at least one instance of $R^{E1}$ is substituted heterocyclyl. In certain embodiments, at least one instance of $R^{E1}$ is unsubstituted heterocyclyl. In certain embodiments, at least one instance of $R^{E1}$ is saturated heterocyclyl. In certain embodiments, at least one instance of $R^{E1}$ is unsaturated heterocyclyl. In certain embodiments, at least one instance of $R^{E1}$ is heterocyclyl including one, two, or three double bonds in the heterocyclic ring. In certain embodiments, at least one instance of $R^{E1}$ is heterocyclyl, wherein one, two, or three atoms in the heterocyclic ring are independently selected from the group consisting of nitrogen, oxygen, and sulfur. In certain embodiments, at least one instance of $R^{E1}$ is 3- to 7-membered, monocyclic heterocyclyl. In certain embodiments, at least one instance of $R^{E1}$ is 5- to 13-membered, bicyclic heterocyclyl. In certain embodiments, at least one instance of $R^{E1}$ is substituted or unsubstituted aryl. In certain embodiments, at least one instance of $R^{E1}$ is 6- to 14-membered aryl. In certain embodiments, at least one instance of $R^{E1}$ is 6- to 10-membered aryl. In certain embodiments, at least one instance of $R^{E1}$ is monocyclic aryl. In certain embodiments, at least one instance of $R^{E1}$ is phenyl. In certain embodiments, at least one instance of $R^{E1}$ is bicyclic aryl. In certain embodiments, at least one instance of $R^{E1}$ is naphthyl. In certain embodiments, at least one instance of $R^{E1}$ is substituted or unsubstituted heteroaryl. In certain embodiments, at least one instance of $R^{E1}$ is heteroaryl, wherein one, two, three, or four atoms in the heteroaryl ring are independently selected from the group consisting of nitrogen, oxygen, and sulfur. In certain embodiments, at least one instance of $R^{E1}$ is monocyclic heteroaryl. In certain embodiments, at least one instance of $R^{E1}$ is 5-membered, monocyclic heteroaryl. In certain embodiments, at least one instance of $R^{E1}$ is 6-membered, monocyclic heteroaryl. In certain embodiments, at least one instance of $R^{E1}$ is pyridyl. In certain embodiments, at least one instance of $R^{E1}$ is bicyclic heteroaryl, wherein the point of attachment may be on any atom of the bicyclic heteroaryl ring system, as valency permits. In certain embodiments, at least one instance of $R^{E1}$ is 9-membered, bicyclic heteroaryl. In certain embodiments, at least one instance of $R^{E1}$ is 10-membered, bicyclic heteroaryl. In certain embodiments, at least one instance of $R^{E1}$ is a nitrogen protecting group when attached to a nitrogen atom. In certain embodiments, at least one instance of $R^{E1}$ is Bn, Boc, Cbz, Fmoc, trifluoroacetyl, triphenylmethyl, acetyl, or Ts when attached to a nitrogen atom. In certain embodiments, $R^{E1}$ is an oxygen protecting group when attached to an oxygen atom. In certain embodiments, $R^{E1}$ is silyl, TBDPS, TBDMS, TIPS, TES, TMS, MOM, THP, t-Bu, Bn, allyl, acetyl, pivaloyl, or benzoyl when attached to an oxygen atom.

In certain embodiments, two instances of $R^{E1}$ are joined to form a substituted or unsubstituted heterocyclic ring. In certain embodiments, two instances of $R^{E1}$ are joined to form a saturated or unsaturated heterocyclic ring. In certain embodiments, two instances of $R^{E1}$ are joined to form a heterocyclic ring including one, two, or three double bonds in the heterocyclic ring. In certain embodiments, two instances of $R^{E1}$ are joined to form a heterocyclic ring, wherein one, two, or three atoms in the heterocyclic ring are independently selected from the group consisting of nitrogen, oxygen, and sulfur. In certain embodiments, two instances of $R^{E1}$ are joined to form a 3- to 7-membered, monocyclic heterocyclic ring. In certain embodiments, two instances of $R^{E1}$ are joined to form a 5- to 13-membered, bicyclic heterocyclic ring.

Compounds of Formula (I) includes linker moiety L. In certain embodiments, L is a bond. In certain embodiments, L is a single bond. In certain embodiments, L is

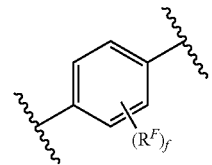

In certain embodiments, L is

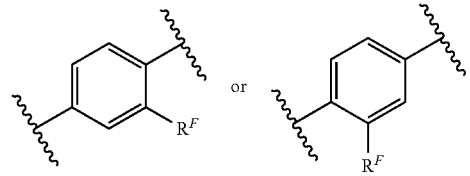

In certain embodiments, L is

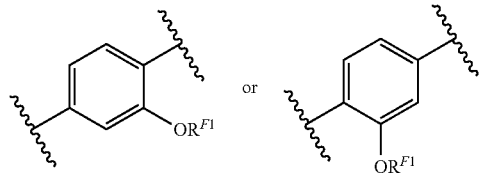

In certain embodiments, L is

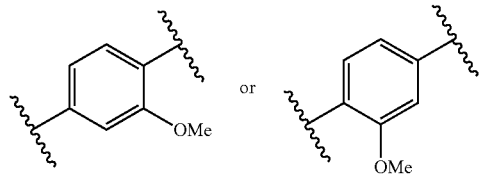

In certain embodiments, L is

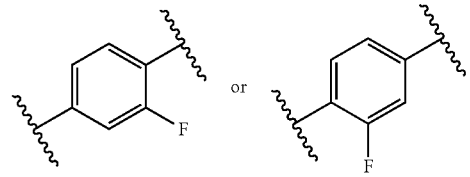

In certain embodiments, L is
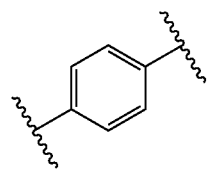
In certain embodiments, L is
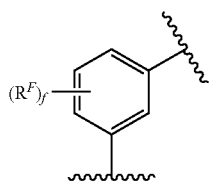
In certain embodiments, L is
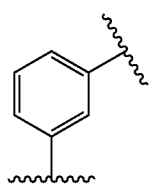
In certain embodiments, L is
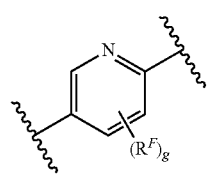
In certain embodiments, L is
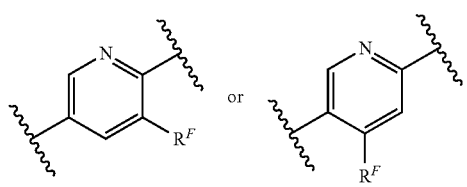 or
In certain embodiments, L is
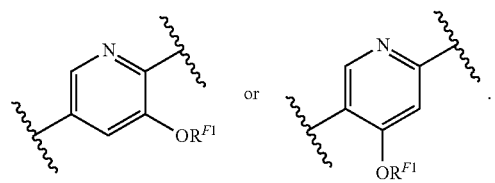 or
In certain embodiments, L is
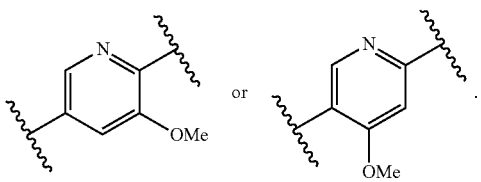 [SMILES: *c1cnc(*)c(OC)c1 ; *c1cc(OC)c(*)cn1] or
In certain embodiments, L is
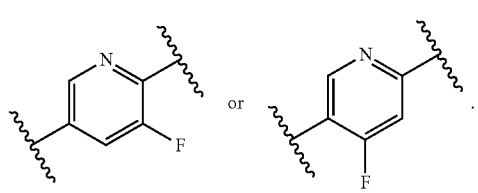 [SMILES: *c1cnc(*)c(F)c1 ; *c1cc(F)c(*)cn1] or
In certain embodiments, L is
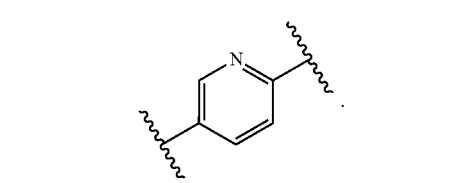 [SMILES: *c1ccc(*)nc1]
In certain embodiments, L is
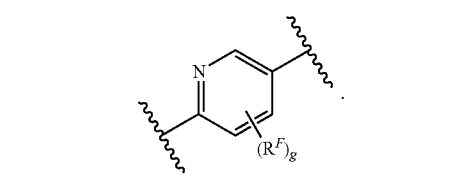
In certain embodiments, L is
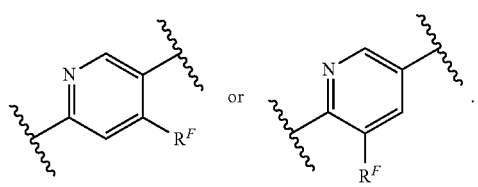 or
In certain embodiments, L is
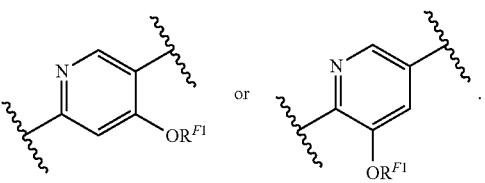 or In certain embodiments, L is
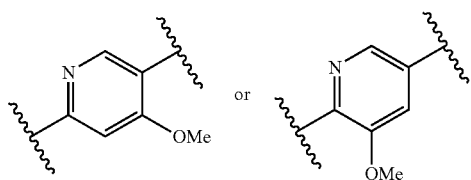 or .
In certain embodiments, L is
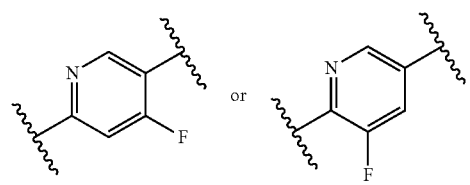 or .
In certain embodiments, L is
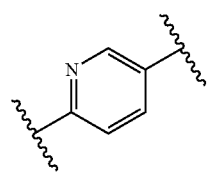.
In certain embodiments, L is
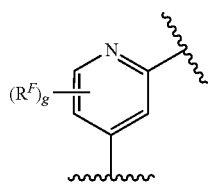.
In certain embodiments, L is
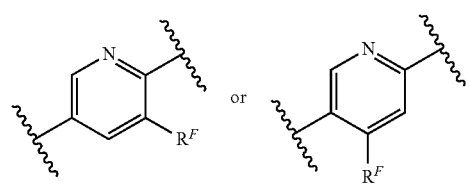 or .
In certain embodiments, L is
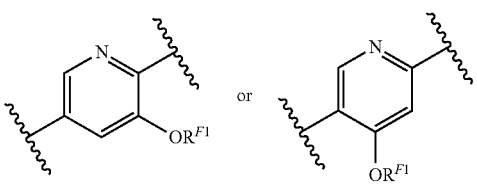 or .
In certain embodiments, L is
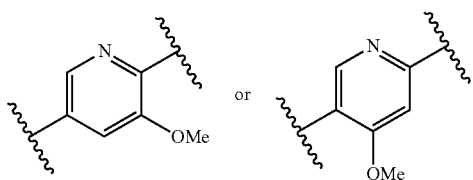 or .
In certain embodiments, L is
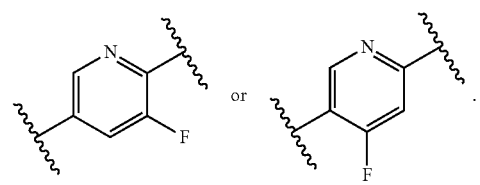 [SMILES: *c1cnc(*)c(F)c1 ; *c1cc(F)c(*)cn1] or .
In certain embodiments, L is
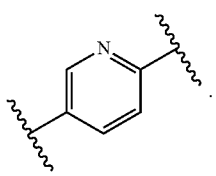.
In certain embodiments, L is
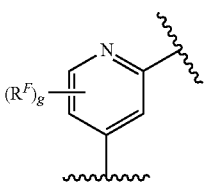.
In certain embodiments, L is
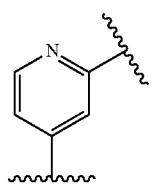.
In certain embodiments, L is
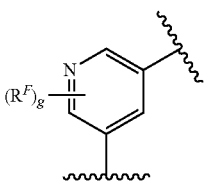.

In certain embodiments, L is

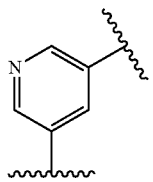

In certain embodiments, L is

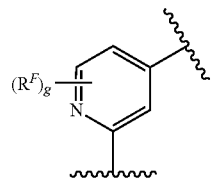

In certain embodiments, L is

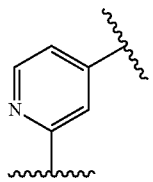

In certain embodiments, L is

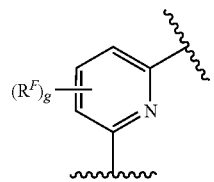

In certain embodiments, L is

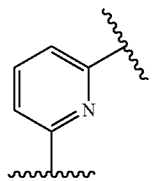

When linker moiety L of compounds of Formula (I) is of the formula:

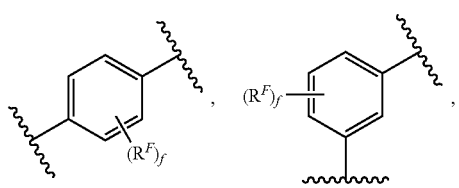

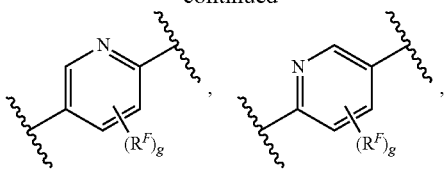

-continued

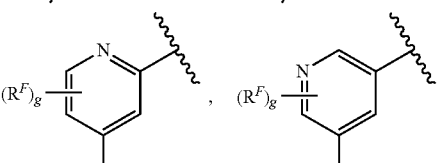

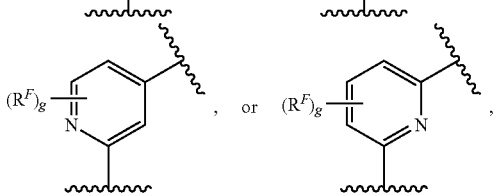

L may include one or more substituent $R^F$. In certain embodiments, at least one instance of $R^F$ is H. In certain embodiments, at least one instance of $R^F$ is halogen. In certain embodiments, at least one instance of $R^F$ is F. In certain embodiments, at least one instance of $R^F$ is Cl. In certain embodiments, at least one instance of $R^F$ is Br. In certain embodiments, at least one instance of $R^F$ is I (iodine). In certain embodiments, at least one instance of $R^F$ is substituted acyl. In certain embodiments, at least one instance of $R^F$ is unsubstituted acyl. In certain embodiments, at least one instance of $R^F$ is substituted alkyl. In certain embodiments, at least one instance of $R^F$ is unsubstituted alkyl. In certain embodiments, at least one instance of $R^F$ is $C_{1-12}$ alkyl. In certain embodiments, at least one instance of $R^F$ is $C_{1-6}$ alkyl. In certain embodiments, at least one instance of $R^F$ is unsubstituted methyl. In certain embodiments, at least one instance of $R^F$ is substituted methyl. In certain embodiments, at least one instance of $R^F$ is —CH$_2$F. In certain embodiments, at least one instance of $R^F$ is —CHF$_2$. In certain embodiments, at least one instance of $R^F$ is —CF$_3$. In certain embodiments, at least one instance of $R^F$ is Bn. In certain embodiments, at least one instance of $R^F$ is unsubstituted ethyl. In certain embodiments, at least one instance of $R^F$ is substituted ethyl. In certain embodiments, at least one instance of $R^F$ is —(CH$_2$)$_2$Ph. In certain embodiments, at least one instance of $R^F$ is propyl. In certain embodiments, at least one instance of $R^F$ is butyl. In certain embodiments, at least one instance of $R^F$ is pentyl. In certain embodiments, at least one instance of $R^F$ is hexyl. In certain embodiments, at least one instance of $R^F$ is substituted alkenyl. In certain embodiments, at least one instance of $R^F$ is unsubstituted alkenyl. In certain embodiments, at least one instance of $R^F$ is vinyl. In certain embodiments, at least one instance of $R^F$ is substituted alkynyl. In certain embodiments, at least one instance of $R^F$ is unsubstituted alkynyl. In certain embodiments, at least one instance of $R^F$ is ethynyl. In certain embodiments, at least one instance of $R^F$ is substituted carbocyclyl. In certain embodiments, at least one instance of $R^F$ is unsubstituted carbocyclyl. In certain embodiments, at least one instance of $R^F$ is saturated carbocyclyl. In certain embodiments, at least one instance of $R^F$ is unsaturated carbocyclyl. In certain embodiments, at least one instance of $R^F$ is carbocyclyl including one, two, or three double bonds in the carbocyclic ring. In certain embodiments, at least one instance of $R^F$ is monocyclic carbocyclyl. In certain embodiments, at least one instance of $R^F$ is 3- to 7-membered, monocyclic carbocyclyl. In certain embodiments, at least one instance of $R^F$ is cylcopropyl. In certain embodiments, at least one instance of $R^F$ is cyclobutyl. In certain embodiments, at least one instance of $R^F$ is cyclopentyl. In certain embodiments, at least one instance of $R^F$ is cyclohexyl. In certain embodiments, at least one instance of $R^F$ is cycloheptyl. In certain embodiments, at least one instance of $R^F$ is bicyclic carbocyclyl. In certain embodiments, at least one instance of $R^F$ is 5- to 13-membered, bicyclic carbocyclyl. In certain embodiments, at least one instance of $R^F$ is substituted heterocyclyl. In certain embodiments, at least one instance of $R^F$ is unsubstituted heterocyclyl. In certain embodiments, at least one instance of $R^F$ is saturated heterocyclyl. In certain embodiments, at least one instance of $R^F$ is unsaturated heterocyclyl. In certain embodiments, at least one instance of $R^F$ is heterocyclyl including one, two, or three double bonds in the heterocyclic ring. In certain embodiments, at least one instance of $R^F$ is heterocyclyl, wherein one, two, or three atoms in the heterocyclic ring are independently selected from the group consisting of nitrogen, oxygen, and sulfur. In certain embodiments, at least one instance of $R^F$ is monocyclic heterocyclyl. In certain embodiments, at least one instance of $R^F$ is 3- to 7-membered, monocyclic heterocyclyl. In certain embodiments, at least one instance of $R^F$ is bicyclic heterocyclyl. In certain embodiments, at least one instance of $R^F$ is 5- to 13-membered, bicyclic heterocyclyl. In certain embodiments, at least one instance of $R^F$ is substituted aryl. In certain embodiments, at least one instance of $R^F$ is unsubstituted aryl. In certain embodiments, at least one instance of $R^F$ is 6- to 14-membered aryl. In certain embodiments, at least one instance of $R^F$ is 6- to 10-membered aryl. In certain embodiments, at least one instance of $R^F$ is substituted phenyl. In certain embodiments, at least one instance of $R^F$ is unsubstituted phenyl. In certain embodiments, at least one instance of $R^F$ is substituted naphthyl. In certain embodiments, at least one instance of $R^F$ is unsubstituted naphthyl. In certain embodiments, at least one instance of $R^F$ is substituted heteroaryl. In certain embodiments, at least one instance of $R^F$ is unsubstituted heteroaryl. In certain embodiments, at least one instance of $R^F$ is heteroaryl, wherein one, two, three, or four atoms in the heteroaryl ring are independently selected from the group consisting of nitrogen, oxygen, and sulfur. In certain embodiments, at least one instance of $R^F$ is monocyclic heteroaryl. In certain embodiments, at least one instance of $R^F$ is 5-membered, monocyclic heteroaryl. In certain embodiments, at least one instance of $R^F$ is 6-membered, monocyclic heteroaryl. In certain embodiments, at least one instance of $R^F$ is pyridyl. In certain embodiments, at least one instance of $R^F$ is bicyclic heteroaryl, wherein the point of attachment may be on any atom of the bicyclic heteroaryl ring system, as valency permits. In certain embodiments, at least one instance of $R^F$ is 9-membered, bicyclic heteroaryl. In certain embodiments, at least one instance of $R^F$ is 10-membered, bicyclic heteroaryl. In certain embodiments, at least one instance of $R^F$ is —$OR^F$. In certain embodiments, at least one instance of $R^F$ is —OMe. In certain embodiments, at least one instance of $R^F$ is —OEt. In certain embodiments, at least one instance of $R^F$ is —OPr. In certain embodiments, at least one instance of $R^F$ is —OBu. In certain embodiments, at least one instance of $R^F$ is —O(pentyl). In certain embodiments, at least one instance of $R^F$ is —O(hexyl). In certain embodiments, at least one instance of $R^F$ is —OPh. In certain embodiments, at least one instance of $R^F$ is —OBn. In certain embodiments, at least one instance of $R^F$ is —O(CH$_2$)$_2$Ph. In certain embodiments, at least one instance of $R^F$ is —OH. In certain embodiments, at least one instance of $R^F$ is —$SR^{F1}$. In certain embodiments, at least one instance of $R^F$ is —SMe. In certain embodiments, at least one instance of $R^F$ is —SH. In certain embodiments, at least one instance of $R^F$ is —N($R^{F1}$)$_2$. In certain embodiments, at least one instance of $R^F$ is —NMe$_2$. In certain embodiments, at least one instance of $R^F$ is —NH$_2$. In certain embodiments, at least one instance of $R^F$ is —CN. In certain embodiments, at least one instance of $R^F$ is —SCN. In certain embodiments, at least one instance of $R^F$ is —C(=$NR^{F1}$)$R^{F1}$, —C(=$NR^{F1}$)$OR^{F1}$, or —C(=$NR^{F1}$)N($R^{F1}$)$_2$. In certain embodiments, at least one instance of $R^F$ is —C(=O)$R^{F1}$, —C(=O)$OR^{F1}$, or —C(=O)N($R^{F1}$)$_2$. In certain embodiments, at least one instance of $R^F$ is —NO$_2$. In certain embodiments, at least one instance of $R^F$ is —$NR^{F1}$C(=O)$R^{F1}$, —$NR^{F1}$C(=O)$OR^{F1}$, or $NR^{F1}$C(=O)N($R^F$)$_2$. In certain embodiments, at least one instance of $R^F$ is OC(=O)$R^{F1}$, —OC(=O)$OR^{F1}$, or —OC(=O)N($R^{F1}$)$_2$.

In compounds of Formula (I), two $R^F$ groups may be joined to form a substituted or unsubstituted carbocyclic ring. In certain embodiments, two instances of $R^F$ are joined to form a saturated or unsaturated carbocyclic ring. In certain embodiments, two instances of $R^F$ are joined to form a carbocyclic ring including one, two, or three double bonds in the carbocyclic ring. In certain embodiments, two instances of $R^F$ are joined to form a 3- to 7-membered, monocyclic carbocyclic ring. In certain embodiments, two instances of $R^F$ are joined to form a 3-membered carbocyclic ring. In certain embodiments, two instances of $R^F$ are joined to form a 4-membered carbocyclic ring. In certain embodiments, two instances of $R^F$ are joined to form a 5-membered carbocyclic ring. In certain embodiments, two instances of $R^F$ are joined to form a 6-membered carbocyclic ring. In certain embodiments, two instances of $R^F$ are joined to form a 7-membered carbocyclic ring. In certain embodiments, two instances of $R^F$ are joined to form a 5- to 13-membered, bicyclic carbocyclic ring.

In certain embodiments, two instances of $R^F$ are joined to form a substituted or unsubstituted heterocyclic ring. In certain embodiments, two instances of $R^F$ are joined to form a saturated or unsaturated heterocyclic ring. In certain embodiments, two instances of $R^F$ are joined to form a heterocyclic ring including one, two, or three double bonds in the heterocyclic ring. In certain embodiments, two instances of $R^F$ are joined to form a heterocyclic ring, wherein one, two, or three atoms in the heterocyclic ring are independently selected from the group consisting of nitrogen, oxygen, and sulfur. In certain embodiments, two instances of $R^F$ are joined to form a 3- to 7-membered, monocyclic heterocyclic ring. In certain embodiments, two instances of $R^F$ are joined to form a 5- to 13-membered, bicyclic heterocyclic ring.

In certain embodiments, two instances of $R^F$ are joined to form a substituted or unsubstituted aryl ring. In certain embodiments, two instances of $R^F$ are joined to form a 6- to 14-membered aryl ring. In certain embodiments, two instances of $R^F$ are joined to form a 6-to 10-membered aryl ring. In certain embodiments, two instances of $R^F$ are joined to form a monocyclic aryl ring. In certain embodiments, two instances of $R^F$ are joined to form a phenyl. In certain embodiments, two instances of $R^F$ are joined to form a bicyclic aryl ring. In certain embodiments, two instances of $R^F$ are joined to form a naphthyl.

In certain embodiments, two instances of $R^F$ are joined to form a substituted or unsubstituted heteroaryl ring. In certain embodiments, two instances of $R^F$ are joined to form a monocyclic heteroaryl ring, wherein one, two, or three atoms in the heteroaryl ring are independently selected from the group consisting of nitrogen, oxygen, and sulfur. In certain embodiments, two instances of $R^F$ are joined to form a 5-membered, monocyclic heteroaryl ring. In certain embodiments, two instances of $R^F$ are joined to form a 6-membered, monocyclic heteroaryl ring. In certain embodiments, two instances of $R^F$ are joined to form a pyridyl. In certain embodiments, two instances of $R^F$ are joined to form a bicyclic heteroaryl ring system, wherein one, two, three, or four atoms in the heteroaryl ring are independently selected from the group consisting of nitrogen, oxygen, and sulfur. In certain embodiments, two instances of $R^F$ are joined to form a 9-membered, bicyclic heteroaryl ring system. In certain embodiments, two instances of $R^F$ are joined to form a 10-membered, bicyclic heteroaryl ring system.

In certain embodiments, at least one instance of $R^F$ is halogen, substituted or unsubstituted alkyl, or —$OR^{F1}$. In certain embodiments, at least one instance of $R^F$ is halogen, unsubstituted alkyl, or —O-(unsubstituted alkyl). In certain embodiments, at least one instance of $R^F$ is halogen, unsubstituted $C_{1-6}$ alkyl, or —O-(unsubstituted $C_{1-6}$ alkyl).

In certain embodiments, at least one instance of $R^{F1}$ is H. In certain embodiments, at least one instance of $R^{F1}$ is substituted acyl. In certain embodiments, at least one instance of $R^{F1}$ is unsubstituted acyl. In certain embodiments, at least one instance of $R^{F1}$ is acetyl. In certain embodiments, at least one instance of $R^{F1}$ is substituted alkyl. In certain embodiments, at least one instance of $R^{F1}$ is unsubstituted alkyl. In certain embodiments, at least one instance of $R^{F1}$ is $C_{1-12}$ alkyl. In certain embodiments, at least one instance of $R^{F1}$ is $C_{1-6}$ alkyl. In certain embodiments, at least one instance of $R^{F1}$ is methyl. In certain embodiments, at least one instance of $R^{F1}$ is ethyl. In certain embodiments, at least one instance of $R^{F1}$ is propyl. In certain embodiments, at least one instance of $R^{F1}$ is butyl. In certain embodiments, at least one instance of $R^{F1}$ is pentyl. In certain embodiments, at least one instance of $R^{F1}$ is hexyl. In certain embodiments, at least one instance of $R^{F1}$ is substituted alkenyl. In certain embodiments, at least one instance of $R^{F1}$ is unsubstituted alkenyl. In certain embodiments, at least one instance of $R^{F1}$ is vinyl. In certain embodiments, at least one instance of $R^{F1}$ is substituted alkynyl. In certain embodiments, at least one instance of $R^{F1}$ is unsubstituted alkynyl. In certain embodiments, at least one instance of $R^{F1}$ is ethynyl. In certain embodiments, at least one instance of $R^{F1}$ is substituted carbocyclyl. In certain embodiments, at least one instance of $R^{F1}$ is unsubstituted carbocyclyl. In certain embodiments, at least one instance of $R^F$ is saturated carbocyclyl. In certain embodiments, at least one instance of $R^{F1}$ is unsaturated carbocyclyl. In certain embodiments, at least one instance of $R^{F1}$ is carbocyclyl including one, two, or three double bonds in the carbocyclic ring. In certain embodiments, at least one instance of $R^{F1}$ is 3- to 7-membered, monocyclic carbocyclyl. In certain embodiments, at least one instance of $R^{F1}$ is cylcopropyl. In certain embodiments, at least one instance of $R^{F1}$ is cyclobutyl. In certain embodiments, at least one instance of $R^{F1}$ is cyclopentyl. In certain embodiments, at least one instance of $R^{F1}$ is cyclohexyl. In certain embodiments, at least one instance of $R^{F1}$ is cycloheptyl. In certain embodiments, at least one instance of $R^{F1}$ is 5- to 13-membered, bicyclic carbocyclyl. In certain embodiments, at least one instance of $R^{F1}$ is substituted heterocyclyl. In certain embodiments, at least one instance of $R^{F1}$ is unsubstituted heterocyclyl. In certain embodiments, at least one instance of $R^{F1}$ is saturated heterocyclyl. In certain embodiments, at least one instance of $R^{F1}$ is unsaturated heterocyclyl. In certain embodiments, at least one instance of $R^{F1}$ is heterocyclyl including one, two, or three double bonds in the heterocyclic ring. In certain embodiments, at least one instance of $R^{F1}$ is heterocyclyl, wherein one, two, or three atoms in the heterocyclic ring are independently selected from the group consisting of nitrogen, oxygen, and sulfur. In certain embodiments, at least one instance of $R^{F1}$ is 3- to 7-membered, monocyclic heterocyclyl. In certain embodiments, at least one instance of $R^{F1}$ is 5- to 13-membered, bicyclic heterocyclyl. In certain embodiments, at least one instance of $R^{F1}$ is substituted or unsubstituted aryl. In certain embodiments, at least one instance of $R^{F1}$ is 6- to 14-membered aryl. In certain embodiments, at least one instance of $R^{F1}$ is 6- to 10-membered aryl. In certain embodiments, at least one instance of $R^{F1}$ is monocyclic aryl. In certain embodiments, at least one instance of $R^{F1}$ is phenyl. In certain embodiments, at least one instance of $R^{F1}$ is bicyclic aryl. In certain embodiments, at least one instance of $R^{F1}$ is naphthyl. In certain embodiments, at least one instance of $R^{F1}$ is substituted or unsubstituted heteroaryl. In certain embodiments, at least one instance of $R^{F1}$ is heteroaryl, wherein one, two, three, or four atoms in the heteroaryl ring are independently selected from the group consisting of nitrogen, oxygen, and sulfur. In certain embodiments, at least one instance of $R^{F1}$ is monocyclic heteroaryl. In certain embodiments, at least one instance of $R^{F1}$ is 5-membered, monocyclic heteroaryl. In certain embodiments, at least one instance of $R^{F1}$ is 6-membered, monocyclic heteroaryl. In certain embodiments, at least one instance of $R^{F1}$ is pyridyl. In certain embodiments, at least one instance of $R^{F1}$ is bicyclic heteroaryl, wherein the point of attachment may be on any atom of the bicyclic heteroaryl ring system, as valency permits. In certain embodiments, at least one instance of $R^{F1}$ is 9-membered, bicyclic heteroaryl. In certain embodiments, at least one instance of $R^{F1}$ is 10-membered, bicyclic heteroaryl. In certain embodiments, at least one instance of $R^{F1}$ is a nitrogen protecting group when attached to a nitrogen atom. In certain embodiments, at least one instance of $R^{F1}$ is Bn, Boc, Cbz, Fmoc, trifluoroacetyl, triphenylmethyl, acetyl, or Ts when attached to a nitrogen atom. In certain embodiments, $R^{F1}$ is an oxygen protecting group when attached to an oxygen atom. In certain embodiments, $R^{F1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{F1}$ is a sulfur protecting group when attached to a sulfur atom. In certain embodiments, $R^{F1}$ is acetamidomethyl, t-Bu, 3-nitro-2-pyridine sulfenyl, 2-pyridine-sulfenyl, or triphenylmethyl when attached to a sulfur atom.

In certain embodiments, two instances of $R^{F1}$ are joined to form a substituted or unsubstituted heterocyclic ring. In certain embodiments, two instances of $R^{F1}$ are joined to form a saturated or unsaturated heterocyclic ring. In certain embodiments, two instances of $R^{F1}$ are joined to form a heterocyclic ring including one, two, or three double bonds in the heterocyclic ring. In certain embodiments, two instances of $R^{F1}$ are joined to form a heterocyclic ring, wherein one, two, or three atoms in the heterocyclic ring are independently selected from the group consisting of nitrogen, oxygen, and sulfur. In certain embodiments, two instances of $R^{F1}$ are joined to form a 3- to 7-membered, monocyclic heterocyclic ring. In certain embodiments, two instances of $R^{F1}$ are joined to form a 5- to 13-membered, bicyclic heterocyclic ring.

In certain embodiments, f is 0. In certain embodiments, f is 1. In certain embodiments, f is 2. In certain embodiments, f is 3. In certain embodiments, f is 4.

In certain embodiments, g is 0. In certain embodiments, g is 1. In certain embodiments, g is 2. In certain embodiments, g is 3.

In certain embodiments, $R^F$ is halogen, substituted or unsubstituted alkyl, or —$OR^{F1}$; and f or g is 1. In certain embodiments, $R^F$ is halogen, unsubstituted alkyl, or —O-(unsubstituted alkyl); and f or g is 1. In certain embodiments, $R^F$ is halogen, unsubstituted $C_{1-6}$ alkyl, or —O-(unsubstituted $C_{1-6}$ alkyl); and f or g is 1. In certain embodiments, $R^F$ is —$OR^{F1}$; and f or g is 1. In certain embodiments, $R^F$ is —O-(unsubstituted alkyl); and f or g is 1. In certain embodiments, $R^F$ is —O-(unsubstituted $C_{1-6}$ alkyl); and f or g is 1. In certain embodiments, $R^F$ is —OMe; and f or g is 1.

Compounds of Formula (I) include substituent $R^B$ on the amino moiety. In certain embodiments, $R^B$ is H. In certain embodiments, $R^B$ is substituted acyl. In certain embodiments, $R^B$ is unsubstituted acyl. In certain embodiments, $R^B$ is substituted alkyl. In certain embodiments, $R^B$ is unsubstituted alkyl. In certain embodiments, $R^B$ is $C_{1-12}$ alkyl. In certain embodiments, $R^B$ is $C_{1-6}$ alkyl. In certain embodiments, $R^B$ is unsubstituted methyl. In certain embodiments, $R^B$ is substituted methyl. In certain embodiments, $R^B$ is —$CH_2F$. In certain embodiments, $R^B$ is $CHF_2$. In certain embodiments, $R^B$ is $CF_3$. In certain embodiments, $R^B$ is Bn. In certain embodiments, $R^B$ is unsubstituted ethyl. In certain embodiments, $R^B$ is substituted ethyl. In certain embodiments, $R^B$ is —$(CH_2)_2Ph$. In certain embodiments, $R^B$ is propyl. In certain embodiments, $R^B$ is n-propy. In certain embodiments, $R^B$ is iso-propyl. In certain embodiments, $R^B$ is butyl. In certain embodiments, $R^B$ is n-butyl. In certain embodiments, $R^B$ is iso-butyl. In certain embodiments, $R^B$ is t-butyl. In certain embodiments, $R^B$ is pentyl. In certain embodiments, $R^B$ is hexyl. In certain embodiments, $R^B$ is substituted alkenyl. In certain embodiments, $R^B$ is unsubstituted alkenyl. In certain embodiments, $R^B$ is vinyl. In certain embodiments, $R^B$ is substituted alkynyl. In certain embodiments, $R^B$ is unsubstituted alkynyl. In certain embodiments, $R^B$ is ethynyl. In certain embodiments, $R^B$ is substituted carbocyclyl. In certain embodiments, $R^B$ is unsubstituted carbocyclyl. In certain embodiments, $R^B$ is saturated carbocyclyl. In certain embodiments, $R^B$ is unsaturated carbocyclyl. In certain embodiments, $R^B$ is carbocyclyl including one, two, or three double bonds in the carbocyclic ring. In certain embodiments, $R^B$ is monocyclic carbocyclyl. In certain embodiments, $R^B$ is 3- to 7-membered, monocyclic carbocyclyl. In certain embodiments, $R^B$ is cylcopropyl. In certain embodiments, $R^B$ is cyclobutyl. In certain embodiments, $R^B$ is cyclopentyl. In certain embodiments, $R^B$ is cyclohexyl. In certain embodiments, $R^B$ is cycloheptyl. In certain embodiments, $R^B$ is bicyclic carbocyclyl. In certain embodiments, $R^B$ is 5- to 13-membered, bicyclic carbocyclyl. In certain embodiments, $R^B$ is substituted heterocyclyl. In certain embodiments, $R^B$ is unsubstituted heterocyclyl. In certain embodiments, $R^B$ is saturated heterocyclyl. In certain embodiments, $R^B$ is unsaturated heterocyclyl. In certain embodiments, $R^B$ is heterocyclyl including one, two, or three double bonds in the heterocyclic ring. In certain embodiments, $R^B$ is heterocyclyl, wherein one, two, or three atoms in the heterocyclic ring are independently selected from the group consisting of nitrogen, oxygen, and sulfur. In certain embodiments, $R^B$ is monocyclic heterocyclyl. In certain embodiments, $R^B$ is 3- to 7-membered, monocyclic heterocyclyl. In certain embodiments, $R^B$ is bicyclic heterocyclyl. In certain embodiments, $R^B$ is 5- to 13-membered, bicyclic heterocyclyl. In certain embodiments, $R^B$ is substituted aryl. In certain embodiments, $R^B$ is unsubstituted aryl. In certain embodiments, $R^B$ is 6- to 14-membered aryl. In certain embodiments, $R^B$ is 6- to 10-membered aryl. In certain embodiments, $R^B$ is substituted phenyl. In certain embodiments, $R^B$ is para-substituted phenyl. In certain embodiments, $R^B$ is of the formula:

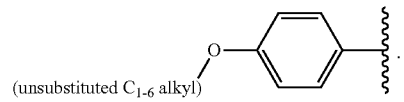

In certain embodiments, $R^B$ is of the formula:

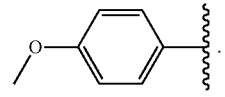

In certain embodiments, RB is unsubstituted phenyl. In certain embodiments, $R^B$ is substituted naphthyl. In certain embodiments, $R^B$ is unsubstituted naphthyl. In certain embodiments, $R^B$ is substituted heteroaryl. In certain embodiments, $R^B$ is unsubstituted heteroaryl. In certain embodiments, $R^B$ is heteroaryl, wherein one, two, three, or four atoms in the heteroaryl ring are independently selected from the group consisting of nitrogen, oxygen, and sulfur. In certain embodiments, $R^B$ is monocyclic heteroaryl. In certain embodiments, $R^B$ is 5-membered, monocyclic heteroaryl. In certain embodiments, $R^B$ is 6-membered, monocyclic heteroaryl. In certain embodiments, $R^B$ is pyridyl. In certain embodiments, $R^B$ is bicyclic heteroaryl, wherein the point of attachment may be on any atom of the bicyclic heteroaryl ring system, as valency permits. In certain embodiments, $R^B$ is 9-membered, bicyclic heteroaryl. In certain embodiments, $R^B$ is 10-membered, bicyclic heteroaryl. In certain embodiments, $R^B$ is —$C(=O)R^{B1}$. In certain embodiments, $R^B$ is —$C(=O)$-(substituted or unsubstituted alkyl). In certain embodiments, $R^B$ is —$C(=O)$-(unsubstituted $C_{1-6}$ alkyl). In certain embodiments, $R^B$ is —$C(=O)$-(t-Bu). In certain embodiments, $R^B$ is —$C(=O)$-(substituted or unsubstituted phenyl). In certain embodiments, $R^B$ is —$C(=O)Ph$. In certain embodiments, $R^B$ is of the formula:

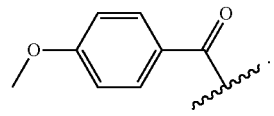 [SMILES: *C(=O)c1ccc(OC)cc1]

In certain embodiments, $R^B$ is —$C(=O)OR^{B1}$. In certain embodiments, $R^B$ is —$C(=O)N(R^{B1})_2$. In certain embodiments, $R^B$ is a nitrogen protecting group. In certain embodiments, $R^B$ is Bn, Boc, Cbz, Fmoc, trifluoroacetyl, triphenylmethyl, acetyl, or Ts.

In certain embodiments, $R^B$ is substituted or unsubstituted acyl, substituted or unsubstituted alkyl, substituted or unsubstituted carbocyclyl, substituted or unsubstituted aryl, —$C(=O)R^{B1}$, —$C(=O)OR^{B1}$, or —$C(=O)N(R^{B1})_2$. In certain embodiments, $R^B$ is substituted or unsubstituted alkyl, substituted or unsubstituted, 3- to 7-membered, monocyclic carbocyclyl, substituted or unsubstituted phenyl, —C(=O)$R^{B1}$, —C(=O)O$R^{B1}$, or —C(=O)N($R^{B1}$)$_2$. In certain embodiments, $R^B$ is substituted or unsubstituted $C_{1-6}$ alkyl, unsubstituted, 3- to 7-membered, monocyclic carbocyclyl, substituted or unsubstituted phenyl, or —C(=O)$R^{B1}$. In certain embodiments, $R^B$ is t-Bu, benzyl, cyclohexyl,

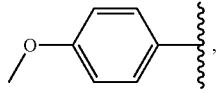

—C(=O)(t-Bu), or —C(=O)Ph. In certain embodiments, $R^B$ is t-Bu, benzyl, cyclohexyl, or

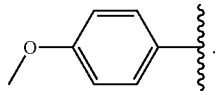 [SMILES: *c1ccc(OC)cc1]

In certain embodiments, $R^B$ and $R^C$ are joined to form a substituted heterocyclic ring. In certain embodiments, $R^B$ and $R^C$ are joined to form an unsubstituted heterocyclic ring. In certain embodiments, $R^B$ and $R^C$ are joined to form a saturated or unsaturated heterocyclic ring. In certain embodiments, $R^B$ and $R^C$ are joined to form a heterocyclic ring including one, two, or three double bonds in the heterocyclic ring. In certain embodiments, $R^B$ and $R^C$ are joined to form a heterocyclic ring, wherein one, two, or three atoms in the heterocyclic ring are independently selected from the group consisting of nitrogen, oxygen, and sulfur. In certain embodiments, $R^B$ and $R^C$ are joined to form a 3- to 7-membered, monocyclic heterocyclic ring. In certain embodiments, $R^B$ and $R^C$ are joined to form a 5- or 6-membered, monocyclic heterocyclic ring wherein one or two atoms in the heterocyclic ring are independently selected from the group consisting of nitrogen or oxygen. In certain embodiments, $R^B$ and $R^C$ are joined to form a heterocyclic ring of the formula:

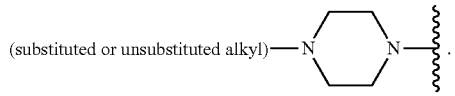

In certain embodiments, $R^B$ and $R^C$ are joined to form a heterocyclic ring of the formula:

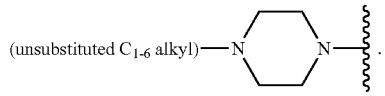

In certain embodiments, $R^B$ and $R^C$ are joined to form a heterocyclic ring of the formula:

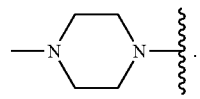

In certain embodiments, $R^B$ and $R^C$ are joined to form a heterocyclic ring of the formula:

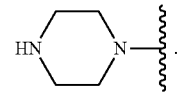

In certain embodiments, $R^B$ and $R^C$ are joined to form a heterocyclic ring of the formula:

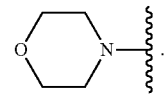

In certain embodiments, $R^B$ and $R^C$ are joined to form a 5- to 13-membered, bicyclic heterocyclic ring system.

In certain embodiments, at least one instance of $R^{B1}$ is H. In certain embodiments, at least one instance of $R^{B1}$ is substituted acyl. In certain embodiments, at least one instance of $R^{B1}$ is unsubstituted acyl. In certain embodiments, at least one instance of $R^B$ is acetyl. In certain embodiments, at least one instance of $R^{B1}$ is substituted alkyl. In certain embodiments, at least one instance of $R^{B1}$ is unsubstituted alkyl. In certain embodiments, at least one instance of $R^{B1}$ is $C_{1-12}$ alkyl. In certain embodiments, at least one instance of $R^{B1}$ is $C_{1-6}$ alkyl. In certain embodiments, at least one instance of $R^{B1}$ is methyl. In certain embodiments, at least one instance of $R^{B1}$ is ethyl. In certain embodiments, at least one instance of $R^{B1}$ is propyl. In certain embodiments, at least one instance of $R^{B1}$ is butyl. In certain embodiments, at least one instance of $R^{B1}$ is pentyl. In certain embodiments, at least one instance of $R^{B1}$ is hexyl. In certain embodiments, at least one instance of $R^{B1}$ is substituted alkenyl. In certain embodiments, at least one instance of $R^{B1}$ is unsubstituted alkenyl. In certain embodiments, at least one instance of $R^{B1}$ is vinyl. In certain embodiments, at least one instance of $R^{B1}$ is substituted alkynyl. In certain embodiments, at least one instance of $R^{B1}$ is unsubstituted alkynyl. In certain embodiments, at least one instance of $R^{B1}$ is ethynyl. In certain embodiments, at least one instance of $R^{B1}$ is substituted carbocyclyl. In certain embodiments, at least one instance of $R^B$ is unsubstituted carbocyclyl. In certain embodiments, at least one instance of $R^{B1}$ is saturated carbocyclyl. In certain embodiments, at least one instance of $R^{B1}$ is unsaturated carbocyclyl. In certain embodiments, at least one instance of $R^{B1}$ is carbocyclyl including one, two, or three double bonds in the carbocyclic ring. In certain embodiments, at least one instance of $R^{B1}$ is 3- to 7-membered, monocyclic carbocyclyl. In certain embodiments, at least one instance of $R^{B1}$ is cylcopropyl. In certain embodiments, at least one instance of $R^{B1}$ is cyclobutyl. In certain embodiments, at least one instance of $R^{B1}$ is cyclopentyl. In certain embodiments, at least one instance of $R^{B1}$ is cyclohexyl. In certain embodiments, at least one instance of $R^{B1}$ is cycloheptyl. In certain embodiments, at least one instance of $R^{B1}$ is 5- to 13-membered, bicyclic carbocyclyl. In certain embodiments, at least one instance of $R^{B1}$ is substituted heterocyclyl. In certain embodiments, at least one instance of $R^{B1}$ is unsubstituted heterocyclyl. In certain embodiments, at least one instance of $R^{B1}$ is saturated heterocyclyl. In certain embodiments, at least one instance of $R^{B1}$ is unsaturated heterocyclyl. In certain embodiments, at least one instance of $R^{B1}$ is heterocyclyl including one, two, or three double bonds in the heterocyclic ring. In certain embodiments, at least one instance of $R^{B1}$ is heterocyclyl, wherein one, two, or three atoms in the heterocyclic ring are independently selected from the group consisting of nitrogen, oxygen, and sulfur. In certain embodiments, at least one instance of $R^{B1}$ is 3- to 7-membered, monocyclic heterocyclyl. In certain embodiments, at least one instance of $R^{B1}$ is 5- to 13-membered, bicyclic heterocyclyl. In certain embodiments, at least one instance of $R^{B1}$ is substituted or unsubstituted aryl. In certain embodiments, at least one instance of $R^{B1}$ is 6- to 14-membered aryl. In certain embodiments, at least one instance of $R^{B1}$ is 6- to 10-membered aryl. In certain embodiments, at least one instance of $R^B$ is monocyclic aryl. In certain embodiments, at least one instance of $R^{B1}$ is phenyl. In certain embodiments, at least one instance of $R^{B1}$ is bicyclic aryl. In certain embodiments, at least one instance of RBI is naphthyl. In certain embodiments, at least one instance of $R^{B1}$ is substituted or unsubstituted heteroaryl. In certain embodiments, at least one instance of $R^{B1}$ is heteroaryl, wherein one, two, three, or four atoms in the heteroaryl ring are independently selected from the group consisting of nitrogen, oxygen, and sulfur. In certain embodiments, at least one instance of $R^{B1}$ is monocyclic heteroaryl. In certain embodiments, at least one instance of $R^{B1}$ is 5-membered, monocyclic heteroaryl. In certain embodiments, at least one instance of $R^{B1}$ is 6-membered, monocyclic heteroaryl. In certain embodiments, at least one instance of $R^{B1}$ is pyridyl. In certain embodiments, at least one instance of $R^{B1}$ is bicyclic heteroaryl, wherein the point of attachment may be on any atom of the bicyclic heteroaryl ring system, as valency permits. In certain embodiments, at least one instance of $R^{B1}$ is 9-membered, bicyclic heteroaryl. In certain embodiments, at least one instance of $R^{B1}$ is 10-membered, bicyclic heteroaryl. In certain embodiments, at least one instance of $R^{B1}$ is a nitrogen protecting group when attached to a nitrogen atom. In certain embodiments, at least one instance of $R^{B1}$ is Bn, Boc, Cbz, Fmoc, trifluoroacetyl, triphenylmethyl, acetyl, or Ts when attached to a nitrogen atom. In certain embodiments, $R^{B1}$ is an oxygen protecting group when attached to an oxygen atom. In certain embodiments, $R^{B1}$ is silyl, TBDPS, TBDMS, TIPS, TES, TMS, MOM, THP, t-Bu, Bn, allyl, acetyl, pivaloyl, or benzoyl when attached to an oxygen atom.

In certain embodiments, two instances of $R^{B1}$ are joined to form a substituted or unsubstituted heterocyclic ring. In certain embodiments, two instances of $R^{B1}$ are joined to form a saturated or unsaturated heterocyclic ring. In certain embodiments, two instances of $R^{B1}$ are joined to form a heterocyclic ring including one, two, or three double bonds in the heterocyclic ring. In certain embodiments, two instances of $R^{B1}$ are joined to form a heterocyclic ring, wherein one, two, or three atoms in the heterocyclic ring are independently selected from the group consisting of nitrogen, oxygen, and sulfur. In certain embodiments, two instances of $R^{B1}$ are joined to form a 3- to 7-membered, monocyclic heterocyclic ring. In certain embodiments, two instances of $R^{B1}$ are joined to form a 5- to 13-membered, bicyclic heterocyclic ring.

Compounds of Formula (I) include substituent $R^C$ on the amino moiety. In certain embodiments, $R^C$ is H. In certain embodiments, $R^C$ is substituted acyl. In certain embodiments, $R^C$ is unsubstituted acyl. In certain embodiments, $R^C$ is substituted alkyl. In certain embodiments, $R^C$ is unsubstituted alkyl. In certain embodiments, $R^C$ is $C_{1-12}$ alkyl. In certain embodiments, $R^C$ is $C_{1-6}$ alkyl. In certain embodiments, $R^C$ is unsubstituted methyl. In certain embodiments, $R^C$ is substituted methyl. In certain embodiments, $R^C$ is —$CH_2F$. In certain embodiments, $R^C$ is —$CHF_2$. In certain embodiments, $R^C$ is —$CF_3$. In certain embodiments, $R^C$ is Bn. In certain embodiments, $R^C$ is unsubstituted ethyl. In certain embodiments, $R^C$ is substituted ethyl. In certain embodiments, $R^C$ is —$(CH_2)_2Ph$. In certain embodiments, $R^C$ is propyl. In certain embodiments, $R^C$ is butyl. In certain embodiments, $R^C$ is t-butyl. In certain embodiments, $R^C$ is pentyl. In certain embodiments, $R^C$ is hexyl. In certain embodiments, $R^C$ is substituted alkenyl. In certain embodiments, $R^C$ is unsubstituted alkenyl. In certain embodiments, $R^C$ is vinyl. In certain embodiments, $R^C$ is substituted alkynyl. In certain embodiments, $R^C$ is unsubstituted alkynyl. In certain embodiments, $R^C$ is ethynyl. In certain embodiments, $R^C$ is substituted carbocyclyl. In certain embodiments, $R^C$ is unsubstituted carbocyclyl. In certain embodiments, $R^C$ is saturated carbocyclyl. In certain embodiments, $R^C$ is unsaturated carbocyclyl. In certain embodiments, $R^C$ is carbocyclyl including one, two, or three double bonds in the carbocyclic ring. In certain embodiments, $R^C$ is monocyclic carbocyclyl. In certain embodiments, $R^C$ is 3- to 7-membered, monocyclic carbocyclyl. In certain embodiments, $R^C$ is cylcopropyl. In certain embodiments, $R^C$ is cyclobutyl. In certain embodiments, $R^C$ is cyclopentyl. In certain embodiments, $R^C$ is cyclohexyl. In certain embodiments, $R^C$ is cycloheptyl. In certain embodiments, $R^C$ is bicyclic carbocyclyl. In certain embodiments, $R^C$ is 5- to 13-membered, bicyclic carbocyclyl. In certain embodiments, $R^C$ is substituted heterocyclyl. In certain embodiments, $R^C$ is unsubstituted heterocyclyl. In certain embodiments, $R^C$ is saturated heterocyclyl. In certain embodiments, $R^C$ is unsaturated heterocyclyl. In certain embodiments, $R^C$ is heterocyclyl including one, two, or three double bonds in the heterocyclic ring. In certain embodiments, $R^C$ is heterocyclyl, wherein one, two, or three atoms in the heterocyclic ring are independently selected from the group consisting of nitrogen, oxygen, and sulfur. In certain embodiments, $R^C$ is monocyclic heterocyclyl. In certain embodiments, $R^C$ is 3- to 7-membered, monocyclic heterocyclyl. In certain embodiments, $R^C$ is bicyclic heterocyclyl. In certain embodiments, $R^C$ is 5- to 13-membered, bicyclic heterocyclyl. In certain embodiments, $R^C$ is substituted aryl. In certain embodiments, $R^C$ is unsubstituted aryl. In certain embodiments, $R^C$ is 6- to 14-membered aryl. In certain embodiments, $R^C$ is 6- to 10-membered aryl. In certain embodiments, $R^C$ is substituted phenyl. In certain embodiments, $R^C$ is unsubstituted phenyl. In certain embodiments, $R^C$ is substituted naphthyl. In certain embodiments, $R^C$ is unsubstituted naphthyl. In certain embodiments, $R^C$ is substituted heteroaryl. In certain embodiments, $R^C$ is unsubstituted heteroaryl. In certain embodiments, $R^C$ is heteroaryl, wherein one, two, three, or four atoms in the heteroaryl ring are independently selected from the group consisting of nitrogen, oxygen, and sulfur. In certain embodiments, $R^C$ is monocyclic heteroaryl. In certain embodiments, $R^C$ is 5-membered, monocyclic heteroaryl. In certain embodiments, $R^C$ is 6-membered, monocyclic heteroaryl. In certain embodiments, $R^C$ is pyridyl. In certain embodiments, $R^C$ is bicyclic heteroaryl, wherein the point of attachment may be on any atom of the bicyclic heteroaryl ring system, as valency permits. In certain embodiments, $R^C$ is 9-membered, bicyclic heteroaryl. In certain embodiments, $R^C$ is 10-membered, bicyclic heteroaryl. In certain embodiments, $R^C$ is —$C(=O)R^{C1}$. In certain embodiments, $R^C$ is —$C(=O)OR^{C1}$. In certain embodiments, $R^C$ is —$C(=O)N(R^{C1})_2$. In certain embodiments, $R^C$ is a nitrogen protecting group. In certain embodiments, $R^C$ is Bn, Boc, Cbz, Fmoc, trifluoroacetyl, triphenylmethyl, acetyl, or Ts.

In certain embodiments, $R^C$ is substituted or unsubstituted acyl, substituted or unsubstituted alkyl, substituted or unsubstituted carbocyclyl, substituted or unsubstituted aryl, —C(=O)$R^{C1}$, —C(=O)O$R^{C1}$, or —C(=O)N($R^{C1}$)$_2$. In certain embodiments, $R^C$ is substituted or unsubstituted alkyl, substituted or unsubstituted carbocyclyl, substituted or unsubstituted aryl, or —C(=O)$R^{C1}$. In certain embodiments, $R^C$ is unsubstituted $C_{1-6}$ alkyl, unsubstituted 3- to 7-membered monocyclic carbocyclyl, substituted or unsubstituted phenyl, or —C(=O)$R^{C1}$.

In certain embodiments, at least one instance of $R^{C1}$ is H. In certain embodiments, at least one instance of $R^{C1}$ is substituted acyl. In certain embodiments, at least one instance of $R^{C1}$ is unsubstituted acyl. In certain embodiments, at least one instance of $R^{C1}$ is acetyl. In certain embodiments, at least one instance of $R^{C1}$ is substituted alkyl. In certain embodiments, at least one instance of $R^{C1}$ is unsubstituted alkyl. In certain embodiments, at least one instance of $R^{C1}$ is $C_{1-12}$ alkyl. In certain embodiments, at least one instance of $R^{C1}$ is $C_{1-6}$ alkyl. In certain embodiments, at least one instance of $R^{C1}$ is methyl. In certain embodiments, at least one instance of $R^{C1}$ is ethyl. In certain embodiments, at least one instance of $R^{C1}$ is propyl. In certain embodiments, at least one instance of $R^{C1}$ is butyl. In certain embodiments, at least one instance of $R^{C1}$ is pentyl. In certain embodiments, at least one instance of $R^{C1}$ is hexyl. In certain embodiments, at least one instance of $R^{C1}$ is substituted alkenyl. In certain embodiments, at least one instance of $R^{C1}$ is unsubstituted alkenyl. In certain embodiments, at least one instance of $R^{C1}$ is vinyl. In certain embodiments, at least one instance of $R^{C1}$ is substituted alkynyl. In certain embodiments, at least one instance of $R^{C1}$ is unsubstituted alkynyl. In certain embodiments, at least one instance of $R^{C1}$ is ethynyl. In certain embodiments, at least one instance of $R^{C1}$ is substituted carbocyclyl. In certain embodiments, at least one instance of $R^{C1}$ is unsubstituted carbocyclyl. In certain embodiments, at least one instance of $R^{C1}$ is saturated carbocyclyl. In certain embodiments, at least one instance of $R^{C1}$ is unsaturated carbocyclyl. In certain embodiments, at least one instance of $R^{C1}$ is carbocyclyl including one, two, or three double bonds in the carbocyclic ring. In certain embodiments, at least one instance of $R^{C1}$ is 3- to 7-membered, monocyclic carbocyclyl. In certain embodiments, at least one instance of $R^{C1}$ is cylcopropyl. In certain embodiments, at least one instance of $R^{C1}$ is cyclobutyl. In certain embodiments, at least one instance of $R^{C1}$ is cyclopentyl. In certain embodiments, at least one instance of $R^{C1}$ is cyclohexyl. In certain embodiments, at least one instance of $R^{C1}$ is cycloheptyl. In certain embodiments, at least one instance of $R^{C1}$ is 5- to 13-membered, bicyclic carbocyclyl. In certain embodiments, at least one instance of $R^C$ is substituted heterocyclyl. In certain embodiments, at least one instance of $R^{C1}$ is unsubstituted heterocyclyl. In certain embodiments, at least one instance of $R^{C1}$ is saturated heterocyclyl. In certain embodiments, at least one instance of $R^C$ is unsaturated heterocyclyl. In certain embodiments, at least one instance of $R^{C1}$ is heterocyclyl including one, two, or three double bonds in the heterocyclic ring. In certain embodiments, at least one instance of $R^{C1}$ is heterocyclyl, wherein one, two, or three atoms in the heterocyclic ring are independently selected from the group consisting of nitrogen, oxygen, and sulfur. In certain embodiments, at least one instance of $R^{C1}$ is 3- to 7-membered, monocyclic heterocyclyl. In certain embodiments, at least one instance of $R^{C1}$ is 5- to 13-membered, bicyclic heterocyclyl. In certain embodiments, at least one instance of $R^{C1}$ is substituted or unsubstituted aryl. In certain embodiments, at least one instance of $R^{C1}$ is 6- to 14-membered aryl. In certain embodiments, at least one instance of $R^{C1}$ is 6- to 10-membered aryl. In certain embodiments, at least one instance of $R^{C1}$ is monocyclic aryl. In certain embodiments, at least one instance of $R^{C1}$ is phenyl. In certain embodiments, at least one instance of $R^{C1}$ is bicyclic aryl. In certain embodiments, at least one instance of $R^{C1}$ is naphthyl. In certain embodiments, at least one instance of $R^C$ is substituted or unsubstituted heteroaryl. In certain embodiments, at least one instance of $R^{C1}$ is heteroaryl, wherein one, two, three, or four atoms in the heteroaryl ring are independently selected from the group consisting of nitrogen, oxygen, and sulfur. In certain embodiments, at least one instance of $R^{C1}$ is monocyclic heteroaryl. In certain embodiments, at least one instance of $R^{C1}$ is 5-membered, monocyclic heteroaryl. In certain embodiments, at least one instance of $R^{C1}$ is 6-membered, monocyclic heteroaryl. In certain embodiments, at least one instance of $R^{C1}$ is pyridyl. In certain embodiments, at least one instance of $R^{C1}$ is bicyclic heteroaryl, wherein the point of attachment may be on any atom of the bicyclic heteroaryl ring system, as valency permits. In certain embodiments, at least one instance of $R^{C1}$ is 9-membered, bicyclic heteroaryl. In certain embodiments, at least one instance of $R^{C1}$ is 10-membered, bicyclic heteroaryl. In certain embodiments, at least one instance of $R^{C1}$ is a nitrogen protecting group when attached to a nitrogen atom. In certain embodiments, at least one instance of $R^{C1}$ is Bn, Boc, Cbz, Fmoc, trifluoroacetyl, triphenylmethyl, acetyl, or Ts when attached to a nitrogen atom. In certain embodiments, $R^{C1}$ is an oxygen protecting group when attached to an oxygen atom. In certain embodiments, $R^{C1}$ is silyl, TBDPS, TBDMS, TIPS, TES, TMS, MOM, THP, t-Bu, Bn, allyl, acetyl, pivaloyl, or benzoyl when attached to an oxygen atom.

In certain embodiments, two instances of $R^{C1}$ are joined to form a substituted or unsubstituted heterocyclic ring. In certain embodiments, two instances of $R^{C1}$ are joined to form a saturated or unsaturated heterocyclic ring. In certain embodiments, two instances of $R^{C1}$ are joined to form a heterocyclic ring including one, two, or three double bonds in the heterocyclic ring. In certain embodiments, two instances of $R^{C1}$ are joined to form a heterocyclic ring, wherein one, two, or three atoms in the heterocyclic ring are independently selected from the group consisting of nitrogen, oxygen, and sulfur. In certain embodiments, two instances of $R^{C1}$ are joined to form a 3- to 7-membered, monocyclic heterocyclic ring. In certain embodiments, two instances of $R^{C1}$ are joined to form a 5- to 13-membered, bicyclic heterocyclic ring.

In certain embodiments, $R^B$ is substituted or unsubstituted acyl, substituted or unsubstituted alkyl, substituted or unsubstituted carbocyclyl, substituted or unsubstituted aryl, —C(=O)$R^{B1}$, —C(=O)O$R^{B1}$, or —C(=O)N($R^{B1}$)$_2$; and $R^C$ is hydrogen. In certain embodiments, $R^B$ is substituted or unsubstituted alkyl, substituted or unsubstituted, 3- to 7-membered, monocyclic carbocyclyl, substituted or unsubstituted phenyl, —C(=O)$R^{B1}$, —C(=O)O$R^{B1}$, or —C(=O)N($R^{B1}$)$_2$; and $R^C$ is hydrogen. In certain embodiments, $R^B$ is substituted or unsubstituted $C_{1-6}$ alkyl, unsubstituted, 3- to 7-membered, monocyclic carbocyclyl, substituted or unsubstituted phenyl, or —C(=O)$R^{B1}$; and $R^C$ is hydrogen. In certain embodiments, $R^B$ is t-Bu, benzyl, cyclohexyl,

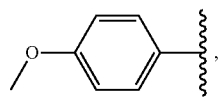

—C(=O)(t-Bu), or —C(=O)Ph; and $R^C$ is hydrogen. In certain embodiments, $R^B$ is t-Bu, benzyl, cyclohexyl, or

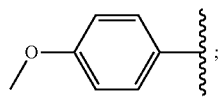

and $R^C$ is hydrogen.

Compounds of Formula (I) may include one or more substituent $R^D$. In certain embodiments, at least one instance of $R^D$ is H. In certain embodiments, at least one instance of $R^D$ is halogen. In certain embodiments, at least one instance of $R^D$ is F. In certain embodiments, at least one instance of $R^D$ is Cl. In certain embodiments, at least one instance of $R^D$ is Br. In certain embodiments, at least one instance of $R^D$ is I (iodine). In certain embodiments, at least one instance of $R^D$ is substituted acyl. In certain embodiments, at least one instance of $R^D$ is unsubstituted acyl. In certain embodiments, at least one instance of $R^D$ is substituted alkyl. In certain embodiments, at least one instance of $R^D$ is unsubstituted alkyl. In certain embodiments, at least one instance of $R^D$ is $C_{1-12}$ alkyl. In certain embodiments, at least one instance of $R^D$ is $C_{1-6}$ alkyl. In certain embodiments, at least one instance of $R^D$ is unsubstituted methyl. In certain embodiments, at least one instance of $R^D$ is substituted methyl. In certain embodiments, at least one instance of $R^D$ is —$CH_2F$. In certain embodiments, at least one instance of $R^D$ is —$CHF_2$. In certain embodiments, at least one instance of $R^D$ is —$CF_3$. In certain embodiments, at least one instance of $R^D$ is Bn. In certain embodiments, at least one instance of $R^D$ is unsubstituted ethyl. In certain embodiments, at least one instance of $R^D$ is substituted ethyl. In certain embodiments, at least one instance of $R^D$ is —$(CH_2)_2Ph$. In certain embodiments, at least one instance of $R^D$ is propyl. In certain embodiments, at least one instance of $R^D$ is butyl. In certain embodiments, at least one instance of $R^D$ is pentyl. In certain embodiments, at least one instance of $R^D$ is hexyl. In certain embodiments, at least one instance of $R^D$ is substituted alkenyl. In certain embodiments, at least one instance of $R^D$ is unsubstituted alkenyl. In certain embodiments, at least one instance of $R^D$ is vinyl. In certain embodiments, at least one instance of $R^D$ is substituted alkynyl. In certain embodiments, at least one instance of $R^D$ is unsubstituted alkynyl. In certain embodiments, at least one instance of $R^D$ is ethynyl. In certain embodiments, at least one instance of $R^D$ is substituted carbocyclyl. In certain embodiments, at least one instance of $R^D$ is unsubstituted carbocyclyl. In certain embodiments, at least one instance of $R^D$ is saturated carbocyclyl. In certain embodiments, at least one instance of $R^D$ is unsaturated carbocyclyl. In certain embodiments, at least one instance of RD is carbocyclyl including one, two, or three double bonds in the carbocyclic ring. In certain embodiments, at least one instance of $R^D$ is monocyclic carbocyclyl. In certain embodiments, at least one instance of $R^D$ is 3- to 7-membered, monocyclic carbocyclyl. In certain embodiments, at least one instance of $R^D$ is cylcopropyl. In certain embodiments, at least one instance of $R^D$ is cyclobutyl. In certain embodiments, at least one instance of $R^D$ is cyclopentyl. In certain embodiments, at least one instance of $R^D$ is cyclohexyl. In certain embodiments, at least one instance of $R^D$ is cycloheptyl. In certain embodiments, at least one instance of $R^D$ is bicyclic carbocyclyl. In certain embodiments, at least one instance of $R^D$ is 5- to 13-membered, bicyclic carbocyclyl. In certain embodiments, at least one instance of $R^D$ is substituted heterocyclyl. In certain embodiments, at least one instance of $R^D$ is unsubstituted heterocyclyl. In certain embodiments, at least one instance of $R^D$ is saturated heterocyclyl. In certain embodiments, at least one instance of $R^D$ is unsaturated heterocyclyl. In certain embodiments, at least one instance of $R^D$ is heterocyclyl including one, two, or three double bonds in the heterocyclic ring. In certain embodiments, at least one instance of $R^D$ is heterocyclyl, wherein one, two, or three atoms in the heterocyclic ring are independently selected from the group consisting of nitrogen, oxygen, and sulfur. In certain embodiments, at least one instance of $R^D$ is monocyclic heterocyclyl. In certain embodiments, at least one instance of $R^D$ is 3- to 7-membered, monocyclic heterocyclyl. In certain embodiments, at least one instance of $R^D$ is bicyclic heterocyclyl. In certain embodiments, at least one instance of $R^D$ is 5- to 13-membered, bicyclic heterocyclyl. In certain embodiments, at least one instance of $R^D$ is substituted aryl. In certain embodiments, at least one instance of $R^D$ is unsubstituted aryl. In certain embodiments, at least one instance of $R^D$ is 6- to 14-membered aryl. In certain embodiments, at least one instance of $R^D$ is 6- to 10-membered aryl. In certain embodiments, at least one instance of $R^D$ is substituted phenyl. In certain embodiments, at least one instance of $R^D$ is unsubstituted phenyl. In certain embodiments, at least one instance of $R^D$ is substituted naphthyl. In certain embodiments, at least one instance of $R^D$ is unsubstituted naphthyl. In certain embodiments, at least one instance of $R^D$ is substituted heteroaryl. In certain embodiments, at least one instance of $R^D$ is unsubstituted heteroaryl. In certain embodiments, at least one instance of $R^D$ is heteroaryl, wherein one, two, three, or four atoms in the heteroaryl ring are independently selected from the group consisting of nitrogen, oxygen, and sulfur. In certain embodiments, at least one instance of $R^D$ is monocyclic heteroaryl. In certain embodiments, at least one instance of $R^D$ is 5-membered, monocyclic heteroaryl. In certain embodiments, at least one instance of $R^D$ is 6-membered, monocyclic heteroaryl. In certain embodiments, at least one instance of $R^D$ is pyridyl. In certain embodiments, at least one instance of $R^D$ is bicyclic heteroaryl, wherein the point of attachment may be on any atom of the bicyclic heteroaryl ring system, as valency permits. In certain embodiments, at least one instance of $R^D$ is 9-membered, bicyclic heteroaryl. In certain embodiments, at least one instance of $R^D$ is 10-membered, bicyclic heteroaryl. In certain embodiments, at least one instance of $R^D$ is —$OR^{D1}$. In certain embodiments, at least one instance of $R^D$ is —O-(substituted or unsubstituted alkyl). In certain embodiments, at least one instance of $R^D$ is —O-(unsubstituted $C_{1-6}$-alkyl). In certain embodiments, at least one instance of $R^D$ is —OMe. In certain embodiments, at least one instance of $R^D$ is —OEt. In certain embodiments, at least one instance of $R^D$ is —OPr. In certain embodiments, at least one instance of $R^D$ is —OBu. In certain embodiments, at least one instance of $R^D$ is —O(pentyl). In certain embodiments, at least one instance of $R^D$ is —O(hexyl). In certain embodiments, at least one instance of $R^D$ is —OPh. In certain embodiments, at least one instance of $R^D$ is —OBn. In certain embodiments, at least one instance of $R^D$ is —$O(CH_2)_2Ph$. In certain embodiments, at least one instance of $R^D$ is —OH. In certain embodiments, at least one instance of $R^D$ is —$SR^{D1}$. In certain embodiments, at least one instance of $R^D$ is —SMe. In certain embodiments, at least one instance of $R^D$ is —SH. In certain embodiments, at least one instance of $R^D$ is —N($R^{D1}$)$_2$. In certain embodiments, at least one instance of $R^D$ is —NMe$_2$. In certain embodiments, at least one instance of $R^D$ is —NH$_2$. In certain embodiments, at least one instance of $R^D$ is —CN. In certain embodiments, at least one instance of $R^D$ is —SCN. In certain embodiments, at least one instance of $R^D$ is —C(=N$R^{D1}$)$R^{D1}$, —C(=N$R^{D1}$)O$R^{D1}$, or —C(=N$R^{D1}$)N($R^{D1}$)$_2$. In certain embodiments, at least one instance of $R^D$ is —C(=O)$R^{D1}$, —C(=O)O$R^{D1}$, or —C(=O)N($R^{D1}$)$_2$. In certain embodiments, at least one instance of $R^D$ is —NO$_2$. In certain embodiments, at least one instance of $R^D$ is —N$R^{D1}$C(=O)$R^{D1}$, —N$R^{D1}$C(=O)O$R^{D1}$ or —N$R^{D1}$C(=O)N($R^{D1}$)$_2$. In certain embodiments, at least one instance of $R^D$ is —OC(=O)$R^D$, —OC(=O)O$R^{D1}$, or —OC(=O)N($R^{D1}$)$_2$.

In compounds of Formula (I), two $R^D$ groups may be joined to form a substituted or unsubstituted carbocyclic ring. In certain embodiments, two instances of $R^D$ are joined to form a saturated or unsaturated carbocyclic ring. In certain embodiments, two instances of $R^D$ are joined to form a carbocyclic ring including one, two, or three double bonds in the carbocyclic ring. In certain embodiments, two instances of $R^D$ are joined to form a 3- to 7-membered, monocyclic carbocyclic ring. In certain embodiments, two instances of $R^D$ are joined to form a 3-membered carbocyclic ring. In certain embodiments, two instances of $R^D$ are joined to form a 4-membered carbocyclic ring. In certain embodiments, two instances of $R^D$ are joined to form a 5-membered carbocyclic ring. In certain embodiments, two instances of $R^D$ are joined to form a 6-membered carbocyclic ring. In certain embodiments, two instances of $R^D$ are joined to form a 7-membered carbocyclic ring. In certain embodiments, two instances of $R^D$ are joined to form a 5- to 13-membered, bicyclic carbocyclic ring system.

In certain embodiments, two instances of $R^D$ are joined to form a substituted or unsubstituted heterocyclic ring. In certain embodiments, two instances of $R^D$ are joined to form a saturated or unsaturated heterocyclic ring. In certain embodiments, two instances of $R^D$ are joined to form a heterocyclic ring including one, two, or three double bonds in the heterocyclic ring. In certain embodiments, two instances of $R^D$ are joined to form a heterocyclic ring, wherein one, two, or three atoms in the heterocyclic ring are independently selected from the group consisting of nitrogen, oxygen, and sulfur. In certain embodiments, two instances of $R^D$ are joined to form a 3- to 7-membered, monocyclic heterocyclic ring. In certain embodiments, two instances of $R^D$ are joined to form a 5- to 13-membered, bicyclic heterocyclic ring system.

In certain embodiments, two instances of $R^D$ are joined to form a substituted or unsubstituted aryl ring. In certain embodiments, two instances of $R^D$ are joined to form a 6- to 14-membered aryl ring. In certain embodiments, two instances of $R^D$ are joined to form a 6-to 10-membered aryl ring. In certain embodiments, two instances of $R^D$ are joined to form a monocyclic aryl ring. In certain embodiments, two instances of $R^D$ are joined to form a phenyl. In certain embodiments, two instances of $R^D$ are joined to form a bicyclic aryl ring system. In certain embodiments, two instances of $R^D$ are joined to form a naphthyl.

In certain embodiments, two instances of $R^D$ are joined to form a substituted or unsubstituted heteroaryl ring. In certain embodiments, two instances of $R^D$ are joined to form a monocyclic heteroaryl ring, wherein one, two, or three atoms in the heteroaryl ring are independently selected from the group consisting of nitrogen, oxygen, and sulfur. In certain embodiments, two instances of $R^D$ are joined to form a 5-membered, monocyclic heteroaryl ring. In certain embodiments, two instances of $R^D$ are joined to form a 6-membered, monocyclic heteroaryl ring. In certain embodiments, two instances of $R^D$ are joined to form a pyridyl ring. In certain embodiments, two instances of $R^D$ are joined to form a bicyclic heteroaryl ring system, wherein one, two, three, or four atoms in the heteroaryl ring are independently selected from the group consisting of nitrogen, oxygen, and sulfur. In certain embodiments, two instances of $R^D$ are joined to form a 9-membered, bicyclic heteroaryl ring system. In certain embodiments, two instances of $R^D$ are joined to form a 10-membered, bicyclic heteroaryl ring system.

In certain embodiments, at least one instance of $R^D$ is halogen, substituted or unsubstituted alkyl, or —O$R^{D1}$. In certain embodiments, at least one instance of $R^D$ is halogen, unsubstituted alkyl, or —O-(unsubstituted alkyl). In certain embodiments, at least one instance of $R^D$ is halogen, unsubstituted $C_{1-6}$ alkyl, or —O-(unsubstituted $C_{1-6}$ alkyl). In certain embodiments, at least one instance of $R^D$ is Cl or —OMe. In certain embodiments, all instances of $R^D$ are hydrogen.

In certain embodiments, at least one instance of $R^{D1}$ is H. In certain embodiments, at least one instance of $R^{D1}$ is substituted acyl. In certain embodiments, at least one instance of $R^{D1}$ is unsubstituted acyl. In certain embodiments, at least one instance of $R^{D1}$ is acetyl. In certain embodiments, at least one instance of $R^{D1}$ is substituted alkyl. In certain embodiments, at least one instance of $R^{D1}$ is unsubstituted alkyl. In certain embodiments, at least one instance of $R^{D1}$ is $C_{1-12}$ alkyl. In certain embodiments, at least one instance of $R^{D1}$ is $C_{1-6}$ alkyl. In certain embodiments, at least one instance of $R^{D1}$ is methyl. In certain embodiments, at least one instance of $R^{D1}$ is ethyl. In certain embodiments, at least one instance of $R^{D1}$ is propyl. In certain embodiments, at least one instance of $R^{D1}$ is butyl. In certain embodiments, at least one instance of $R^{D1}$ is pentyl. In certain embodiments, at least one instance of $R^{D1}$ is hexyl. In certain embodiments, at least one instance of $R^{D1}$ is substituted alkenyl. In certain embodiments, at least one instance of $R^{D1}$ is unsubstituted alkenyl. In certain embodiments, at least one instance of $R^{D1}$ is vinyl. In certain embodiments, at least one instance of $R^{D1}$ is substituted alkynyl. In certain embodiments, at least one instance of $R^{D1}$ is unsubstituted alkynyl. In certain embodiments, at least one instance of $R^{D1}$ is ethynyl. In certain embodiments, at least one instance of $R^{D1}$ is substituted carbocyclyl. In certain embodiments, at least one instance of $R^{D1}$ is unsubstituted carbocyclyl. In certain embodiments, at least one instance of $R^{D1}$ is saturated carbocyclyl. In certain embodiments, at least one instance of $R^{D1}$ is unsaturated carbocyclyl. In certain embodiments, at least one instance of $R^{D1}$ is carbocyclyl including one, two, or three double bonds in the carbocyclic ring. In certain embodiments, at least one instance of $R^{D1}$ is 3- to 7-membered, monocyclic carbocyclyl. In certain embodiments, at least one instance of $R^{D1}$ is cylcopropyl. In certain embodiments, at least one instance of $R^{D1}$ is cyclobutyl. In certain embodiments, at least one instance of $R^{D1}$ is cyclopentyl. In certain embodiments, at least one instance of $R^{D1}$ is cyclohexyl. In certain embodiments, at least one instance of $R^D$ is cycloheptyl. In certain embodiments, at least one instance of $R^{D1}$ is 5- to 13-membered, bicyclic carbocyclyl. In certain embodiments, at least one instance of $R^{D1}$ is substituted heterocyclyl. In certain embodiments, at least one instance of $R^{D1}$ is unsubstituted heterocyclyl. In certain embodiments, at least one instance of $R^{D1}$ is saturated heterocyclyl. In certain embodiments, at least one instance of $R^{D1}$ is unsaturated heterocyclyl. In certain embodiments, at least one instance of $R^{D1}$ is heterocyclyl including one, two, or three double bonds in the heterocyclic ring. In certain embodiments, at least one instance of $R^{D1}$ is heterocyclyl, wherein one, two, or three atoms in the heterocyclic ring are independently selected from the group consisting of nitrogen, oxygen, and sulfur. In certain embodiments, at least one instance of $R^{D1}$ is 3- to 7-membered, monocyclic heterocyclyl. In certain embodiments, at least one instance of $R^{D1}$ is 5- to 13-membered, bicyclic heterocyclyl. In certain embodiments, at least one instance of $R^{D1}$ is substituted or unsubstituted aryl. In certain embodiments, at least one instance of $R^{D1}$ is 6- to 14-membered aryl. In certain embodiments, at least one instance of $R^{D1}$ is 6- to 10-membered aryl. In certain embodiments, at least one instance of $R^{D1}$ is monocyclic aryl. In certain embodiments, at least one instance of $R^{D1}$ is phenyl. In certain embodiments, at least one instance of $R^{D1}$ is bicyclic aryl. In certain embodiments, at least one instance of $R^{D1}$ is naphthyl. In certain embodiments, at least one instance of $R^{D1}$ is substituted or unsubstituted heteroaryl. In certain embodiments, at least one instance of $R^{D1}$ is heteroaryl, wherein one, two, three, or four atoms in the heteroaryl ring are independently selected from the group consisting of nitrogen, oxygen, and sulfur. In certain embodiments, at least one instance of $R^{D1}$ is monocyclic heteroaryl. In certain embodiments, at least one instance of $R^{D1}$ is 5-membered, monocyclic heteroaryl. In certain embodiments, at least one instance of $R^{D1}$ is 6-membered, monocyclic heteroaryl. In certain embodiments, at least one instance of $R^{D1}$ is pyridyl. In certain embodiments, at least one instance of $R^{D1}$ is bicyclic heteroaryl, wherein the point of attachment may be on any atom of the bicyclic heteroaryl ring system, as valency permits. In certain embodiments, at least one instance of $R^{D1}$ is 9-membered, bicyclic heteroaryl. In certain embodiments, at least one instance of $R^{D1}$ is 10-membered, bicyclic heteroaryl. In certain embodiments, at least one instance of $R^{D1}$ is a nitrogen protecting group when attached to a nitrogen atom. In certain embodiments, at least one instance of $R^{D1}$ is Bn, Boc, Cbz, Fmoc, trifluoroacetyl, triphenylmethyl, acetyl, or Ts when attached to a nitrogen atom. In certain embodiments, $R^{D1}$ is an oxygen protecting group when attached to an oxygen atom. In certain embodiments, $R^{D1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D1}$ is a sulfur protecting group when attached to a sulfur atom. In certain embodiments, $R^{D1}$ is acetamidomethyl, t-Bu, 3-nitro-2-pyridine sulfenyl, 2-pyridine-sulfenyl, or triphenylmethyl when attached to a sulfur atom.

In certain embodiments, two instances of $R^{D1}$ are joined to form a substituted or unsubstituted heterocyclic ring. In certain embodiments, two instances of $R^{D1}$ are joined to form a saturated or unsaturated heterocyclic ring. In certain embodiments, two instances of $R^{D1}$ are joined to form a heterocyclic ring including one, two, or three double bonds in the heterocyclic ring. In certain embodiments, two instances of $R^{D1}$ are joined to form a heterocyclic ring, wherein one, two, or three atoms in the heterocyclic ring are independently selected from the group consisting of nitrogen, oxygen, and sulfur. In certain embodiments, two instances of $R^{D1}$ are joined to form a 3- to 7-membered, monocyclic heterocyclic ring. In certain embodiments, two instances of $R^{D1}$ are joined to form a 5- to 13-membered, bicyclic heterocyclic ring system.

In certain embodiments, d is 0. In certain embodiments, d is 1. In certain embodiments, d is 2.

In certain embodiments, $R^D$ is halogen, substituted or unsubstituted alkyl, or $-OR^{D1}$; and d is 1. In certain embodiments, $R^D$ is halogen, unsubstituted alkyl, or $-O$-(unsubstituted alkyl); and d is 1. In certain embodiments, $R^D$ is halogen, unsubstituted $C_{1-6}$ alkyl, or $-O$-(unsubstituted $C_{1-6}$ alkyl); and d is 1. In certain embodiments, $R^D$ is halogen; and d is 1. In certain embodiments, $R^D$ is Cl; and d is 1. In certain embodiments, $R^D$ is $-OR^{D1}$; and d is 1. In certain embodiments, $R^D$ is $-OMe$; and d is 1.

In certain embodiments, the compound of Formula (I) is of the formula:

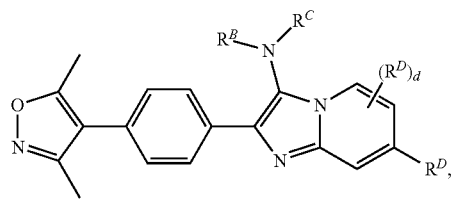

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

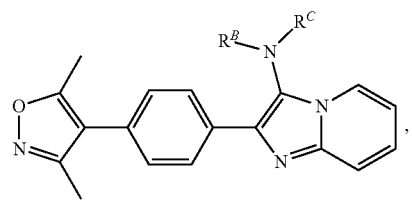

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

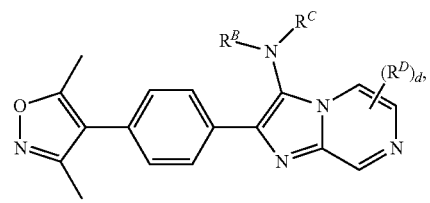

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

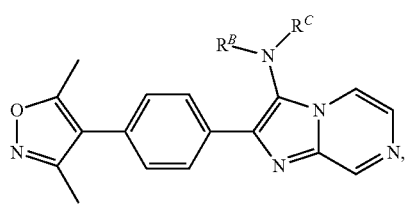

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

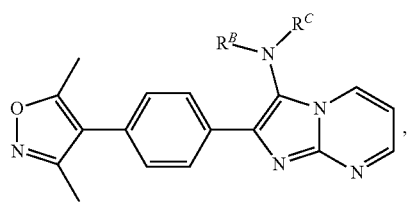

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

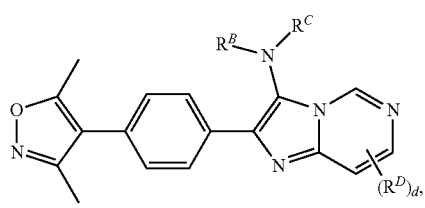

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

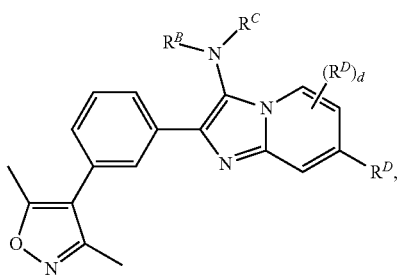

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

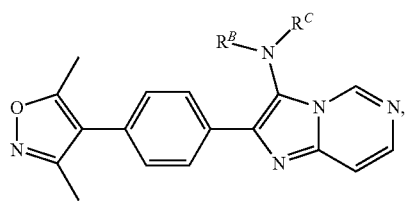

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

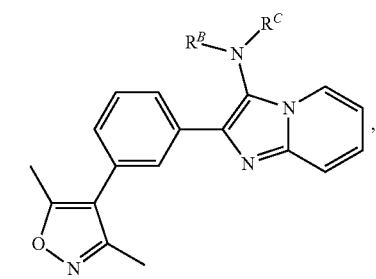

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

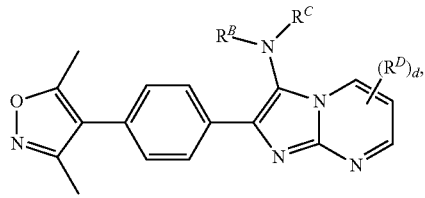

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

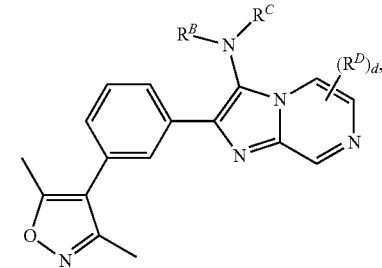

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

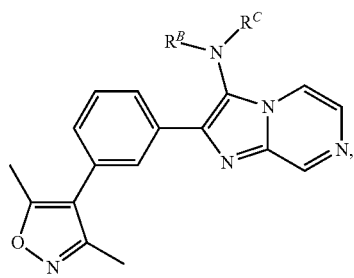

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

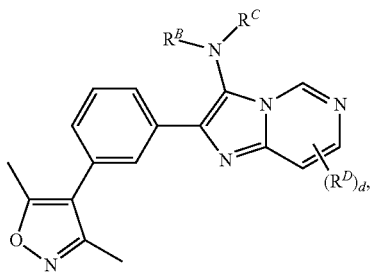

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

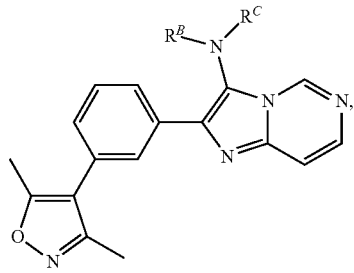

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

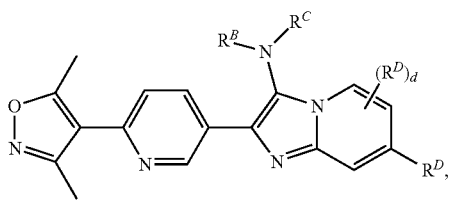

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

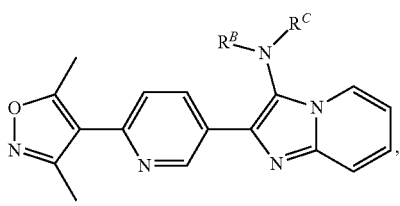

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

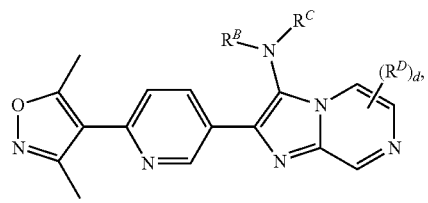

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

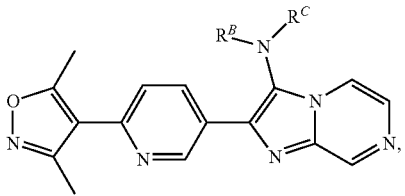

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

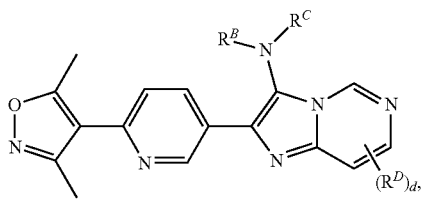

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

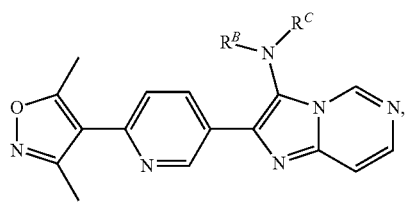

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

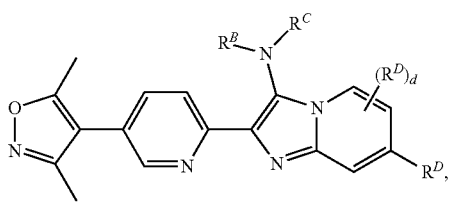

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

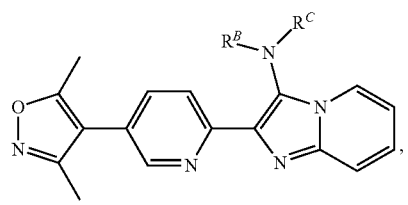

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

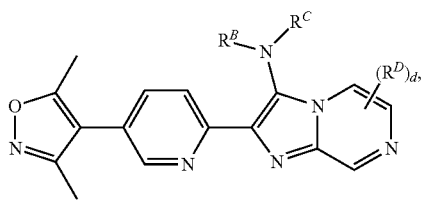

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

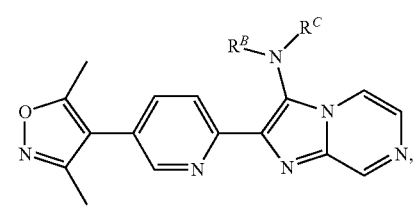

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

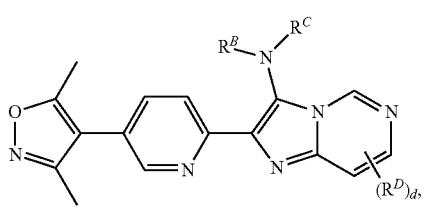

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

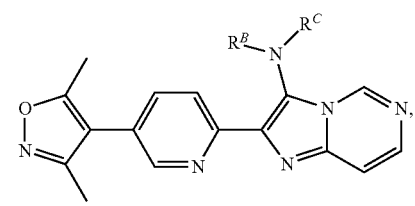

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

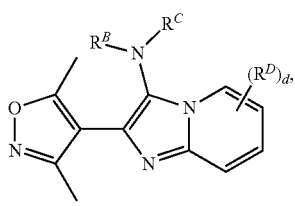

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

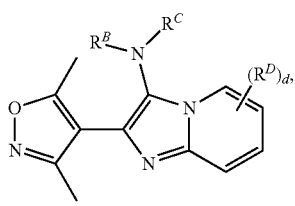

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

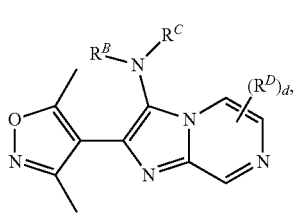

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

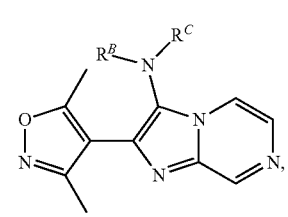

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

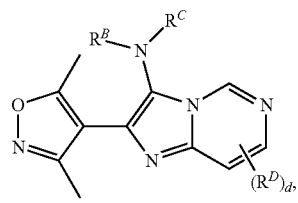

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

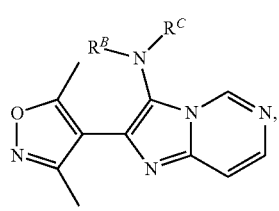

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

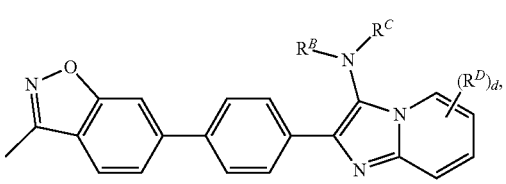

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

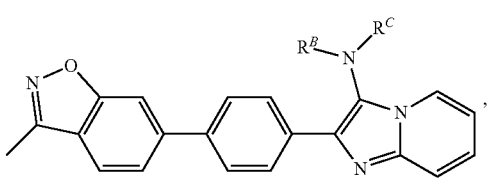

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

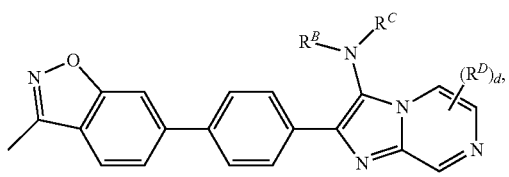

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

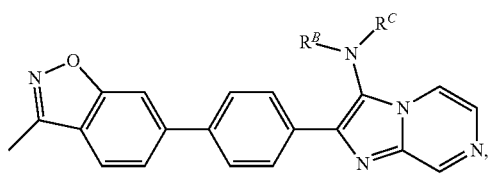

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

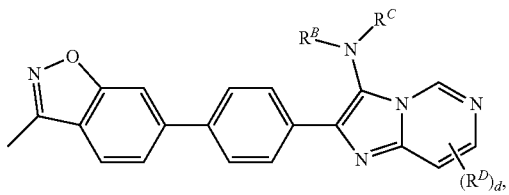

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

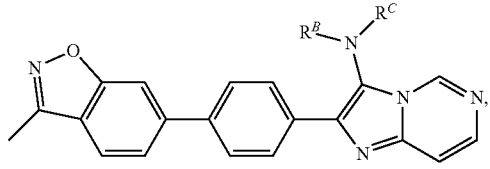

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

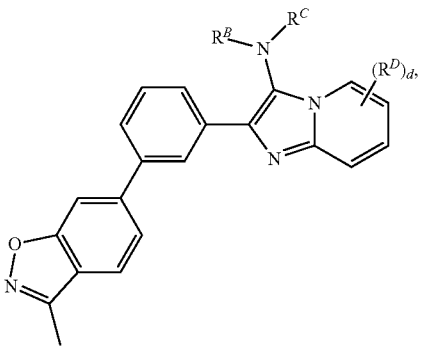

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

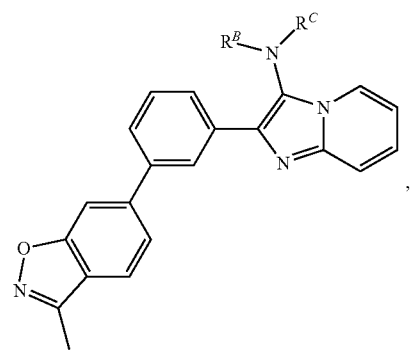

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

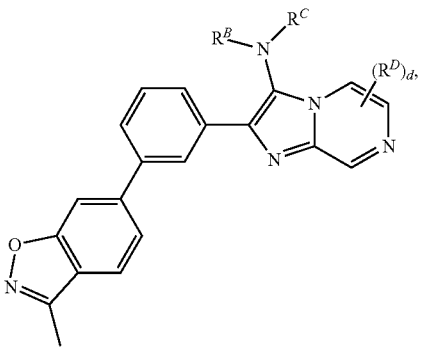

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

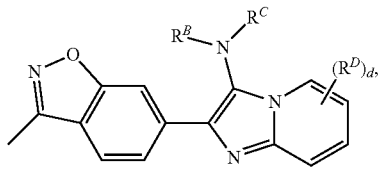

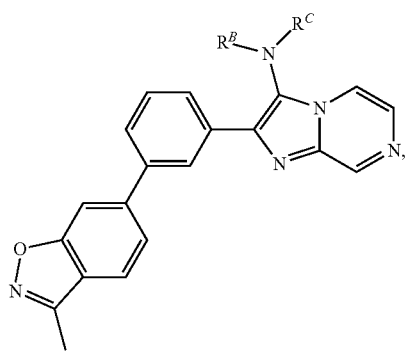

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

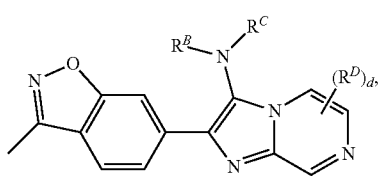

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

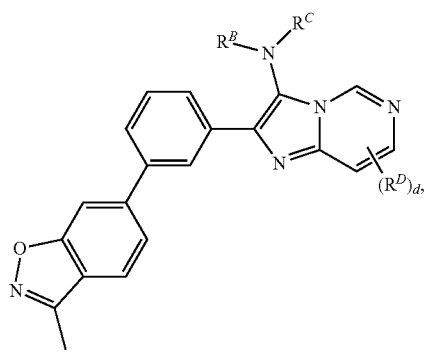

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

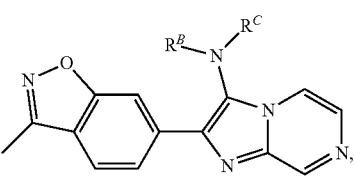

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

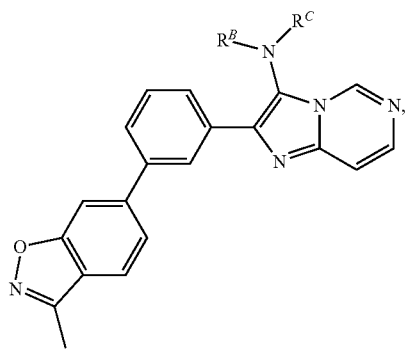

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

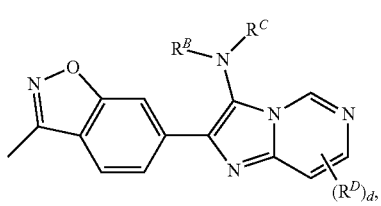

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

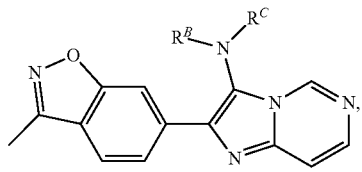

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

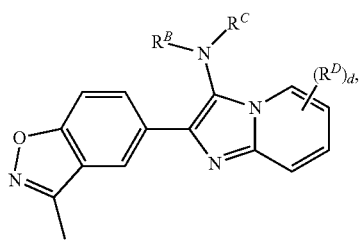

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

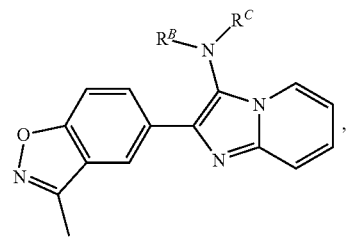

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

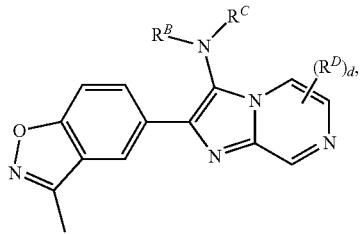

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

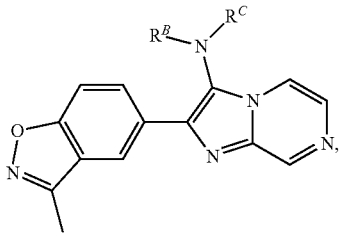

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

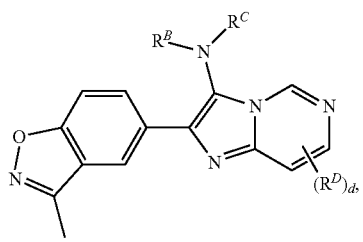

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

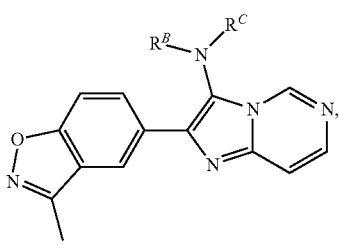

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

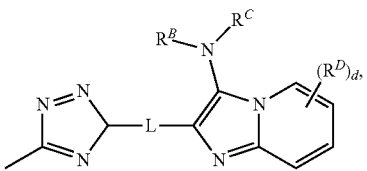

In certain embodiments, the compound of Formula (I) is of the formula:

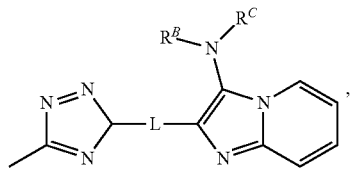

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

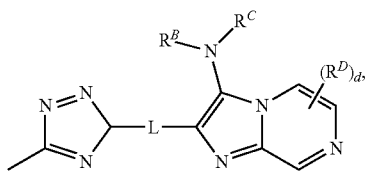

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

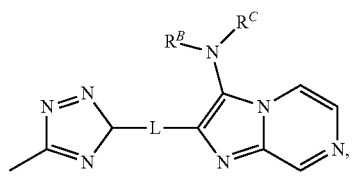

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

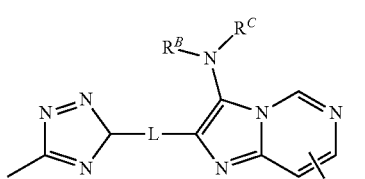

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

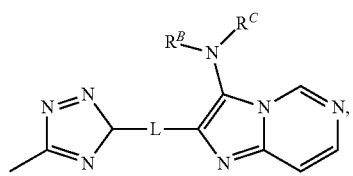

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

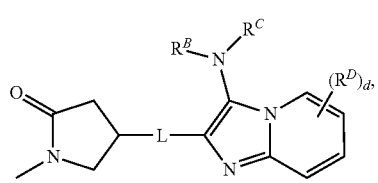

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

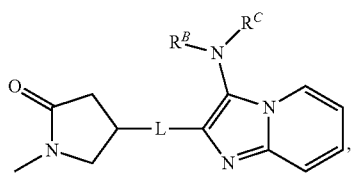

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

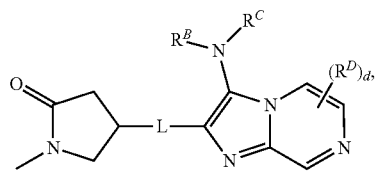

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

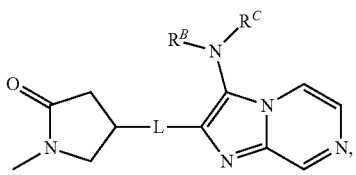

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

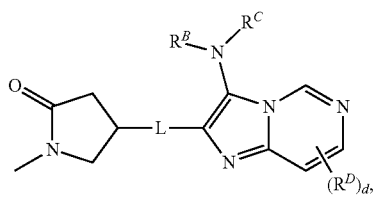

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

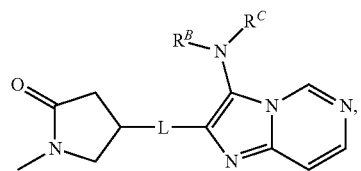

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

(UMB11)
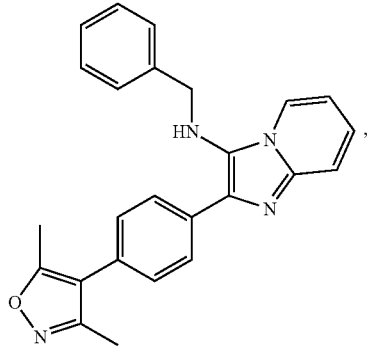

(UMB20)
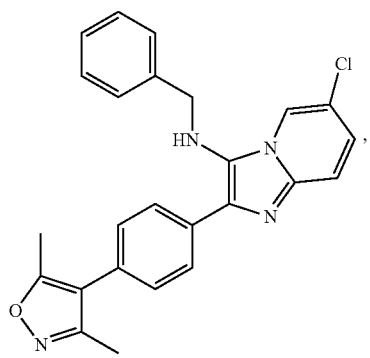

(UMB21)
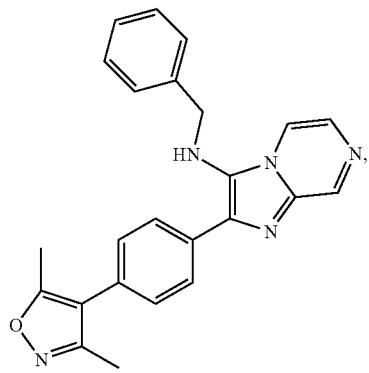

(UMB22)
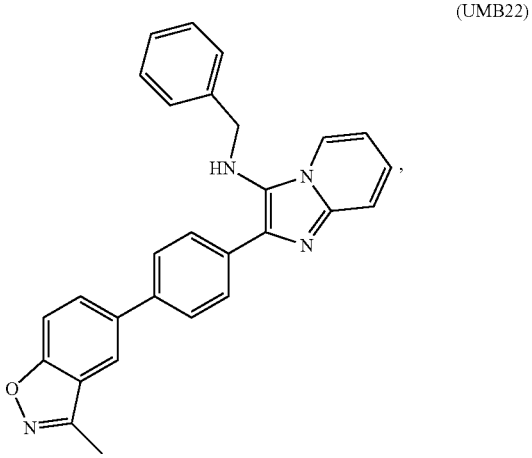

(UMB23)
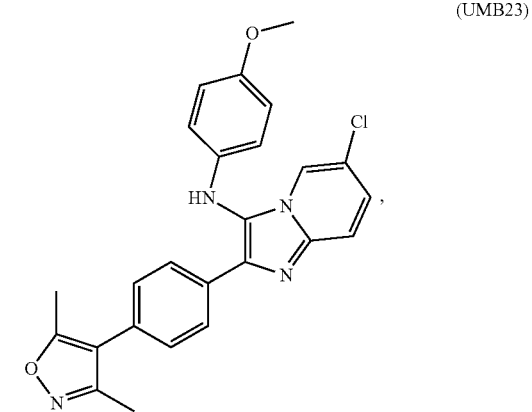

(UMB24)
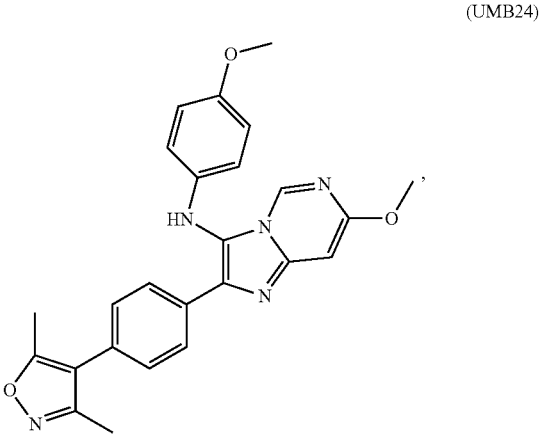

-continued
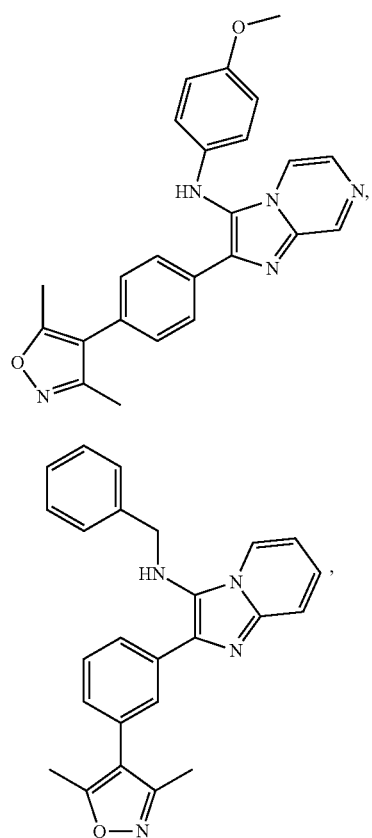
(UMB25)
(UMB26)
(UMB28)
(UMB29)
-continued
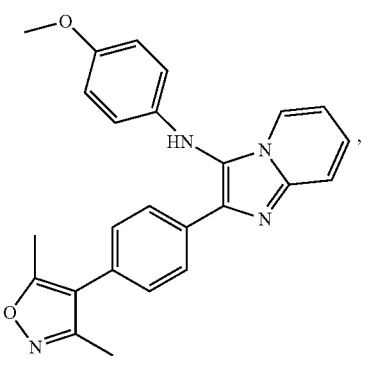
(UMB30)
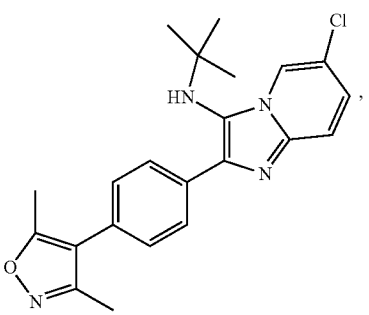
(UMB31)
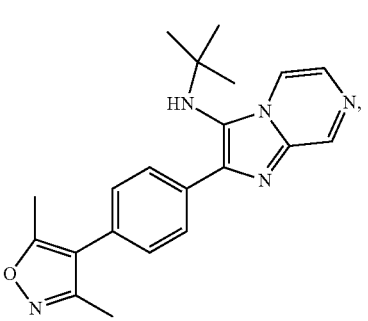
(UMB32)
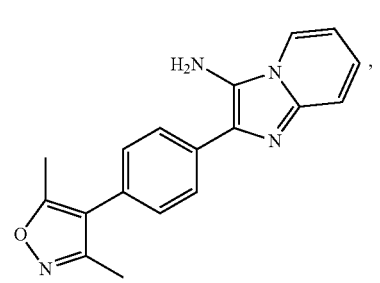
(12a)
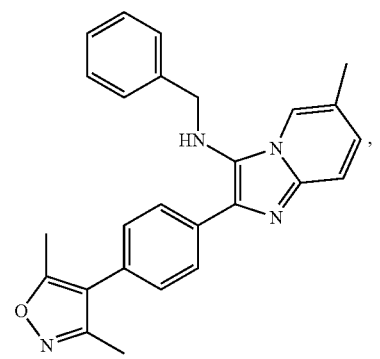
(13a)

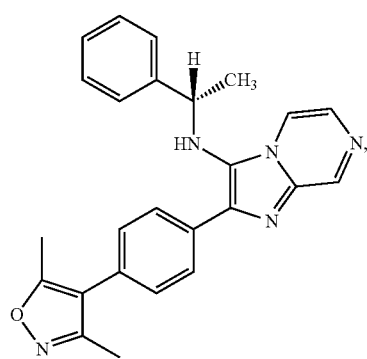
(21a)
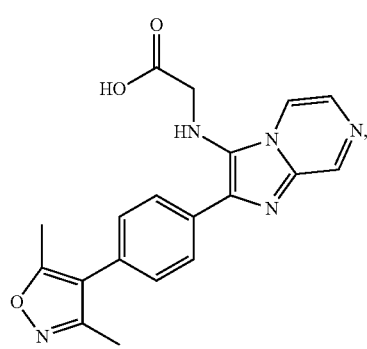
(22a)
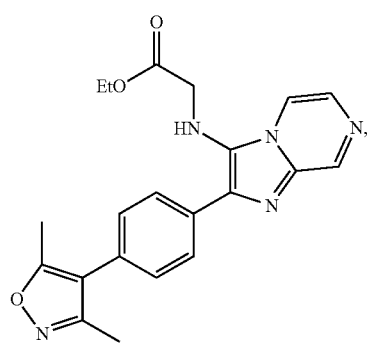
(23a)
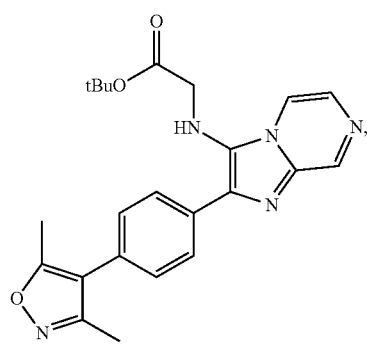
(24a)
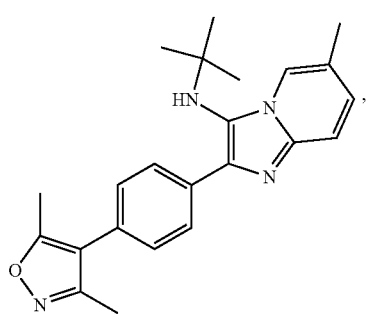
(27a)
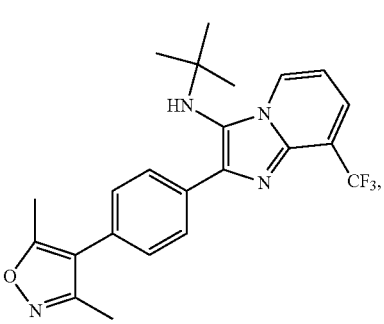
(28a)
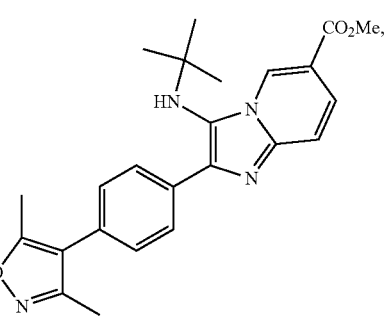
(29a)
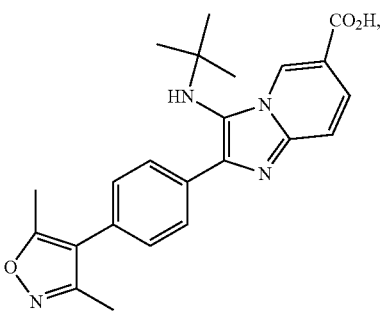
(30a)
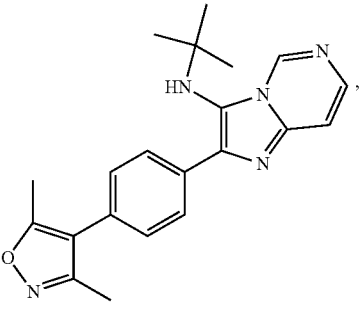
(UMB56)

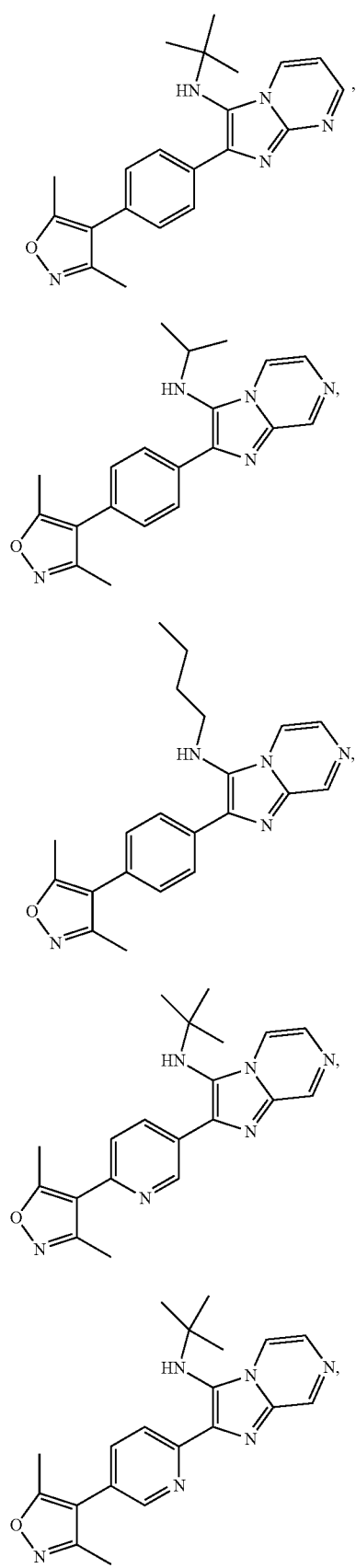
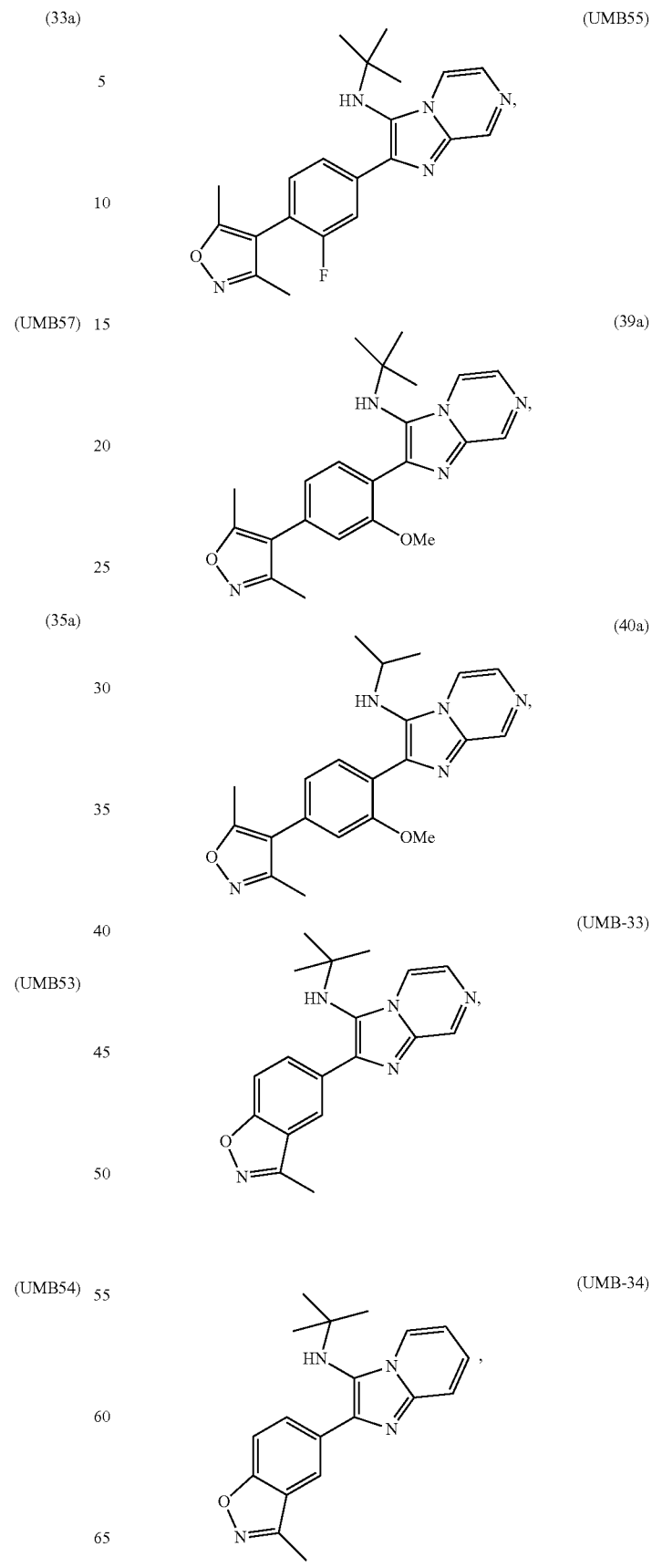

-continued

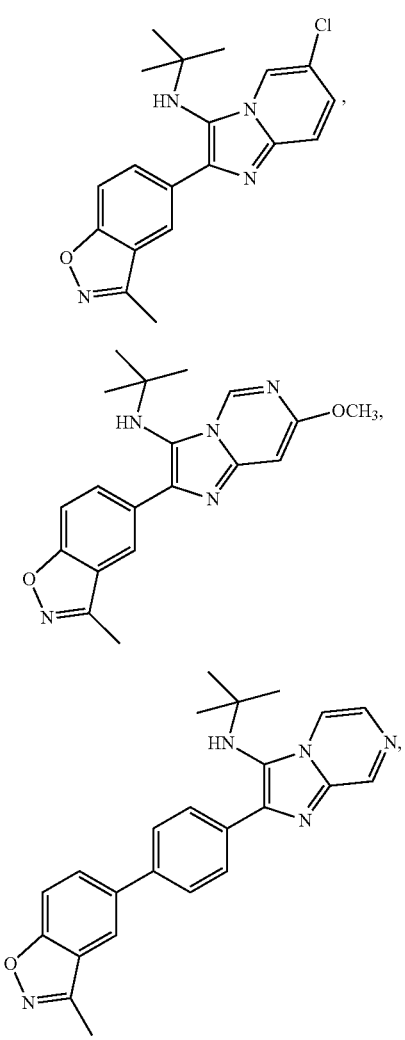

(UMB-35)

(UMB-36)

(UMB-42)

or a pharmaceutically acceptable salt, solvate, hydrate, polymorph, co-crystal, tautomer, stereoisomer, isotopically labeled derivative, or prodrug thereof.

The present invention also provides the compound of Formula (II):

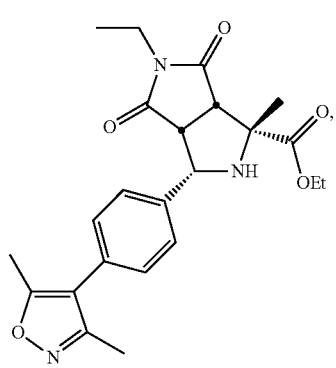

(II)

and pharmaceutically acceptable salts, solvates, hydrates, polymorphs, co-crystals, tautomers, stereoisomers, isotopically labeled derivatives, and prodrugs thereof. In certain embodiments, the present invention provides the compound of Formula (II), and pharmaceutically acceptable salts thereof.

The present invention also provides the compound of Formula (III):

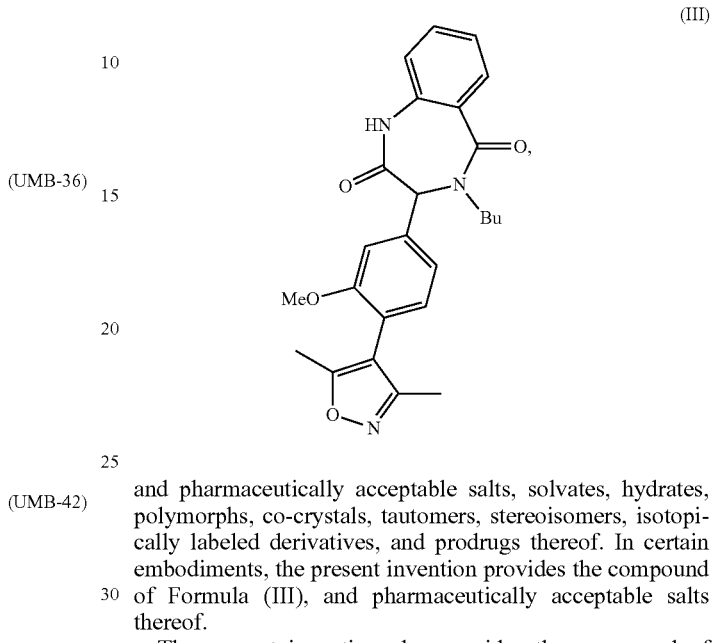

(III)

and pharmaceutically acceptable salts, solvates, hydrates, polymorphs, co-crystals, tautomers, stereoisomers, isotopically labeled derivatives, and prodrugs thereof. In certain embodiments, the present invention provides the compound of Formula (III), and pharmaceutically acceptable salts thereof.

The present invention also provides the compound of Formula (IV):

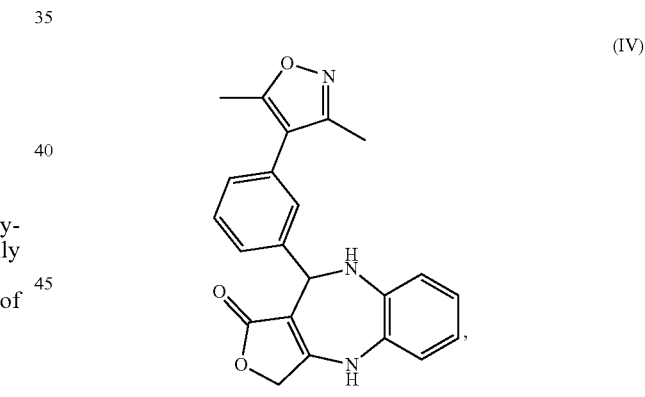

(IV)

and pharmaceutically acceptable salts, solvates, hydrates, polymorphs, co-crystals, tautomers, stereoisomers, isotopically labeled derivatives, and prodrugs thereof. In certain embodiments, the present invention provides the compound of Formula (IV), and pharmaceutically acceptable salts thereof.

In certain embodiments, compounds of the invention are compounds described herein, and pharmaceutically acceptable salts, solvates, hydrates, polymorphs, co-crystals, tautomers, stereoisomers, isotopically labeled derivatives, and prodrugs thereof. In certain embodiments, compounds of the invention are compounds described herein, and pharmaceutically acceptable salts thereof. In certain embodiments, compounds of the invention are compounds of any one of Formulae (I) to (IV), and pharmaceutically acceptable salts, solvates, hydrates, polymorphs, co-crystals, tautomers, stereoisomers, isotopically labeled derivatives, and prodrugs thereof. In certain embodiments, compounds of the invention are compounds of any one of Formulae (I) to (IV), and pharmaceutically acceptable salts thereof. In certain embodiments, compounds of the invention are compounds of Formula (I), and pharmaceutically acceptable salts, solvates, hydrates, polymorphs, co-crystals, tautomers, stereoisomers, isotopically labeled derivatives, and prodrugs thereof. In certain embodiments, compounds of the invention are compounds of Formula (I), and pharmaceutically acceptable salts thereof.

Compounds of the invention are inhibitors of bromodomain-containing proteins. In certain embodiments, the compounds of the invention bind to a bromodomain-containing protein. Without wishing to be bound by any particular theory, the compounds of the invention are thought to bind in a binding pocket of a bromodomain of a bromodomain-containing protein. In certain embodiments, the compounds of the invention bind to the binding pocket of the bromodomain by mimicking the contact between a histone acetyl-lysine residue and the binding pocket. In certain embodiments, the compounds of the invention bind to the apo binding pocket of the bromodomain. In certain embodiments, the compounds of the invention covalently bind to the bromodomain-containing protein. In certain embodiments, the compounds of the invention non-covalently bind to the bromodomain-containing protein. In certain embodiments, the compounds of the invention reversibly bind to the bromodomain-containing protein. In certain embodiments, the compounds of the invention non-reversibly bind to the bromodomain-containing protein. In certain embodiments, the compounds of the invention inhibit the activity of a bromodomain-containing protein. In certain embodiments, the compounds of the invention inhibit the activity of a bromodomain-containing protein because of the binding of the compound to the bromodomain-containing protein. In certain embodiments, the compounds of the invention inhibit the activity of a bromodomain-containing protein because of the binding of the compounds to a bromodomain of the bromodomain-containing protein. In certain embodiments, the inventive compounds specifically bind to a bromodomain-containing protein. In certain embodiments, the inventive compounds specifically bind to a bromodomain of a bromodomain-containing protein. In certain embodiments, the inventive compounds that specifically bind to a bromodomain-containing protein show a greater binding affinity to the bromodomain-containing protein than to one or more other proteins or one or more other bromodomain-containing proteins. In certain embodiments, the inventive compounds non-specifically bind to a bromodomain-containing protein. In certain embodiments, the inventive compounds non-specifically bind to a bromodomain of a bromodomain-containing protein. In certain embodiments, the compounds of the invention reduce transcriptional elongation. In certain embodiments, the compounds of the invention disrupt the subcellular localization of a bromodomain-containing protein. In certain embodiments, the compounds of the invention reduce chromatin binding. In certain embodiments, the compounds of the invention inhibit the binding of Histone H4 Kac peptide to a bromodomain of a bromodomain-containing protein. In certain embodiments, the compounds of the invention form one or more hydrogen bonds with an evolutionarily conserved asparagine in a bromodomain of a bromodomain-containing protein. In certain embodiments, the bromodomain-containing protein is BRD4 or BRD2; and the asparagine is Asn140 in BRD4(1) and Asn429 in BRD2(2). In certain embodiments, the compounds of the invention bind competitively with chromatin in a cellular environment. It is thus expected that the compounds of the invention may be useful in the treatment of a disease associated with the activity a bromodomain-containing protein (e.g., a proliferative disease).

The bromodomain-containing proteins that may be bound, and whose activity may be inhibited, by the inventive compounds include, but are not limited to, the bromodomain-containing proteins described herein. In certain embodiments, the bromodomain-containing protein is a bromo and extra terminal protein (BET). In certain embodiments, the bromodomain-containing protein is BRD2. In certain embodiments, the bromodomain-containing protein is BRD2(1). In certain embodiments, the bromodomain-containing protein is BRD2(2). In certain embodiments, the bromodomain-containing protein is BRD3. In certain embodiments, the bromodomain-containing protein is BRD3(1). In certain embodiments, the bromodomain-containing protein is BRD3(2). In certain embodiments, the bromodomain-containing protein is BRD4. In certain embodiments, the bromodomain-containing protein is BRD4(1). In certain embodiments, the bromodomain-containing protein is BRD4(2). In certain embodiments, the bromodomain-containing protein is BRDT. In certain embodiments, the bromodomain-containing protein is BRDT(1). In certain embodiments, the bromodomain-containing protein is BRDT(2). In certain embodiments, the bromodomain-containing protein is a TBP (TATA box binding protein)-associated factor protein (TAF). In certain embodiments, the bromodomain-containing protein is TAF1. In certain embodiments, the bromodomain-containing protein is TAF1L. In certain embodiments, the bromodomain-containing protein is CREB-binding protein (CBP). In certain embodiments, the bromodomain-containing protein is E1A binding protein p300 (EP300).

The binding affinity of a compound of the invention to a bromodomain-containing protein may be measured by the dissociation constant ($K_d$) value of an adduct of the compound of the invention and the bromodomain-containing protein using methods known in the art (e.g., isothermal titration calorimetry (ITC)). In certain embodiments, the adduct comprises the compound of the invention and the bromodomain-containing protein, which are bound (e.g., covalently or non-covalently) to each other. In certain embodiments, the $K_d$ value of the adduct is at most about 100 µM, at most about 30 µM, at most about 10 µM, at most about 3 µM, at most about 1 µM, at most about 300 nM, at most about 100 nM, at most about 30 nM, at most about 10 nM, at most about 3 nM, or at most about 1 nM. In certain embodiments, the $K_d$ value of the adduct is at least about 1 nM, at least about 10 nM, at least about 100 nM, at least about 1 µM, at least about 10 µM, or at least about 100 µM. Combinations of the above-referenced ranges (e.g., at most about 10 µM and at least about 1 nM) are also within the scope of the invention. Other ranges are also possible. In certain embodiments, the $K_d$ value of the adduct is at most about 10 µM. In certain embodiments, the $K_d$ value of the adduct is at most about 300 nM. In certain embodiments, the $K_d$ value of the adduct is at most about 100 nM.

In certain embodiments, the activity of the bromodomain-containing proteins described herein is inhibited by the inventive compounds. The inhibition of the activity of a bromodomain-containing protein by an inventive compound may be measured by the half maximal inhibitory concentration ($IC_{50}$) value of a compound of the invention when the inventive compound, or a pharmaceutical composition thereof, is contacted, directly or indirectly, with the bromodomain-containing protein. The $IC_{50}$ values may be obtained using methods known in the art, e.g., by competing the PEG-biotinylated JQ1 off from a BRD protein in an alpha assay. In certain embodiments, the $IC_{50}$ value of a compound of the invention is at most about 1 mM, at most about 300 μM, at most about 100 μM, at most about 30 μM, at most about 10 μM, at most about 3 μM, at most about 1 μM, at most about 300 nM, at most about 100 nM, at most about 30 nM, at most about 10 nM, at most about 3 nM, or at most about 1 nM. In certain embodiments, the $IC_{50}$ value of a compound of the invention is at least about 1 nM, at least about 3 nM, at least about 10 nM, at least about 30 nM, at least about 100 nM, at least about 300 nM, at least about 1 μM, at least about 3 μM, at least about 10 μM, at least about 30 μM, at least about 100 μM, at least about 300 μM, or at least 1 mM. Combinations of the above-referenced ranges (e.g., at most about 300 μM and at least about 1 μM) are also within the scope of the invention. Other ranges are also possible. In certain embodiments, the $IC_{50}$ value of a compound of the invention is at most about 300 μM. In certain embodiments, the $IC_{50}$ value of a compound of the invention is at most about 30 μM. In certain embodiments, the $IC_{50}$ value of a compound of the invention is at most about 10 μM.

The compounds of the invention may selectively inhibit the activity of a bromodomain-containing protein. In certain embodiments, the inventive compounds that selectively inhibit the activity of a bromodomain-containing protein show a greater inhibitory activity against the bromodomain-containing protein than against one or more other proteins or one or more other bromodomain-containing proteins.

The selectivity of an inventive compound for a bromodomain-containing protein over another protein (e.g., another bromodomain-containing protein) may be measured by the quotient of the $IC_{50}$ value of the inventive compound in inhibiting the activity of the another protein over the $IC_{50}$ value of the inventive compound in inhibiting the activity of the bromodomain-containing protein. The selectivity of an inventive compound for a bromodomain-containing protein over another protein (e.g., another bromodomain-containing protein) may also be measured by the quotient of the $K_d$ value of an adduct of the inventive compound and the another protein over the $K_d$ value of an adduct of the inventive compound and the bromodomain-containing protein. In certain embodiments, the selectivity is at least about 1-fold, at least about 2-fold, at least about 5-fold, at least about 10-fold, at least about 30-fold, at least about 100-fold, at least about 300-fold, at least about 1,000-fold, at least about 3,000-fold, at least about 10,000-fold, at least about 30,000-fold, or at least about 100,000-fold. In certain embodiments, the selectivity is at most about 100,000-fold, at most about 10,000-fold, at most about 1,000-fold, at most about 100-fold, at most about 10-fold, or at most about 1-fold. Combinations of the above-referenced ranges (e.g., and at least about 2-fold and at most about 10,000-fold) are also within the scope of the invention. Other ranges are also possible. In certain embodiments, the selectivity is at least about 2-fold. In certain embodiments, the selectivity is at least about 10-fold. In certain embodiments, the selectivity is at least about 100-fold. In certain embodiments, the compounds of the invention selectively inhibit a bromodomain-containing protein described herein. In certain embodiments, the compounds of the invention selectively inhibit a BET protein. In certain embodiments, the compounds of the invention selectively inhibit BRD2. In certain embodiments, the compounds of the invention selectively inhibit BRD3. In certain embodiments, the compounds of the invention selectively inhibit BRD4. In certain embodiments, the compounds of the invention selectively inhibit BRDT. In certain embodiments, the compounds of the invention selectively inhibit a TAF protein (e.g., TAF1 or TAF1L), CBP, and/or EP300. In certain embodiments, the compound of the inventions are non-selective inhibitors of two or more bromodomain-containing proteins.

It is known in the art that a bromodomain-containing protein is implicated in a wide range of diseases. For example, BRD3 and BRD4 are related to BRD3 NUT midline carcinoma and BRD4 NUT midline carcinoma, respectively, BRDT is related to sperm formation, and CBP is related to mixed-lineage leukemia (MLL). Therefore, the inventive compounds are expected to be useful in treating and/or preventing diseases associated with bromodomain-containing proteins or as a male contraceptive drug.

Pharmaceutical Compositions, Kits, and Administration

The present invention provides pharmaceutical compositions comprising a compound of the invention (e.g., a compound of any one of Formulae (I)-(IV), or a pharmaceutically acceptable salt, solvate, hydrate, polymorph, co-crystal, tautomer, stereoisomer, isotopically labeled derivative, or prodrug thereof), and optionally a pharmaceutically acceptable excipient. In certain embodiments, the pharmaceutical composition of the invention comprises a compound of Formula (I), or a pharmaceutically acceptable salt thereof, and optionally a pharmaceutically acceptable excipient. In certain embodiments, the pharmaceutical composition of the invention comprises a compound of Formula (I), or a pharmaceutically acceptable salt thereof, and a pharmaceutically acceptable excipient. In certain embodiments, the pharmaceutical composition of the invention comprises the compound of Formula (II), or a pharmaceutically acceptable salt thereof, and optionally a pharmaceutically acceptable excipient. In certain embodiments, the pharmaceutical composition of the invention comprises the compound of Formula (II), or a pharmaceutically acceptable salt thereof, and a pharmaceutically acceptable excipient. In certain embodiments, the pharmaceutical composition of the invention comprises the compound of Formula (III), or a pharmaceutically acceptable salt thereof, and optionally a pharmaceutically acceptable excipient. In certain embodiments, the pharmaceutical composition of the invention comprises the compound of Formula (III), or a pharmaceutically acceptable salt thereof, and a pharmaceutically acceptable excipient. In certain embodiments, the pharmaceutical composition of the invention comprises the compound of Formula (IV), or a pharmaceutically acceptable salt thereof, and optionally a pharmaceutically acceptable excipient. In certain embodiments, the pharmaceutical composition of the invention comprises the compound of Formula (IV), or a pharmaceutically acceptable salt thereof, and a pharmaceutically acceptable excipient.

In certain embodiments, the compound of the invention is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating and/or preventing a disease (e.g., a disease described herein). In certain embodiments, the effective amount is an amount effective for treating a disease. In certain embodiments, the effective amount is an amount effective for treating and/or preventing a disease associated with a bromodomain-containing protein. In certain embodiments, the effective amount is an amount effective for treating a disease associated with a bromodomain-containing protein. In certain embodiments, the effective amount is an amount effective for treating and/or preventing a proliferative disease (e.g., a proliferative disease described herein). In certain embodiments, the effective amount is an amount effective for treating a proliferative disease. In certain embodiments, the effective amount is an amount effective for treating and/or preventing cancer (e.g., a cancer described herein). In certain embodiments, the effective amount is an amount effective for treating cancer. In certain embodiments, the effective amount is an amount effective for treating and/or preventing lung cancer (e.g., small-cell lung cancer or non-small-cell lung cancer). In certain embodiments, the effective amount is an amount effective for treating lung cancer. In certain embodiments, the effective amount is an amount effective for treating and/or preventing a benign neoplasm (e.g., a benign neoplasm described herein). In certain embodiments, the effective amount is an amount effective for treating a benign neoplasm. In certain embodiments, the effective amount is an amount effective for treating and/or preventing a diseases or process associated with angiogenesis. In certain embodiments, the effective amount is an amount effective for treating a disease or process associated angiogenesis. In certain embodiments, the effective amount is an amount effective for treating and/or preventing an inflammatory disease (e.g., an inflammatory disease described herein). In certain embodiments, the effective amount is an amount effective for treating an inflammatory disease. In certain embodiments, the effective amount is an amount effective for treating and/or preventing an autoimmune disease (e.g., an autoimmune disease described herein). In certain embodiments, the effective amount is an amount effective for treating an autoimmune disease. In certain embodiments, the effective amount is an amount effective for treating and/or preventing diabetes (e.g., type 1 diabetes, type 2 diabetes, and gestational diabetes), obesity, fatty liver (NASH or otherwise), multiple myoloma, neuroblastoma, medullo, therosclerosis, arterial stent occlusion, heart failure, cachexia, graft versus host disease, an infection disease associated with a bromodomain-containing protein, an infection disease caused by a parasite, malaria, trypanosomes, an inflammatory disease, or male fertility.

An effective amount of a compound may vary from about 0.001 mg/kg to about 1000 mg/kg in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

An effective amount of a compound of the invention may be an amount effective for inhibiting the activity of a bromodomain-containing protein in a subject or cell. An effective amount of a compound of the invention may also be an amount effective for inhibiting the binding of a bromodomain of a bromodomain-containing protein to an acetyl-lysine residue of a histone in a subject or cell. An effective amount of a compound of the invention may further be an amount effective for modulating (e.g., down-regulating) the expression (e.g., transcription) of a gene that is regulated by a bromodomain-containing protein in a subject or cell. In certain embodiments, the effective amount is an amount effective for inhibiting the activity of a bromodomain-containing protein, the binding of a bromodomain of a bromodomain-containing protein to an acetyl-lysine residue of a histone, and/or the transcription of a gene that is regulated by a bromodomain-containing protein by at least about 10%, at least about 20%, at least about 30%, at least about 40%, at least about 50%, at least about 60%, at least about 70%, at least about 80%, or at least about 90%. In certain embodiments, the effective amount is an amount effective for inhibiting the activity of a bromodomain-containing protein, the binding of a bromodomain of a bromodomain-containing protein to an acetyl-lysine residue of a histone, and/or the transcription of a gene that is regulated by a bromodomain-containing protein by at most about 90%, at most about 80%, at most about 70%, at most about 60%, at most about 50%, at most about 40%, at most about 30%, at most about 20%, or at most about 10%. Combinations of the ranges described herein (e.g., at least about 20% and at most about 50%) are also within the scope of the invention. In certain embodiments, the activity of a bromodomain-containing protein, the binding of a bromodomain of a bromodomain-containing protein to an acetyl-lysine residue of a histone, and/or the transcription of a gene that is regulated by a bromodomain-containing protein are inhibited by a percentage or a range of percentage described herein by an effective amount of a compound of the invention.

In certain embodiments, the gene regulated by a bromodomain-containing protein is a gene regulated by a bromo and extra terminal protein (BET). In certain embodiments, the gene regulated by a bromodomain-containing protein is BRD2. In certain embodiments, the gene regulated by a bromodomain-containing protein is BRD2(1). In certain embodiments, the gene regulated by a bromodomain-containing protein is BRD2(2). In certain embodiments, the gene regulated by a bromodomain-containing protein is BRD3. In certain embodiments, the gene regulated by a bromodomain-containing protein is BRD3(1). In certain embodiments, the gene regulated by a bromodomain-containing protein is BRD3(2). In certain embodiments, the gene regulated by a bromodomain-containing protein is BRD4. In certain embodiments, the gene regulated by a bromodomain-containing protein is BRD4(1). In certain embodiments, the gene regulated by a bromodomain-containing protein is BRD4(2). In certain embodiments, the gene regulated by a bromodomain-containing protein is BRDT. In certain embodiments, the gene regulated by a bromodomain-containing protein is BRDT(1). In certain embodiments, the gene regulated by a bromodomain-containing protein is BRDT(2). In certain embodiments, the gene regulated by a bromodomain-containing protein is a gene regulated by a TBP (TATA box binding protein)-associated factor protein (TAF). In certain embodiments, the gene regulated by a bromodomain-containing protein is TAF1. In certain embodiments, the gene regulated by a bromodomain-containing protein is TAF1L. In certain embodiments, the gene regulated by a bromodomain-containing protein is a gene regulated by a CREB-binding protein (CBP). In certain embodiments, the gene regulated by a bromodomain-containing protein is a gene regulated by an E1A binding protein p300 (EP300).

Pharmaceutical compositions described herein can be prepared by any method known in the art of pharmacology. In general, such preparatory methods include the steps of bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound of this invention may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Alternatively or additionally, conventional syringes can be used in the classical mantoux method of intradermal administration. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition of the invention is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds described herein may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease associated with a bromodomain-containing protein in a subject in need thereof, in preventing a disease associated with a bromodomain-containing protein in a subject in need thereof, in reducing the risk to have a disease associated with a bromodomain-containing protein in a subject in need thereof, in inhibiting the activity of a bromodomain-containing protein in a subject or cell, in inhibiting the binding of a bromodomain of a bromodomain-containing protein to an acetyl-lysine residue of a histone in a subject or cell, in modulating the transcription of a gene that is regulated by a bromodomain-containing protein in a subject or cell), bioavailability, and/or safety, reduce drug resistance, reduce and/or modify their metabolism, inhibit their excretion, and/or modify their distribution within the body of a subject. It will also be appreciated that the therapy employed may achieve a desired effect for the same disorder, and/or it may achieve different effects. In certain embodiments, an inventive pharmaceutical composition including a compound of the invention and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease described herein. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agent(s) and/or the desired therapeutic and/or prophylactic effect to be achieved. In general, it is expected that the additional pharmaceutical agent(s) utilized in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, anti-diabetic agents, anti-allergic agents, and pain-relieving agents. In certain embodiments, the additional pharmaceutical agent is an inhibitor of a bromodomain-containing protein. In certain embodiments, the additional pharmaceutical agent is selected from the group consisting of (+)-JQ1, (−)-JQ1, I-BET, and PFI-1. See, e.g., international PCT patent application publication, WO 2011/143669. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine kinase inhibitors), modulators of protein stability (e.g., proteasome inhibitors), Hsp90 inhibitors, glucocorticoids, all-trans retinoic acids, and other agents that promote differentiation. In certain embodiments, the inventive compounds or pharmaceutical compositions can be administered in combination with an anti-cancer therapy including, but not limited to, surgery, radiation therapy, and chemotherapy.

Also encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the first container and the second container are combined to form one unit dosage form.

Thus, in one aspect, provided are kits including a first container comprising a compound described herein, or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the kits are useful for treating and/or preventing a disease described herein (e.g., a disease associated with bromodomain-containing proteins, such as a proliferative disease) in a subject in need thereof. In certain embodiments, the kits are useful for treating a disease described herein (e.g., a disease associated with bromodomain-containing proteins, such as a proliferative disease) in a subject in need thereof. In certain embodiments, the kits are useful for preventing a disease described herein (e.g., a disease associated with bromodomain-containing proteins, such as a proliferative disease) in a subject in need thereof. In certain embodiments, the kits are useful for reducing the risk of having a disease described herein (e.g., a disease associated with bromodomain-containing proteins, such as a proliferative disease) in a subject in need thereof. In certain embodiments, the kits are useful for inhibiting the activity of a bromodomain-containing protein in a subject or cell. In certain embodiments, the kits are useful for inhibiting the binding of a bromodomain of a bromodomain-containing protein to an acetyl-lysine residue of a histone in a subject or cell. In certain embodiments, the kits are useful for modulating (e.g., down-regulating) the transcription of a gene that is regulated by a bromodomain-containing protein in a subject or cell. In certain embodiments, the kits are useful for screening a library of compounds to identify a compound that is useful in the methods of the invention (e.g., useful for inhibiting the activity of a bromodomain-containing protein). In certain embodiments, the kits further include instructions for administering the compound or pharmaceutical composition of the invention. The kits may also include information as required by a regulatory agency such as the U.S. Food and Drug Administration (FDA). In certain embodiments, the information included in the kits is prescribing information. In certain embodiments, the kits and instructions provide for treating and/or preventing a disease described herein (e.g., a disease associated with bromodomain-containing proteins, such as a proliferative disease) in a subject in need thereof. In certain embodiments, the kits and instructions provide for treating a disease described herein (e.g., a disease associated with bromodomain-containing proteins, such as a proliferative disease) in a subject in need thereof. In certain embodiments, the kits and instructions provide for preventing a disease described herein (e.g., a disease associated with bromodomain-containing proteins, such as a proliferative disease) in a subject in need thereof. In certain embodiments, the kits and instructions provide for reducing the risk of having a disease described herein (e.g., a disease associated with bromodomain-containing proteins, such as a proliferative disease) in a subject in need thereof. In certain embodiments, the kits and instructions provide for inhibiting the activity of a bromodomain-containing protein in a subject or cell. In certain embodiments, the kits and instructions provide for inhibiting the binding of a bromodomain of a bromodomain-containing protein to an acetyl-lysine residue of a histone in a subject or cell. In certain embodiments, the kits and instructions provide for modulating (e.g., down-regulating) the transcription of a gene that is regulated by a bromodomain-containing protein in a subject or cell. In certain embodiments, the kits and instructions provide for screening a library of compounds to identify a compound that is useful in the methods of the invention (e.g., useful for inhibiting the activity of a bromodomain-containing protein). The kit of the invention may include one or more additional pharmaceutical agents described herein as a separate composition.

Methods of Treatment and Uses

The present invention provides methods that are useful for the treatment of a disease associated with a bromodomain-containing protein, such as a proliferative disease. The invention also provides methods of inhibiting the activity of a bromodomain-containing protein, methods of inhibiting the binding of a bromodomain of a bromodomain-containing protein to an acetyl-lysine residue of a histone, and methods of modulating the expression (e.g., transcription) of a gene that is regulated by a bromodomain-containing protein.

It has been reported that compound JQ1 is a cell-permeable, potent, small-molecule bromodomain inhibitor with biochemical selectivity for the BET family of bromodomain-containing proteins and that compounds related to JQ1 are capable of regulating bromodomain-containing proteins. See, e.g., international PCT patent application publication, WO 2011/143669. Lysine acetylation has emerged as a signaling modification of broad relevance to cellular and disease biology. Targeting the enzymes which reversibly mediate side-chain acetylation has been an active area of drug discovery for many years. To date, successful efforts have been limited to the "writers" (acetyl transferases) and "erasers" (histone deacetylases) of covalent modifications arising in the context of nuclear chromatin. Inhibitors of acetyl-lysine recognition modules, or bromodomains, are less studied. The recent characterization of a co-crystal structure of JQ1-BRD4 revealed excellent shape complementarity of JQ1 with the acetyl-lysine binding cavity of BRD4. Binding of JQ1 to the tandem bromodomains of BRD4 is acetyl-lysine competitive and displaces BRD4 from chromatin in human cells. Recurrent translocation of BRD4 has been observed in an incurable, genetically-defined subtype of human squamous cell carcinoma. Competitive binding of JQ1 to the BRD4 fusion oncoprotein has resulted in immediate squamous differentiation and specific anti-proliferative effects in patient-derived cell lines and in a murine model of BRD4-dependent carcinoma. Similar properties of compound I-BET, another bromodomain inhibitor, have also been reported (Nicodeme et al., Nature 2010, 468, 1119-1123). These data have established the feasibility of targeting protein-protein interactions of epigenetic "readers" and have suggested a versatile chemical scaffold for the development of chemical probes more broadly throughout the bromodomain protein family.

Gene regulation is fundamentally governed by reversible, non-covalent assembly of macromolecules. Signal transduction to RNA polymerase requires higher-ordered protein complexes, spatially regulated by assembly factors capable of interpreting the post-translational modification states of chromatin. Epigenetic readers are structurally diverse proteins, and each of the epigenetic readers possesses one or more evolutionarily conserved effector modules, which recognize covalent modifications of histone proteins or DNA. The $\epsilon$-N-acetylation of lysine residues (Kac) on histone tails is associated with an open chromatin architecture and transcriptional activation. Context-specific molecular recognition of acetyl-lysine is principally mediated by bromodomains.

Bromodomain-containing proteins are of substantial biological interest, as components of transcription factor complexes (e.g., TBP (TATA box binding protein)-associated factor 1 (TAF1), CREB-binding protein (CBP or CREBBP), P300/CBP-associated factor (PCAF), and Gcn5) and determinants of epigenetic memory. There are 41 human proteins containing a total of 57 diverse bromodomains. Despite large sequence variations, all bromodomains share a conserved fold comprising a left-handed bundle of four alpha helices ($\alpha_z$, $\alpha_A$, $\alpha_B$, and $\alpha_C$), linked by diverse loop regions (ZA and BC loops) that determine substrate specificity. Co-crystal structures with peptidic substrates showed that the acetyl-lysine is recognized by a central hydrophobic cavity and is anchored by a hydrogen bond with an asparagine residue present in most bromodomains. The bromo and extra-terminal (BET) family (e.g., BRD2, BRD3, BRD4 and BRDT) shares a common domain architecture comprising two N-terminal bromodomains that exhibit high level of sequence conservation, and a more divergent C-terminal recruitment domain.

Recent research has established a compelling rationale for targeting BRD4 in cancer. BRD4 functions to facilitate cell cycle progression and knock-down in cultured cancer cell lines prompts G1 arrest. BRD4 is an important mediator of transcriptional elongation, functioning to recruit the positive transcription elongation factor complex (P-TEFb). Cyclin dependent kinase-9, a core component of P-TEFb, is a validated target in chronic lymphocytic leukemia, and has recently been linked to c-Myc dependent transcription. Bromodomains present in BRD4 recruit P-TEFb to mitotic chromosomes resulting in increased expression of growth promoting genes. BRD4 remains bound to transcriptional start sites of genes expressed during M/G1 but has not been found present at start sites that are expressed later in the cell cycle. Knockdown of BRD4 in proliferating cells has been shown to lead to G1 arrest and apoptosis by decreasing expression levels of genes important for mitotic progression and survival.

Importantly, BRD4 has recently been identified as a component of a recurrent t(15;19) chromosomal translocation in an aggressive form of human squamous cell carcinoma. Such translocations express the tandem N-terminal bromodomains of BRD4 as an in-frame chimera with the nuclear protein in testis (NUT) protein, genetically defining the NUT midline carcinoma (NMC). Functional studies in patient-derived NMC cell lines have validated the essential role of the BRD4-NUT oncoprotein in maintaining the characteristic proliferation advantage and differentiation block of this malignancy. Notably, RNA silencing of BRD4-NUT gene expression arrests proliferation and prompts squamous differentiation with a marked increase in cytokeratin expression. A bromodomain may also down-regulates Myc and other transcripitional factors, such as interleukin 7 receptor (IL7R). These observations underscore the utility and therapeutic potential of an inhibitor of bromodomain-containing proteins.

In one aspect, the present invention provides methods of inhibiting the activity of a bromodomain-containing protein in a subject or cell. In certain embodiments, the bromodomain-containing protein is a bromodomain-containing protein described herein (e.g., a BET protein, such as BRD2, BRD3, BRD4, or BRDT). In certain embodiments, the activity of a bromodomain-containing protein in a subject or cell is inhibited by the inventive methods. In certain embodiments, the activity of a bromodomain-containing protein in a subject or cell is inhibited by the inventive methods by at least about 1%, at least about 3%, at least about 10%, at least about 20%, at least about 30%, at least about 40%, at least about 50%, at least about 60%, at least about 70%, at least about 80%, or at least about 90%. In certain embodiments, the activity of a bromodomain-containing protein in a subject or cell is inhibited by the inventive methods by at most about 90%, at most about 80%, at most about 70%, at most about 60%, at most about 50%, at most about 40%, at most about 30%, at most about 20%, at most about 10%, at most about 3%, or at most about 1%. Combinations of the above-referenced ranges (e.g., at least about 10% and at most about 50%) are also within the scope of the invention. Other ranges are also possible. In some embodiments, the activity of a bromodomain-containing protein in a subject or cell is selectively inhibited by the inventive methods. In other embodiments, the activity of a bromodomain-containing protein in a subject or cell is non-selectively inhibited by the inventive methods. In certain embodiments, the cytokine level and/or histamine release are reduced by the inventive methods.

In certain embodiments, the subject described herein is a human. In certain embodiments, the subject is a human diagnosed as having a disease associated with a bromodomain-containing protein. In certain embodiments, the subject is a human diagnosed as being at a higher-than-normal risk to have a disease associated with a bromodomain-containing protein. In certain embodiments, the subject is a human suspected of having a disease associated with a bromodomain-containing protein. In certain embodiments, the subject is an animal. The animal may be of either sex and may be at any stage of development. In certain embodiments, the subject is a fish. In certain embodiments, the subject is a mammal. In certain embodiments, the subject is a non-human mammal. In certain embodiments, the subject is a human or non-human mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

In certain embodiments, the cell is in vitro. In certain embodiments, the cell is ex vivo. In certain embodiments, the cell is in vivo.

In certain embodiments, the methods of the invention include administering to a subject in need thereof an effective amount of a compound or pharmaceutical composition of the invention. In certain embodiments, the methods of the invention include administering to a subject in need thereof a therapeutically effective amount of a compound or pharmaceutical composition of the invention. In certain embodiments, the methods of the invention include administering to a subject in need thereof an effective amount of a pharmaceutical composition of the invention. In certain embodiments, the methods of the invention include administering to a subject in need thereof a therapeutically effective amount of a pharmaceutical composition of the invention. In certain embodiments, the methods of the invention include contacting a cell with an effective amount of a compound or pharmaceutical composition of the invention. In certain embodiments, the methods of the invention include contacting a cell with an effective amount of a pharmaceutical composition of the invention.

In certain embodiments, the inventive methods are in vitro methods. In certain embodiments, the inventive methods are ex vivo methods. In certain embodiments, the inventive methods are in vivo methods.

Another aspect of the present invention relates to methods of inhibiting the binding of a bromodomain of a bromodomain-containing protein to an acetyl-lysine residue of a histone in a subject or cell. In certain embodiments, the histone is selected from the group consisting of H1, H2A, H2B, H3, H4, and H5. In certain embodiments, the binding of a bromodomain of the bromodomain-containing protein to an acetyl-lysine residue of the histone is inhibited by the inventive methods.

In another aspect, the present invention provides methods of modulating the transcription of a gene (e.g., a gene described herein) that is regulated by a bromodomain-containing protein in a subject or cell. In certain embodiments, the present invention provides methods of down-regulating the transcription of a gene that is regulated by a bromodomain-containing protein in a subject or cell. Without wishing to be bound by any particular theory, the inventive compounds and pharmaceutical compositions may be able to interfere with the binding of a bromodomain-containing protein to a transcriptional start site of the gene. In certain embodiments, the inventive compounds and pharmaceutical compositions interfere with the acetyl-lysine recognition during the transcription of the gene. In certain embodiments, the inventive compounds and pharmaceutical compositions interfere with the acetyl-lysine anchoring during the transcription of the gene. In certain embodiments, the transcription of a gene that is regulated by a bromodomain-containing protein in a subject or cell is modulated by the inventive methods. In certain embodiments, the transcription of a gene that is regulated by a bromodomain-containing protein in a subject or cell is down-regulated by the inventive methods. In certain embodiments, the gene that is regulated by a bromodomain-containing protein is an oncogene.

Another aspect of the present invention relates to methods of treating a disease associated with a bromodomain-containing protein in a subject in need thereof. In certain embodiments, the disease associated with a bromodomain-containing protein is treated by the inventive methods.

In certain embodiments, the disease associated with a bromodomain-containing protein is a disease associated with the activity of the bromodomain-containing protein. In certain embodiments, the disease associated with a bromodomain-containing protein is a disease associated with the function of a bromodomain of the bromodomain-containing protein. In certain embodiments, the disease associated with a bromodomain-containing protein is a disease associated with a bromodomain of the bromodomain-containing protein. In certain embodiments, the disease associated with a bromodomain-containing protein is driven by a transcriptional activator. In certain embodiments, the transcriptional activator is Myc. In certain embodiments, the disease associated with a bromodomain-containing protein is associated with a NUT rearrangement. In certain embodiments, the disease associated with a bromodomain-containing protein is a proliferative disease (e.g., a proliferative disease described herein). In certain embodiments, the disease associated with a bromodomain-containing protein is cancer (e.g., a cancer described herein). In certain embodiments, the disease associated with a bromodomain-containing protein is lung cancer, multiple myoloma, neuroblastoma, colon cancer, or ovary cancer. In certain embodiments, the disease associated with a bromodomain-containing protein is lung cancer (e.g., small-cell lung cancer or non-small-cell lung cancer). In certain embodiments, the disease associated with a bromodomain-containing protein is selected from the group consisting of Burkitt's lymphoma, breast cancer, colon cancer, neuroblastoma, glial blastoma multiforme, MLL-driven leukemia, chronic lymphocytic leukemia, NUT midline carcinoma, and squamous cell carcinoma. In certain embodiments, the disease associated with a bromodomain-containing protein is a benign neoplasm (e.g., a benign neoplasm described herein). In certain embodiments, the disease associated with a bromodomain-containing protein is an inflammatory disease (e.g., an inflammatory disease described herein). In certain embodiments, the disease associated with a bromodomain-containing protein is a disease that involves an inflammatory response to an infection with a bacterium, virus, fungus, parasite, and/or protozoon. In certain embodiments, the disease associated with a bromodomain-containing protein is selected from the group consisting of osteoarthritis, acute gout, multiple sclerosis, an inflammatory bowel disease (e.g., Crohn's disease and ulcerative colitis), neuroinflammation, asthma, a chronic obstructive airways disease, pneumonitis, myocarditis, pericarditis, myositis, eczema, dermatitis, acne, cellulitis, an occlusive disease, a cardiac valvular disease, stenosis, restenosis, in-stent-stenosis, a coronary arterial disease, congestive heart failure, angina pectoris, myocardial ischemia, thrombosis, alopecia, nephritis, vasculitis, atherosclerosis, retinitis, uveitis, scleritis, sclerosing cholangitis, hypophysitis, thyroiditis, sepsis, sepsis syndrome, septic shock, systemic inflammatory response syndrome (SIRS), toxic shock syndrome, acute lung injury, ARDS (adult respiratory distress syndrome), acute renal failure, hepatitis (e.g., fulminant hepatitis), burns, pancreatitis (e.g., acute pancreatitis), post-surgical syndromes, sarcoidosis, Herxheimer reactions, encephalitis, myelitis, meningitis, malaria, and SIRS associated with viral infections (such as influenza, herpes zoster, herpes simplex, and coronavirus). In certain embodiments, the disease associated with a bromodomain-containing protein is acute or chronic pancreatitis. In certain embodiments, the disease associated with a bromodomain-containing protein is burns. In certain embodiments, the disease associated with a bromodomain-containing protein is an inflammatory bowel disease. In certain embodiments, the disease associated with a bromodomain-containing protein is neuroinflammation. In certain embodiments, the disease associated with a bromodomain-containing protein is an autoimmune disease (e.g., an autoimmune disease described herein). In certain embodiments, the disease associated with a bromodomain-containing protein is rheumatoid arthritis. In certain embodiments, the disease associated with a bromodomain-containing protein is selected from the group consisting of psoriasis, systemic lupus erythematosus, vitiligo, a bullous skin disease, hepatic cirrhosis, biliary cirrhosis, Addison's disease, acute rejection of transplanted organs, endotoxemia, and multi-organ dysfunction syndrome. In certain embodiments, the disease associated with a bromodomain-containing protein is a disease associated with ischemia-reperfusion injury. In certain embodiments, the disease associated with a bromodomain-containing protein is selected from the group consisting of myocardial infarction, cerebrovascular ischemia (stroke), acute coronary syndromes, renal reperfusion injury, organ transplantation, coronary artery bypass grafting, a cardio-pulmonary bypass procedure, or pulmonary, renal, hepatic, gastro-intestinal, or peripheral limb embolism. In certain embodiments, the disease associated with a bromodomain-containing protein is a disorder of lipid metabolism via the regulation of apolipoprotein A1 (APOA1). In certain embodiments, the disease associated with a bromodomain-containing protein is selected from the group consisting of hypercholesterolemia, atherosclerosis, and Alzheimer's disease. In certain embodiments, the disease associated with a bromodomain-containing protein is a viral infection. In certain embodiments, the disease associated with a bromodomain-containing protein is selected from the group consisting of infectious diseases caused by herpes virus, human papilloma virus, adenovirus, and/or poxvirus. In certain embodiments, the disease associated with a bromodomain-containing protein is a fibrotic condition. In certain embodiments, the disease associated with a bromodomain-containing protein is selected from the group consisting of idiopathic pulmonary fibrosis, renal fibrosis, post-operative stricture, keloid formation, scleroderma, and cardiac fibrosis. In certain embodiments, the disease associated with a bromodomain-containing protein is selected from the group consisting of diabetes (e.g., type 1 diabetes, type 2 diabetes, and gestational diabetes), obesity, fatty liver (NASH or otherwise), therosclerosis, arterial stent occlusion, heart failure, cachexia, graft versus host disease, an infection disease associated with a bromodomain-containing protein, an infection disease caused by a parasite, malaria, trypanosomes, an inflammatory disease, and male fertility. In certain embodiments, the disease associated with a bromodomain-containing protein is a disease associated with aberrant Myc function. In certain embodiments, the disease associated with a bromodomain-containing protein is a disease associated with interleukin 7 receptor (IL7R).

In yet another aspect, the present invention provides methods of reducing the risk to have a disease associated with a bromodomain-containing protein in a subject in need thereof. In certain embodiments, the risk to have the disease associated with a bromodomain-containing protein is reduced by the inventive methods.

Another aspect of the invention relates to methods of inhibiting the interaction between a bromodomain-containing protein and an immunoglobulin (Ig) regulatory element in a subject or cell.

Another aspect of the invention relates to methods of screening a library of compounds, and pharmaceutical acceptable salts thereof, to identify a compound, or a pharmaceutical acceptable salt thereof, that is useful in the methods of the invention. In certain embodiments, the compound identified is useful for treating and/or preventing a disease associated with a bromodomain-containing protein in a subject in need thereof. In certain embodiments, the compound identified is useful for treating a disease associated with a bromodomain-containing protein in a subject in need thereof. In certain embodiments, the compound identified is useful for treating a proliferative disease in a subject in need thereof. In certain embodiments, the compound identified is useful for treating cancer in a subject in need thereof. In certain embodiments, the compound identified is useful for treating a benign neoplasm in a subject in need thereof. In certain embodiments, the compound identified is useful for treating pathological angiogenesis in a subject in need thereof. In certain embodiments, the compound identified is useful for treating an inflammatory disease in a subject in need thereof. In certain embodiments, the compound identified is useful for treating an autoimmune disease in a subject in need thereof. In certain embodiments, the compound identified is useful for reducing the risk to have a disease associated with a bromodomain-containing protein in a subject in need thereof. In certain embodiments, the compound identified is useful for inhibiting the activity of a bromodomain-containing protein in a subject or cell. In certain embodiments, the compound identified is useful for inhibiting the binding of a bromodomain of a bromodomain-containing protein to an acetyl-lysine residue of a histone in a subject or cell. In certain embodiments, the compound identified is useful for modulating the transcription of a gene that is regulated by a bromodomain-containing protein in a subject or cell. In certain embodiments, the library of compounds is a library of the compounds of the invention. In certain embodiments, the methods of screening a library include obtaining at least two different compounds of the invention; and performing at least one assay using the different compounds of the invention. In certain embodiments, at least one assay is useful in identifying a compound that is useful in the inventive methods.

Typically, the methods of screening a library of compounds involve at least one assay. In certain embodiments, the assay is performed to detect one or more characteristics associated with the treatment and/or prevention of a disease described herein, with the inhibition of the activity of a bromodomain-containing protein, with the inhibition of the binding of a bromodomain of a bromodomain-containing protein to an acetyl-lysine residue of a histone, and/or with the modulation the transcription of a gene that is regulated by a bromodomain-containing protein. The characteristics may be desired characteristics (e.g., a disease having been treated, a disease having been prevented, the risk to have a disease having been reduced, the activity of a bromodomain-containing protein having been inhibited, the binding of a bromodomain of a bromodomain-containing protein to an acetyl-lysine residue of a histone having been inhibited, or the transcription of a gene that is regulated by a bromodomain-containing protein having been modulated). The characteristics may be undesired characteristics (e.g., a disease not having been treated, a disease not having been prevented, the risk to have a disease not having been reduced, the activity of a bromodomain-containing protein not having been inhibited, the binding of a bromodomain of a bromodomain-containing protein to an acetyl-lysine residue of a histone not having been inhibited, or the transcription of a gene that is regulated by a bromodomain-containing protein not having been modulated). The assay may be an immunoassay, such as a sandwich-type assay, competitive binding assay, one-step direct test, two-step test, or blot assay. The step of performing at least one assay may be performed robotically or manually. In certain embodiments, the assay comprises (a) contacting a library of compounds with a bromodomain-containing protein; and (b) detecting the binding of the library of compounds to the bromodomain-containing protein. In certain embodiments, the assay comprises detecting the specific binding of the library of compounds to the bromodomain-containing protein. In certain embodiments, the assay comprises detecting the specific binding of the library of compounds to a bromodomain of the bromodomain-containing protein. In certain embodiments, the detected binding of the library of compounds to the bromodomain-containing protein is useful in identifying the compound that is useful in the methods of the invention. In certain embodiments, the step of detecting the binding comprises using differential scanning fluorimetry (DSF), isothermal titration calorimetry (ITC), and/or an amplified luminescence proximity homogeneous assay (ALPHA). The step of performing at least one assay may be performed in a cell (e.g., a cancer cell) in vitro, ex vivo, or in vivo. In certain embodiments, the step of performing at least one assay is performed in a cell (e.g., a cancer cell) in vitro. In certain embodiments, the assay comprises (a) contacting a library of compounds with a cell; and (b) detecting a decrease in cell proliferation, an increase in cell death, and/or an increase in cell differentiation. In certain embodiments, the cell death is apoptotic cell death. In certain embodiments, the cell differentiation is identified by detecting an increase in cytokeratin expression. In certain embodiments, the step of performing at least one assay further comprises detecting a reduction in transcriptional elongation.

In another aspect, the present invention provides uses of the inventive compounds and pharmaceutical compositions in treating and/or preventing a disease described herein in a subject in need thereof. In certain embodiments, the invention provides uses of the inventive compounds and pharmaceutical compositions in treating a disease described herein in a subject in need thereof.

Another aspect of the present invention relates to uses of the inventive compounds and pharmaceutical compositions in reducing the risk to have a disease described herein in a subject in need thereof.

In yet another aspect, the present invention provides uses of the inventive compounds and pharmaceutical compositions in inhibiting the activity of a bromodomain-containing protein in a subject or cell.

Another aspect of the present invention relates to uses of the inventive compounds and pharmaceutical compositions in inhibiting the binding of a bromodomain of a bromodomain-containing protein to an acetyl-lysine residue of a histone in a subject or cell.

In still another aspect, the present invention provides uses of the inventive compounds and pharmaceutical compositions in modulating the transcription of a gene that is regulated by a bromodomain-containing protein in a subject or cell.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Example 1

Preparation of Compounds

Compounds of Formula (I) (e.g., compounds of Formula (I-A)), and pharmaceutically acceptable salts, solvates, hydrates, polymorphs, co-crystals, tautomers, stereoisomers, isotopically labeled derivatives, and prodrugs thereof, may be prepared by methods similar to the one reported in Lu et al., *QSAR Comb. Sci.* 2004, 23, 827-835, such as the synthetic sequence outlined below in Scheme 1, wherein $X^A$, $X^B$, Ring A, $R^B$, $R^D$, $R^F$, d, and f are as defined herein. The compounds of Formula (I) (e.g., compounds of Formula (I-B)), and pharmaceutically acceptable salts, solvates, hydrates, polymorphs, co-crystals, tautomers, stereoisomers, isotopically labeled derivatives, and prodrugs thereof, may also be synthesized according to the method shown in Scheme 2. Alternatively, compounds of Formula (I), and pharmaceutically acceptable salts, solvates, hydrates, polymorphs, co-crystals, tautomers, stereoisomers, isotopically labeled derivatives, and prodrugs thereof, may be prepared by other methods described herein or known in the art.

Scheme 1. Exemplary synthesis of compounds of Formula (I).

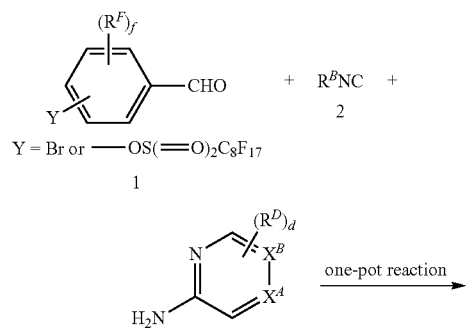

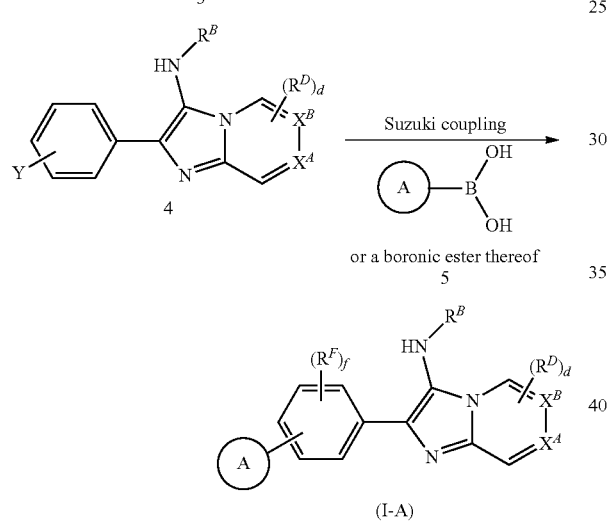

Scheme 2. Exemplary synthesis of compounds of Formula (I).

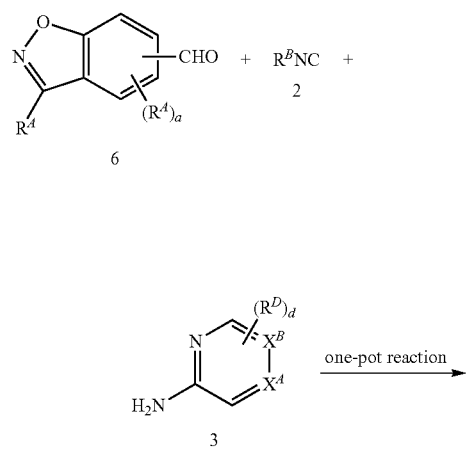

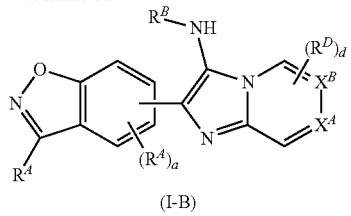

The compound of Formula (II), or a pharmaceutically acceptable salt, solvate, hydrate, polymorph, co-crystal, tautomer, stereoisomer, isotopically labeled derivative, or prodrug thereof, may be prepared by methods similar to the one reported in Zhang et al., *Tetrahedron Lett.* 2005, 46, 1807-1810, such as the synthetic sequence outlined below in Scheme 3. Alternatively, the compound of Formula (II), or a pharmaceutically acceptable salt, solvate, hydrate, polymorph, co-crystal, tautomer, stereoisomer, isotopically labeled derivative, or prodrug thereof, may be prepared by other methods described herein or known in the art.

Scheme 3. Exemplary synthesis of compounds of Formula (II).

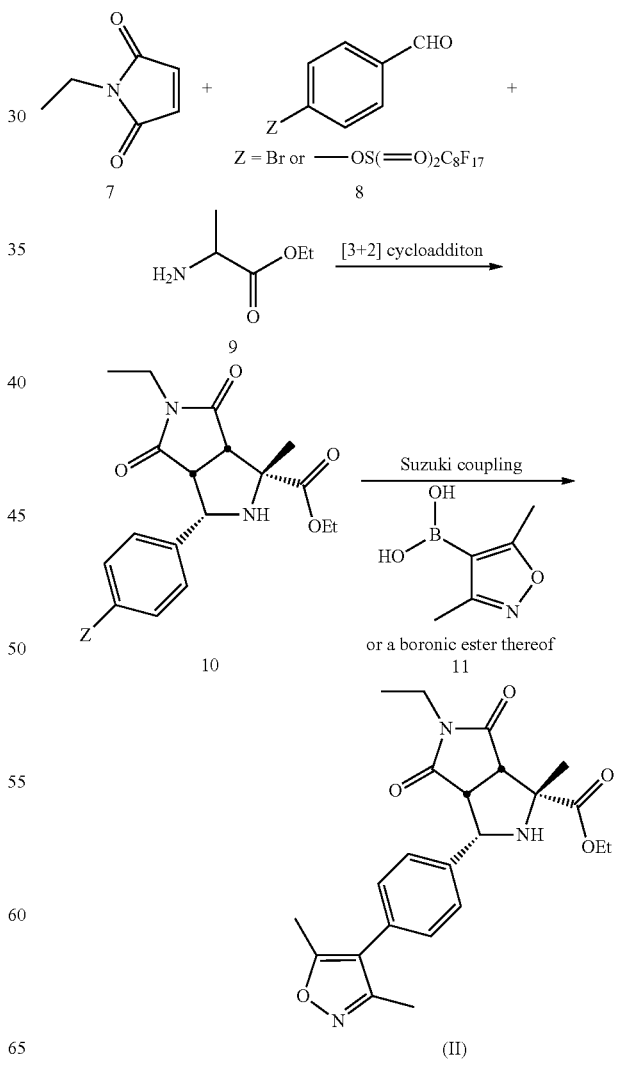

Isoxazole probe compounds were prepared using Suzuki-type coupling reactions followed by purification of reaction intermediates using fluorous-solid phase extraction (F-SPE). In this case, aryl perfluorooctylsulfonates (ArOSO$_2$(CF$_2$)$_7$CF$_3$) were reacted with 3,5-dimethylisoxazole-4-boronic acid pinacol esters to produce a low-molecular weight chemical series. The resulting compounds were purified using F-SPE. Initial compounds included positional isomers of carbonyl functionalities around the phenyl ring system.

Scheme 4. Exemplary synthesis of isoxazole probe compounds.

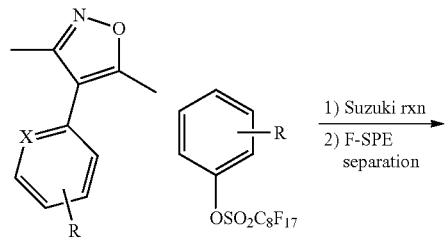

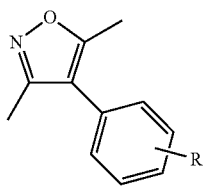

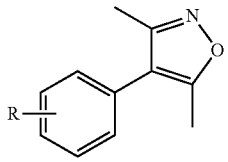

1a

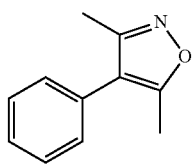

2a

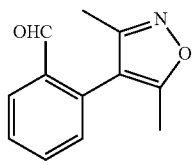

3a

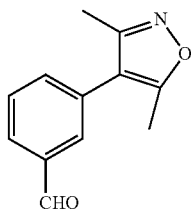

4a

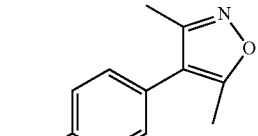

5a

General Methods

All chemical reagents (including solvents) were purchased from commercial suppliers and used as received. $^1$H NMR (300 MHz) and $^{13}$C NMR (75 MHz) spectra were recorded on a Varian NMR spectrometer. LC-MS were performed on an Agilent 2100 system with a C$_{18}$ LC column (5.0 µm, 6.0×50 mm). The mobile phase was a mixture of MeOH (containing 0.05% trifluoroacetic acid) and water (containing 0.05% trifluoroacetic acid). A linear gradient was started from 75:25 MeOH—H$_2$O to 100% MeOH in 5.0 min at a flow rate of 0.7 mL/min. The chromatograms were recorded at UV 210 nm, 254 nm, and 365 nm. Low resolution mass spectra (LRMS) were recorded in APCI (atmospheric pressure chemical ionization). Flash chromatography separations were performed on a YAMAZEN AI-580 system with Agela silica gel (12 g or 20 g, 230-400 µm) cartridges. The microwave reactions were performed on a Biotage Initiator 8 system.

Procedures for the Synthesis of Compounds 1a-5a.

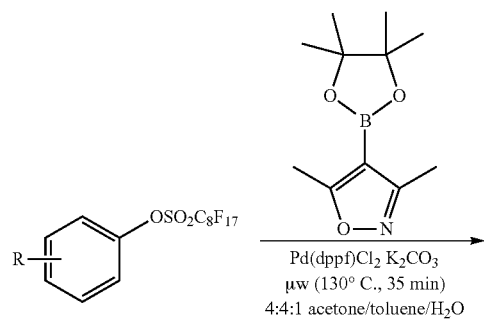

These compounds were prepared by direct Suzuki coupling of fluorous arylsulfonates with the boronic ester. The Suzuki coupling reactions were carried out following the general procedure as shown.

3,5-Dimethyl-4-phenylisoxazole (1a). Yellow oily compound, 58% yield, $^1$H NMR (300 MHz, CDCl$_3$) δ 7.15-7.62 (m, 5H), 2.41 (s, 3H), 2.25 (s, 3H); MS(APCI) m/z 174.1 (M$^+$+1).

2-(3,5-Dimethylisoxazol-4-yl)benzaldehydes (2a). Yellow oily compound, 17% yield, $^1$H NMR (300 MHz, CDCl$_3$) δ 9.92 (s, 1H), 8.06 (d, J=7.2 Hz, 1H), 7.69 (m, 1H), 7.54 (m, 2H), 2.28 (s, 3H), 2.16 (s, 3H); MS(APCI) m/z 202.1 (M$^+$+1).

3-(3,5-Dimethylisoxazol-4-yl)benzaldehydes (3a). Yellow oily compound, 63%, yield, $^1$H NMR (300 MHz, CDCl$_3$) δ 10.3 (s, 1H), 7.91 (d, 1H), 7.78 (s, 1H), 7.71 (d, 1H), 7.64 (t, 1H), 2.42 (s, 3H), 2.27 (s, 3H). MS (APCI) m/z 202.2 (M$^+$+1).

4-(3,5-dimethylisoxazol-4-yl)benzaldehyde (4a). Yellow oily compound, 35% yield; $^1$H NMR (300 MHz, CDCl$_3$) δ 10.07 (s, 1H), 7.99 (m, 2H), 7.46 (d, J=6.6 Hz, 2H), 2.47 (s, 3H), 2.31 (s, 3H); MS(APCI) m/z 202.1 (M$^+$+1).

1-(4-(3,5-Dimethylisoxazol-4-yl)phenyl)ethanone (5a). Yellow oily compound, 60% yield, $^1$H NMR (300 MHz, CDCl$_3$) δ 8.05 (d, J=8.7 Hz, 2H), 7.38 (d, J=8.7 Hz, 2H), 2.64 (s, 3H), 2.44 (s, 3H), 2.30 (s, 3H). MS(APCI) m/z 216.2 (M$^+$+1).

N-cyclohexyl-2-(4-(3,5-dimethylisoxazol-4-yl)phenyl)imidazo[1,2-a]pyrdin-3-amine (UMB28)

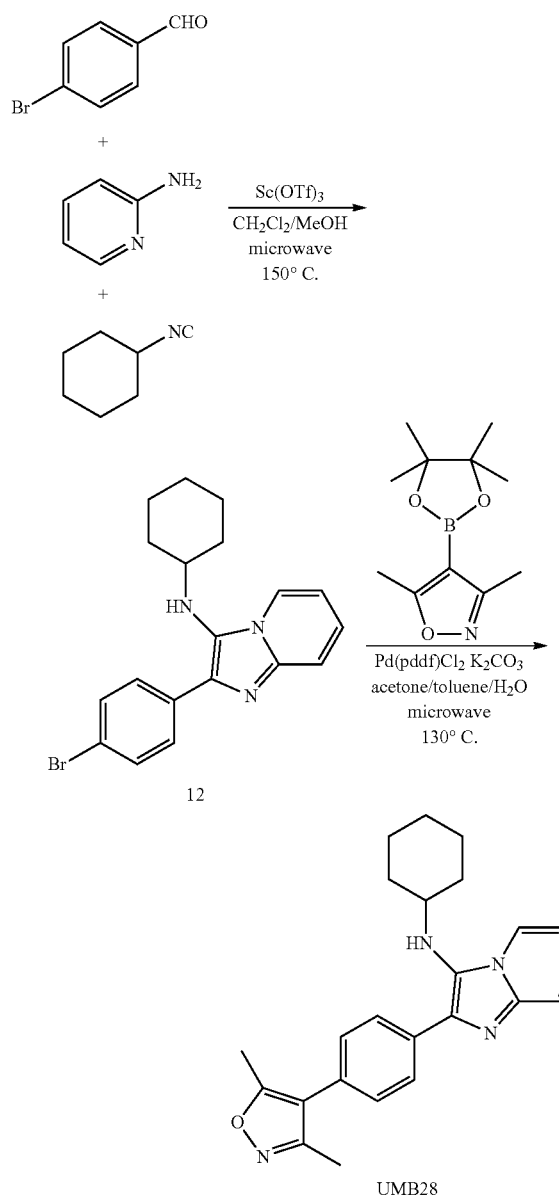

A mixture of 4-bromobenzaldehyde (37 mg, 0.4 mmol), 2-aminopyridine (24 mg, 0.5 mmol), cyclohexyl isocyanide (32 μL, 0.5 mmol), and catalyst Sc(OTf)$_3$ (10 mg, 0.04 mmol) in 2 mL of 3:1 CH$_2$Cl$_2$:H$_2$O was heated under microwave at 150° C. for 60 min. See, e.g., Lu et al., QSAR Comb. Sci. 2004, 23, 827-835. The reaction mixture was filtered, and the residue was washed with ethyl acetate. The concentrated filtrate was purified by flash chromatography (7:3 hexanes:EtOAc) to afford intermediate 12 (88 mg, 60% yield). MS (APCI) m/z: 371.1 (M+1)$^+$.

A mixture of intermediate 12 (37 mg, 0.1 mmol), 3,5-dimethylisoxazole-4-boronic acid pinacol ester (33.6 mg, 0.15 mmol), catalyst Pd(pddf)Cl$_2$ (8.2 mg, 0.01 mmol), and base K$_2$CO$_3$ (27.6 mg, 0.2 mmol) in 2 mL of a solvent of 4:4:1 acetone:toluene:H$_2$O was heated under microwave at 130° C. for 60 min. See, e.g., Lu et al., QSAR Comb. Sci. 2004, 23, 827-835. The reaction mixture was filtered, and the residue was washed with ethyl acetate. The concentrated filtrate was purified by flash chromatography (5:5 hexanes: EtOAc) to afford compound UMB28 (25 mg, 65% yield). $^1$H NMR (300 MHz, CDCl$_3$) δ 8.18 (m, 4H), 7.58 (d, J=6.0 Hz, 1 H), 7.38 (m, 2 H), 7.16 (m, 1 H), 2.24 (s, 3 H), 2.36 (s, 3 H), 1.6 (m, 6 H), 1.2 (m, 5 H) ppm. $^{13}$C NMR (75 MHz, CDCl$_3$) δ 195.2, 165.1, 152.8, 129.2, 128.4, 124.0, 122.8, 116.6, 112.0, 57.6, 34.0, 25.2, 7.4 ppm. MS (APCI) m/z: 387.2 (M+1)$^+$.

N-(tert-butyl)-2-(4-(3,5-dimethylisoxazol-4-yl)phenyl)imidazo[1,2-a]pyridin-3-amine (UMB29)

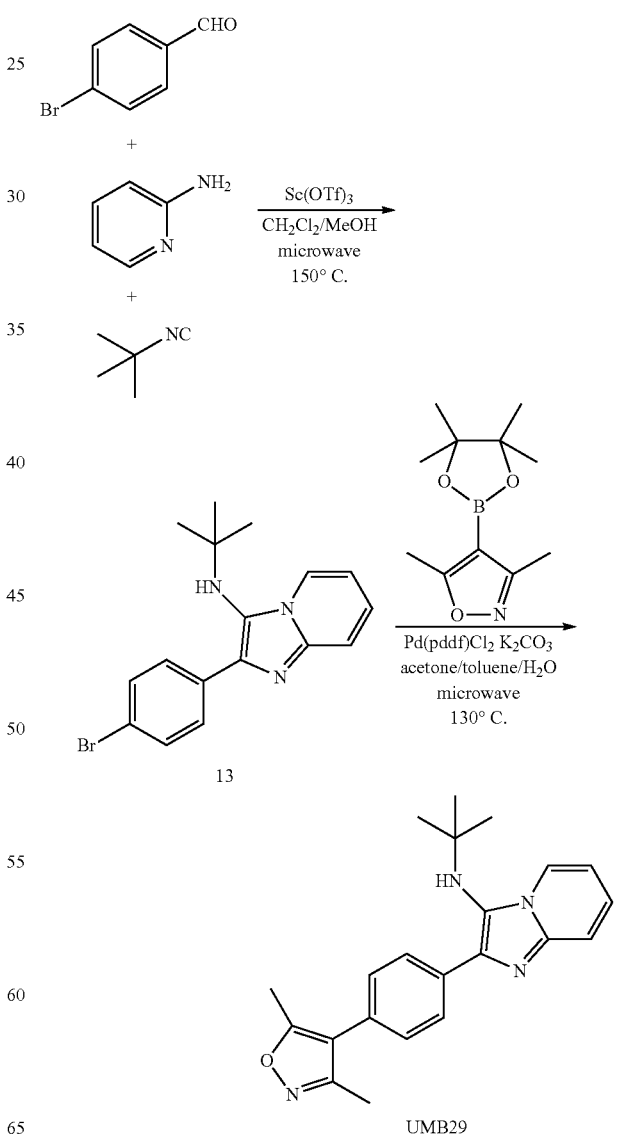

A mixture of 4-bromobenzaldehyde (37 mg, 0.4 mmol), 2-aminopyridine (45.2 mg, 0.48 mmol), tert-butyl isocyanide (54.3 μL, 0.48 mmol), and catalyst Sc(OTf)$_3$ (10 mg, 0.04 mmol) in 2 mL of 3:1 CH$_2$Cl$_2$:H$_2$O was heated under microwave at 150° C. for 60 min. The reaction mixture was filtered, and the residue was washed with ethyl acetate. The concentrated filtrate was purified by flash chromatography (7:3 hexanes:EtOAc) to afford intermediate 13 (110 mg, 79% yield). MS (APCI) m/z: 345.1 (M+1)$^+$.

A mixture of intermediate 13 (30 mg, 0.09 mmol), 3,5-dimethylisoxazole-4-boronic acid pinacol ester (30 mg, 0.135 mmol), catalyst Pd(pddf)Cl$_2$ (5.7 mg, 0.007 mmol), and base K$_2$CO$_3$ (25 mg, 0.18 mmol) in 2 mL of 4:4:1 acetone:toluene:H$_2$O was heated under microwave at 130° C. for 60 min. The reaction mixture was filtered, and the residue was washed with ethyl acetate. The concentrated filtrate was purified by flash chromatography (7:3 hexanes:EtOAc) to afford compound UMB29 (18.2 mg, 56% yield). $^1$H NMR (300 MHz, CDCl$_3$) δ 8.18 (m, 1 H), 7.96 (m, 2 H), 7.47 (m, 1 H), 7.26 (m, 2 H), 7.12 (m, 1 H), 6.75 (m, 1 H), 2.39 (s, 3 H), 2.25 (s, 3 H), 1.00 (s, 9 H) ppm. $^{13}$C NMR (75 MHz, CDCl$_3$) δ 215.9, 201.1, 200.7, 177.8, 128.9, 128.4, 123.4, 118.2. 30.4, 24.5, 11.7, 7.7 ppm. MS (APCI) m/z: 361.2 (M+1)$^+$.

N-(tert-butyl)-2-(4-(3,5-dimethylisoxazol-4-yl)phenyl)imidazo[1,2-a]pyrazin-3-amine (UMB32)

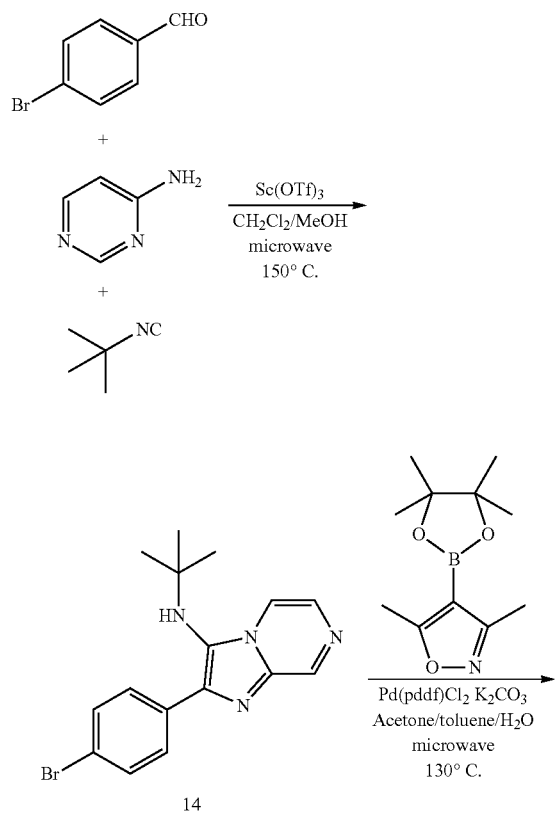

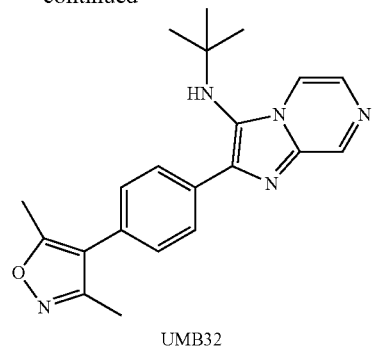

UMB32

A mixture of 4-bromobenzaldehyde (37 mg, 0.4 mmol), 4-aminopyrimidine (45.6 mg, 0.48 mmol), tert-butyl isocyanide (54.3 μL, 0.48 mmol), and catalyst Sc(OTf)$_3$ (10 mg, 0.04 mmol) in 2 mL of 3:1 CH$_2$Cl$_2$:H$_2$O was heated under microwave at 150° C. for 60 min. The reaction mixture was filtered, and the residue was washed with ethyl acetate. The concentrated filtrate was purified by flash chromatography (7:3 hexanes:EtOAc) to afford intermediate 14 (96 mg, 72% yield). MS (APCI) m/z: 346.1 (M+1)$^+$.

A mixture of intermediate 14 (30 mg, 0.09 mmol), 3,5-dimethylisoxazole-4-boronic acid pinacol ester (30 mg, 0.135 mmol), catalyst Pd(pddf)Cl$_2$ (5.7 mg, 0.007 mmol), and base K$_2$CO$_3$ (25 mg, 0.18 mmol) in 2 mL of 4:4:1 acetone:toluene:H$_2$O was heated under microwave at 130° C. for 60 min. The reaction mixture was filtered, and the residue was washed with ethyl acetate. The concentrated filtrate was purified by flash chromatography (7:3 hexanes:EtOAc) to afford compound UMB32 (16.3 mg, 50% yield). $^1$H NMR (300 MHz, CDCl$_3$) δ 8.93 (s, 1 H), 8.10 (d, J=6.0 Hz, 1 H), 7.95-8.08 (m, 2 H), 7.80 (d, J=6.6 Hz, 1 H), 7.28 (d, J=6.6 Hz, 2 H), 2.38 (s, 3 H), 2.24 (s, 3 H), 1.00 (s, 9 H) ppm. $^{13}$C NMR (75 MHz, CDCl$_3$) δ 216.1, 201.2, 164.1, 129.2, 128.7, 118.2, 116.5, 30.6, 11.10, 7.81 ppm. MS (APCI) m/z: 362.2 (M+1)$^+$.

(1R,3S,3aR,6aS)-ethyl 3-(4-(3,5-dimethylisoxazol-4-yl)phenyl)-5-ethyl-1-methyl-4,6-dioxooctahydropyrrolo[3,4-c]pyrrole-1-carboxylate (UMB17)

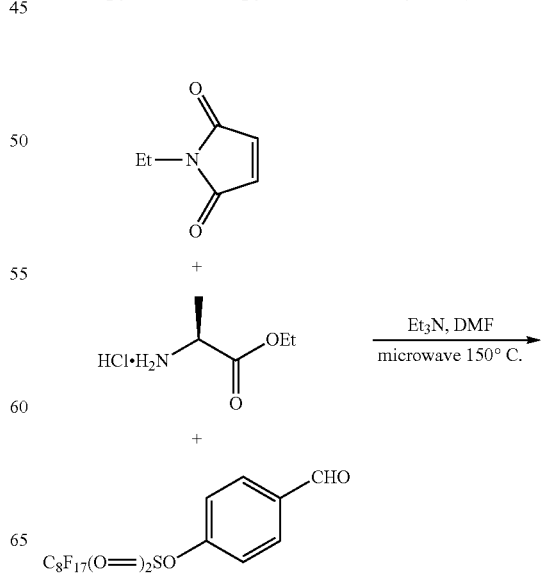

135

-continued

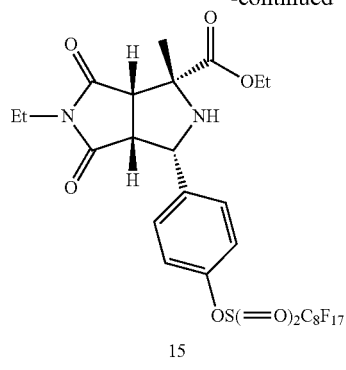 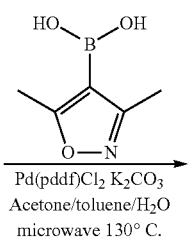

15

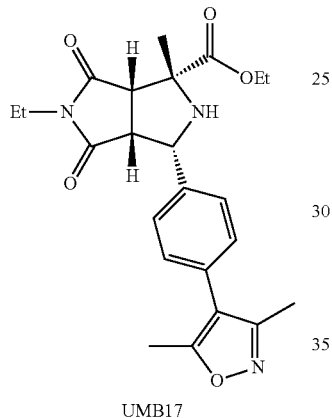

UMB17

A mixture of N-ethylmaleimide (37.5 mg, 0.3 mmol), L-alanine ethyl ester hydrochloride (37 mg, 0.24 mmol), flourous benzaldehyde (120.5 mg, 0.2 mmol), and triethylamine (69 µL, 0.48 mmol) in 2 mL DMF was heated under microwave at 150° C. for 15 min. After aqueous workup, the concentrated crude product was purified by flash chromatography (8:2 hexanes:EtOAc) to give the perfluorooctylsulfate intermediate 15 (124.3 mg, 75% yield).

The perfluorooctylsulfate intermediate 15 (82.8 mg, 0.1 mmol), 3,5-dimethylisoxazole-4-yl boronic acid (21.1 mg, 0.15 mmol), Pd(pddf)Cl$_2$ (a catalyst, 65.1 mg, 0.08 mmol), and K$_2$CO$_3$ (a base, 27.6 mg, 0.2 mmol) in 2 mL of 4:4:1 acetone:toluene:H$_2$O was heated under microwave at 130° C. for 30 min. The reaction mixture was filtered, and the residue was washed with ethyl acetate. The filtrate was concentrated, and the resulting residue was purified by flash chromatography (7:3 hexanes:EtOAc) to afford compound UMB17. MS (APCI) m/z: 426.5 (M+1)$^+$.

136

2-Butyl-3-(4-(3,5-dimethylisoxazol-4-yl)-3-methoxyphenyl)-2,3-dihydro-1H-benzo[e][1,4]diazepine-1,4(5H)-dione (UMB18)

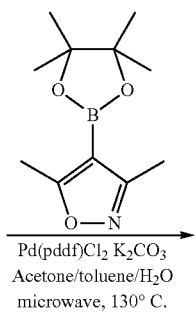

16

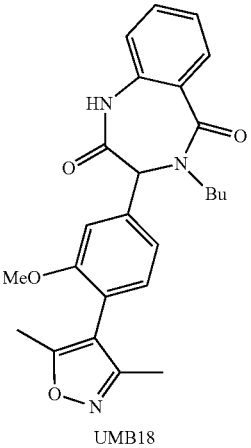

UMB18

The fluorous sulfonate starting material 16 was synthesized following a procedure reported in Zhou et al., *J. Comb. Chem.* 2010, 12, 206-214. A mixture of fluorous sulfonate 16 (167.3 mg, 0.2 mmol), 3,5-dimethylisoxazole-4-boroic acid pinacol ester (67.2 mg, 0.3 mmol), Pd(pddf)Cl$_2$ (a catalyst, 16.4 mg, 0.02 mmol), and K$_2$CO$_3$ (a base, 55.2 mg, 0.4 mmol) in 2 mL of 4:4:1 acetone:toluene:H$_2$O was heated under microwave at 130° C. for 60 min. The reaction mixture was filtered, and the residue was washed with ethyl acetate. The filtrate was concentrated, and the resulting residue was purified by flash chromatography (7:3 hexanes: EtOAc) to afford compound UMB18. MS (APCI) m/z: 434.2 (M+1)$^+$.

10-(3-(3,5-Dimethylisoxazol-4-yl)phenyl)-3,4,9,10-tetrahydro-1H-benzo[b]furo[3,4-e][1,4]diazepin-1-one (UMB27)

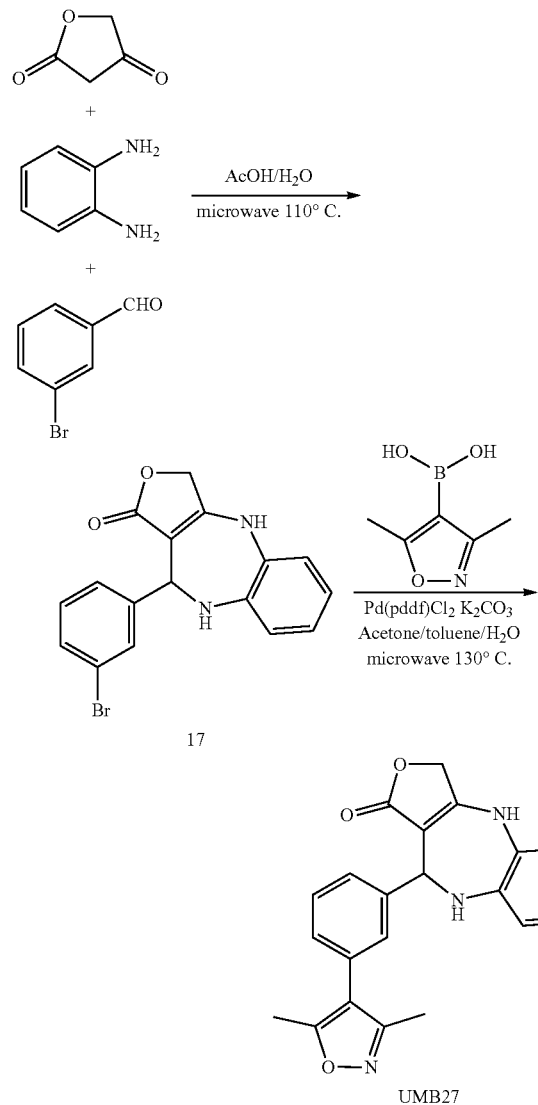

UMB27

A mixture of benzene-1,2-diamine (54 mg, 0.5 mmol), tetronic acid (53.5 mg, 0.5 mmol), and acetic acid (3 μL, 0.05 mmol) in 1 mL of H$_2$O was stirred at room temperature for 30 min. Then 3-bromobenzaldehyde (92.5 mg, 0.5 mmol) was added. The reaction mixture was heated under microwave at 110° C. for 10 min. See, e.g., Wang et al., *Tetrahedron* 2011, 25, 4485-4493. The reaction mixture was filtered, and the residue was washed with 1 mL of 50% ethanol. The solid obtained was purified by flash chromatography (6:4 EtOAc:hexanes) to afford intermediate 17 (87 mg, 49% yield). MS (APCI) m/z: 357.2 (M+1)$^+$.

A mixture of the intermediate 17 (32 mg, 0.09 mmol), 3,5-dimethylisoxazole-4-yl boronic acid (19 mg, 0.135 mmol), Pd(pddf)Cl$_2$ (a catalyst, 5.7 mg, 0.007 mmol), and K$_2$CO$_3$ (a base, 25 mg, 0.18 mmol) in 2 mL of 4:4:1 acetone:toluene:H$_2$O was heated under microwave at 130° C. for 30 min. The reaction mixture was filtered, and the residue was washed with ethyl acetate. The filtrate was concentrated, and the resulting residue was purified by flash chromatography (6:4 EtOAc:hexanes) to afford compound UMB27 (18 mg, 54% yield). MS (APCI) m/z: 374.1 (M+1)$^+$.

Additional UMB Analog Synthesis and Characterization

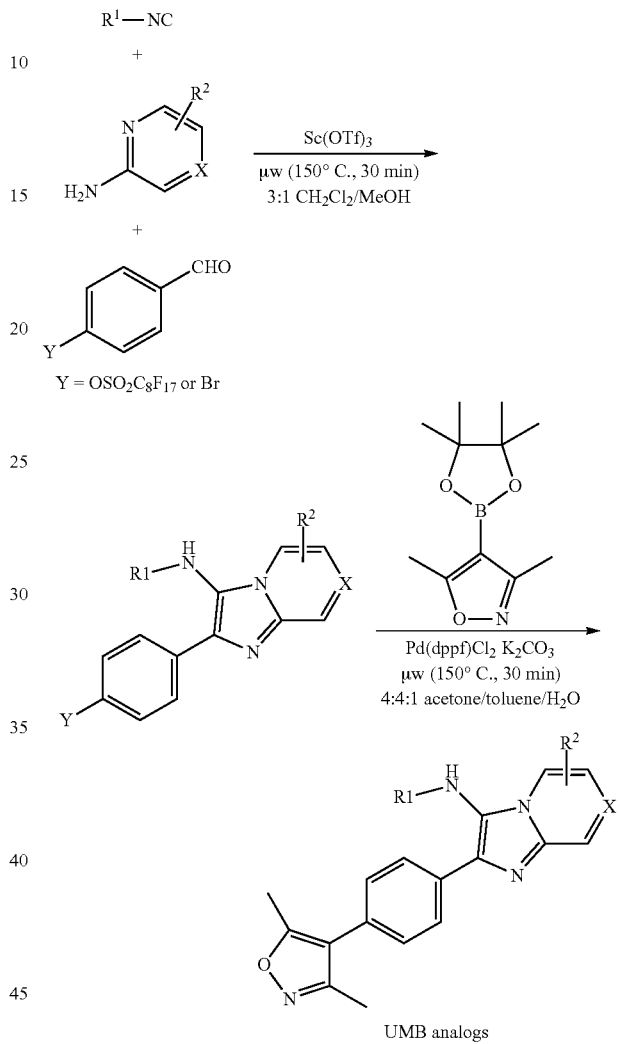

UMB analogs

| product | X | R$^1$ | R$^2$ |
|---|---|---|---|
| UMB11 | CH4 | PhCH$_2$ | H |
| 12a | CH | H | H |
| 13a | CH | PhCH$_2$ | Me |
| UMB20 | CH | PhCH$_2$ | Cl |
| UMB21 | 7-N | PhCH$_2$ | H |
| UMB28 | CH4 | c-C$_6$H$_{11}$ | H |
| UMB30 | CH | p-EtC$_6$H$_4$ | H |
| UMB23 | CH | p-MeOC$_6$H$_4$ | Cl |
| UMB24 | 6-N | p-MeOC$_6$H$_4$ | 7-OMe |
| UMB25 | 7-N | p-MeOC$_6$H$_4$ | H |
| 21a | 7-N | (S)-1-PhEt | H |
| 24a | 7-N | —CH$_2$CO$_2$tBu | H |
| UMB29 | CH | t-Bu | H |
| UMB31 | CH | t-Bu | Cl |
| 27a | CH | t-Bu | 6-Me |
| 28a | CH | t-Bu | 8-CF$_3$ |
| 29a | CH | t-Bu | 6-CO$_2$CH$_2$ |
| 30a | CH | t-Bu | 6-COOH |

| product | X | R¹ | R² |
|---|---|---|---|
| UMB56 | 6-N | t-Bu | H |
| UMB32 | 7-N | t-Bu | H |
| 33a | 8-N | t-Bu | H |
| UMB57 | 7-N | i-Pr | H |
| 35a | 7-N | n-Bu | H |

N-Benzyl-2-(4-(3,5-dimethylisoxazol-4-yl)phenyl)imidazo[1,2-α]pyridin-3-amine (UMB11). Yellowish brown solid, 52% yield, $^1$H NMR (300 MHz, CDCl$_3$) δ 8.24 (d, 1H), 7.72 (d, 2H), 7.66 (d, 1H), 7.58 (d, 2H), 7.53 (t, 1H), 7.42 (t, 1H), 7.22 (m, 5H), 4.21 (s, 2H), 3.15 (s, 1H), 2.42 (s, 3H), 2.37 (s, 3H); MS(APCI) m/z 395.2 (M$^+$+1).

2-(4-(3,5-Dimethylisoxazol-4-yl)phenyl)imidazo[1,2-a]pyridin-3-amine (12a). 36% yield, $^1$H-NMR (300 MHz, CDCl$_3$) δ 8.06 (m, 3H), 7.55 (m, 2H), 7.36 (d, J=6.3 Hz, 2H), 7.15 (m, 1H), 6.83 (m, 1H), 3.45 (2, 2H), 2.44 (s, 3H), 2.31 (s, 3H). MS (APCI) m/z 305.1 (M$^+$+1).

N-Benzyl-2-(4-(3,5-dimethylisoxazol-4-yl)phenyl)-6-methylimidazo[1,2-α]pyridine-3-amine (13a). Yellow solid, 45% yield, $^1$H NMR (300 MHz, CDCl$_3$) δ 7.99 (d, 1H), 7.96 (d, 1H), 7.62 (s, 1H), 7.39 (d, 2H), 7.27 (m, 5H), 6.97 (d, 2H), 4.14 (s, 2H), 3.42 (s, 1H), 2.44 (s, 3H), 2.36 (s, 3H), 2.28 (s, 3H). MS(APCI) m/z 409.2 (M$^+$+1).

N-Benzyl-6-chloro-2-(4-(3,5-dimethylisoxazol-4-yl)phenyl)imidazo[1,2-α]pyridin-3-amine (UMB20). 15% yield, $^1$H NMR (300 MHz, CDCl$_3$) δ 8.85 (s, 1H), 8.12 (d, 2H), 8.05 (d, 1H), 8.02 (d, 1H), 7.96 (d, 2H), 7.34 (m, 5H) 4.22 (s, 2H), 3.51 (s, 1H), 2.42 (s, 3H), 2.37 (s, 3H); MS(APCI) m/z 429.1 (M$^+$+1).

N-Benzyl-2-(4-(3,5-dimethylisoxazol-4-yl)phenyl)imidazo[1,2-α]-pyrazin-3-amine (UMB21). 16% yield, $^1$H NMR (300 MHz, CDCl$_3$) δ 8.11 (d, 1H), 8.05 (d, 1H), 8.01 (s, 1H), 7.92 (d, 2H), 7.52 (d, 2H), 7.42 (t, 1H), 7.28 (m, 5H), 4.22 (s, 2H), 3.51 (s, 1H), 2.43 (s, 3H), 2.37 (s, 3H); MS(APCI) m/z 396.2 (M$^+$+1).

N-Cyclohexyl-2-(4-(3,5-dimethylisoxazol-4-yl)phenyl)imidazo[1,2-α]pyridin-3-amine (UMB28). 19% yield, $^1$H NMR (300 MHz, CDCl$_3$) δ 8.11 (d, 1H), 8.05 (d, 2H), 7.57 (d, 1H), 7.35 (d, 2H), 7.08 (t, 1H), 6.81 (t, 1H), 3.01 (s, 1H), 2.42 (s, 3H), 2.27 (s, 3H), 1.12 (m, 11H); MS(APCI) m/z 387.2 (M$^+$+1).

2-(4-(3,5-Dimethylisoxazol-4-yl)phenyl)-N-(4-methoxyphenyl)imidazo-[1,2-α]pyridin-3-amine (UMB30). 20% yield, $^1$H NMR (300 MHz, CDCl$_3$) δ 8.03 (d, J=8.4 Hz, 2H), 7.80 (d, J=6.6 Hz, 1H), 7.59 (d, J=9 Hz, 1H), 7.21 (d, J=8.4 Hz, 2H), 7.17 (t, 1H), 6.75 (d, J=6.6 Hz, 2H), 6.73 (t, 1H), 6.50 (d, J=6.6 Hz, 2H), 5.43 (s, 1H), 3.68 (s, 3H), 2.33 (s, 3H), 2.20 (s, 3H), 1.01 (s, 9H); MS(APCI) m/z 411.2 (M$^+$+1).

6-Chloro-2-(4-(3,5-dimethylisoxazol-4-yl)phenyl)-N-(4-methoxy-phenyl)imidazo-[1,2-α]pyridine-3-amine (UMB23). 15% yield, $^1$H NMR (300 MHz, CDCl$_3$) δ 8.07 (s, 1H), 8.02 (d, 1H), 7.62 (d, 1H), 7.40 (d, 2H), 7.38 (d, 2H), 7.30 (d, 2H), 7.23 (d, 2H), 0.3.77 (s, 3H), 2.42 (s, 3H), 2.28 (s, 3H); MS(APCI) m/z 445.9 (M$^+$+1).

2-(4-(3,5-Dimethylisoxazol-4-yl)phenyl)-7-methoxy-N-(4-methoxy-phenyl)imidazo[1,2-c]pyrimidin-3-amine (UMB24). 11% yield, $^1$H NMR (300 MHz, CDCl$_3$) δ 8.51 (s, 1H), 8.09 (d, J=8.4 Hz, 2H), 7.31 (d, J=8.4 Hz, 2H), 6.85 (d, J=8.7 Hz, 2H), 6.78 (d, J=6.6 Hz, 2H), 6.65 (d, J=8.7 Hz, 2H), 5.38 (s, 1H), 3.97 (s, 3H), 3.76 (s, 3H), 2.42 (s, 3H), 2.29 (s, 3H); MS(APCI) m/z 442.4 (M$^+$+1).

2-(4-(3,5-Dimethylisoxazol-4-yl)phenyl)-N-(4-methoxyphenyl)imidazo[1,2-a]pyrazin-3-amine (UMB25). 42% yield, $^1$H NMR (400 MHz, CD$_3$OD) δ 9.07 (s, 1H), 8.14 (m, 2H), 8.09 (d, 1H), 7.92 (d, 1H), 7.42 (m, 2H), 6.80 (m, 6.80), 6.57 (m, 2H), 3.70 (s, 3H), 2.42 (s, 3H), 2.26 (s, 3H); MS(APCI) m/z 412.2 (M$^+$+1).

(S)-2-(4-(3,5-dimethylisoxazol-4-yl)phenyl)-N-(1-phenylethyl)imidazo[1,2-a]pyrazin-3-amine (21a). 24% yield, $^1$H-NMR (300 MHz, CDCl$_3$) δ 8.96 (s, 1H), 8.05 (m, 2H), 7.78 (d, J=9.6 Hz, 2H), 7.36 (d, J=2.1 Hz, 2H), 7.27 (m, 5H), 4.38 (m, 1H), 2.48 (s, 3H), 2.35 (s, 3H), 1.51 (s, 3H). MS (APCI) m/z 410.2 (M$^+$+1).

Tert-butyl (2-(4-(3,5-dimethylisoxazol-4-yl)phenyl)imidazo[1,2-a]pyrazin-3-yl)glycinate (24a). 19% yield, $^1$H-NMR (300 MHz, CDCl$_3$) δ 9.01 (s, 1H), 8.19 (m, 3H), 7.89 (d, J=4.5 Hz, 1H), 7.38 (d, J=7.2 Hz, 2H), 3.77 (s, 2H), 2.46 (s, 3H), 2.33 (s, 3H), 1.47 (s, 9H). MS (APCI) m/z 420.2 (M$^+$+1).

N-(t-Butyl)-2-(4-(3,5-dimethylisoxazol-4-yl)phenyl)imidazo[1,2-α]pyridin-3-amine (UMB29). 20% yield, $^1$H NMR (300 MHz, CDCl$_3$) δ 8.15 (d, 1H), 7.99 (d, 2H), 7.45 (d, 1H), 7.22 (d, 2H), 7.03 (t, 1H), 6.71 (t, 1H), 3.01 (s, 1H), 2.40 (s, 3H), 2.25 (s, 3H), 1.01 (s, 9H); MS(APCI) m/z 361.2 (M$^+$+1).

N-(t-Butyl)-6-chloro-2-(4-(3,5-dimethylisoxazol-4-yl)phenyl)-imidazo-[1,2-α]pyridin-3-amine (UMB31). 18% yield, $^1$H NMR (300 MHz, CDCl$_3$) δ 8.19 (s, 1H), 7.93 (d, J=6.6 Hz, 2H), 7.44 (d, J=9.6 Hz, 1H), 7.27 (d, J=6.6 Hz, 2H), 7.07 (d, J=9.6 Hz, 1H), 3.03 (s, 1H), 2.35 (s, 3H), 2.25 (s, 3H), 1.01 (s, 9H); MS(APCI) m/z 395.2 (M$^+$+1).

N-(tert-butyl)-2-(4-(3,5-dimethylisoxazol-4-yl)phenyl)-6-methylimidazo[1,2-a]pyridin-3-amine (27a). 33% yield, $^1$H-NMR (300 MHz, CDCl$_3$) δ 8.06 (m, 3H), 7.55 (m, 2H), 7.36 (d, J=6.3 Hz, 2H), 7.15 (m, 1H), 6.83 (m, 1H), 3.45 (2, 2H), 2.44 (s, 3H), 2.31 (s, 3H). MS (APCI) m/z 305.1 (M$^+$+1).

N-(tert-butyl)-2-(4-(3,5-dimethylisoxazol-4-yl)phenyl)-8-(trifluoromethyl)imidazo[1,2-a]pyridin-3-amine (28a). 32% yield, $^1$H-NMR (400 MHz, CD$_3$OD) δ 8.67 (d, 1H), 8.12 (m, 2H), 7.67 (d, 1H), 7.45 (d, 2H), 7.03 (m, 1H), 2.46 (s, 3H), 2.30 (s, 3H), 1.04 (s, 9H). MS (APCI) m/z 429.2 (M$^+$+1).

Methyl 3-(tert-butylamino)-2-(4-(3,5-dimethylisoxazol-4-yl)phenyl)imidazo[1,2-a]pyridine-6-carboxylate (29a). 35% yield, $^1$H-NMR (400 MHz, DMSO-d6) δ 9.08 (s, 1H), 8.35 (d, 2H), 7.59 (m, 2H), 7.45 (d, 2H), 4.96 (s, 1H), 3.92 (s, 3H), 2.45 (s, 3H), 2.27 (s, 3H), 1.06 (s, 9H). MS (APCI) m/z 419.2 (M$^+$+1).

3-(Tert-butylamino)-2-(4-(3,5-dimethylisoxazol-4-yl)phenyl)imidazo[1,2-a]pyridine-6-carboxylic acid (30a). 30% yield, $^1$H-NMR (400 MHz, CD$_3$OD) δ 9.03 (s, 1H), 8.13 (d, 2H), 7.82 (m, 1H), 7.42 (m, 3H), 2.46 (s, 3H), 2.30 (s, 3H), 1.07 (s, 9H). MS (APCI) m/z 405.1 (M$^+$+1).

N-(Tert-butyl)-2-(4-(3,5-dimethylisoxazol-4-yl)phenyl)imidazo[1,2-c]pyrimidin-3-amine (UMB56). 18% yield, H-NMR (400 MHz, CD$_3$OD) δ 9.05 (s, 1H), 7.87 (d, 1H), 7.71 (m, 2H), 7.59 (m, 2H), 7.40 (m, 1H), 2.48 (s, 3H), 2.33 (s, 3H), 1.45 (s, 9H). MS (APCI) m/z 361.9 (M$^+$+1).

N-(Tert-butyl)-2-(4-(3,5-dimethylisoxazol-4-yl)phenyl)imidazo[1,2-a]pyrimidin-3-amine (33a). 15% yield, $^1$H-NMR (400 MHz, CD$_3$OD) δ 8.83 (d, 1H), 8.53 (d, 1H), 8.18 (m, 2H), 7.43 (m, 3H), 7.06 (m, 1H), 2.45 (s, 3H), 2.30 (s, 3H), 1.07 (s, 9H). MS (APCI) m/z 361.4 (M$^+$+1).

2-(4-(3,5-dimethylisoxazol-4-yl)phenyl)-N-isopropylimidazo[1,2-a]pyrazin-3-amine (UMB57). 19% yield, $^1$H-NMR (400 MHz, CD$_3$OD) δ 8.88 (d, 1H), 8.37 (d, 1H), 8.25 (m, 2H), 7.88 (d, 1H), 7.49 (m, 2H), 3.42 (m, 1H), 2.47 (s, 3H), 2.31 (s, 3H), 1.13, (d, 6H). MS (APCI) m/z 347.9 (M⁺+1).

N-butyl-2-(4-(3,5-dimethylisoxazol-4-yl)phenyl)imidazo[1,2-a]pyrazin-3-amine (35a). 27% yield, ¹H-NMR (300 MHz, CDCl₃) δ 9.02 (s, 1H), 8.07 (d, J=8.4 Hz, 2H), 7.98 (d, J=4.2 Hz, 1H), 7.89 (d, J=7.8 Hz, 1H), 7.39 (d, J=8.1 Hz, 2H), 3.15 (s, 2H), 2.46 (s, 3H), 2.34 (s, 3H), 1.64 (m, 2H), 1.48 (m, 2H), 0.95 (t, 3H). MS (APCI) m/z 362.2 (M⁺+1).

2-((2-(4-(3,5-Dimethylisoxazol-4-yl)phenyl)imidazo[1,2-a]pyrazin-3-yl)amino)acetic acid (22a)

Compound 24a (0.284 g, 0.677 mmol, 1 eq) was dissolved in DCM (2.7 mL) and TFA (2.7 mL) and stirred at room temperature. After 12 hours, the mixture was concentrated, and purified by preparative HPLC (5 to 95% MeCN/water with 0.1% TFA) and lyophilized to yield the product as an orange powder (187 mg, 0.515 mmol, 76%).

¹H NMR (400 MHz, MeOD) δ 9.08 (s, 1H), 8.69 (d, J=5.3 Hz, 1H), 8.16 (d, J=8.2 Hz, 2H), 7.94 (d, J=5.1 Hz, 1H), 7.66-7.46 (m, 2H), 3.99 (s, 2H), 2.48 (s, 3H), 2.32 (s, 3H). MS (ESI) 364.76 (M+H).

Ethyl 2-((2-(4-(3,5-dimethylisoxazol-4-yl)phenyl)imidazo[1,2-a]pyrazin-3-yl)amino)acetate (23a)

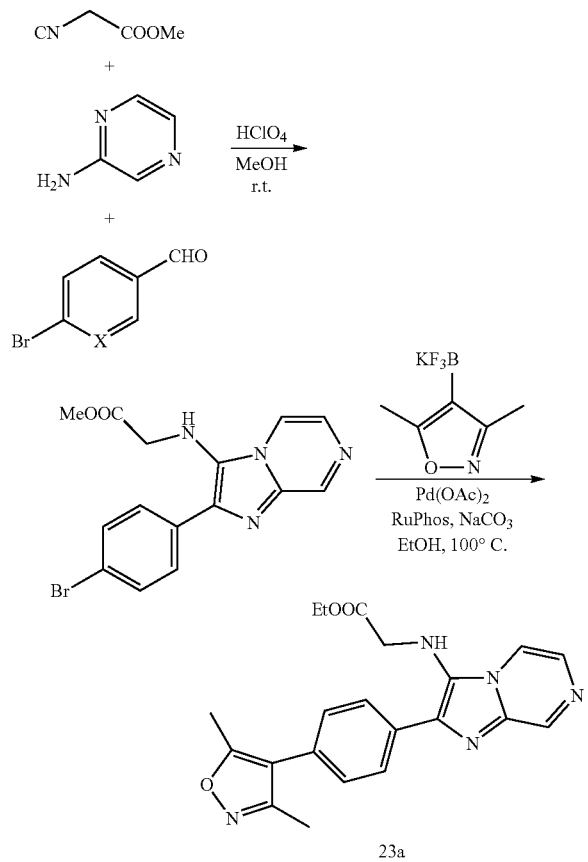

Methyl 2-((2-(4-bromophenyl)imidazo[1,2-a]pyrazin-3-yl)amino)acetate

Aminopyrazine (95.2 mg, 1.00 mmol, 1 eq), 4-bromobenzaldehyde (278 mg, 1.50 mmol, 1.5 eq) and methyl isocyanoacetate (0.105 mL, 1.15 mmol, 1.15 eq) were dissolved in methanol (2 mL). A 1M solution of perchloric acid in methanol (0.20 mL, 0.10 eq) was added and the solution was stirred for 12 hours at room temperature. The mixture was then diluted with EtOAc and washed with saturated sodium bicarbonate, water and brine. The crude material was purified by automated column chromatography (50 to 100% EtOAc/hexanes) to yield a cream colored solid (0.21 g, 0.581 mmol, 58%).

¹H NMR (400 MHz, CDCl₃) δ 8.99 (d, J=1.5 Hz, 1H), 8.18 (dd, J=4.6, 1.5 Hz, 1H), 8.02-7.93 (m, 2H), 7.90 (d, J=4.6 Hz, 1H), 7.68-7.51 (m, 2H), 3.83 (d, J=5.6 Hz, 2H), 3.74 (s, 3H). MS (ESI) 361.69 (M+H).

Ethyl 2-((2-(4-(3,5-dimethylisoxazol-4-yl)phenyl)imidazo[1,2-a]pyrazin-3-yl)amino)acetate (23a)

Methyl 2-((2-(4-bromophenyl)imidazo[1,2-a]pyrazin-3-yl)amino)acetate (147 mg, 0.408 mmol, 1 eq), potassium 3,5-dimethylisoxazole-4-trifluoroborate (108 mg, 0.530 mmol, 1.3 eq), palladium (II) acetate (4.5 mg, 0.020 mmol, 5 mol %) RuPhos (19.1 mg, 0.041 mmol, 10 mol %) and sodium carbonate (86.5 mg, 0.816 mmol, 2 eq) were dissolved in ethanol (2.1 mL) and degassed with nitrogen for roughly 1 minute. The mixture was placed in a heat block at 100° C. After 16 hours, the mixture was filtered through a silica plug and concentrated. The crude mixture was purified by automated column chromatography (30 to 100% EtOAc/hexanes) to yield the ethyl ester (as a result of transesterification during the course of the cross-coupling) as a brown solid (88.9 mg, 0.227 mmol, 56%).

¹H NMR (400 MHz, CDCl₃) δ 8.96 (d, J=1.3 Hz, 1H), 8.21 (dd, J=4.6, 1.4 Hz, 1H), 8.18-8.10 (m, 2H), 7.85 (d, J=4.6 Hz, 1H), 7.39-7.31 (m, 2H), 4.18 (q, J=7.2 Hz, 2H), 4.05 (t, J=5.7 Hz, 1H), 3.86 (d, J=5.7 Hz, 2H), 2.43 (s, 3H), 2.29 (s, 3H), 1.22 (t, J=7.2 Hz, 3H). MS (ESI) 392.90 (M+H).

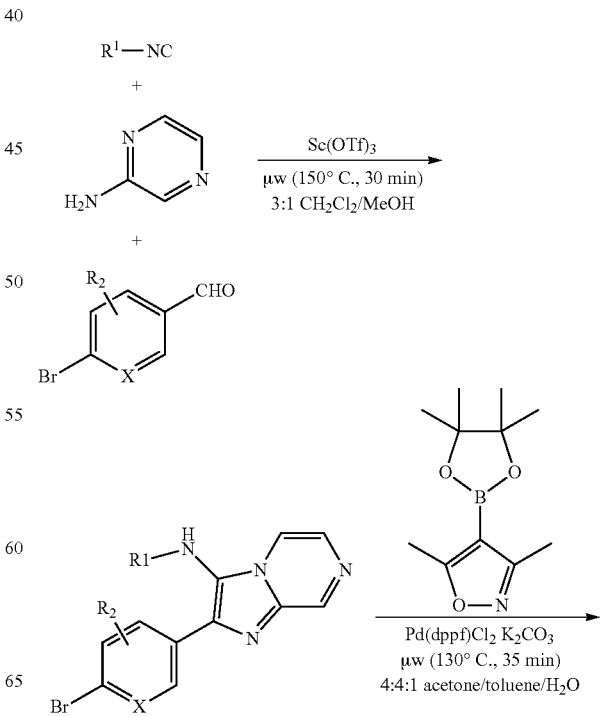

-continued

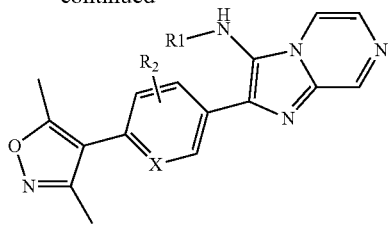

| Compound | R¹ | R² | X |
|---|---|---|---|
| UMB53 | t-Bu | H | 2-N |
| UMB54 | t-Bu | H | 3-N |
| UMB55 | t-Bu | 2-F | CH |
| 39a | t-Bu | 3-OMe | CH |
| 40a | i-Pr | 3-OMe | CH |

N-(tert-butyl)-2-(6-(3,5-dimethylisoxazol-4-yl)pyridin-3-yl)imidazo[1,2-a]pyrazin-3-amine (UMB53). 25% yield, $^1$H-NMR (300 MHz, CDCl$_3$) δ 8.92 (s, 1H), 8.84 (d, J=2.1 Hz, 1H), 7.87 (m, 1H), 7.52 (d, J=8.1 Hz, 1H), 7.35 (d, J=4.8 Hz, 1H), 2.65 (s, 3H), 2.50 (s, 3H), 1.46 (s, 9H); MS (APCI) m/z 363.1 (M$^+$+1).

N-(tert-butyl)-2-(5-(3,5-dimethylisoxazol-4-yl)pyridin-2-yl)imidazo[1,2-a]pyrazin-3-amine (UMB54). 31% yield, $^1$H-NMR (300 MHz, CDCl$_3$) δ 9.54 (s, 1H), 8.55 (s, 1H), 7.93 (d, J=6.3 Hz, 1H), 7.65 (m, 2H), 7.35 (d, J=4.5 Hz, 1H), 2.48 (s, 3H), 2.34 (s, 3H), 1.25 (s, 9H); MS (APCI) m/z 363.1 (M$^+$+1).

N-(tert-butyl)-2-(4-(3,5-dimethylisoxazol-4-yl)-3-fluorophenyl)imidazo[1,2-a]pyrazin-3-amine (UMB55). 20% yield, $^1$H-NMR (300 MHz, CDCl$_3$) δ 9.04 (s, 1H), 7.88 (d, J=5.4 Hz, 1H), 7.36 (m, 4H), 2.43 (s, 3H), 2.31 (s, 3H), 1.51 (s, 9H); MS (APCI) m/z 380.1 (M$^+$+1).

N-(tert-butyl)-2-(4-(3,5-dimethylisoxazol-4-yl)-2-methoxyphenyl)imidazo[1,2-a]pyrazin-3-amine (39a). 21% yield, $^1$H-NMR (300 MHz, CDCl$_3$) δ 9.00 (s, 1H), 8.22 (d, J=4.5 Hz, 1H), 7.88 (m, 2H), 7.05 (d, J=7.8 Hz, 1H), 6.89 (s, 1H), 3.94 (s, 3H), 3.82 (s, 1H), 2.47 (s, 3H), 2.33 (s, 3H), 1.01 (s, 9H); MS (APCI) m/z 392.2 (M$^+$+1).

2-(4-(3,5-dimethylisoxazol-4-yl)-2-methoxyphenyl)-N-isopropylimidazo[1,2-a]pyrazin-3-amine (40a). 19% yield, $^1$H-NMR (300 MHz, CDCl$_3$) δ 9.00 (s, 1H), 8.05 (m, 1H), 7.89 (m, 2H), 7.05 (d, J=6.6 Hz, 1H), 6.91 (s, 1H), 7.05 (d, J=7.8 Hz, 1H), 3.94 (s, 3H), 3.15 (m, 1H), 2.48 (s, 3H), 2.34 (s, 3H), 1.03 (d, 6H); MS (APCI) m/z 378.1 (M$^+$+1).

Example 2

Biochemical and Cellular Assays of the Compounds

In Vitro AlphaScreen® Protein Binding Assay

Assays were performed with minor modifications from the manufacturer's protocol (PerkinElmer, USA). All reagents were diluted in 50 mM HEPES, 150 mM NaCl, 0.1% w/v BSA, and 0.01% w/v Tween® 20 at pH 7.5 and allowed to equilibrate to room temperature prior to addition to plates. After addition of Alpha beads to master solutions, all subsequent steps were performed in low light conditions. A 2× solution of components with final concentrations of a BRD protein (e.g., BRD4) at 40 nM, Ni-coated Acceptor Bead at 25 µg/ml, and 20 nM biotinylated JQ1 was added in 10 µL to 384-well plates (AlphaPlate-384, PerkinElmer, USA). Biotinylated JQ1 was synthesized as described herein or according to methods known in the art. After a 1000-rpm spin-down for 1 minute, 100 nL of the solutions of compounds of the invention in DMSO from stock plates were added by pin transfer using a Janus Workstation (PerkinElmer, USA). The streptavidin-coated donor beads (25 µg/ml final) were added as with previous solution in a 2×, 10 µL volume. Following this addition, the plates were sealed with foil to block light exposure and to prevent evaporation. The plates were spun down again at 1000 rpm for 1 minute. Next, the plates were incubated in the room with the plate reader (for temperature equilibration) for 1 hour prior to reading the assay. Signal is stable for up to 3 hours after donor bead addition. AlphaScreen® measurements were performed on an Envision 2104 (PerkinElmer, USA) utilizing the manufacturer's protocol.

Acetyl-Histone Binding Assay

Assays were performed with minor modifications from the manufacturer's protocol (PerkinElmer, USA). All reagents were diluted in 50 mM HEPES, 150 mM NaCl, 0.1% w/v BSA, and 0.01% w/v Tween® 20 at pH 7.5 and allowed to equilibrate to room temperature prior to addition to plates. After addition of Alpha beads to master solutions, all subsequent steps were performed in low light conditions. A 2× solution of components with final concentrations of BRD4.1 at 80 nM, Ni-coated Acceptor Bead at 25 µg/ml, and 80 nM biotinylated H4-tetra acetyl was added in 10 µL to 384-well plates (AlphaPlate-384, PerkinElmer, USA). Biotinylated peptide for BRD4.1 was synthesized in-house on a CEM Liberty 9008005 microwave peptide synthesizer: H4-tetra acetyl, biotin-PEG2-SGRGKacGGKacGLGKacG-GAKacRHRK—COOH. Addition to wells was performed with either a multichannel pipet (for optimization experiments) or a Biotek EL406 liquid handler. After a 1000-rpm spin-down for 1 minute, 100 nL of the solutions of the compounds of the invention from stock plates were added by pin transfer using a Janus Workstation (PerkinElmer, USA). The streptavidin-coated donor beads (25 µg/ml final) were added as with previous solution in a 2×, 10 µL volume. Following this addition, the plates were sealed with foil to block light exposure and to prevent evaporation. The plates were spun down again at 1000 rpm for 1 minute. Next, the plates were incubated in the room with the plate reader (for temperature equilibration) for 1.5 hour prior to reading the assay. AlphaScreen® measurements were performed on an Envision 2104 (PerkinElmer, USA) utilizing the manufacturer's protocol.

Cellular Assay

The compounds of the invention are also evaluated in the BRD4 dependant cell line for the cellular activity to generate cellular IC$_{50}$ values.

Cells (e.g., BRD4 dependant cells) were counted and adjusted to 60,000 cells/mL. Using a Biotek EL406, 50 µL of the cells in media were distributed into 384 well white plates from Thermo. Immediately after plating, compounds of the invention in DMSO were distributed to plates. For large plate sets, cells were returned to a 37° C. incubator while not in use. The compounds were added to plates using a 100 nL 384 well pin transfer manifold on a Janus workstation. Stocks were arrayed in 10 point quadruplicate dose response in DMSO stock in 384-well Greiner compound plates. After addition of the compounds, plates were incubated for three days in a 37° C. incubator. Cell viability was read out using ATPlite from Perkin Elmer. Plates were removed from the incubator and brought to room temperature prior to use. Lyophilized powder was resuspended in lysis buffer and diluted 1:2 with DI water. 25 µL of this solution was added to each well using the Biotek liquid handler. Plates were sealed with adherent aluminum seals prior to vortexing and spinning down at 1000 g for 1 minute. Plates were incubated for 15 minutes at room temperature before signal was read on an Envision Plate Reader.

Biologic and Biochemical Compound Evaluation Reagents

Endogenous BRD4-NUT-expressing midline carcinoma cell lines, 797 was described previously (Toretsky et al., Am. J. Clin. Oncol. 2003, 26, 300). Media, trypsin, and antibiotics for tissue culture were purchased from MediatechCloning. cDNA encoding human BRD2, BRD3, BRD4, BRDT, CREBBP and WDR9 (NCBI accession number NP 005095, NP 031397.1, NP 055114.1, NP 001717.2, NP 004371.1, NP 061836.2) were obtained from different sources (BRD2: Synthetic, BRD3: Origene, BRD4: FivePrime, BRDT: IMAGE collection, CREBBP: Synthetic, WDR9: synthetic) and used as templates to amplify the bromodomain regions of the above proteins, using the polymerase chain reaction (PCR) in the presence of Platinum® Pfx DNA polymerase (Invitrogen™, UK). PCR products were purified (QIAquick PCR Purification Kit, Qiagen Ltd. UK) and further subcloned into a pET28 derived expression vector, pNIC28-Bsa4, using ligation independent cloning (Stols et al., Protein Expr. Purif. 2002, 25, 8). The constructs were transformed into competent Mach1™ cells (Invitrogen™, UK) to yield the final plasmid DNA. This vector includes sites for ligation-independent cloning and a Tobacco Etch Virus (TEV)-cleavable N-terminal His6-tag (extension MHHHHHHSSGVDLGTENLYFQ*SM-) After digestion with TEV protease, the protein retains an additional serine and methionine on the N-terminus.

Protein Expression and Purification

The first bromodomain of Brd4 (Brd4-BD1, residues 42-168) was subcloned into a modified pET-15b(+) vector with an N-terminal $His_6$ tag followed by a Tobacco Etch Virus cleavage site. The encoded protein was expressed in the E. coli BL21(DE3) strain. E. coli cells transformed with the vector were grown 4 hours at 37° C. to an $OD_{600}$ of 1.0, in 1 liter LB media containing ampicillin (0.1 mg/ml). After 0.1 mM IPTG induction at 20° C., cells were cultured overnight, and collected by centrifugation at 4,000 g. The pellet was suspended in 40 ml lysis buffer containing 50 mM HEPES, pH 7.4, 500 mM NaCl, 5 mM 3-mercaptoethanol, and 1 mM PMSF. Cells were lysed on ice by sonication and cell debris was precipitated by centrifugation at 15,000 g for 30 minutes. Brd4-BD1 was purified by affinity chromatography on an Ni-NTA agarose column (Qiagen), using an elution buffer of 50 mM HEPES, pH 7.4, 500 mM NaCl, 5 mM b-mercaptoethanol, and 50 mM of imidazole. After overnight TEV cleavage of the $His_6$-tag, the cleaved tag was captured on affinity resin, and Brd4-BD1 was then purified to homogeneity by gel filtration before concentration to roughly 12 mg/ml in storage buffer (20 mM HEPES, pH 7.4, and 150 mM NaCl). Samples for isothermal calorimetry were dialysed over night at 4° C. in a D-Tube™ Dialyser Midi, MWCO 3.5 kDa to a final buffer of 50 mM HEPES, pH 7.4 (at 25° C.), 150 mM NaCl. Protein handling was carried out on ice or in a cold room in all the above steps.

Isothermal Titration Calorimetry (ITC)

Experiments were carried out on a VP-ITC titration microcalorimeter from MicroCal™, LLC (Northampton, Mass.). All experiments were carried out at 15° C. while stirring at 295 rpm, in ITC buffer (50 mM HEPES pH 7.4 at 25° C., 150 mM NaCl). The microsyringe (250 μL) was loaded with a solution of the protein sample (300 μM protein for the BETs, 950 μM protein for CREBBP and 600 μM for WDR9(2), in ITC buffer). All titrations were conducted using an initial control injection of 2 μl followed by 34 identical injections of 8 μl with a duration of 16 sec (per injection) and a spacing of 250 sec between injections. The heat of dilution was determined by independent titrations (protein into buffer) and was subtracted from the experimental data. The collected data were implicated in the MicroCal™ Origin software supplied with the instrument to yield enthalpies of binding (ΔH) and binding constants ($K_B$) as previously described by Wiseman and co-workers (Wiseman et al., Anal. Biochem. 1989, 179, 131). Thermodynamic parameters were calculated ($\Delta G = \Delta H - T\Delta S = -RT \ln K_B$, where ΔG, ΔH and ΔS are the changes in free energy, enthalpy and entropy of binding respectively). In all cases a single binding site model was employed.

Results

Shown in Table 1 are in vitro $IC_{50}$ values, obtained through AlphaScreen®, of exemplary compounds of Formula (I) or (IV) in inhibiting the activity of BRD4. All compounds in Table 1 inhibit the activity of BRD4.

TABLE 1

In vitro $IC_{50}$ values of exemplary compounds of Formula (I) or (IV) in inhibiting the activity of BRD4.

| Compound | $IC_{50}$ (M) |
| --- | --- |
| UMB11 | 1.10E−05 |
| UMB20 | 1.18E−05 |
| UMB21 | 1.88E−05 |
| UMB22 | 6.83E−05 |
| UMB23 | 3.15E−05 |
| UMB24 | 2.89E−06 |
| UMB25 | 7.86E−06 |
| UMB26 | 5.10E−06 |
| UMB27 | 2.05E−06 |
| UMB28 | 9.04E−07 |
| UMB29 | 4.79E−07 |
| UMB30 | 2.76E−06 |
| UMB31 | 1.17E−06 |
| UMB32 | 2.56E−07 |

Table 2 shows in vitro $IC_{50}$ values, obtained through AlphaScreen®, of exemplary compounds of Formula (I) or (II) in inhibiting BRD and CBP, and cellular $IC_{50}$ values of the compounds in lung carcinoma cell line H2171. Compound UMB11 shows good selectivity toward BRD4 over CBP. Compounds UMB11 and UMB17 show cellular activity in H2171.

TABLE 2

In vitro $IC_{50}$ values of exemplary compounds of Formula (I) or (II) in inhibiting BRD and CBP, and cellular $IC_{50}$ values of the compounds in lung carcinoma cell line H2171.

| Compound | BRD4 $IC_{50}$ (μM) | CBP $IC_{50}$ (μM) | H2171 $IC_{50}$ (μM) |
| --- | --- | --- | --- |
| UMB11 | 0.51 | 11 | 0.76 |
| UMB17 | 122 | 30 | 55 |

Table 3 shows the in vitro $IC_{50}$ value, obtained through AlphaScreen®, of an exemplary compound of Formula (I) in inhibiting the activity of BRD4. Also shown in Table 3 is the compound's cellular $EC_{50}$ value obtained from a cellular assay where a BRD4 dependant cell line was treated with the compound. Compound UMB32 is active in inhibiting the activity of BRD4 in vitro and also shows cellular activity in the BRD4 dependant cell line.

TABLE 3

In vitro $IC_{50}$ value of an exemplary compound of Formula (I) in inhibiting the activity of BRD4, and cellular $EC_{50}$ value of the compound in a BRD4 dependant cell line.

| Compound | BRD4 $IC_{50}$ (µM) | BRD4 $EC_{50}$ (µM) |
| --- | --- | --- |
| UMB32 | 0.26 | 1.1 |

Shown in Table 4 are cellular $EC_{50}$ values obtained from a cellular assay where a BRD4 (site 1) dependant cell line was treated with exemplary compounds of Formula (I) or (IV). All compounds tested show cellular activity in the BRD4 dependant cell line.

TABLE 4

Cellular $EC_{50}$ values of exemplary compounds of Formula (I) or (IV) in a BRD4 dependant cell line.

| Compound | $EC_{50}$ (M) |
| --- | --- |
| UMB11 | 1.41E-05 |
| UMB20 | 1.84E-05 |
| UMB21 | 4.91E-05 |
| UMB22 | 1.24E-05 |
| UMB23 | 2.07E-05 |
| UMB24 | 1.18E-05 |
| UMB25 | 3.28E-05 |
| UMB26 | 2.02E-05 |
| UMB27 | 2.07E-04 |
| UMB28 | 5.07E-06 |
| UMB29 | 2.04E-06 |
| UMB30 | 7.36E-06 |
| UMB31 | 2.19E-06 |
| UMB32 | 1.13E-06 |

A diverse set of molecules was synthesized using reactions previously developed around fluorous-tagged multi-component reactions. These reactions created structural diversity by changing the substituent groups on each fractional component, allowing generation of diverse small-molecule libraries around a biasing element. The perfluoro-alkyl tags can substituted with a binding motif of choice via Suzuki coupling. Synthesized compounds included tertiary amines, pyrimidines and fused heterocyclic ring systems in order to explore the optimal shape for exploiting protein-inhibitor contour interactions. In addition to biochemical IC50, these compounds were selectively evaluated in a BRD4-dependent cell viability study (see Table 5). The EC50s were collected by assessing viability using PerkinElmer ATPlite kits against the BRD4-dependent Nut-Midline Carcinoma line 797. The use of a fluorous-tagged Groebke-Blackburn-Bienayme multi-component reaction was used to develop the para-imidazo[1,2-a]pyridine scaffold (UMB11), which was found have biochemical and cellular inhibitory values of 11.0 µM and 14.1 µM, respectively. In addition, the UMB11 scaffold is accessible at a variety of positions for diversification to drive potency and develop understanding of SAR.

TABLE 5

Exploration of Compound Scaffold Region.

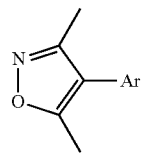

| Compound | Ar | BRD4--$IC_{50}$ (µM) | 797--$EC_{50}$ (µM) |
| --- | --- | --- | --- |
| II | 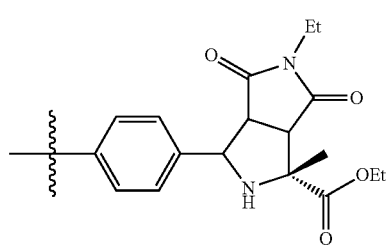 [SMILES: *c1ccc(C2N[C@@](C)(C(=O)OCC)C3C(=O)N(CC)C(=O)C23)cc1] | >100 | 9.42 |
| III | 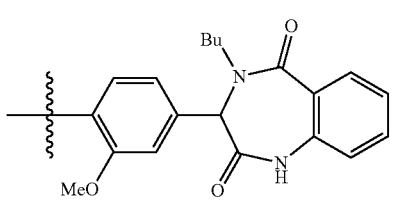 | 13.0 | 9.91 |

TABLE 5-continued

Exploration of Compound Scaffold Region.

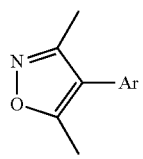

| Compound | Ar | BRD4--IC$_{50}$ (μM) | 797--EC$_{50}$ (μM) |
|---|---|---|---|
| IV | (structure) | 2.05 | >100 |
| UMB11 | (structure) | 11.0 | 14.1 |

Further analogs were synthesized to explore the functional role of both sterics and electronics of the fused bicyclic scaffold on inhibitor function (see Table 6). Variations of $R^B$ from the benzyl group to bulky, non-aromatic groups like cyclohexane and t-Bu improved potency. Ring-nitrogens at the 7 and 8 position resulted in little biochemical potency change. Cellular potency, however, modestly improved upon substitution of a 7-N.

TABLE 6

Exploration of Compound Scaffold Region.

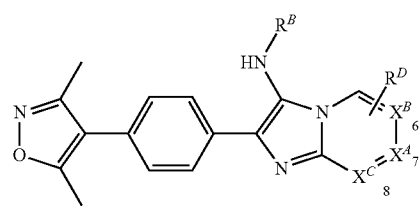

| Compound | $R^B$ | $R^D$ | X | BRD4--IC$_{50}$ (μM) | 797--EC$_{50}$ (μM) |
|---|---|---|---|---|---|
| 12a | H | H | CH | 3.89 | |
| 13a | Bn | 6-Me | CH | >100 | |
| UMB20 | Bn | 6-Cl | CH | 11.8 | 18.4 |
| UMB21 | Bn | H | 7-N | 18.8 | 49.1 |
| UMB28 | cyclohexane | H | CH | 0.904 | 5.07 |
| UMB30 | 4-(OMe)Ph | H | CH | 2.76 | 7.36 |
| UMB23 | 4-(OMe)Ph | 6-Cl | CH | 31.5 | 20.7 |
| UMB24 | 4-(OMe)Ph | 7-OMe | 6-N | 2.89 | 11.8 |
| UMB25 | 4-(OMe)Ph | H | 7-N | 7.86 | 32.8 |
| 21a | (S)-1-PhEt | H | 7-N | 2.86 | |
| 22a | —CH$_2$CO$_2$H | H | 7-N | >100 | |
| 23a | —CH$_2$CO$_2$Et | H | 7-N | 4.53 | |
| 24a | —CH$_2$CO$_2$tBu | H | 7-N | 4.96 | |
| UMB29 | t-Bu | H | CH | 0.479 | 2.04 |
| UMB31 | t-Bu | 6-Cl | CH | 1.17 | 2.19 |
| 27a | t-Bu | 6-Me | CH | 3.17 | |
| 28a | t-Bu | 8-CF$_3$ | CH | 11.9 | |
| 29a | t-Bu | 6-CO$_2$CH$_2$ | CH | 1.62 | |
| 30a | t-Bu | 6-COOH | CH | 0.968 | |
| UMB56 | t-Bu | H | 6-N | 20.7 | 2.06 |
| UMB32 | t-Bu | H | 7-N | 0.637 | 0.724 |
| 33a | t-Bu | H | 8-N | 0.860 | |
| UMB57 | i-Pr | H | 7-N | 0.807 | 0.494 |
| 35a | n-Bu | H | 7-N | 1.66 | |

Limited structural study around the linking phenyl ring is shown below (see Table 7). Electron-donating methoxy substituents appear to be mildly beneficial in biochemical assays. Additional work regarding this linking region of the molecule will be a focus of continued medicinal chemistry.

TABLE 7

Variations to UMB-32 linker.

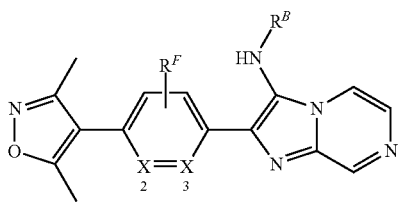

| Compound | $R^B$ | $R^F$ | X | BRD4--IC$_{50}$ (µM) | 797--EC$_{50}$ (µM) |
|---|---|---|---|---|---|
| UMB53 | t-Bu | H | 2-N | 51.9 | >100 |
| UMB54 | t-Bu | H | 3-N | 12.9 | 8.29 |
| UMB55 | t-Bu | 2-F | CH | 13.0 | 12.8 |
| 39a | t-Bu | 3-OMe | CH | 0.562 | |
| 40a | i-Pr | 3-OMe | H | 0.474 | |

Example 3

Selectivity of the Compounds for Different Bromodomain-Containing Proteins

Figure 3A:
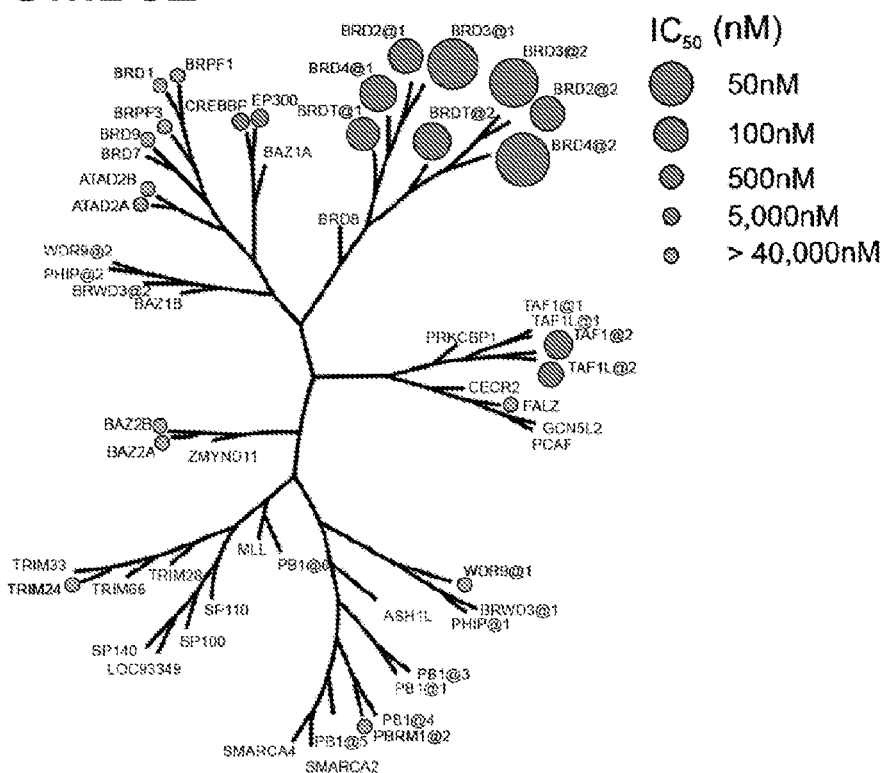
FIGS. 3A-3B show the selectivity of exemplary compounds of Formula (I) (e.g., compounds UMB11 and UMB32) for different bromodomain-containing proteins.
Figure 3B:
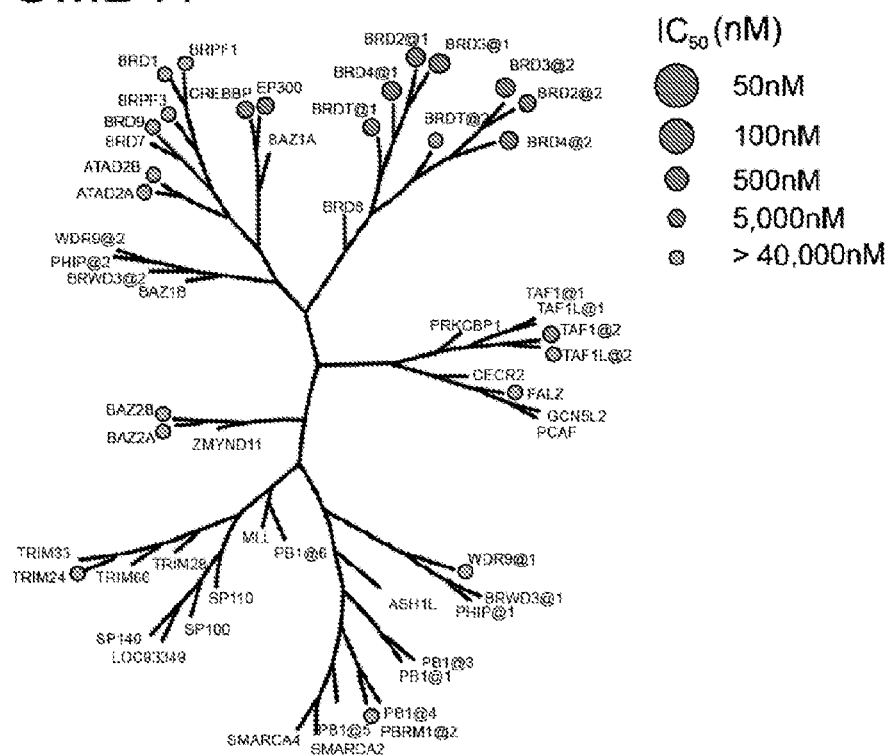
Figure 4:
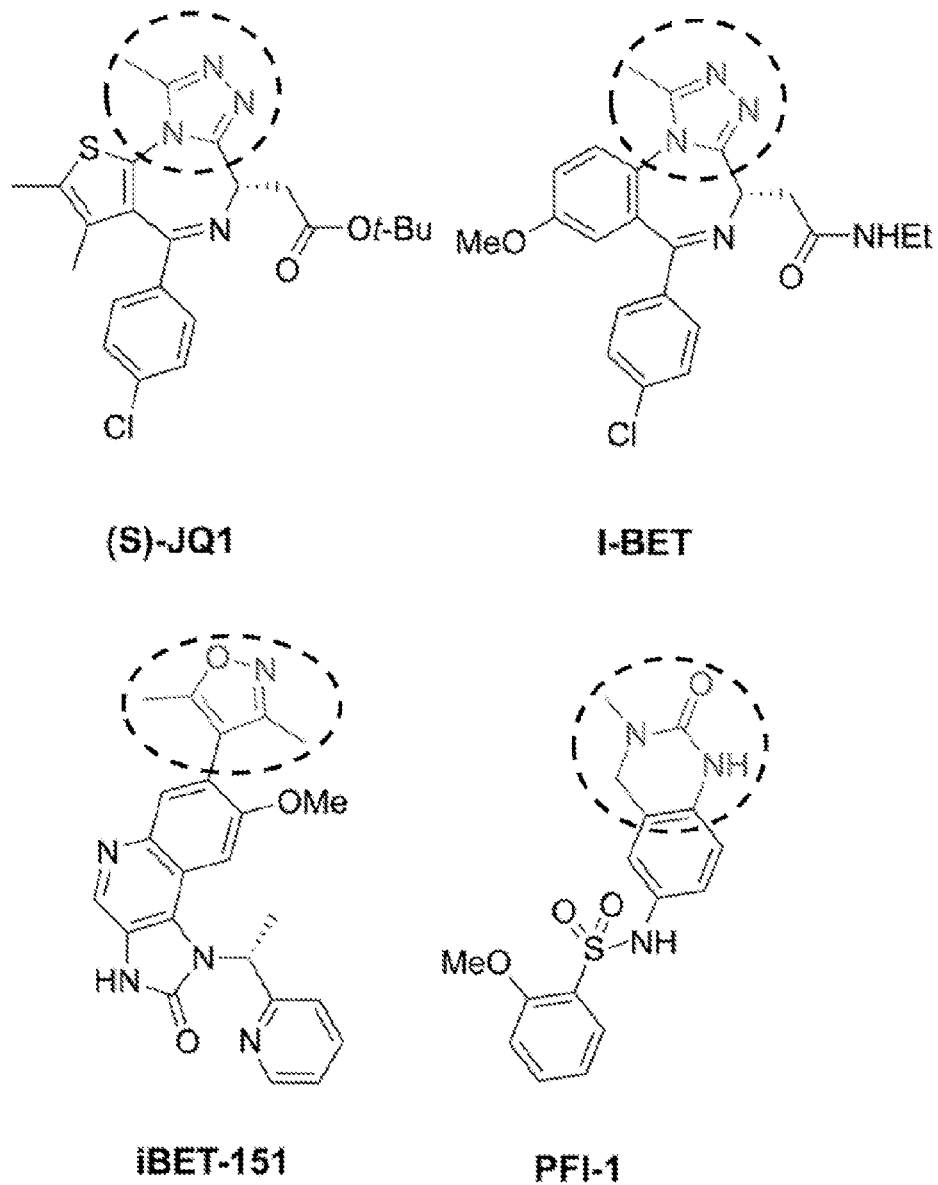
FIG. 4 shows existing BET bromodomain inhibitors with their biasing moieties highlighted by dashed circles.
Figure 5:
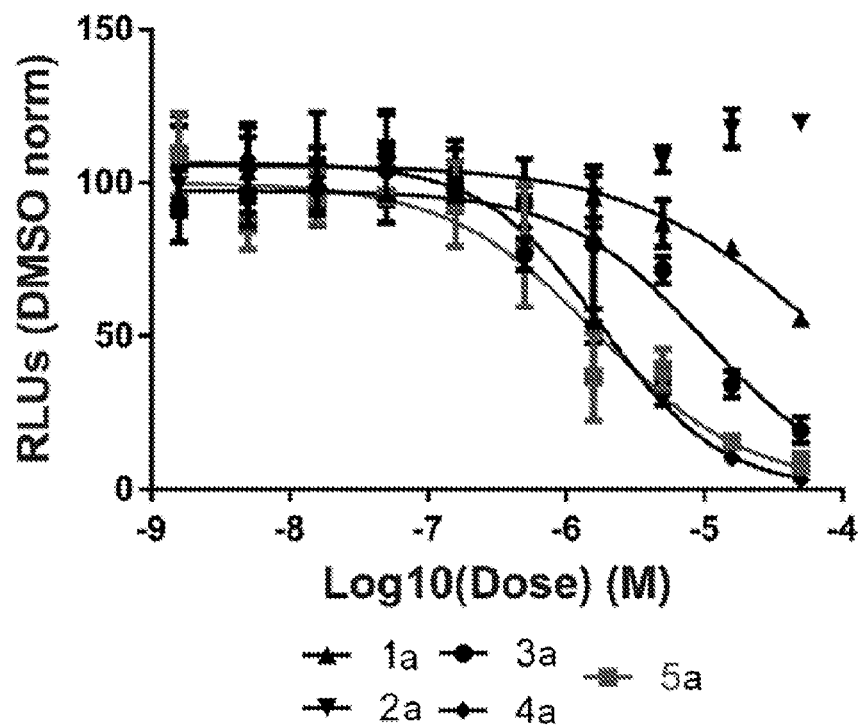
Figure 5:
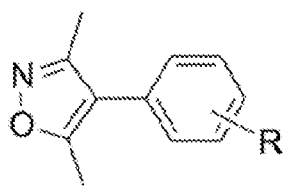
Figure 6A:
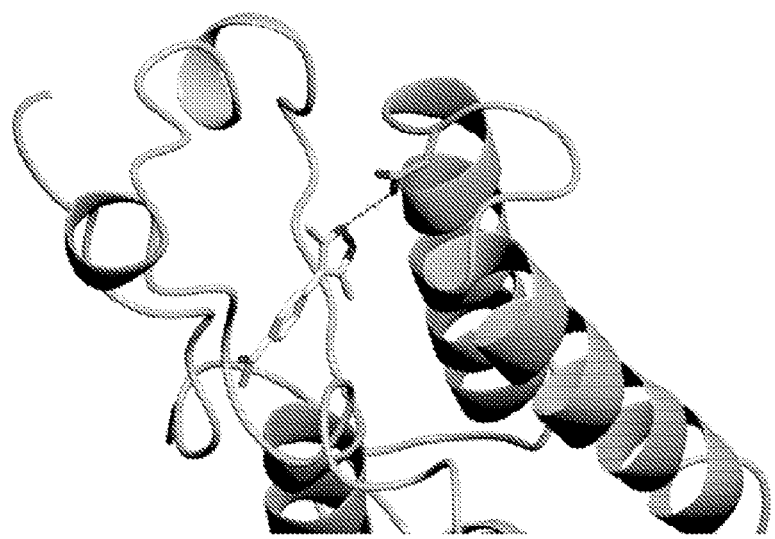
FIG. 6A shows the docking of compound 5a into BRD4 crystal structure (PDB: 3MXF).
Figure 6B:
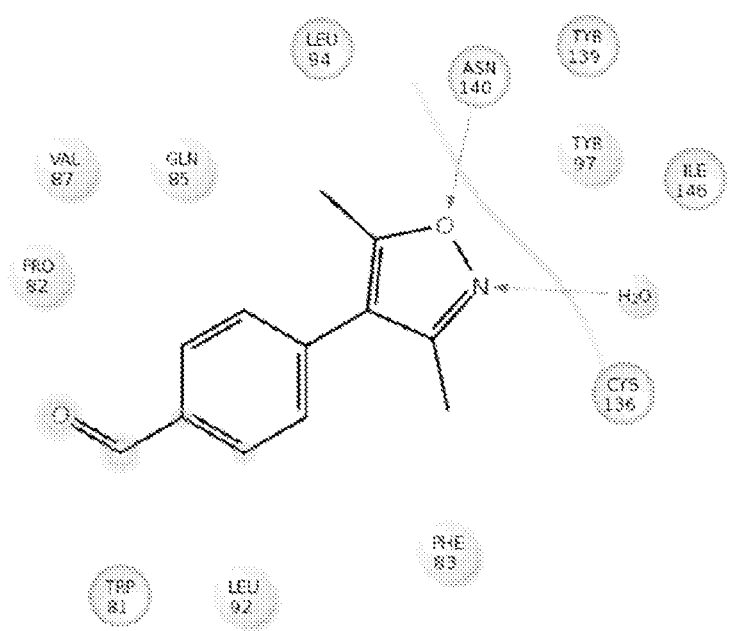
FIG. 6B shows the ligand interaction diagram of compound 5a and BRD4.
Figure 7:
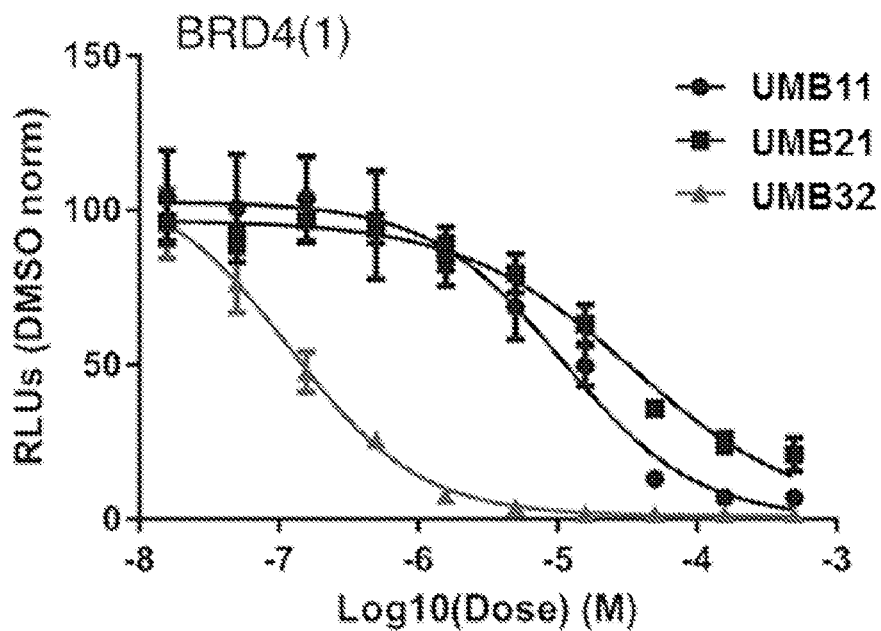
FIG. 7 shows representative biochemical inhibitory curves (top) and 797 viability (bottom) for compounds UMB11, UMB21, and UMB32.
Figure 7:
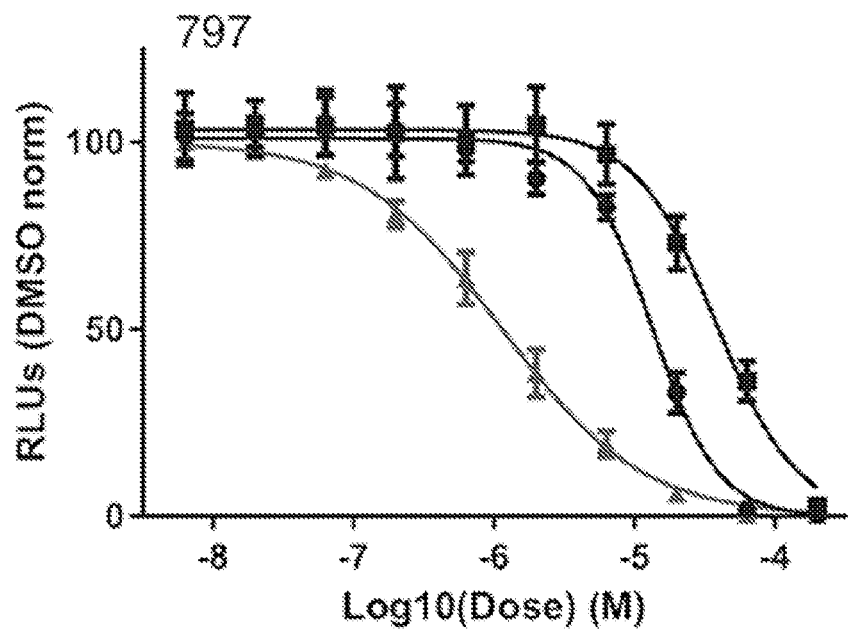
Figure 8:
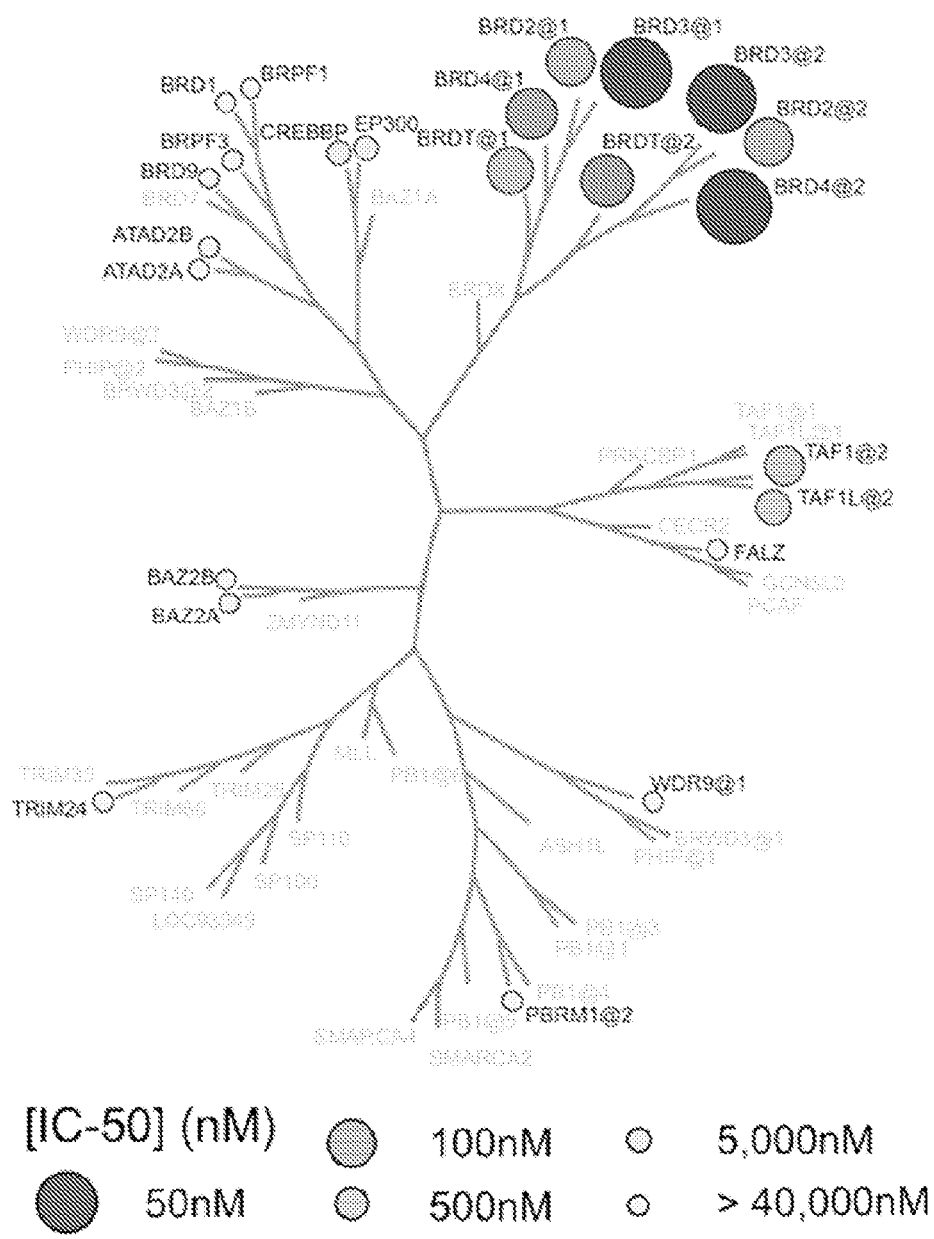
FIG. 8 shows the evaluation of compound UMB32 selectivity against a panel of bromodomains.
Figure 9:
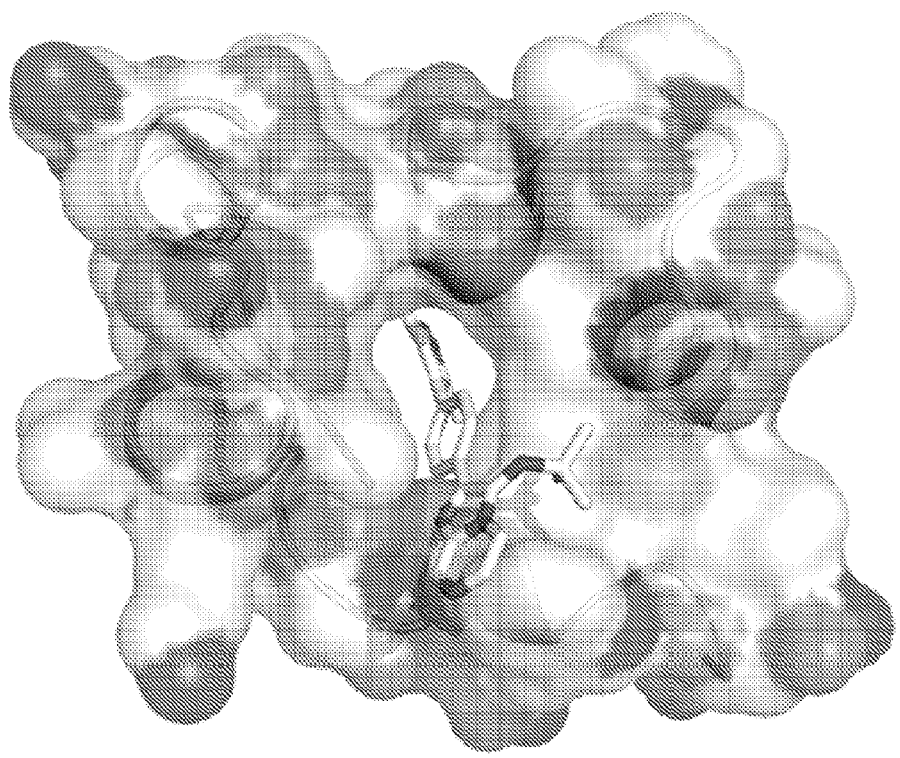
FIG. 9 shows the crystal structure of UMB32 in BRD4. Shaded areas are oxygen and nitrogen atoms.
Figure 10:
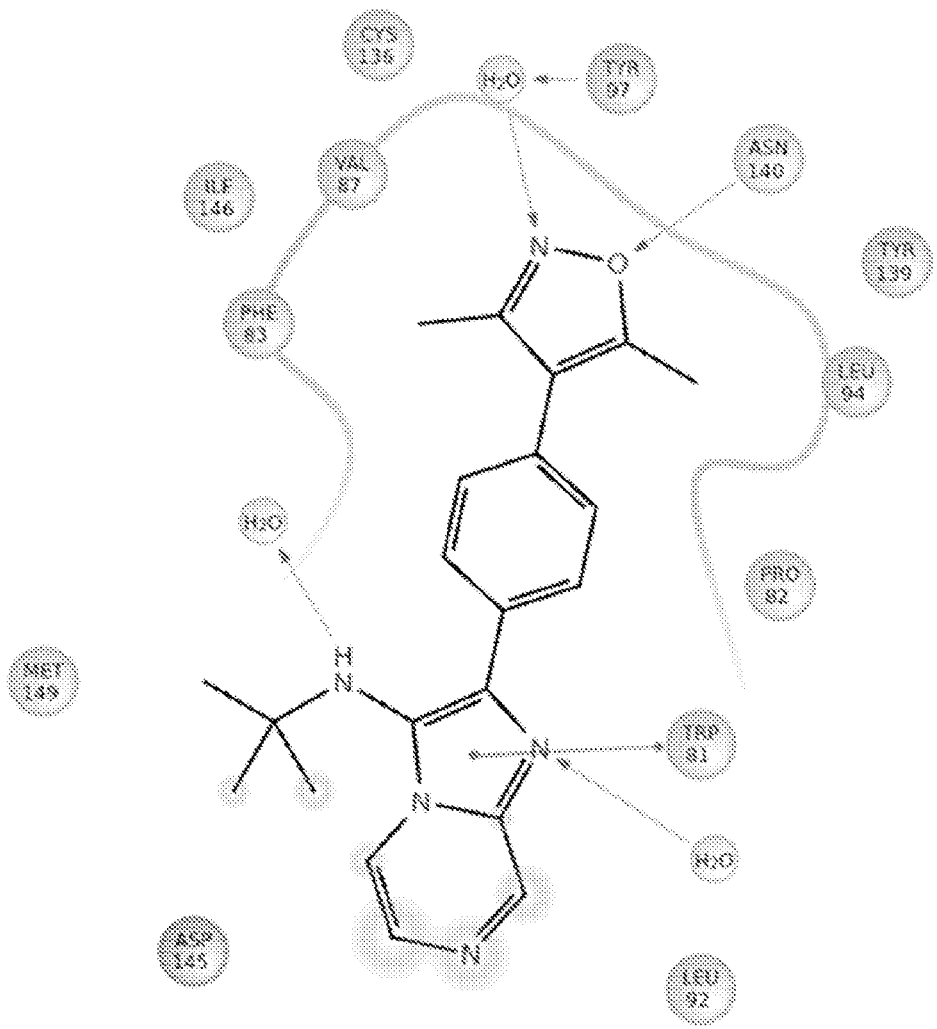
FIG. 10 shows the ligand interaction diagram of UMB32 in the BRD4 crystal.
Figure 11:
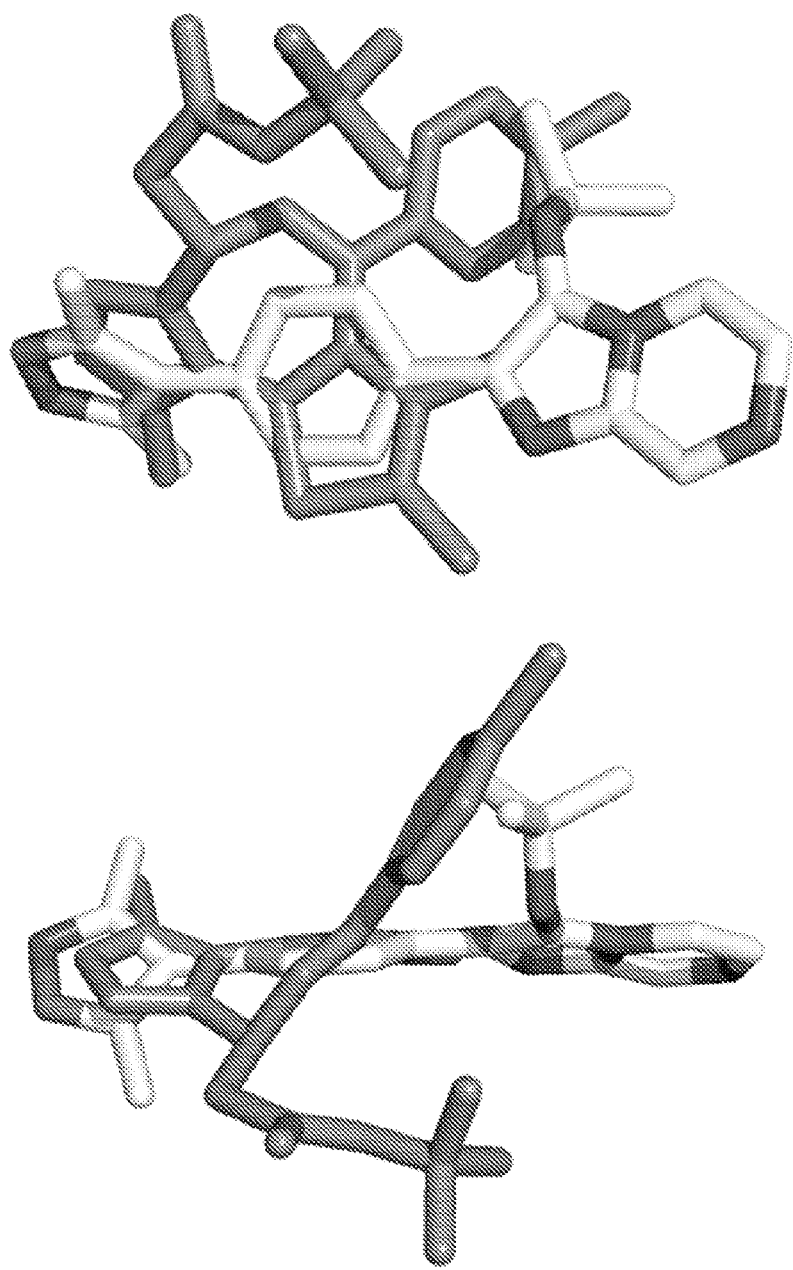
FIG. 11 shows the crystal structure of UMB32 overlaid on JQ1 (top) and rotated 90° (bottom).
Figure 12:
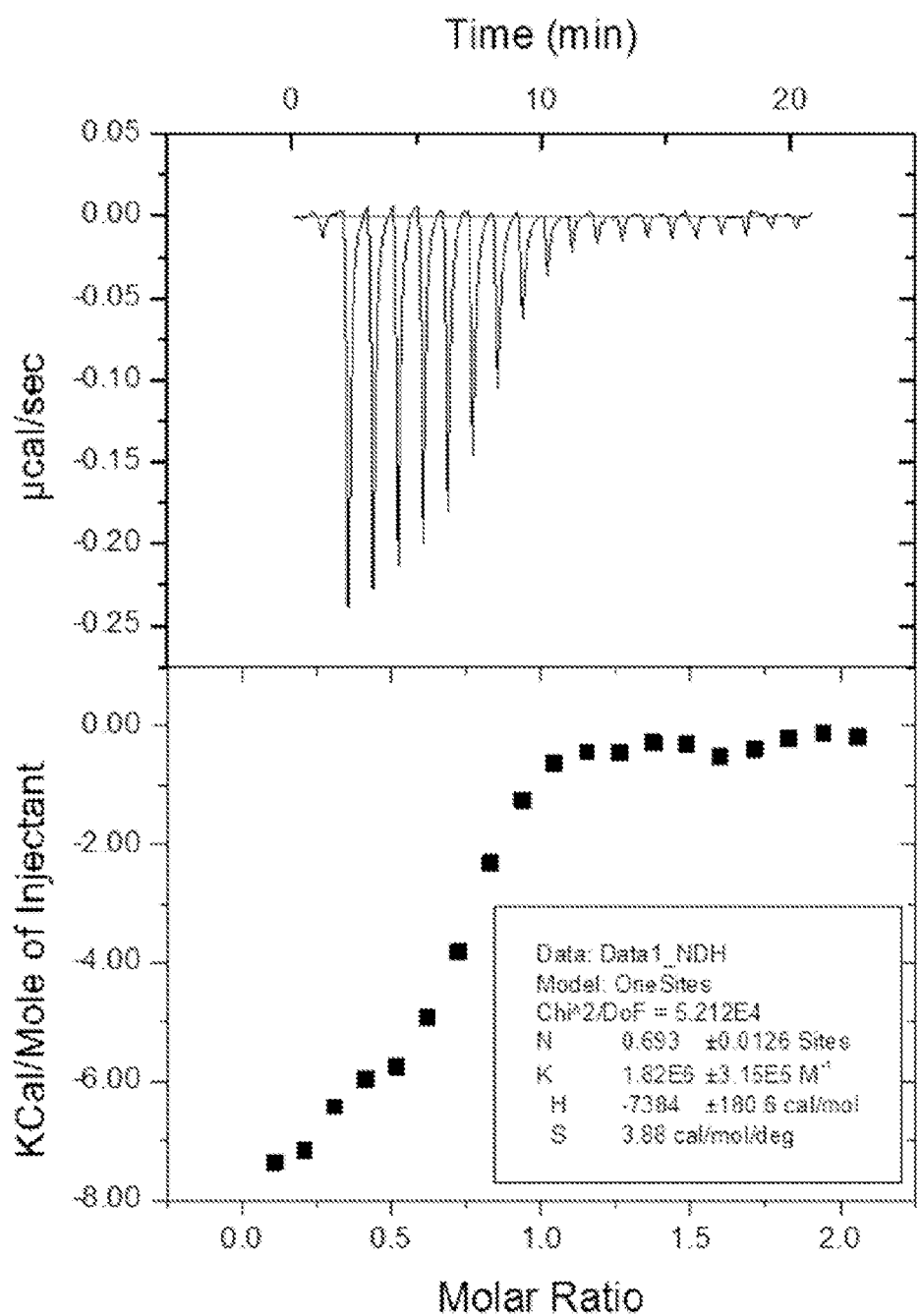
FIG. 12 shows isothermal titration calorimetry of UMB-32 and BRD4 protein.
Figure 13:
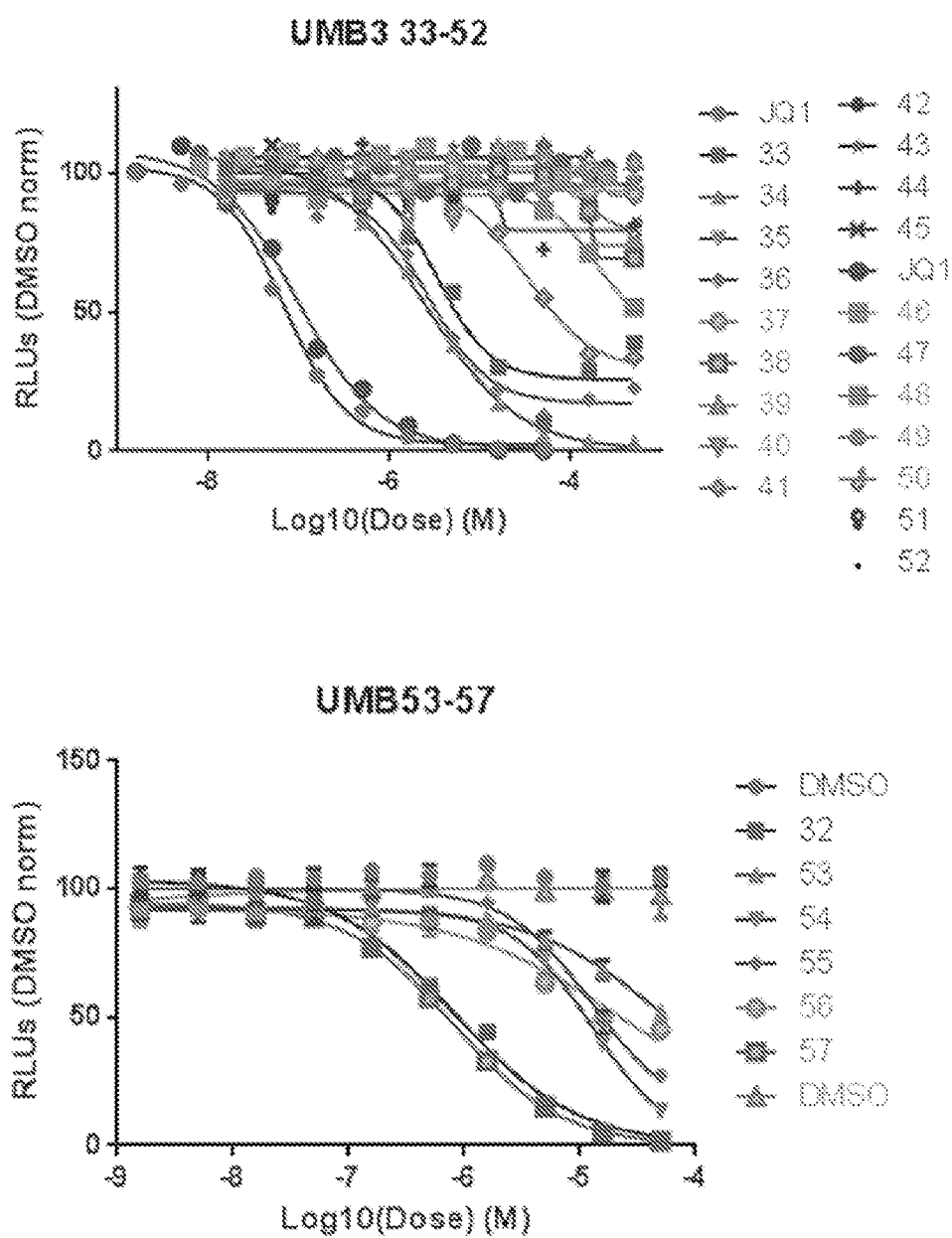
FIG. 13 shows the dose-response curves of exemplary compounds of Formula (I) or (IV) for inhibiting BRD4(1). The response was measured in relative luminescence units (RLUs) and was normalized against DMSO.
Figure 14:
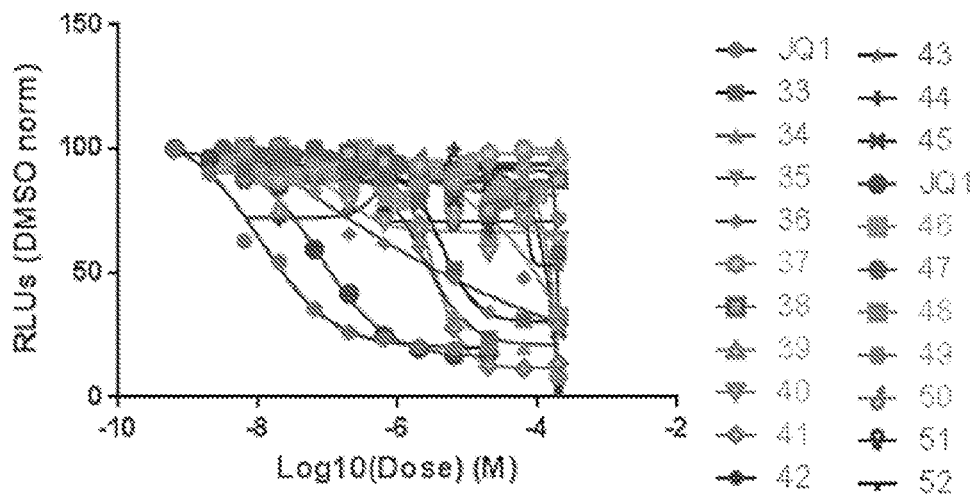
FIG. 14 shows the dose-response curves of exemplary compounds of Formula (I) or (IV) for inhibiting the growth of cancer cell line 797, a nuclear protein in testis (NUT) midline carcinoma. The response was measured in relative luminescence units (RLUs) and was normalized against DMSO.
Figure 14:
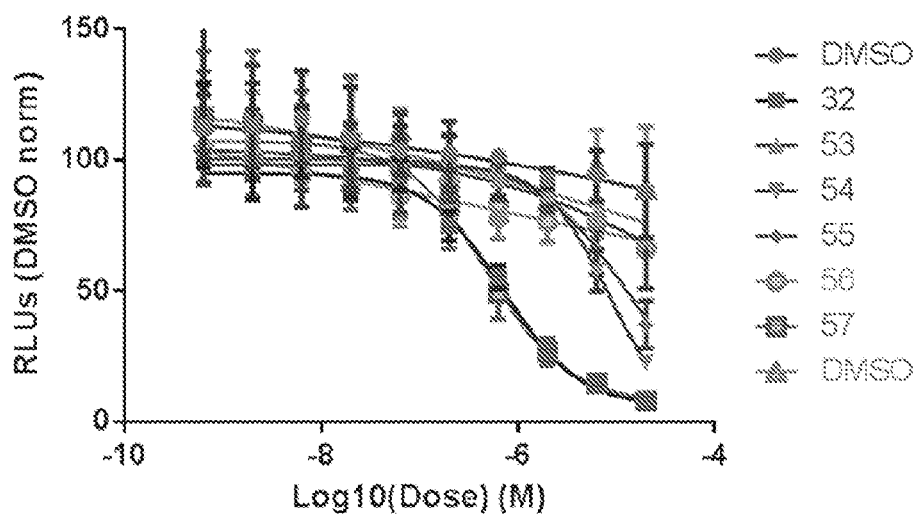

The compounds of the invention (e.g., UMB11 and UMB32) were profiled with a panel of bromodomain-containing proteins for selectivity and were also fully characterized by isothermal titration calorimetry (ITC) (FIG. 12). The results show that the compounds of the invention are active against bromodomain-containing proteins such as TAF1 and TAF1L, which may be validated targets for cancer therapy (Tables 8 and 9 and FIGS. 3A-3B).

TABLE 8

Selectivity of exemplary compounds of Formula (I) for different bromodomain-containing proteins measured by dissociation constant ($K_d$) values.

| Bromodomain-containing protein | JQ1 | I-BET | UMB32 | UMB11 |
|---|---|---|---|---|
| | | $K_d$ (nM) | | |
| ATAD2A | 40000 | 40000 | 40000 | 40000 |
| ATAD2B | 40000 | 40000 | 40000 | 40000 |
| BAZ2A | 40000 | 40000 | 40000 | 40000 |
| BAZ2B | 40000 | 40000 | 40000 | 40000 |
| BRD1 | 40000 | 40000 | 40000 | 40000 |
| BRD2(1) | 27 | 79 | 94 | 2400 |
| BRD2(2) | 18 | 23 | 95 | 5800 |
| BRD3(1) | 14 | 34 | 35 | 1300 |
| BRD3(2) | 19 | 27 | 38 | 1800 |
| BRD4(1) | 14 | 59 | 80 | 2500 |
| BRD4(2) | 8 | 11 | 31 | 3500 |
| BRD9 | 40000 | 40000 | 40000 | 40000 |
| BRDT(1) | 47 | 160 | 110 | 6000 |
| BRDT(2) | 35 | 45 | 75 | 40000 |
| BRPF1 | 40000 | 40000 | 40000 | 40000 |
| BRPF3 | 40000 | 40000 | 40000 | 40000 |
| CBP | 24000 | 76000 | 4500 | 6800 |
| EP300 | 51000 | 71000 | 4500 | 5800 |
| FALZ | 40000 | 40000 | 40000 | 40000 |
| PERM1(2) | 40000 | 40000 | 40000 | 40000 |
| TAF1(2) | 40000 | 40000 | 560 | 9700 |
| TAF1L(2) | 40000 | 40000 | 1300 | 40000 |
| TRIM24(PHD Bromo.) | 40000 | 40000 | 40000 | 40000 |
| TRIM33(PHD Bromo.) | 40000 | 40000 | 40000 | 40000 |
| WDR9(2) | 40000 | 40000 | 40000 | 40000 |

TABLE 9

BromoScan selectivity profile ($K_d$, nM) of compounds UMB11 and UMB32.

| | Compound UMB11 | Compound UMB32 |
|---|---|---|
| ATAD2A | 40000 | 40000 |
| ATAD2B | 40000 | 40000 |
| BAZ2A | 40000 | 40000 |
| BAZ2B | 40000 | 40000 |
| BRD1 | 40000 | 40000 |
| BRD2(1) | 2400 | 94 |
| BRD2(2) | 5800 | 95 |
| BRD3(1) | 1300 | 35 |
| BRD3(2) | 1800 | 38 |
| BRD4(1) | 2500 | 80 |
| BRD4(2) | 3500 | 31 |
| BRD9 | 40000 | 40000 |
| BRDT(1) | 6000 | 110 |
| BRDT(2) | 40000 | 75 |
| BRPF1 | 40000 | 40000 |
| BRDF3 | 40000 | 40000 |
| CREBBP | 6800 | 4500 |
| EP300 | 5800 | 4500 |
| FALZ | 40000 | 40000 |
| PERM1(2) | 40000 | 40000 |
| TAF1(2) | 9700 | 560 |
| TAF1L(2) | 40000 | 1300 |
| TRIM24(PHD, Bromo.) | 40000 | 40000 |
| TRIM33(PHD, Bromo.) | 40000 | 40000 |
| WDR9(2) | 40000 | 40000 |

Example 4

Computational Methods

Computational Methods

All computational work was performed in Schrodinger Suite (Schrodinger, LLC). Conformational analysis of lead compounds was performed using Schrodinger's Conformational Search function. Possible poses were prepared for docking by Ligprep. In both cases, default settings were used (OPLS2005 force field, water solvent). Docking was conducted using Glide. The co-crystal of BRD4 and JQ1 (PDB: 3MXF) was used to define the ligand receptor grid. Water molecules outside the binding pocket were excluded, and hydrogen bonding interactions were optimized prior to docking.

Results

Computational modeling was performed to better understand the modality of binding and inform further medicinal chemistry. Using previously published crystal structures of both JQ1 and iBET151, fragments were docked into the structure. As is the case with iBET151, compound 5a is thought to bind through a conserved hydrogen bond with N-140 through the ring oxygen, while the ring nitrogen coordinates through a structured water interacting with the hydroxyl group of Y-97. Based on this interaction, further analogs were built off the 4-position of the phenyl ring to improve potency by optimizing protein surface interactions near the BC loop region.

Example 5

X-Ray Crystallography

Crystallization and Diffraction Data Collection

Crystallization was conducted using the sitting drop vapor diffusion method at 22° C. Crystals of inhibitor-free BRD4-BD1 were first obtained in a drop with equal volumes of BD1 at 12 mg/ml and a precipitant solution containing 100 mM sodium nitrate, 5% ethylene glycol, and 18% (w/v) PEG3350, as precipitant. Rod-like crystals were typically grown in 10 days reaching a maximal size of 0.05×0.05×0.4 mm$^3$. Then, native crystals were transferred and soaked in 1 mM UMB32 in the same crystallization buffer for 7 days. For data collection, a single crystal was flash frozen with a precipitant solution containing 20% (v/v) glycerol. Diffraction data for BD1-UMB32 complex were collected from a flash-cooled crystal at 100° K using the 24ID-E beam lines at the NE-CAT, Argonne National Laboratory and were processed, integrated, and scaled together with HKL2000 (Otwinowski et al., *Methods Enzymol* 1997, 276, 307).

Structure Determination and Refinement

The structure of the BD1-UMB32 complex was solved by molecular replacement (MR) as implemented in Phenix[5] using the previous BD1-JQ1 structure (PDB 3MXF) as the search model. Structure refinement was carried out using conjugate-gradient energy minimization, torsion-constrained molecular dynamics simulated annealing, group B factor refinement, and individual B factor refinement protocols in Phenix[5] with 5% of the reflections omitted for free R factor calculation. Electron density peaks in difference Fourier maps at a height of above 3σ were assigned as water molecules in later refinement stages if they had reasonable geometry in relation to hydrogen bond donors or acceptors and their B-factors did not rise above 50 Å$^2$ during subsequent refinement. Model building was performed in Coot[6] guided by $\sigma_A$-weighted 2Fo-Fc and Fo-Fc maps and composite omit maps.

Data Collection and Refinement Statistics

| Beam line | X19 |
| --- | --- |
| Wavelength (Å) | 0.9792 |
| Resolution range (Å) | 35.45-1.56 (1.616-1.56) |
| Space group | P212121 |
| Unit cell | 43.562 49.21 60.991 90 90 90 |
| Unique reflections | 19177 (1862) |
| Redundancy | 3.9 (3.9) |
| Completeness (%) | 99.58 (100) |
| Mean I/sigma(I) | 9.88 (1.8) |
| R-work | 0.1697 (0.2587) |
| R-free | 0.201 (0.2661) |
| Number of non-hydrogen atoms | 1248 |
| macromolecules | 1047 |
| ligands | 47 |
| water | 154 |
| Protein residues | 127 |
| RMS(bonds) | 0.007 |
| RMS(angles) | 1.32 |
| Ramachandran favored (%) | 99 |
| Ramachandran allowed (%) | 1 |
| Ramachandran outliers (%) | 0 |
| Clashscore | 0.92 |
| Average B-factor | 19.6 |
| macromolecules | 17.5 |
| ligands | 22.5 |
| solvent | 32.9 |

EQUIVALENTS AND SCOPE

Those skilled in the art will recognize, or be able to ascertain using no more than routine experimentation, many equivalents to the specific embodiments, described herein. The scope of the present invention is not intended to be limited to the above Description, but rather is as set forth in the appended claims.

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any supercharged protein; any nucleic acid; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

What is claimed is:
1. A compound of Formula (I):

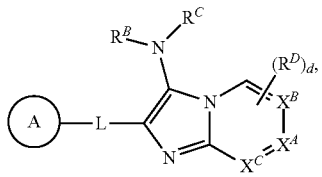

or a pharmaceutically acceptable salt thereof;
wherein:
$X^A$ is $C(R^D)$ or N;
$X^B$ is $C(R^D)$ or N;
$X^C$ is $C(R^D)$ or N;
wherein no more than two of $X^A$, $X^B$, and $X^C$ can be N;
Ring A is of the formula:

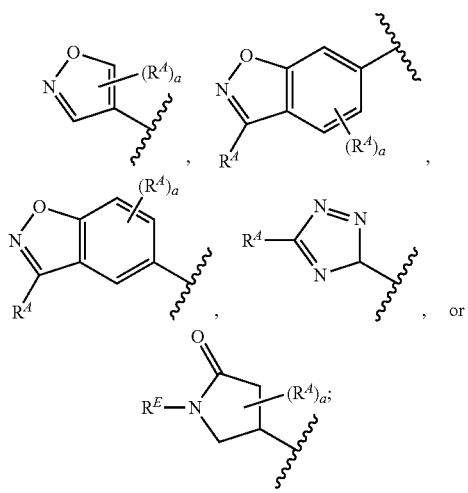

L is a bond or of the formula:

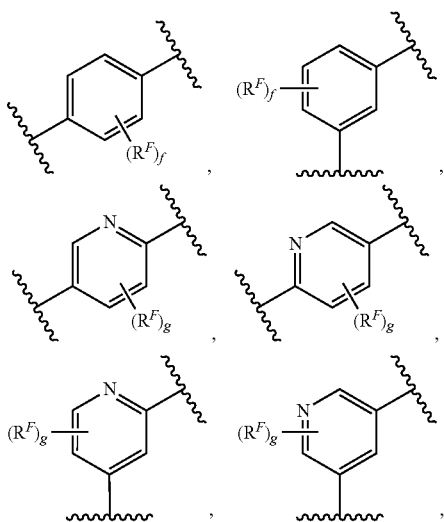

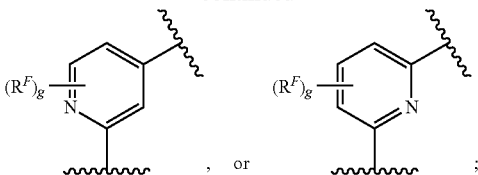

each instance of $R^A$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A1}$, —$N(R^{A1})_2$, —$SR^{A1}$, —CN, —SCN, —$C(=NR^{A1})R^{A1}$, —$C(=NR^{A1})OR^{A1}$, —$C(=NR^{A1})N(R^{A1})_2$, —$C(=O)R^{A1}$, —$C(=O)OR^{A1}$, —$C(=O)N(R^{A1})_2$, —$NO_2$, —$NR^{A1}C(=O)R^{A1}$, —$NR^{A1}C(=O)OR^{A1}$, —$NR^{A1}C(=O)N(R^{A1})_2$, —$OC(=O)R^{A1}$, —$OC(=O)OR^{A1}$, or —$OC(=O)N(R^{A1})_2$, or two instances of $R^A$ are joined to form a substituted or unsubstituted carbocyclic, substituted or unsubstituted heterocyclic, substituted or unsubstituted aryl, or substituted or unsubstituted heteroaryl ring;

each instance of $R^{A1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1}$ are joined to form a substituted or unsubstituted heterocyclic ring;

$R^B$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted aryl, —$C(=O)R^{B1}$, —$C(=O)OR^{B1}$, —$C(=O)N(R^{B1})_2$, or a nitrogen protecting group, or $R^B$ and $R^C$ are joined to form a substituted or unsubstituted heterocyclic ring;

each instance of $R^{B1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or an oxygen protecting group when attached to an oxygen atom, or two instances of $R^{B1}$ are joined to form a substituted or unsubstituted heterocyclic ring;

$R^C$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted aryl, —$C(=O)R^{C1}$, —$C(=O)OR^{C1}$, —$C(=O)N(R^{C1})_2$, or a nitrogen protecting group, or $R^C$ and $R^B$ are joined to form a substituted or unsubstituted heterocyclic ring;

each instance of $R^{C1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or an oxygen protecting group when attached to an oxygen atom, or two instances of $R^{C1}$ are joined to form a substituted or unsubstituted heterocyclic ring;

each instance of $R^D$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{D1}$, $-N(R^{D1})_2$, $-SR^{D1}$, $-CN$, $-SCN$, $-C(=NR^{D1})R^{D1}$, $-C(=NR^{D1})OR^{D1}$, $-C(=NR^{D1})N(R^{D1})_2$, $-C(=O)R^{D1}$, $-C(=O)OR^{D1}$, $-C(=O)N(R^{D1})_2$, $-NO_2$, $-NR^{D1}C(=O)R^{D1}$, $-NR^{D1}C(=O)OR^{D1}$, $-NR^{D1}C(=O)N(R^{D1})_2$, $-OC(=O)R^{D1}$, $-OC(=O)OR^{D1}$, or $-OC(=O)N(R^{D1})_2$, or two instances of $R^D$ are joined to form a substituted or unsubstituted carbocyclic, substituted or unsubstituted heterocyclic, substituted or unsubstituted aryl, or substituted or unsubstituted heteroaryl ring;

each instance of $R^{D1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{D1}$ are joined to form a substituted or unsubstituted heterocyclic ring;

$R^E$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-C(=O)R^{E1}$, $-C(=O)OR^{E1}$, $-C(=O)N(R^{E1})_2$, or a nitrogen protecting group;

each instance of $R^{E1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or an oxygen protecting group when attached to an oxygen atom, or two instances of $R^{E1}$ are joined to form a substituted or unsubstituted heterocyclic ring;

each instance of $R^F$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{F1}$, $-N(R^{F1})_2$, $-SR^{F1}$, $-CN$, $-SCN$, $-C(=NR^{F1})R^{F1}$, $-C(=NR^{F1})OR^{F1}$, $-C(=NR^{F1})N(R^{F1})_2$, $-C(=O)R^{F1}$, $-C(=O)OR^{F1}$, $-C(=O)N(R^{F1})_2$, $-NO_2$, $-NR^{F1}C(=O)R^{F1}$, $-NR^{F1}C(=O)OR^{F1}$, $-NR^{F1}C(=O)N(R^{F1})_2$, $-OC(=O)R^{F1}$, $-OC(=O)OR^{F1}$, or $-OC(=O)N(R^{F1})_2$, or two instances of $R^F$ are joined to form a substituted or unsubstituted carbocyclic, substituted or unsubstituted heterocyclic, substituted or unsubstituted aryl, or substituted or unsubstituted heteroaryl ring;

each instance of $R^{F1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{F1}$ are joined to form a substituted or unsubstituted heterocyclic ring;

a is 0, 1, 2, 3, 4, or 5;

d is 0, 1, or 2;

f is 0, 1, 2, 3 or 4; and g is 0, 1, 2, or 3.

2. The compound of claim 1 of Formula (Ia):

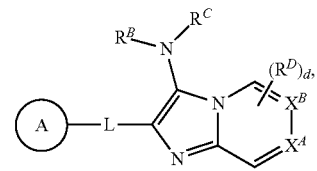

or a pharmaceutically acceptable salt thereof;

wherein:

L is a bond or of the formula:

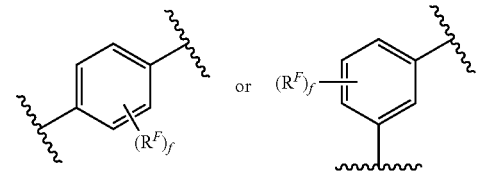

3. The compound of claim 1, wherein the compound is of the formula:

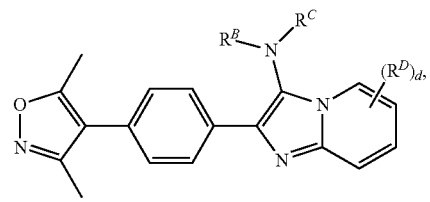

-continued

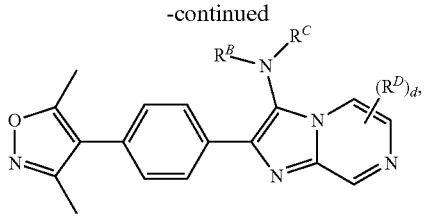

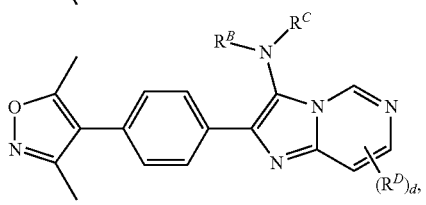

or a pharmaceutically acceptable salt thereof.

4. The compound of claim 1, wherein the compound is of the formula:

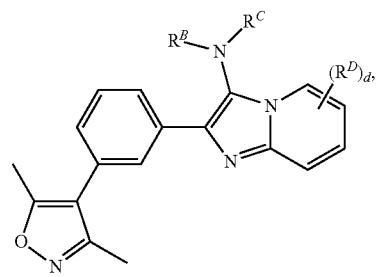

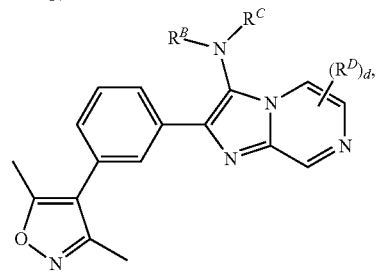

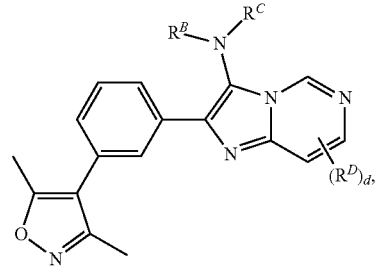

or a pharmaceutically acceptable salt thereof.

5. The compound of claim 1, wherein the compound is of the formula:

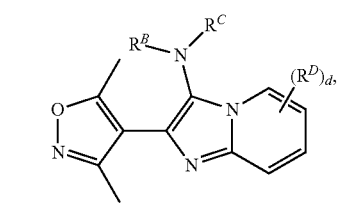

-continued

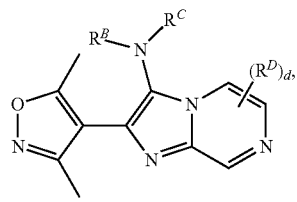

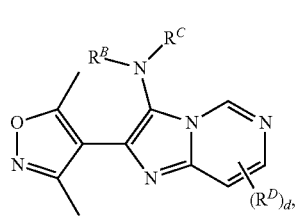

or a pharmaceutically acceptable salt thereof.

6. The compound of claim 1, wherein the compound is of the formula:

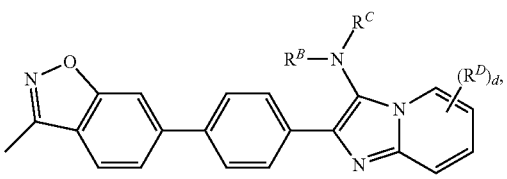

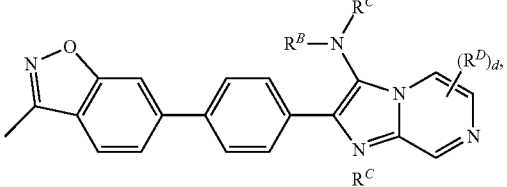

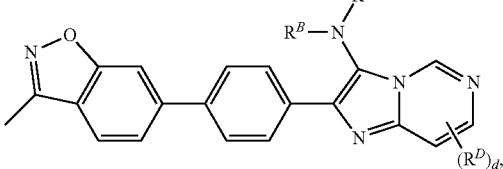

or a pharmaceutically acceptable salt thereof.

7. The compound of claim 1, wherein the compound is of the formula:

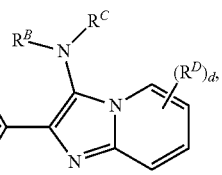

-continued

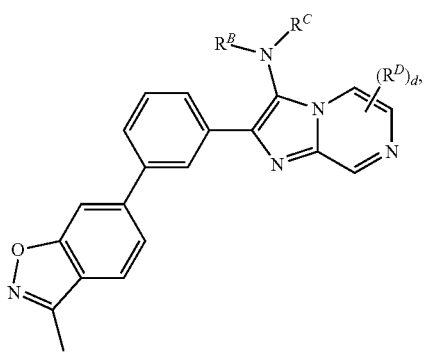

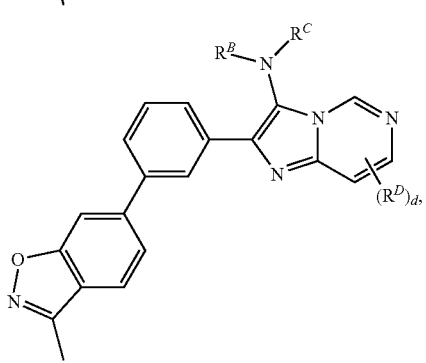

or a pharmaceutically acceptable salt thereof.

8. The compound of claim 1, wherein the compound is of the formula:

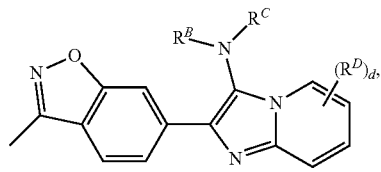

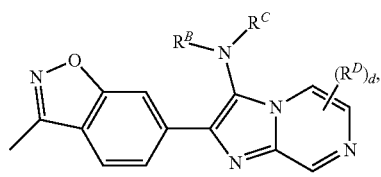

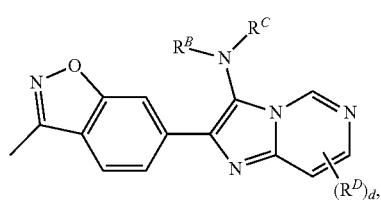

or a pharmaceutically acceptable salt thereof.

9. The compound of claim 1, wherein the compound is of the formula:

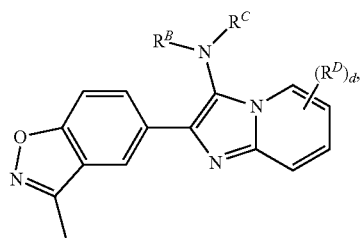

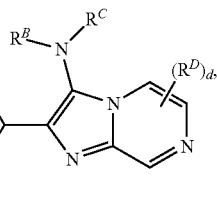

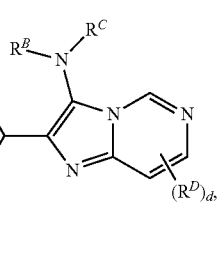

or a pharmaceutically acceptable salt thereof.

10. The compound of claim 1, wherein the compound is of the formula:

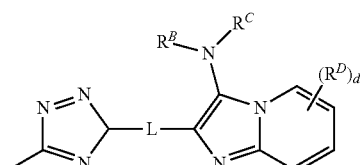

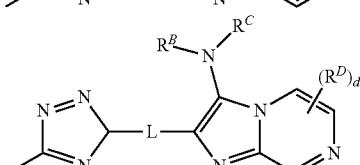

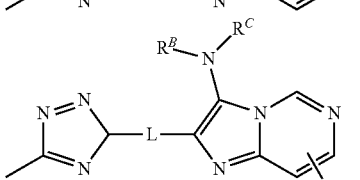

or a pharmaceutically acceptable salt thereof.

11. The compound of claim 1, wherein the compound is of the formula:

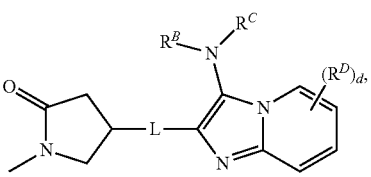

-continued

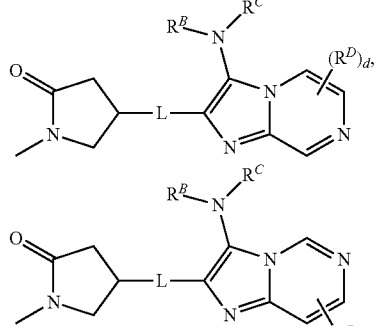

or a pharmaceutically acceptable salt thereof.

12. The compound of claim 1, wherein Ring A is of the formula:

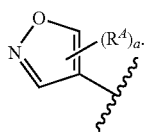

13. The compound of claim 1, wherein Ring A is of the formula:

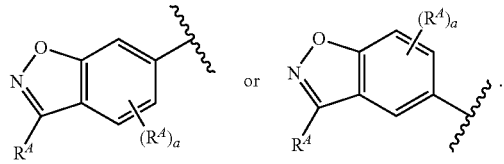

14. The compound of claim 1, wherein Ring A is of the formula:

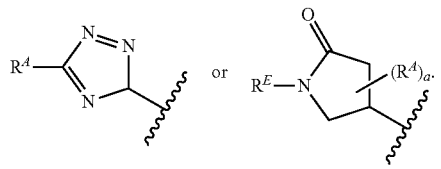

15. The compound of claim 1, wherein L is a bond.

16. The compound of claim 1, wherein L is of the formula:

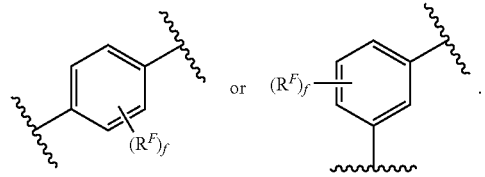

17. The compound of claim 1, wherein $R^B$ is substituted or unsubstituted acyl, substituted or unsubstituted alkyl, substituted or unsubstituted carbocyclyl, substituted or unsubstituted aryl, —C(=O)$R^{B1}$, —C(=O)O$R^{B1}$, or —C(=O)N($R^{B1}$)$_2$.

18. The compound of claim 1, wherein $R^C$ is hydrogen.

19. The compound of claim 1, wherein at least one instance of $R^D$ is halogen, substituted or unsubstituted alkyl, or —O$R^{D1}$.

20. The compound of claim 1, wherein the compound is of the formula:

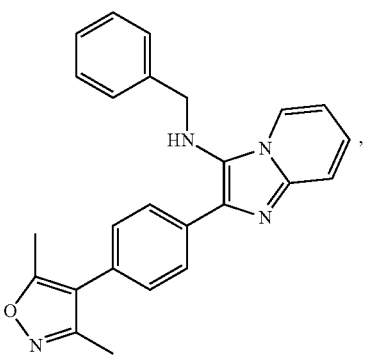
(UMB11)

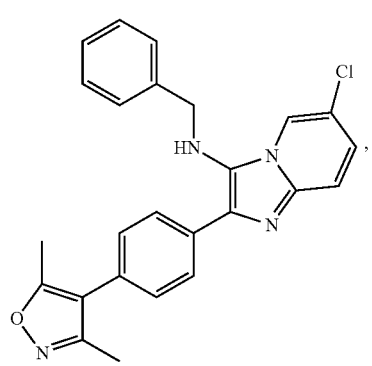
(UMB20)

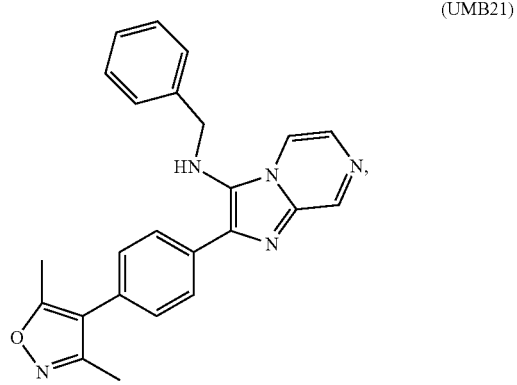
(UMB21)

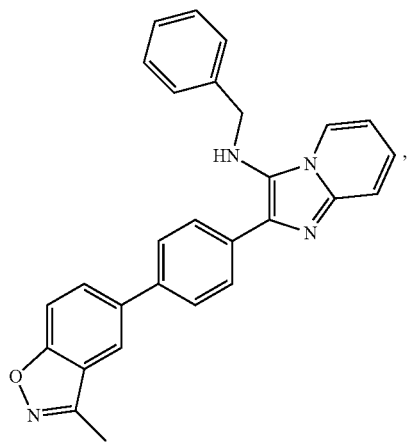
(UMB22)
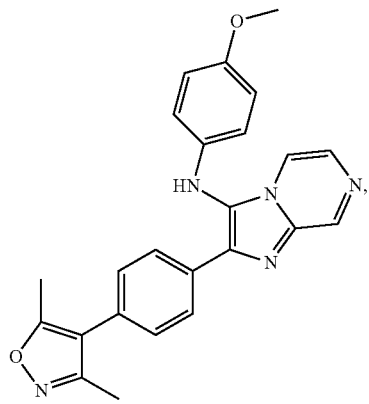
(UMB25)
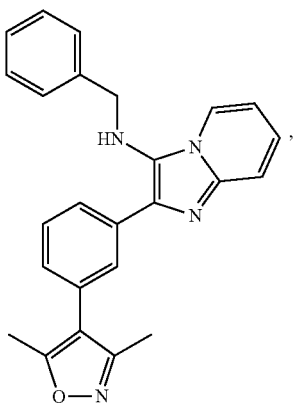
(UMB26)
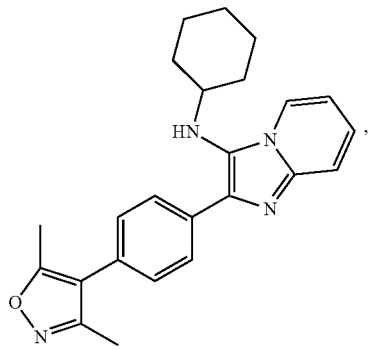
(UMB28)
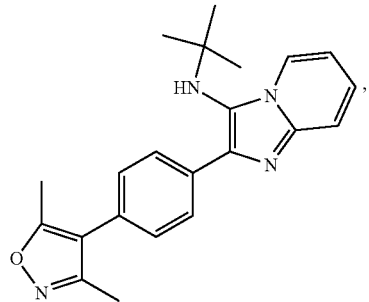
(UMB29)

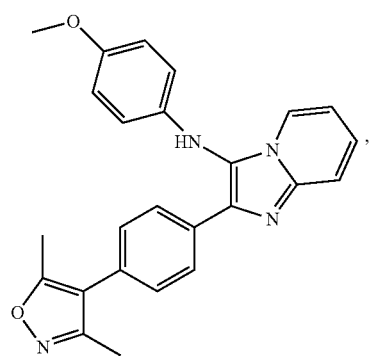
(UMB30)
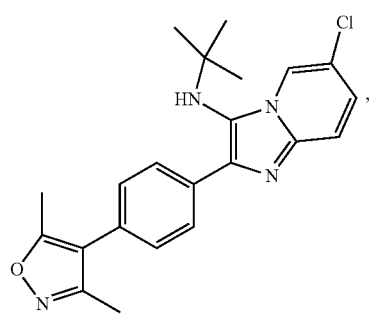
(UMB31)
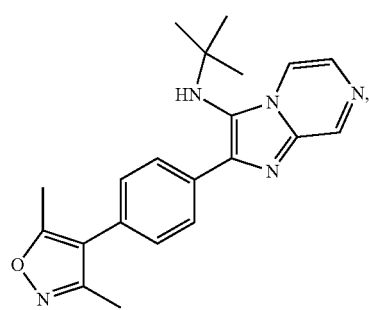
(UMB32)
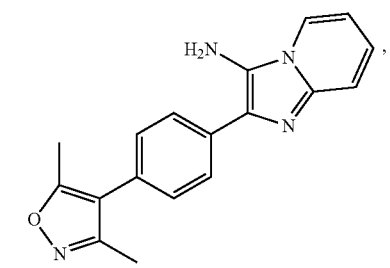
(12a)
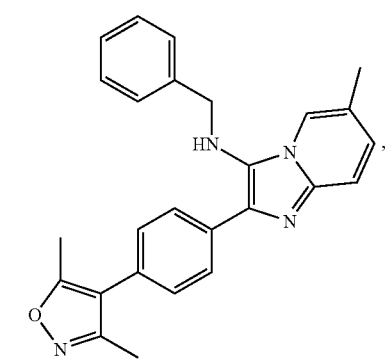
(13a)
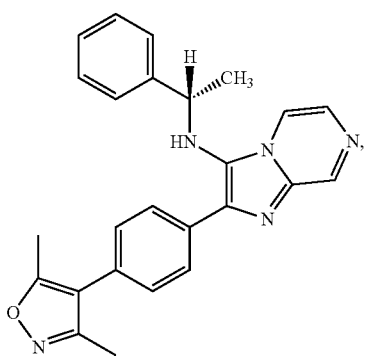
(21a)
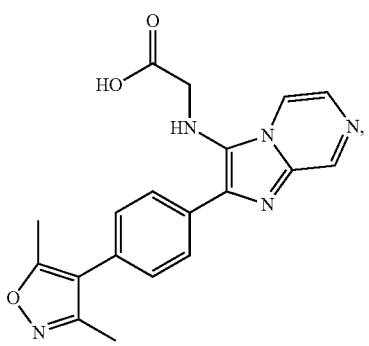
(22a)
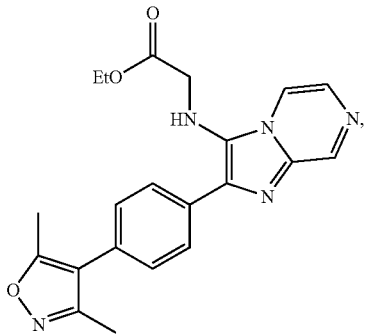
(23a)
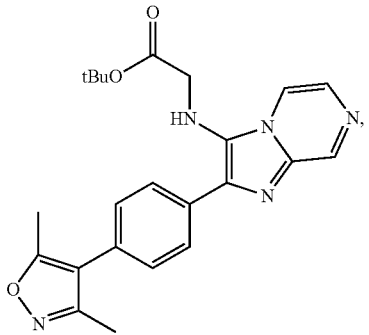
(24a)

-continued
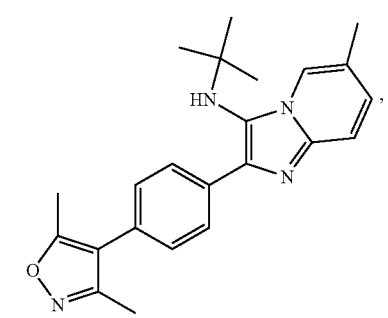
(27a)
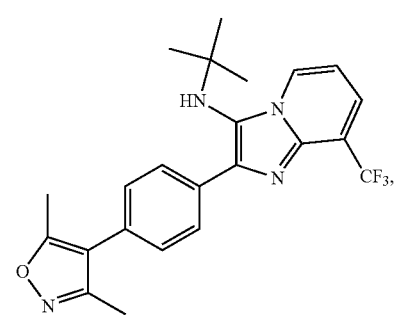
(28a)
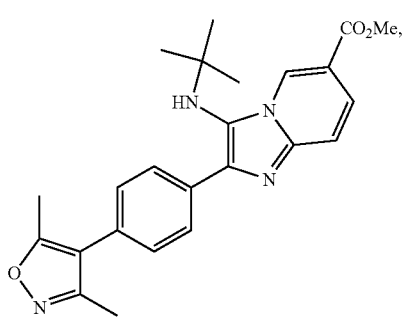
(29a)
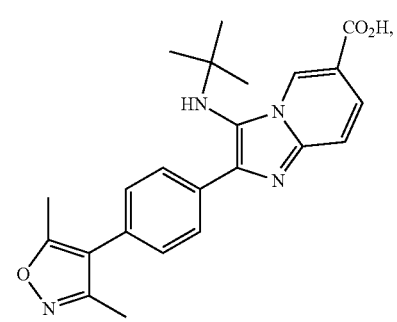
(30a)
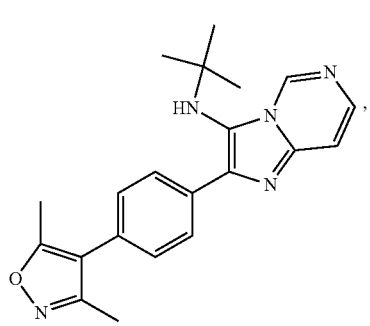
(UMB56)
-continued
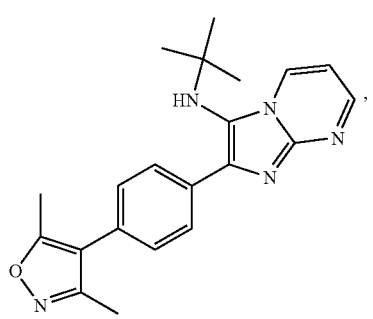
(33a)
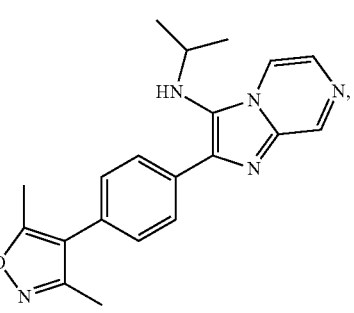
(UMB57)
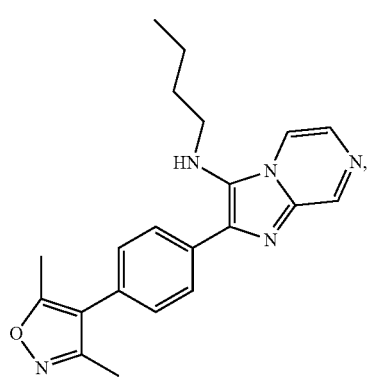
(35a)
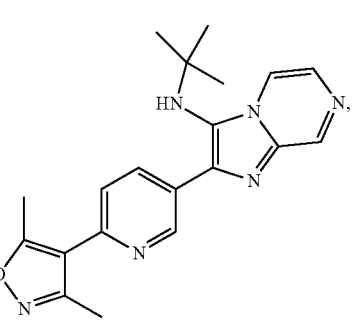
(UMB53)
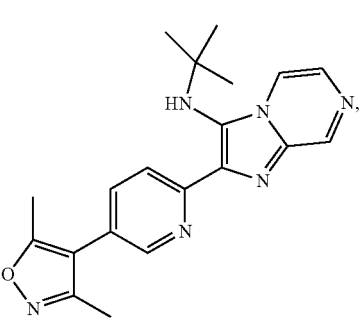
(UMB54)

(UMB55)
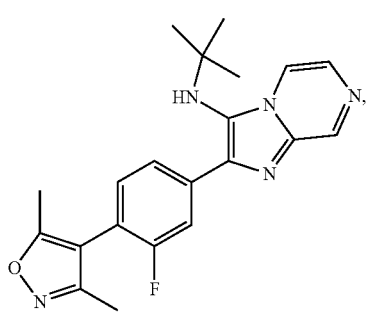

(39a)
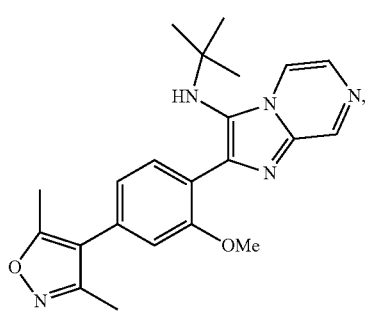

(40a)
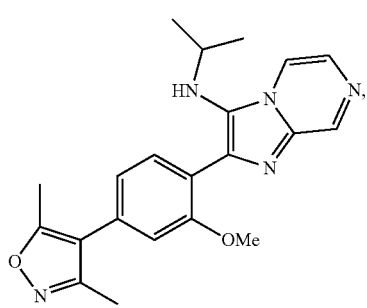

(UMB-33)
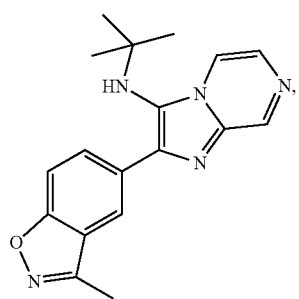

(UMB-34)
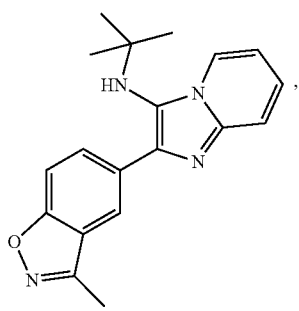

(UMB-35)
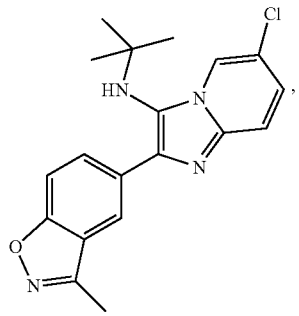

(UMB-36)
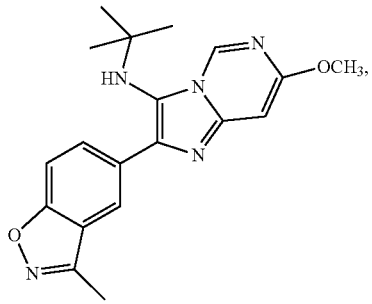

(UMB-42)
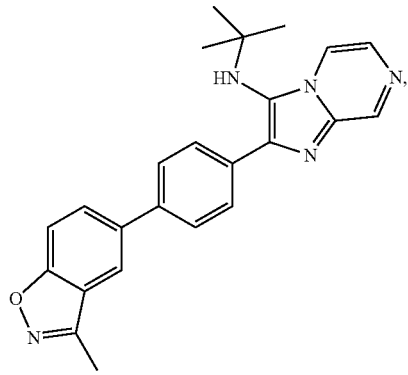

or a pharmaceutically acceptable salt thereof.

21. A pharmaceutical composition comprising a compound of claim 1, or a pharmaceutically acceptable salt thereof, and optionally a pharmaceutically acceptable excipient.

22. The compound of claim 1, wherein the compound is of the formula:

(UMB32)
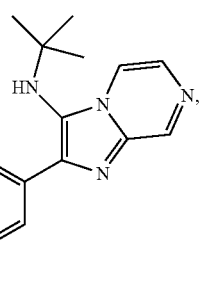

or a pharmaceutically acceptable salt thereof.

23. The compound of claim 1 wherein the compound is of the formula:

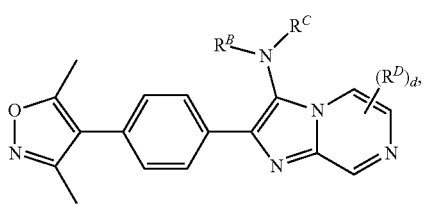

or a pharmaceutically acceptable salt thereof.

24. The compound of claim 1, wherein $X^A$ is N.
25. The compound of claim 1, wherein $X^B$ is $C(R^D)$.
26. The compound of claim 1, wherein $X^C$ is $C(R^D)$.
27. The compound of claim 1, wherein at least one instance of $R^A$ is substituted or unsubstituted $C_{1-6}$ alkyl.
28. The compound of claim 27, wherein at least one instance of $R^A$ is methyl.

29. The compound of claim 1, wherein L is of the formula:

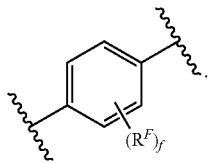

30. The compound of claim 17, wherein $R^B$ is substituted or unsubstituted $C_{1-6}$ alkyl.
31. The compound of claim 17, wherein $R^B$ is t-Bu.
32. The compound of claim 17, wherein $R^B$ is benzyl.
33. The compound of claim 17, wherein $R^B$ is substituted or unsubstituted phenyl.

* * * * *

```
                        SEQUENCE LISTING

<160> NUMBER OF SEQ ID NOS: 3

<210> SEQ ID NO 1
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: biotin-PEG2
<220> FEATURE:
<221> NAME/KEY: MOD_RES
<222> LOCATION: (5)..(5)
<223> OTHER INFORMATION: ACETYLATION
<220> FEATURE:
<221> NAME/KEY: MOD_RES
<222> LOCATION: (8)..(8)
<223> OTHER INFORMATION: ACETYLATION
<220> FEATURE:
<221> NAME/KEY: MOD_RES
<222> LOCATION: (12)..(12)
<223> OTHER INFORMATION: ACETYLATION
<220> FEATURE:
<221> NAME/KEY: MOD_RES
<222> LOCATION: (16)..(16)
<223> OTHER INFORMATION: ACETYLATION

<400> SEQUENCE: 1

Ser Gly Arg Gly Lys Gly Gly Lys Gly Leu Gly Lys Gly Gly Ala Lys
1               5                   10                  15

Arg His Arg Lys
            20

<210> SEQ ID NO 2
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 2

Met His His His His His His Ser Ser Gly Val Asp Leu Gly Thr Glu
1               5                   10                  15

Asn Leu Tyr Phe Gln Ser Met
            20

<210> SEQ ID NO 3
<211> LENGTH: 6
<212> TYPE: PRT
<213> ORGANISM: Artificial Sequence
<220> FEATURE:
<223> OTHER INFORMATION: Synthetic Oligopeptide

<400> SEQUENCE: 3

His His His His His His
1               5
```